(12) United States Patent
Tahri et al.

(10) Patent No.: US 9,617,289 B2
(45) Date of Patent: Apr. 11, 2017

(54) RSV ANTIVIRAL COMPOUNDS

(71) Applicant: JANSSEN R&D IRELAND, Little Island, County Cork (IE)

(72) Inventors: Abdellah Tahri, Anderlecht (BE); Sandrine Marie Helene Vendeville, Woluwe-Saint-Pierre (BE); Tim Hugo Maria Jonckers, Heist-op-den-Berg (BE); Pierre Jean-Marie Bernard Raboisson, Rosieres (BE); Lili Hu, Mechelen (BE); Samuël Dominique Demin, Antwerp (BE); Ludwig Paul Cooymans, Beerse (BE)

(73) Assignee: JANSSEN SCIENCES IRELAND UC, Little Island, County Cork (IE)

( * ) Notice: Subject to any disclaimer, the term of this patent is extended or adjusted under 35 U.S.C. 154(b) by 0 days.

(21) Appl. No.: 14/435,604

(22) PCT Filed: Oct. 15, 2013

(86) PCT No.: PCT/EP2013/071525
§ 371 (c)(1),
(2) Date: Apr. 14, 2015

(87) PCT Pub. No.: WO2014/060411
PCT Pub. Date: Apr. 24, 2014

(65) Prior Publication Data
US 2015/0259367 A1     Sep. 17, 2015

(30) Foreign Application Priority Data

Oct. 16, 2012 (EP) ..................... 12188694
Mar. 15, 2013 (EP) ..................... 13159431

(51) Int. Cl.
| | | |
|---|---|---|
| C07D 403/06 | (2006.01) |
| C07D 403/14 | (2006.01) |
| C07D 471/04 | (2006.01) |
| C07D 471/20 | (2006.01) |
| C07D 491/107 | (2006.01) |
| C07D 491/20 | (2006.01) |
| C07D 493/20 | (2006.01) |
| C07D 519/00 | (2006.01) |
| C07D 487/10 | (2006.01) |
| C07F 9/6506 | (2006.01) |
| C07D 471/10 | (2006.01) |
| C07D 495/20 | (2006.01) |

(52) U.S. Cl.
CPC ........ *C07F 9/65068* (2013.01); *C07D 403/06* (2013.01); *C07D 403/14* (2013.01); *C07D 471/04* (2013.01); *C07D 471/10* (2013.01); *C07D 471/20* (2013.01); *C07D 487/10* (2013.01); *C07D 491/107* (2013.01); *C07D 495/20* (2013.01); *C07D 491/20* (2013.01); *C07D 495/20* (2013.01); *C07D 519/00* (2013.01)

(58) Field of Classification Search
CPC .. C07D 403/06; C07D 403/14; C07D 471/04; C07D 471/20; C07D 491/107; C07D 491/20; C07D 493/20; C07D 519/00; C07D 487/10
See application file for complete search history.

(56) References Cited

U.S. PATENT DOCUMENTS

2014/0308282 A1* 10/2014 Cockerill ............. C07D 401/06
424/134.1

FOREIGN PATENT DOCUMENTS

| CL | 3245-04 | 3/2003 |
|---|---|---|
| WO | WO 2004/069256 A1 | 8/2004 |
| WO | WO 2004/076455 A1 | 9/2004 |
| WO | WO 2012/080446 A1 | 6/2012 |
| WO | WO 2012/080447 A1 | 6/2012 |
| WO | WO 2012/080449 A1 | 6/2012 |
| WO | WO 2012/080450 A1 | 6/2012 |
| WO | WO 2012/080451 A1 | 6/2012 |
| WO | WO 2013/068769 A1 | 5/2013 |

OTHER PUBLICATIONS

Cockerill et al., caplus an 2013:763544 (2013).*
Wang et al., caplus an 2016:384936, 2016.*
Combrink et al., "Respiratory syncytial virus fusion inhibitors. Part 6: An examination of the effect of structural variation of the benzimidazol-2-one heterocycle moiety", Bioorganic & Medicinal Chemistry Letters, 17:4784-4790 (2007).
Hallak et al, "Glycosaminoglycan sulfation requirements for respiratory syncytial virus infection", Journal of Virology 74(22):10508-10513 (Nov. 2000).

(Continued)

*Primary Examiner* — Sun Jae Yoo

(57) ABSTRACT

Inhibitors of RSV replication of formula RI

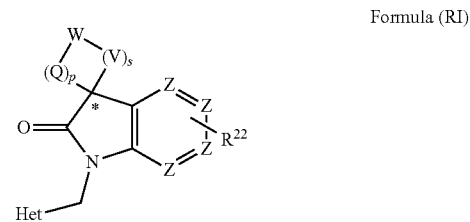

Formula (RI)

including stereochemically isomeric forms, and salts or solvates thereof, wherein $R^{22}$, W, Q, V, Z p, s, and Het have the meaning as defined herein.

The present invention also relates to processes for preparing said compounds, pharmaceutical compositions containing them and their use, alone or in combination with other RSV inhibitors, in RSV therapy.

17 Claims, No Drawings

(56) References Cited

OTHER PUBLICATIONS

Lee et al, "Improved catalysts for the Palladium-catalyzed synthesis of oxindoles by amide α-arylation. Rate of acceleration, use of aryl chloride substates, and a new carbine ligand for asymmetric transformations", J. Org. Chem. 66(10): 3402-3415 (2001).
Teno et al., "Novel scaffold for cathepsin K inhibitors", Bioorganic & Medicinal Chemistry Letters, 17:6096-6100 (2007).
Teno et al., "Effect of cathespin K inhibitors on bone resorption", J. Med. Chem., 51:5459-5462 (2008).
Wang et al, "Respiratory syncytial virus fusion inhibitors. Park 5: Optimization of benzimidazole substitution patterns towards derivatives with improved activity", Bioorganic & Medicinal Chemistry Letters, 17:4592-4598 (2007).
Wyde et al, "CL387626 exhibits marked and unusual antiviral activity against respiratory syncytial virus in tissue culture and in cotton rats", Antiviral Research 38:31-42 (1998).
Extended European search report dated Jan. 18, 2013, for corresponding European application 12188694.9.
Extended European search report dated Jan. 17, 2013, for corresponding European application 13159431.9.
International search report dated Dec. 13, 2013, for corresponding international application PCT/EP2013/071525.
Iqbal et al "Synthesis and Am/Eu extraction of novel TODGA derivatives" Supramolecular Chemistry 2010 vol. 22(11-12) pp. 827-837.
Parsons David G. "Synthesis of ten isomers of a macrocyclic polyether, tetramethyldibenzo-18-crown-6, and their complexes with salts of alkali metals" Journal of the Chemical Society, Perkin Transactions 1: Organic and Bio-Organic Chemistry (1972-1999) 1975 vol. 3 pp. 245-250.

\* cited by examiner

RSV ANTIVIRAL COMPOUNDS

CROSS REFERENCE TO RELATED APPLICATIONS

This application is the national stage under 35 U.S.C. 371 of PCT Application No. PCT/EP2013/071525, filed Oct. 15, 2013, which application claims priority from European Patent Application Nos. EP 13159431.9, filed Mar. 15, 2013, and EP 12188694.9, filed Oct. 16, 2012, the entire disclosures of which are hereby incorporated by reference in their entirety.

FIELD OF THE INVENTION

The invention concerns novel spiro compounds having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with Bovine Respiratory Syncytial Virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference on structure-activity relations, in respect of RSV inhibition, of 5-substituted benzimidazole compounds is X. A. Wang et al., Bioorganic and Medicinal Chemistry Letters 17 (2007) 4592-4598.

Compounds that exhibit anti-RSV activity are disclosed in WO2012/080446, WO2012/080447, WO2012/080449, WO2012/080450 and WO2012/080451.

WO-2004/069256 discloses 2-cyanopyrrolopyrimidines and WO-2004/076455 discloses spiro-substituted 2-cyanopyrrolopyrimidines as capthepsin K or S inhibitors useful in the treatment of various pain disorders. Teno N. et al. in *Bioorganic & Medicinal Chemistry Letters*, vol. 17, 6096-6100 (2007) and Teno N. et al. in *J. Med. Chem.*, vol. 51, 5459-5462 (2008) disclose 2-cyanopyrrolopyrimidines as cathepsin K inhibitors.

Potential problems which RSV antivirals may encounter are toxicity, mutagenicity, lack of selectivity, poor efficacy, poor bioavailability, and difficulty of synthesis.

It is desired to provide new compounds that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art, and preferably at a level of about the most active, more preferably of even stronger activity, than compounds disclosed in the art. A further desire is to find compounds having oral antiviral activity.

There is a need for additional RSV inhibitors that may overcome at least one of these disadvantages or having one of the desired effects.

SUMMARY OF THE INVENTION

In order to better address one or more of the foregoing desires, the invention, in one aspect, presents antiviral compounds represented by Formula (RI), Formula (RI)

or any stereoisomeric form thereof, wherein:

Het is a heterocycle of either of the following formula (a), (b), (c), (d):

(a)

(b)

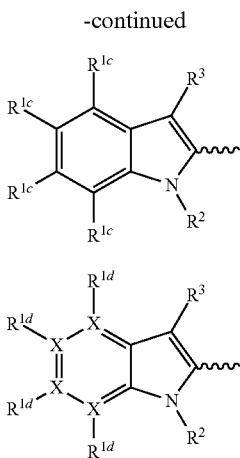

(c)

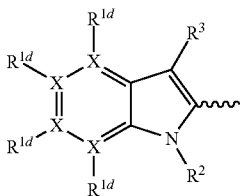

(d)

each X independently is C or N; provided that at least two X is C;
each of $R^{1a}$, $R^{1b}$, $R^{1c}$ or $R^{1d}$ is independently selected from the group consisting of H, halogen, $C_1$-$C_6$alkyl, $C_3$-$C_7$cycloalkyl, $C_1$-$C_6$alkyloxy, $N(R^6)_2$, $CO(R^2)$, $CH_2NH_2$, $CH_2OH$, CN, $C(=NOH)NH_2$, $C(=NOCH_3)NH_2$, $C(=NH)NH_2$, $CF_3$ and $OCF_3$;
$R^{1b}$ or $R^{1d}$ is absent when the X to which it is bound is N;
each $R^2$ is —$(CR^8R^9)_m$—$R^{10}$;
m is an integer from 0 to 6;
each $R^3$ is independently selected from the group consisting of H, halogen, aryl, heteroaryl, $C_1$-$C_6$alkyl, $C_3$-$C_7$cycloalkyl, $C_1$-$C_6$alkyloxy and $CO(R^7)$;
each $R^6$ is independently selected from the group consisting of H, $C_1$-$C_6$alkyl, $COOCH_3$ and $CONHSO_2CH_3$;
each $R^7$ is independently selected from the group consisting of H, $C_1$-$C_6$alkyl, OH, $C_1$-$C_6$alkyloxy, $NH_2$, $NHSO_2N(C_1$-$C_6$alkyl$)_2$, $NHSO_2NHCH_3$, $NHSO_2(C_1$-$C_6$alkyl), $NHSO_2(C_3$-$C_7$cycloalkyl) and $N(C_1$-$C_6$-alkyl$)_2$ $NR^8R^9$ and $NR^9R^{10}$;
each $R^8$ and $R^9$ are independently selected from the group consisting of H, and $C_3$-$C_7$cycloalkyl; or $R^8$ and $R^9$ taken together form a 4 to 6 membered saturated ring that optionally contains one or more heteroatoms selected from the group consisting of N, S and O;
each $R^{10}$ is independently selected from the group consisting of H, halogen, OH, CN, $CF_2H$, $CF_3$, $C_1$-$C_6$ alkyl, $C_3$-$C_7$cycloalkyl, $C(=O)C_1$-$C_6$alkyl, $C(=O)C_3$-$C_7$cycloalkyl, $C(=O)NR^8R^9$, $C(=O)OR^8$, $SO_2R^8$, $C(=O)N(R^8)SO_2R^9$, $C(=O)N(R^8)SO_2N(R^8R^9)$, $NR^8R^9$, $NR^8C(=O)OR^9$, $OC(=O)R^8$, O-benzyl, $NR^8SO_2R^9$, $SO_2NR^8R^9$, $SO_2R^8$, $OC(=O)NR^8R^9$, $OC(=O)NR^8R^{12}$, $N(R^8)C(=O)N(R^8R^9)$, $R^{11}$, $N(R^8)C(=O)OR^{12}$, $OR^{11}$, $C(=O)R^{11}$ and a 4 to 6 membered saturated ring containing one oxygen atom;
$R^{11}$ is phenyl, pyridinyl or pyrazolyl; each of which can be optionally substituted with one or more substituents each independently selected from the group consisting of $CF_3$, $CH_3$, $OCH_3$, $OCF_3$ and halogen;
$R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;
each Z independently is C or N, provided that at least two Z is C;
Q and V each independently represent C=O, $SO_2$ or $CR^{20}R^{21}$;

p and s independently represent an integer from 0 to 3, wherein the sum of p and s minimally should be 2, and when p=0 or s=0 then the carbon atom marked with * is directly bound to W;
$R^{20}$ and $R^{21}$ are independently selected from the group consisting of hydrogen, hydroxyl, $C_1$-$C_3$alkyl, $C_3$-$C_7$cycloalkyl, $CF_3$, $OCH_3$, $OCF_3$ and halogen;
$R^{22}$ is selected from the group consisting of hydrogen, hydroxyl, $C_1$-$C_6$alkyl, $C_3$-$C_7$cycloalkyl, $CF_3$, $OCH_3$, $OCF_3$ and halogen;
W is selected from the group consisting of SO, $SO_2$, S, C, O and N, wherein such C or N is optionally substituted with one or more $R^{23}$;
$R^{23}$ is selected from the group consisting of hydrogen, hydroxyl, $C_1$-$C_6$alkyl, $C_3$-$C_7$cycloalkyl, $C_1$-$C_6$alkyl-$R^{24}$, $SO_2R^{24}$, $SO_2N(R^{24})_2$, aryl, heteroaryl, $C(=O)OR^{24}$, $OR^{24}$, $C(=O)R^{24}$, $C(=O)N(R^{24})_2$, $OC(=O)N(R^{24})_2$, $P(=O)$—$(O$—$C_1$-$C_6$-alkyl$)_2$, $N(R^{24})_2$, $NR^{25}C(=O)OR^{24}$, $NR^{25}C(=O)N(R^{24})_2$, $NR^{25}SO_2R^{24}$ and a 4 to 6 membered saturated ring containing one oxygen atom, wherein any of such $C_1$-$C_6$alkyl, $C_3$-$C_7$cycloalkyl, aryl or heteroaryl is optionally substituted with one or more of the substituents selected from the group consisting of halogen, OH, CN, $OCH_3$;
$R^{24}$ is selected from the group of hydrogen, OH, halogen, $C_1$-$C_6$alkyl, $C_3$-$C_7$cycloalkyl, $C(=O)$ $C_1$-$C_6$alkyl, $C(=O)$ $C_3$-$C_7$cycloalkyl, aryl, heteroaryl, benzyl, and a 4 to 6 membered saturated ring containing one oxygen atom wherein any of such $C_1$-$C_6$alkyl, $C_3$-$C_7$cycloalkyl, $C(=O)$ $C_1$-$C_6$alkyl, $C(=O)$ $C_3$-$C_7$cycloalkyl, aryl, heteroaryl, benzyl is optionally substituted with one or more substituents selected from the group consisting of halogen, $CF_3$, OH, CN, $OCH_3$, $OC(=O)CH_3$) and $C_1$-$C_3$alkyl substituted with at least one CN;
$R^{25}$ is selected from the group consisting of hydrogen and $C_1$-$C_3$ alkyl;
aryl represents phenyl or naphthalenyl;
heteroaryl represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N;
provided that Het does not satisfy a formula d(x)

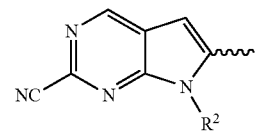

d(x)

or a pharmaceutically acceptable addition salt or a solvate thereof.

Preferably, $R^{23}$ is selected from the group consisting of hydrogen, hydroxyl, $C_1$-$C_6$alkyl, $C_3$-$C_7$cycloalkyl, $C_1$-$C_6$alkyl-$R^{24}$, $SO_2N(R^{24})_2$, aryl, heteroaryl, $C(=O)OR^{24}$, $OR^{24}$, $C(O)R^{24}$, $C(=O)N(R^{24})_2$, $OC(=O)N(R^{24})_2$ and a 4 to 6 membered saturated ring containing one oxygen atom, wherein any of such $C_1$-$C_6$alkyl, $C_3$-$C_7$cycloalkyl, aryl or heteroaryl is optionally substituted with one or more of the substituents selected from the group consisting of halogen, OH, CN, $OCH_3$;

$R^{24}$ is selected from the group of hydrogen, OH, halogen, $C_1$-$C_6$alkyl, $C_3$-$C_7$cycloalkyl, C(=O) $C_1$-$C_6$alkyl, C(=O) $C_3$-$C_7$cycloalkyl, aryl, heteroaryl, benzyl, and a 4 to 6 membered saturated ring containing one oxygen atom wherein any of such $C_1$-$C_6$alkyl, $C_3$-$C_7$cycloalkyl, C(=O) $C_1$-$C_6$alkyl, C(=O) $C_3$-$C_7$cycloalkyl, aryl, heteroaryl, benzyl is optionally substituted with one or more substituents selected from the group consisting of halogen, $CF_3$, OH, CN, $OCH_3$, and OC(=O)$CH_3$).

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The invention, in a broad sense, is based on the judicious recognition that the compounds of Formula (RI) generally possess an interesting RSV inhibitory activity.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

As used herein "$C_1$-$C_6$alkyl" as a group or part of a group defines straight or branched chain saturated hydrocarbon radicals having from 1 to 6 (1, 2, 3, 4, 5 or 6) carbon atoms such as methyl, ethyl, propyl, 1-methylethyl, butyl, pentyl, hexyl, 2-methylbutyl and the like.

"$C_1$-$C_{10}$alkyl" as a group or part of a group defines straight or branched chain saturated hydrocarbon radicals having from 1 to 10 carbon atoms such as the groups defined for $C_1$-$C_6$alkyl and heptyl, octyl, nonyl, 2-methylhexyl, 2-methylheptyl, decyl, 2-methylnonyl, and the like.

"$C_1$-$C_4$alkyloxy" or "$C_1$-$C_4$alkoxy", as a group or part of a group defines an O—$C_1$-$C_4$alkyl radical, wherein $C_1$-$C_4$alkyl has, independently, the meaning given above.

"$C_1$-$C_6$alkyloxy" or "$C_1$-$C_6$alkoxy", as a group or part of a group defines an O—$C_1$-$C_6$alkyl radical, wherein $C_1$-$C_6$alkyl has, independently, the meaning given above.

The term "$C_3$-$C_7$cycloalkyl" alone or in combination, refers to a cyclic saturated hydrocarbon radical having from 3 to 7 carbon atoms. Non-limiting examples of suitable $C_3$-$C_7$cycloalkyl include cyclopropyl, cyclobutyl, cyclopentyl, cyclohexyl and cycloheptyl.

The term "—$(CR^8R^9)_m$—" used herein defines m repetitions of the $CR^8R^9$ subgroup, wherein each of these subgroups is independently defined.

The term "halo" or "halogen" as a group or part of a group is generic for fluoro, chloro, bromo, iodo unless otherwise is indicated or is clear from the context.

A term of the form NRCOOR is identical to N(R)COOR.

Preferred examples of a 4 to 6 membered aliphatic ring optionally containing one or more heteroatoms selected from the group consisting of N, S and O are; cyclobutyl, cyclopentyl, cyclohexyl, piperidinyl, oxetanyl, tetrahydrofuranyl, tetrahydropyranyl, piperidinyl, azetidinyl, thiolanyl, piperazinyl and pyrrolidinyl.

Heteroaryl represents a monocyclic 5 to 6 membered aromatic heterocycle containing one or more heteroatoms each independently selected from the group consisting of 0, S and N; or a bicyclic 8 to 12 membered aromatic heterocycle containing one or more heteroatoms each independently selected from the group consisting of O, S and N. Examples of such heteroaryl are furanyl, thiophenyl, pyridinyl, pyridazinyl, pyrimidinyl, pyrazinyl, quinoxalinyl, and benzimidazolyl.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Hereinbefore and hereinafter, the term "compound of Formula (RI)" or "compounds of Formula (RI)" is meant to include the tautomers and stereoisomeric forms thereof, and the pharmaceutically acceptable addition salts, and the solvates thereof.

The terms "stereoisomers", "stereoisomeric forms" or "stereochemically isomeric forms" hereinbefore or hereinafter are used interchangeably.

The term "stereochemically isomeric forms" as used hereinbefore defines all the possible compounds made up of the same atoms bonded by the same sequence of bonds but having different three-dimensional structures which are not interchangeable, which the compounds of Formula (RI) may possess.

It will be appreciated that some of the compounds of Formula (RI) may contain one or more centers of chirality and exist as stereochemically isomeric forms.

The invention includes all stereoisomers of the compound of Formula (RI) and tautomers thereof, either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (RI) is for instance specified as (R), this means that the compound is substantially free of the (S) isomer; when a compound of Formula (RI) is for instance specified as E, this means that the compound is substantially free of the Z isomer; when a compound of Formula (RI) is for instance specified as cis, this means that the compound is substantially free of the trans isomer.

Some of the compounds according to Formula (RI) may also exist in their tautomeric form. Such forms although not explicitly indicated in the above formula are intended to be included within the scope of the present invention.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates of this invention may be obtained by the application of art-known procedures. The diastereomeric racemates of Formula (RI) can be obtained separately by conventional methods.

For some of the compounds of Formula (RI), tautomers and stereoisomeric forms thereof, and the pharmaceutically acceptable addition salts, and the solvates thereof; and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (RI) which contains at least one radioactive atom. For example, a compound can be labelled with positron or with gamma emitting radioactive isotopes. For radioligand-binding techniques, the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and 123I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br.

For therapeutic use, salts of the compounds of Formula (RI) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of Formula (RI) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of Formula (RI) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term solvate comprises the hydrates and solvent addition forms which the compounds of Formula (RI) are able to form, as well as the salts thereof. Examples of such forms are e.g. hydrates, alcoholates and the like.

Without detracting from the overall scope of the invention, certain embodiments are discussed in more detail below.

The terms described above and others used in the specification are well understood to those in the art.

Preferred features of the compounds of this invention are now set forth.

The present invention concerns novel compounds of Formula (RI),

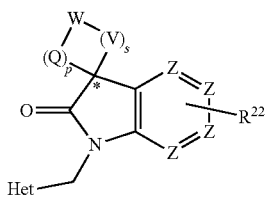

Formula (RI)

or any stereoisomeric form thereof, wherein:
Het is a heterocycle of either of the following formula (a), (b), (c), (d):

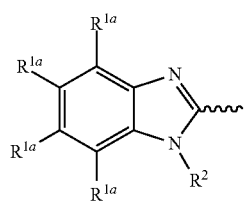

(a)

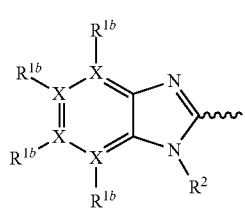

(b)

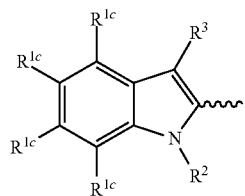

(c)

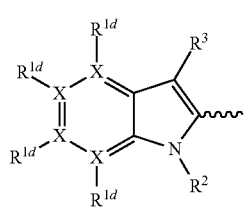

(d)

each X independently is C or N; provided that at least two X is C;
each of $R^{1a}$, $R^{1b}$, $R^{1c}$ or $R^{1d}$ is independently selected from the group consisting of H, halogen, $C_1$-$C_6$alkyl, $C_3$-$C_7$cycloalkyl, $C_1$-$C_6$alkyloxy, $N(R^6)_2$, $CO(R^2)$, $CH_2NH_2$, $CH_2OH$, CN, $C(=NOH)NH_2$, $C(=NOCH_3)NH_2$, $C(=NH)NH_2$, $CF_3$ and $OCF_3$;
$R^{1b}$ or $R^{1d}$ is absent when the X to which it is bound is N;
each $R^2$ is —$(CR^8R^9)_m$—$R^{10}$;
m is an integer from 0 to 6;
each $R^3$ is independently selected from the group consisting of H, halogen, aryl, heteroaryl, $C_1$-$C_6$alkyl, $C_3$-$C_7$cycloalkyl, $C_1$-$C_6$alkyloxy and $CO(R^2)$;
each $R^6$ is independently selected from the group consisting of H, $C_1$-$C_6$alkyl, $COOCH_3$ and $CONHSO_2CH_3$;
each $R^7$ is independently selected from the group consisting of H, $C_1$-$C_6$alkyl, OH, $C_1$-$C_6$alkyloxy, $NH_2$, $NHSO_2N$ ($C_1$-$C_6$alkyl)$_2$, $NHSO_2NHCH_3$, $NHSO_2(C_1$-$C_6$alkyl), $NHSO_2(C_3$-$C_7$cycloalkyl) and $N(C_1$-$C_6$-alkyl)$_2$ $NR^8R^9$ and $NR^9R^{10}$;

each $R^8$ and $R^9$ are independently selected from the group consisting of H, $C_1$-$C_{10}$alkyl and $C_3$-$C_7$cycloalkyl; or $R^8$ and $R^9$ taken together form a 4 to 6 membered saturated ring that optionally contains one or more heteroatoms selected from the group consisting of N, S and O;

each $R^{10}$ is independently selected from the group consisting of H, halogen, OH, CN, $CF_2H$, $CF_3$, $C_1$-$C_6$ alkyl, $C_3$-$C_7$cycloalkyl, $C(=O)C_1$-$C_6$alkyl, $C(=O)C_3$-$C_7$cycloalkyl, $C(=O)NR^8R^9$, $C(=O)OR^8$, $SO_2R^8$, $C(=O)N(R^8)SO_2R^9$, $C(=O)N(R^8)SO_2N(R^8R^9)$, $NR^8R^9$, $NR^8C(=O)OR^9$, $OC(=O)R^8$, O-benzyl, $NR^8SO_2R^9$, $SO_2NR^8R^9$, $SO_2R^8$, $OC(=O)NR^8R^9$, $OC(=O)NR^8R^{12}$, $N(R^8)C(=O)N(R^8R^9)$, $R^{11}$, $N(R^8)C(=O)OR^{12}$, $OR^{11}$, $C(=O)R^{11}$ and a 4 to 6 membered saturated ring containing one oxygen atom;

$R^{11}$ is phenyl, pyridinyl or pyrazolyl; each of which can be optionally substituted with one or more substituents each independently selected from the group consisting of $CF_3$, $CH_3$, $OCH_3$, $OCF_3$ and halogen;

$R^{12}$ is $C_1$-$C_6$ alkyl or $C_3$-$C_7$cycloalkyl; each substituted with one or more substituents each independently selected from the group consisting of $CF_3$, $CH_3$, $OCH_3$, $OCF_3$ and halogen;

each Z independently is C or N, provided that at least two Z is C;

Q and V each independently represent C=O, $SO_2$ or $CR^{20}R^{21}$;

p and s independently represent an integer from 0 to 3, wherein the sum of p and s minimally should be 2, and when p=0 or s=0 then the carbon atom marked with * is directly bound to W;

$R^{20}$ and $R^{21}$ are independently selected from the group consisting of hydrogen, hydroxyl, $C_1$-$C_3$alkyl, $C_3$-$C_7$cycloalkyl, $CF_3$, $OCH_3$, $OCF_3$ and halogen;

$R^{22}$ is selected from the group consisting of hydrogen, hydroxyl, $C_1$-$C_6$alkyl, $C_3$-$C_7$cycloalkyl, $CF_3$, $OCH_3$, $OCF_3$ and halogen; $R^{22}$ is attached to one Z that is not N;

W is selected from the group consisting of SO, $SO_2$, S, C, O and N, wherein such C or N is optionally substituted with one or more $R^{23}$;

$R^{23}$ is selected from the group consisting of hydrogen, hydroxyl, $C_1$-$C_6$alkyl, $C_3$-$C_7$cycloalkyl, $C_1$-$C_6$alkyl-$R^{24}$, $SO_2R^{24}$, $SO_2N(R^{24})_2$, aryl, heteroaryl, $C(=O)OR^{24}$, $OR^{24}$, $C(=O)R^{24}$, $C(=O)N(R^{24})_2$, $OC(=O)N(R^{24})_2$, $P(=O)$—$(O$—$C_1$-$C_6$-alkyl)$_2$, $N(R^{24})_2$, $NR^{25}C(=O)OR^{24}$, $NR^{25}C(=O)N(R^{24})_2NR^{25}SO_2R^{24}$ and a 4 to 6 membered saturated ring containing one oxygen atom, wherein any of such $C_1$-$C_6$alkyl, $C_3$-$C_7$cycloalkyl, aryl or heteroaryl is optionally substituted with one or more of the substituents selected from the group consisting of halogen, OH, CN, $OCH_3$;

$R^{24}$ is selected from the group of hydrogen, OH, halogen, $C_1$-$C_6$alkyl, $C_3$-$C_7$cycloalkyl, $C(=O)$ $C_1$-$C_6$alkyl, $C(=O)$ $C_3$-$C_7$cycloalkyl, aryl, heteroaryl, benzyl, and a 4 to 6 membered saturated ring containing one oxygen atom wherein any of such $C_1$-$C_6$alkyl, $C_3$-$C_7$cycloalkyl, $C(=O)$ $C_1$-$C_6$alkyl, $C(=O)$ $C_3$-$C_7$cycloalkyl, aryl, heteroaryl, benzyl is optionally substituted with one or more substituents selected from the group consisting of halogen, $CF_3$, OH, CN, $OCH_3$, $OC(=O)CH_3$) and $C_1$-$C_3$alkyl substituted with at least one CN;

$R^{25}$ is selected from the group consisting of hydrogen and $C_1$-$C_3$ alkyl;

aryl represents phenyl or naphthalenyl;

heteroaryl represents a monocyclic 5 to 6 membered aromatic heterocycle containing one or more heteroatoms each independently selected from the group consisting of O, S and N; or a bicyclic 8 to 12 membered aromatic heterocycle containing one or more heteroatoms each independently selected from the group consisting of O, S and N;

provided that Het does not satisfy a formula d(x)

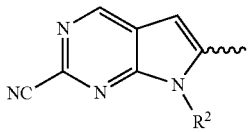

(d(x))

or a pharmaceutically acceptable addition salt or a solvate thereof.

In an embodiment the present invention relates to compounds of formula (RI)

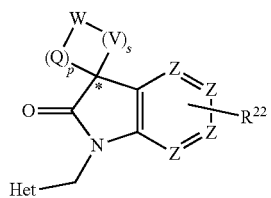

Formula (RI)

or any stereoisomeric form thereof, wherein

Het is a heterocycle of either of the following formula (a), (b), (c), (d):

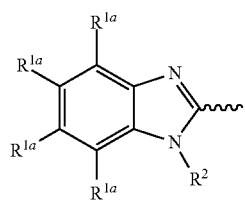

(a)

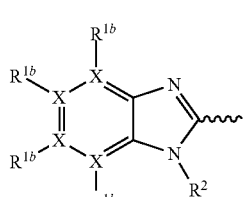

(b)

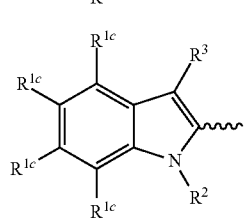

(c)

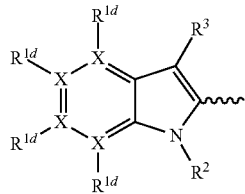

(d)

each X independently is C or N; provided that at least two X is C;

each of $R^{1a}$, $R^{1b}$, $R^{1c}$ or $R^{1d}$ is independently selected from the group consisting of H, halogen, $C_1$-$C_6$alkyl, $C_1$-$C_6$alkyloxy, $CF_3$ and $OCF_3$;

$R^{1b}$ or $R^{1d}$ is absent when the X to which it is bound is N;

each $R^2$ is $—(CR^8R^9)_m—R^{10}$;

m is an integer from 2 to 6;

each $R^3$ is H, halogen or $C_1$-$C_6$alkyl;

each $R^8$ and $R^9$ are independently selected from the group consisting of H and $C_1$-$C_{10}$alkyl;

each $R^{10}$ is independently selected from the group consisting of H, halogen, OH, CN, $CF_2H$, $CF_3$, $C_1$-$C_6$ alkyl, $C_3$-$C_7$cycloalkyl, $C(=O)NR^8R^9$, $C(=O)OR^8$, and $SO_2R^8$;

each Z independently is C or N, provided that at least two Z is C;

Q and V each independently represent $CR^{20}R^{21}$;

p and s independently represent an integer from 0 to 3, wherein the sum of p and s minimally should be 2, and when p=0 or s=0 then the carbon atom marked with * is directly bound to W;

$R^{20}$ and $R^{21}$ are hydrogen;

$R^{22}$ is selected from the group consisting of hydrogen, hydroxyl, $C_1$-$C_6$alkyl, $CF_3$, $OCH_3$, $OCF_3$ and halogen;

W is selected from the group consisting of $SO_2$, C, O and N, wherein such C or N is optionally substituted with one or more $R^{23}$;

$R^{23}$ is selected from the group consisting of hydrogen, hydroxyl, $C_1$-$C_6$alkyl, $C_3$-$C_7$cycloalkyl, $C_1$-$C_6$alkyl-$R^{24}$, $SO_2R^{24}$, $SO_2N(R^{24})_2$, aryl, heteroaryl, $C(=O)OR^{24}$, $OR^{24}$, $C(=O)R^{24}$, $C(=O)N(R^{24})_2$, $OC(=O)N(R^{24})_2$, $P(=O)—(O—C_1-C_6\text{-alkyl})_2$, $N(R^{24})_2$, $NR^{25}C(=O)OR^{24}$, $NR^{25}C(=O)N(R^{24})_2NR^{25}SO_2R^{24}$ and a 4 to 6 membered saturated ring containing one oxygen atom, wherein any of such $C_1$-$C_6$alkyl, $C_3$-$C_7$cycloalkyl, aryl or heteroaryl is optionally substituted with one or more of the substituents selected from the group consisting of halogen, OH, CN, $OCH_3$;

$R^{24}$ is selected from the group of hydrogen, OH, halogen, $C_1$-$C_6$alkyl, $C_3$-$C_7$cycloalkyl, $C(=O)C_1$-$C_6$alkyl, $C(=O)$ $C_3$-$C_7$cycloalkyl, aryl, heteroaryl, benzyl, and a 4 to 6 membered saturated ring containing one oxygen atom wherein any of such $C_1$-$C_6$alkyl, $C_3$-$C_7$cycloalkyl, $C(=O)$ $C_1$-$C_6$alkyl, $C(=O)$ $C_3$-$C_7$cycloalkyl, aryl, heteroaryl, benzyl is optionally substituted with one or more substituents selected from the group consisting of halogen, $CF_3$, OH, CN, $OCH_3$, $OC(=O)CH_3$) and $C_1$-$C_3$alkyl substituted with at least one CN;

$R^{25}$ is selected from the group consisting of hydrogen and $C_1$-$C_3$ alkyl;

aryl represents phenyl or naphthalenyl;

heteroaryl is furanyl, thiophenyl, pyridinyl, pyridazinyl, pyrimidinyl, pyrazinyl, quinoxalinyl, or benzimidazolyl;

or a pharmaceutically acceptable addition salt or a solvate thereof.

Embodiments of compounds RI according to the present invention are represented by formula Ia, Ib, Ic and Id respectively.

Formula (Ia)

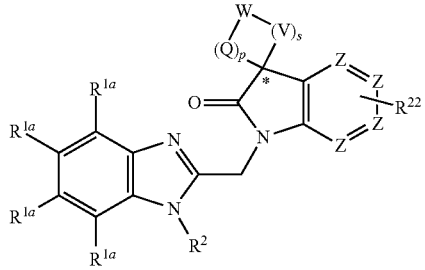

Formula (Ib)

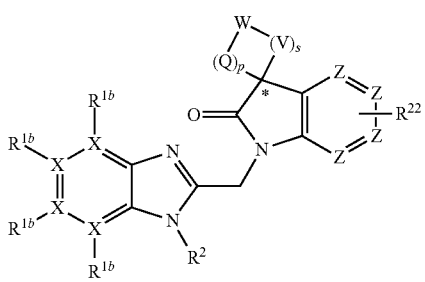

Formula (Ic)

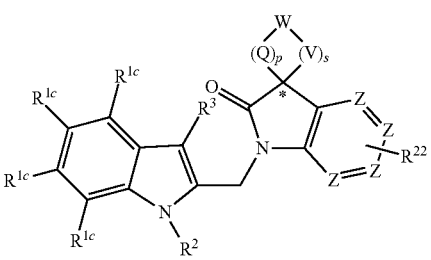

Formula (Id)

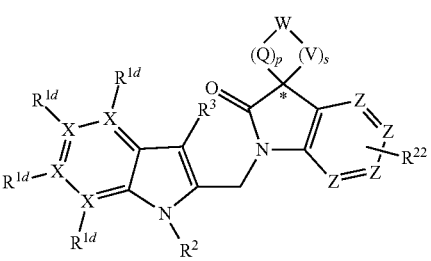

In one embodiment, $R^{1d}$ is independently selected from the group consisting of H, halogen, $C_1$-$C_6$alkyl, $C_3$-$C_7$cycloalkyl, $C_1$-$C_6$alkyloxy, $N(R^6)_2$, $CO(R^7)$, $CH_2NH_2$, $CH_2OH$, $C(=NOH)NH_2$, $C(=NOCH_3)NH_2$, $C(=NH)NH_2$, $CF_3$ and $OCF_3$ Preferably, in any of the embodiments defined herein, Het does not satisfy a formula d(x)

d(x)

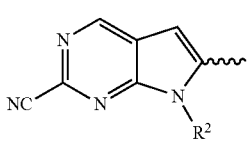

wherein $R^2$ is as defined herein in any of the embodiments.

In an even more preferred embodiment, Het does not satisfy a formula d(y)

d(y)

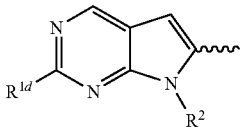

wherein $R^{1d}$ and $R^2$ are as defined herein in any of the embodiments.

In another embodiment, Het is represented by formula (a'), (b'), (c') or (d'):

(a')

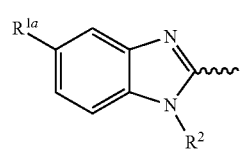

(b')

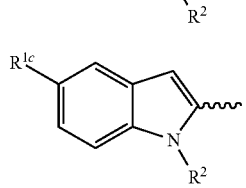

(c')

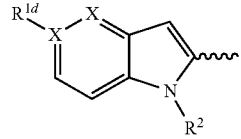

(d')

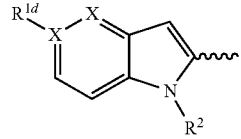

wherein at least one X is N. More preferably, for Formula (b') and (d') only one X is N.

$R^{1a}$, $R^{1b}$, $R^{1c}$ or $R^{1d}$ are independently selected from the group consisting of H and halogen, more preferably from chloro, bromo and fluoro. Most preferred is chloro.

Compounds according to the present invention have a radical $R^2$ that is $—(CR^8R^9)_m—R^{10}$ and wherein m is an integer from 0 to 6, 1 to 4 or 3 or 4.

Preferably each $R^8$ and $R^9$ are independently chosen from H or $C_1$-$C_6$alkyl. In a particular embodiment, $R^2$ is $C_1$-$C_6$ alkyl-$R^{10}$. In an sub-embodiment, $R^2$ is $C_3$-$C_4$ alkyl-$R^{10}$ Each $R^{10}$ is independently selected from the group consisting of H, halogen, OH, CN, $CF_2H$, $CF_3$, $C_1$-$C_6$ alkyl, $C_3$-$C_7$cycloalkyl, $C(=O)C_1$-$C_6$alkyl, $C(=O)C_3$-$C_7$cycloalkyl, $C(=O)NR^8R^9$, $C(=O)OR^8$, $SO_2R^8$, $C(=O)N(R^8)SO_2R^9$, $C(=O)N(R^8)SO_2N(R^8R^9)$, $NR^8R^9$, $NR^8C(=O)OR^9$, $OC(=O)R^8$, O-benzyl, $NR^8SO_2R^9$, $SO_2NR^8R^9$, $SO_2R^8$, $OC(=O)NR^8R^9$, $OC(=O)NR^8R^{12}$, $N(R^8)C(=O)N(R^8R^9)$, $R^{11}$, $N(R^8)C(=O)OR^{12}$, $OR^{11}$, $C(=O)R^{11}$ and a 4 to 6 membered saturated ring containing one oxygen atom.

In a specific embodiment, $R^{10}$ is selected from the group consisting of $C_1$-$C_3$ alkyl, H, OH, CN, F, $CF_2H$, $CF_3$, $SO_2$—$C_1$-$C_3$alkyl, $SO_2C_3$-$C_6$cycloalkyl.

A particular embodiment of the invention relates to compounds having Formula RII, RIII, RIV, RV, RVI or RVII;

Formula RII

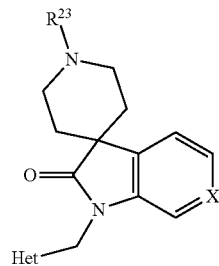

Formula RIII

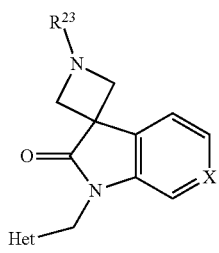

Formula RIV

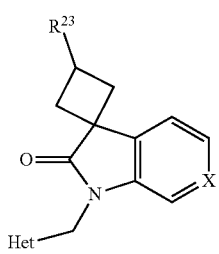

Formula RV

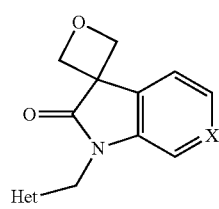

Formula RVI

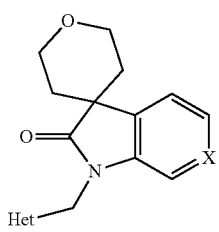

Formula RVII

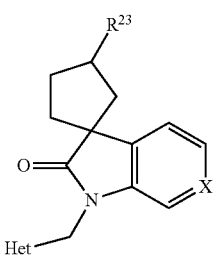

or any stereoisomeric form thereof, wherein Het, X and $R^{23}$ are defined as in any of the described embodiments.

In another embodiment of compounds of Formula RI, RII, RIII, RIV, RV or RVI, $R^{23}$ is selected from the group consisting of hydrogen, hydroxyl, $C_1$-$C_6$alkyl, $C_1$-$C_3$alkyl-$R^{24}$, $SO_2R^{24}$, O—$R^{24}$, phenyl, pyridinyl pyrimidyl, pyrazolyl, $C(=O)OR^{24}$, $C(=O)R^{24}$, wherein any of such $C_1$-$C_6$alkyl, phenyl, pyridinyl, pyrimidyl, pyrazolyl is optionally substituted with one or more of the following substituents; $OCH_3$, halogen, OH and CN.

General Synthetic Schemes

Compounds of formula RI, or their pharmaceutically acceptable salts, can be prepared according to the reaction schemes discussed herein below using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Unless otherwise indicated, the substituent in the schemes are defined as above. Isolation and purification of the products is accomplished by standard procedures, which are known to a chemist of ordinary skill.

The following schemes are exemplary of the processes for making compounds of formula RI. In the schemes below, the numerals used, including numerals from I to XXVIII, are used for convenience to designate the formulae in the schemes.

The compounds of formula (Ia) can be synthesized for instance using one of the methods shown in Scheme 1. In general, a fragment A or B is coupled with a fragment C resulting in derivatives of formula (Ia).

Scheme 1. General synthesis of compounds of formula (Ia)

Method 1

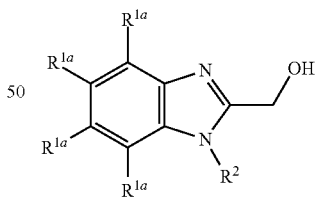

fragment A

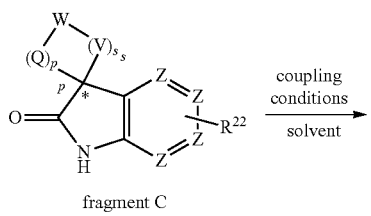

fragment C

-continued

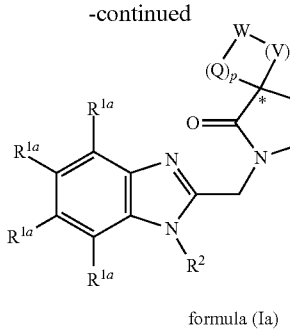

formula (Ia)

Method 2

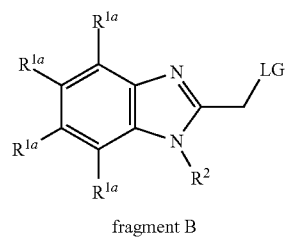

fragment B

LG = Cl, Br, OTos, OMs

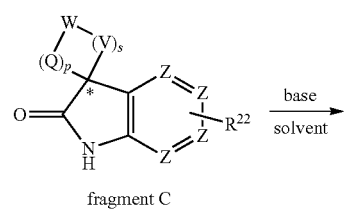

fragment C

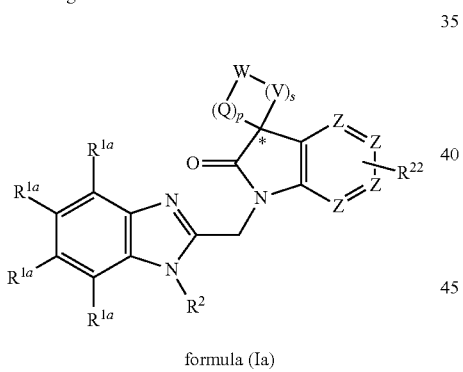

formula (Ia)

For method 1, an example of suitable "coupling conditions" to react a fragment A with a fragment C to form formula (Ia) type compounds is a Mitsunobu reaction. A suitable solvent for this type of reaction is THF (tetrahydrofuran).

Alternatively (but not limited to), a fragment B type compound wherein the LG is a leaving group, such as halide, preferably chlorine, or sulfonate, can be reacted with a fragment C type compound through a base mediated coupling reaction. (Method 2) Possible bases to effect this reaction (but not limited to) are $K_2CO_3$, $Cs_2CO_3$, triethylamine, sodium hydride. A suitable solvent (but not limited to) for this type of base mediated coupling is DMF (dimethylformamide) or THF (tetrahydrofurane).

Fragment A type compounds can be generally prepared as depicted in scheme 2.

Scheme 2. General synthesis of fragment A type compounds

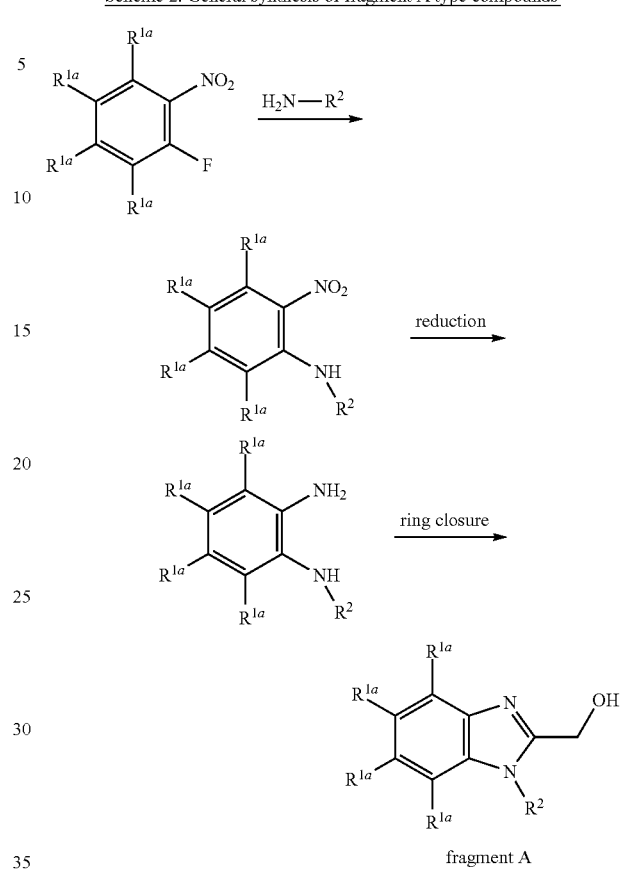

fragment A

In general, fragment B type compounds can be prepared from fragment A type compounds through reaction with reagents like (but not limited to) $SOCl_2$, $PBr_3$, p-TsCl, MsCl.

Scheme 3. General synthesis of fragment B type compounds

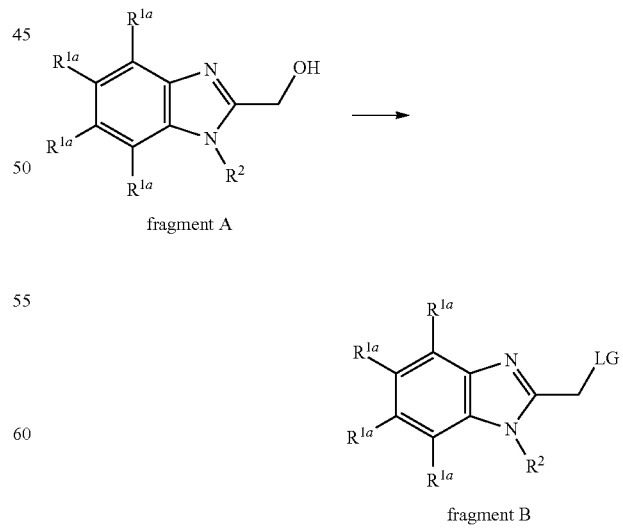

fragment B

Fragment C type intermediates of formula (VI) can be prepared as depicted in Scheme 4.

Scheme 4. General synthesis of fragment C (VI) type compounds

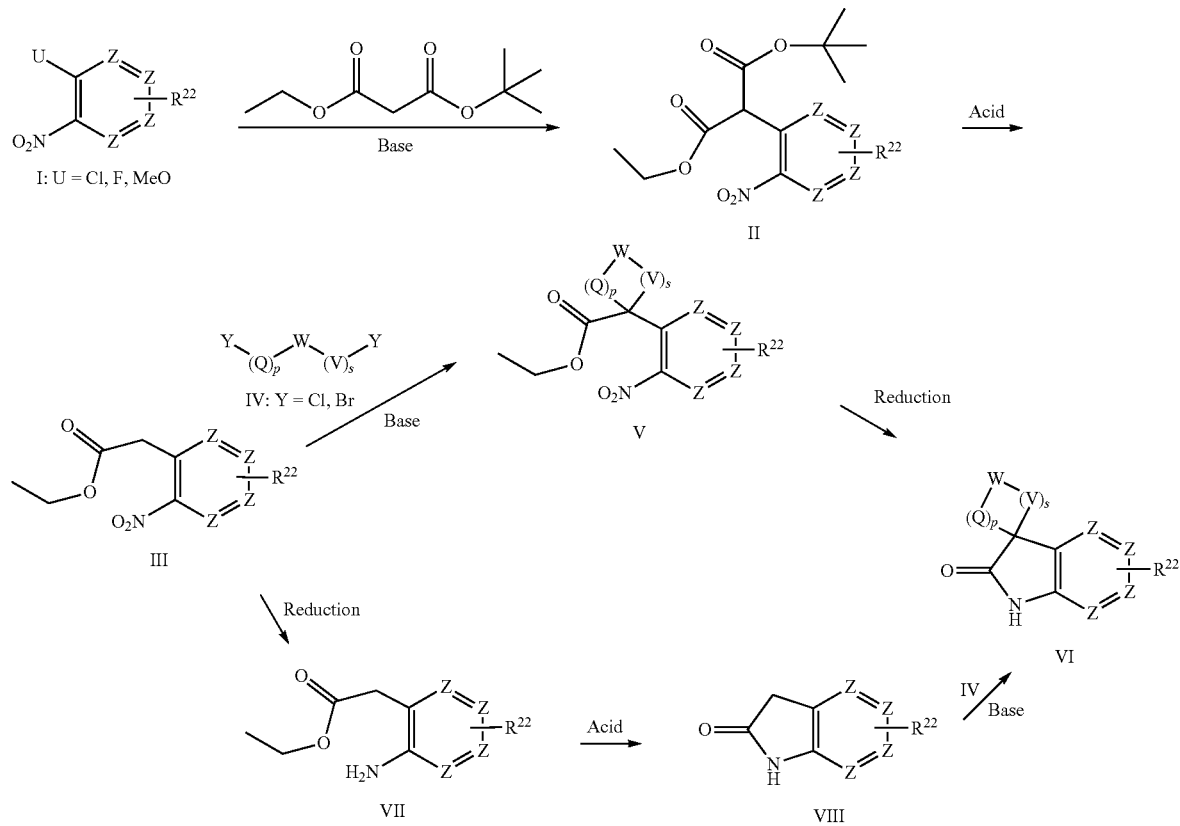

The Synthesis of spiro-2-oxo-indole derivatives and spiro-2-oxo-azaindole derivatives is shown in scheme 4. Intermediates of formula VI can be synthesized using the procedure depicted in scheme 4. Displacement of (U), which is a halide, preferably fluorine, or an alkyloxy group, preferably methoxy, of the nitro pyridine or of nitro aryl of formula I with tert-butyl ethyl malonate, in a suitable solvent such as THF or DMF, in the presence of a base such as sodium hydride or potassium carbonate, gives an intermediate of formula (II). The treatment of intermediate II with an acid such as trifluoroacetic acid or dry hydrochloric acid gives intermediate III. The latter can be transformed to intermediate V by a condensation with a bis halo compound IV preferably bromo in the presence of a suitable base such as potassium carbonate, sodium carbonate, sodium hydride and the like in a suitable solvent such as DMF, THF or a like. Reduction of the nitro group of the intermediate V when it's done in a stoichiometric way using iron in the presence of ammonium chloride or tin chloride in the presence of concentrated hydrochloric acid gives directly compound VI. Alternatively, the intermediate of formula III can be reduced first in a catalytic way using hydrogen in the presence of a catalyst such as palladium or platinum, in a suitable solvent such as methanol, to give intermediate VII. The latter can be transformed to intermediate VIII in acidic conditions using hydrochloric acid or a like in a suitable solvents such as alcohols for example isopropanol. The condensation of intermediate VIII with a bis halo compound IV, preferably chloro or bromo, is performed in the presence of a suitable inorganic base such as potassium carbonate, sodium carbonate, sodium hydride or a like in a suitable solvent such as DMF, THF or a like or using an organic base such as sodium hexamethyldisilazide (NaHMDS) or alkyl lithium bases e.g. nBuLi in a suitable solvents such THF or ether to give intermediate VI.

Scheme 5. General synthesis of fragment C (VI) type compounds

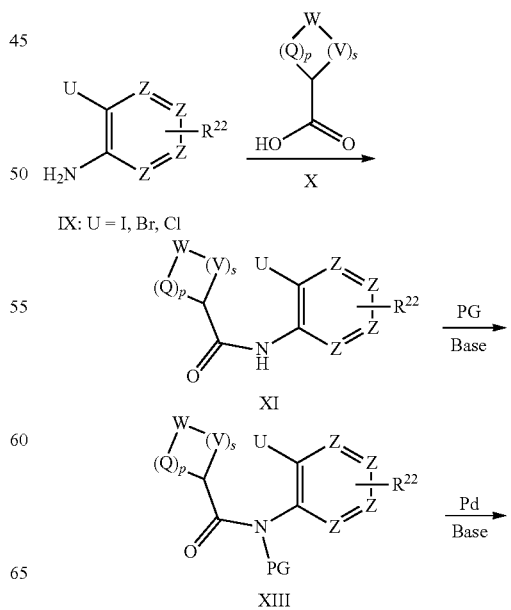

-continued

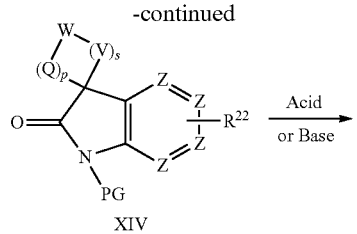

XIV

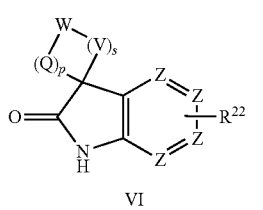

VI

Alternatively compounds of formula VI can be prepared, but not limited to, by general procedures illustrated by scheme 5.

The starting material IX can be commercially available or prepared using known in the art procedures. The acid X can be activated as the Weinreb amide using standard peptide coupling procedures e.g. EDCI/HOBT, HATU, DCC, etc. Once the acid is activated as the ester or Weinreb amide, the aniline IX can be added to convert it to intermediate XI.

The reaction of the intermediate XI with PG where PG, is a protecting group such as para-methoxybenzyl, benzyl, tert-butoxycarbonyl, mesyl or tosyl, in the presence of a suitable base such as potassium carbonate, cesium carbonate or sodium hydride in a suitable solvent such as DMF or THF gives intermediate XIII. Intermediate XIV was prepared according to the procedure reported in Lee, S. and J. F. Hartwig (2001). J. Org. Chem. 66(10): 3402-3415. The displacement of (U) which is an halo, preferably bromine, using Palladium (II) acetate as catalyst in presence of a base such as potassium tert-butoxide and a ligant such as tricyclohexylphosphene in a solvent such as 1,4-dioxane gives intermediate XIV. The removal of protecting group in intermediate XIV, can be performed using the conditions described in Green and Wurts, Protecting groups in Organic Synthesis 3$^{rd}$ Edition, to give intermediate VI.

Scheme 6 illustrates a method for the preparation of compounds of formula Ib, where $R^{1b}$, $R^2$, $R^{22}$, Q, V, W, X and Z are defined as above.

Referring to scheme 6, a compound of formula Ib can be synthesized by coupling 2-hydroxymethylene imidazopyridines XV-a with spiro oxo-indole or spiro oxo-azaindole VI in a known in the art method such as a Mitsunobu reaction which uses for example azadiisopropyldicarboxylate and triphenyl phosphine in a suitable solvent such as DMF or THF. Alternatively, compound of formula Ib may be prepared by displacement of (LG) where (LG) is a leaving group, which is a halide, preferably chlorine XV-b, or a sulfonate such as mesylate XV-c in the presence of a base such as sodium hydride, potassium carbonate or cesium carbonate in a suitable solvent such as DMF or THF.

Scheme 6

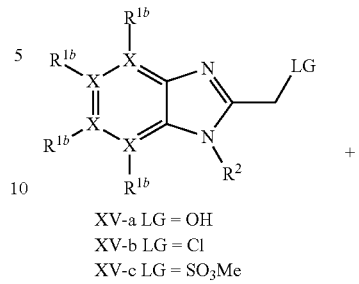

XV-a LG = OH
XV-b LG = Cl
XV-c LG = SO$_3$Me

+

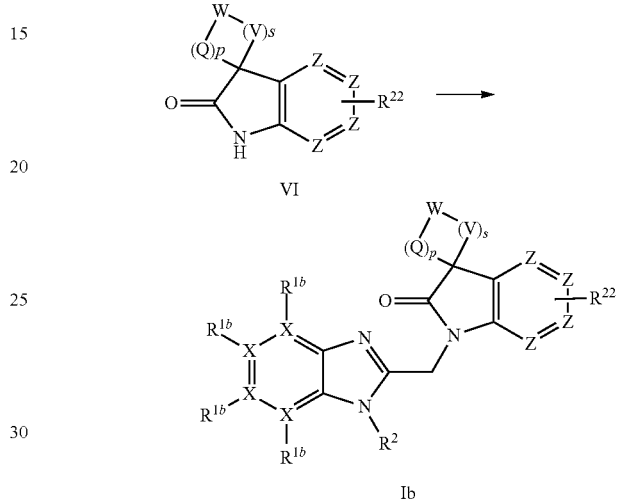

Preparation of compound XV-b and XV-c

Treatment of the alcohol XV-a with thionyl chloride provides 2-chloromethyl imidazopyridines XV-b. Alternatively, alcohol XV-a may be transformed to the intermediate XV-c by a reaction with methane sulfonyl chloride in the presence of an organic base such as triethyl amine or diisopropyl ethyl amine in a suitable solvent such as dichloromethane (scheme 7).

Scheme 7
Preparation of compound XV-a

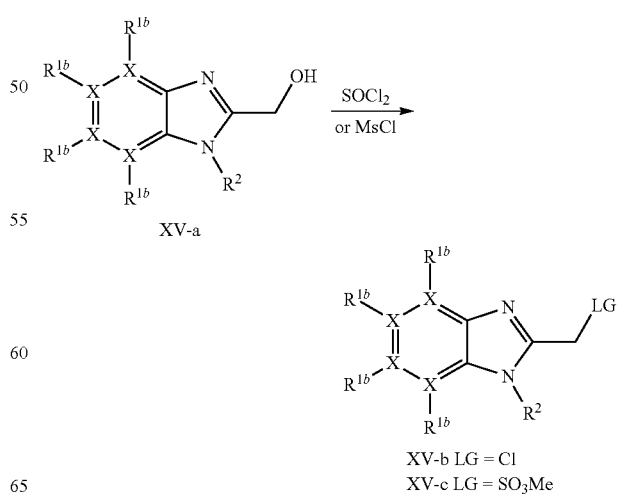

XV-b LG = Cl
XV-c LG = SO$_3$Me

Compounds of formula XV-a are either commercially available or can be prepared, but not limited to, by general procedures illustrated by scheme 8, wherein $R^{1b}$, $R^2$, X are defined as above. Referring to scheme 8 below, haloheteroaryls XVI, where (U) is an halide preferably fluorine, can be treated with primary amines of formula XVII in the presence of a suitable base such as potassium carbonate and the like, in a suitable solvent such as ethanol or dichloromethane at a reaction temperature ranging from room temperature to 100° C. to give compounds of formula XVIII. Hydrogenation of the nitro group using well-precedented conditions such as Pd/C, or other catalyst, under hydrogen or Fe/EtOH/CaCl$_2$ can yield diamine of formula XIX. Alternatively, the hydrogenation of the nitro group of compound XX using well-precedented conditions such as Pd/C, or another catalyst, under hydrogen atmosphere or Fe/EtOH/CaCl$_2$ yield diamine of formula XXI. This can be treated with the aldehydes of formula XXII in the presence of suitable reducing agents such as NaBH(OAc)$_3$, or Na(CN)BH$_3$ in solvents such as methylene chloride, DMF or THF, at about room temperature to give compounds of formula XIX. The imidazol ring can be formed by treating diamines XIX with glycolic acid or an ester like XXV under strong acidic conditions, such as aqueous hydrochloric acid, at elevated temperature such as reflux to yield the alcohols of formula XV-a.

Alternatively, diamines XIX can be condensed with dialkoxyacetate of formula XXIV, in the presence of acetic acid, in a suitable solvent such as methanol gives the acetal XV-e. The acetal of compounds XV-e can be removed with acids such as hydrochloric acid to give the aldehydes of formula XV-f. The resulting aldehydes of formula XV-f can be reduced to alcohols using a suitable reducing agent such as NaBH$_4$ or LiAlH$_4$ in a suitable solvent such as ethanol or THF to yield the desired alcohols of formula XV-a. In addition, diamines XIX can be cyclized with dialkyl oxalate of formula XXIII in a suitable solvent such as ethanol at elevated temperature with or without microwave heating to produce imidazoles of formula XV-d. Alternatively, compounds of formula XV-d may be prepared in a two steps synthesis starting from diamines XIX. Firstly diamine XIX may be reacted with an alkyl trihaloacetimidate, preferably methyl 2,2,2-trichloroacetimidate, in an acidic media, preferably acetic acid, at a temperature ranging between 25 and 50° C. to yield compound of formula XV-g. Secondly a reaction of compounds of formula XV-g with metalcarbonate, preferably sodium carbonate in a suitable solvent such as methanol, lead to compounds of formula XV-d. Compounds XV-d can be subsequently reduced to the desired alcohols of formula XV-a using a suitable reducing agent such as NaBH$_4$ or LiAlH$_4$ in a suitable solvent such as ethanol or THF.

Scheme 8

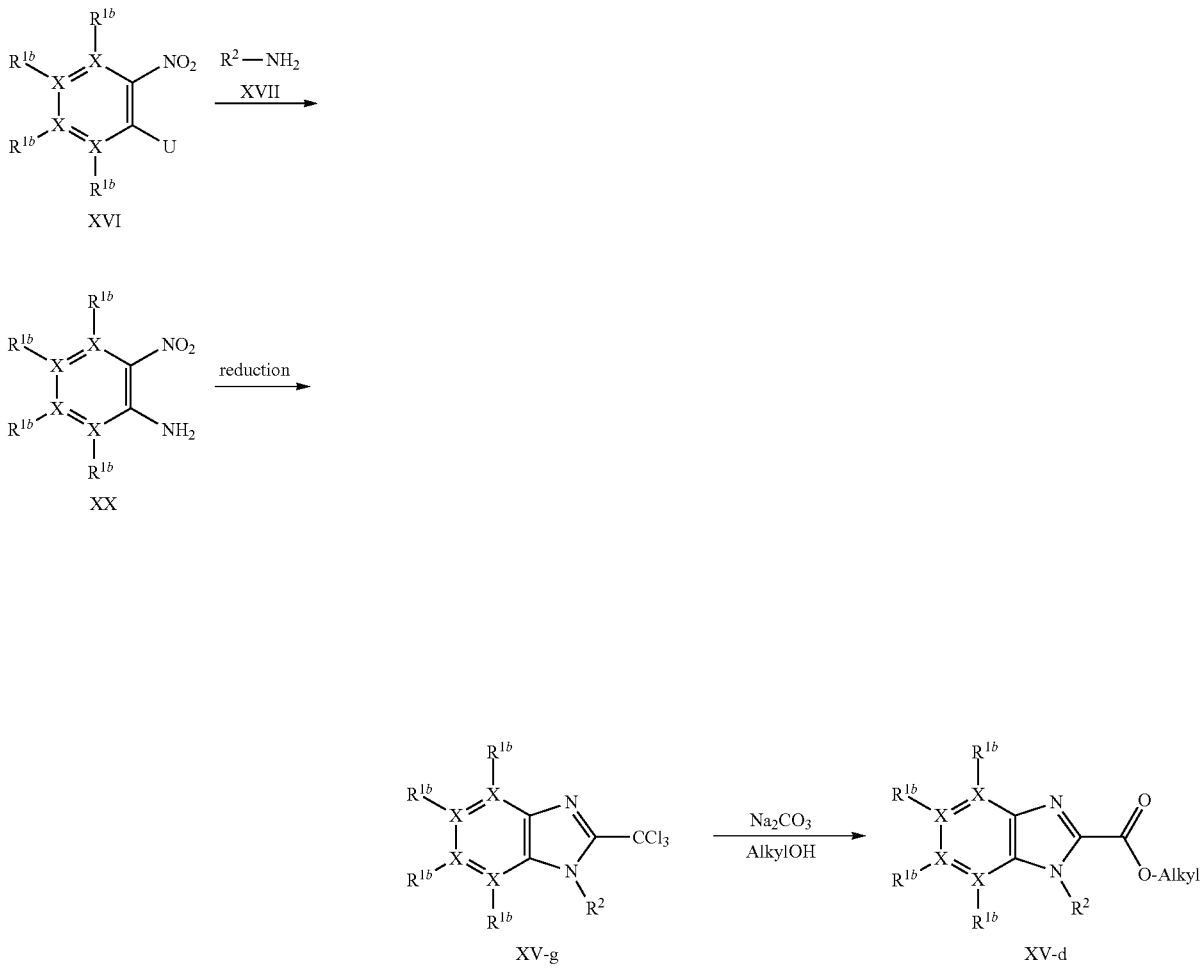

-continued

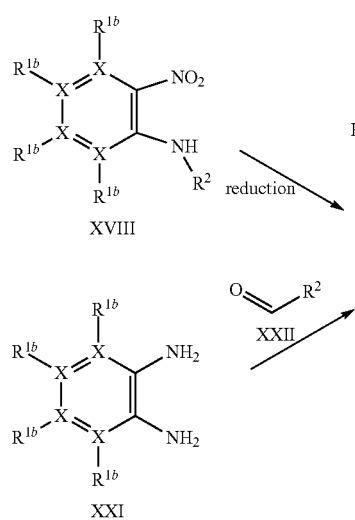

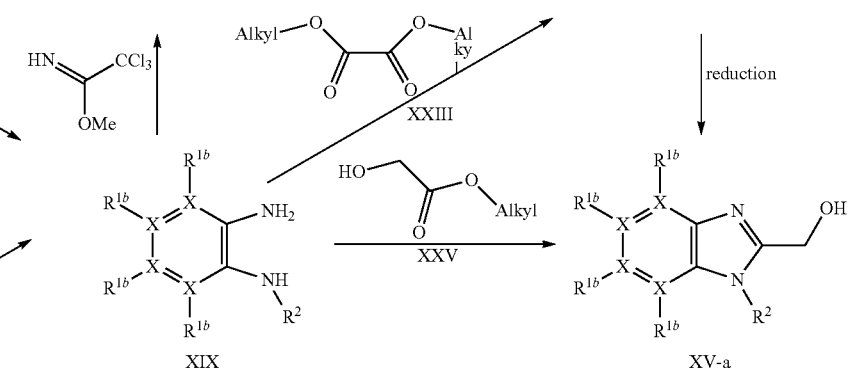

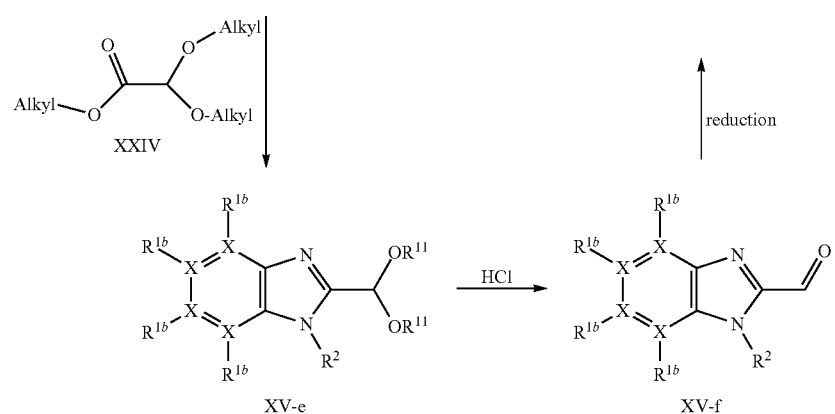

An alternative route for the preparation of compounds of type XV-a is depicted in scheme 9. Diamine XXI may be first coupled to an alkyl glycolic acid or an ester like XXV under strong acidic conditions, such as aqueous hydrochloric acid, at elevated temperature such as reflux to yield the alcohols of formula XXVI. This alcohol may be protected by a PG, where PG is a protecting group such as, but not limiting to, a trityl which consequently results in compounds XXVII. A suitable solvent for this type of reactions can be, but not limiting to, dichloromethane. The treatment of compound XXVII with compound XXVIII, wherein the LG is a leaving group, such as halide, preferably bromine, or sulfonate, in the presence of a base such as sodium hydride, potassium carbonate or cesium carbonate in a suitable solvent such as DMF or THF, gives compound XV-h. The removal of the PG in compound XV-h may be done in the presence of an acid such as hydrochloric acid in the presence of a solvent, not limited to, such as dioxane to yield compound XV-a.

Scheme 9

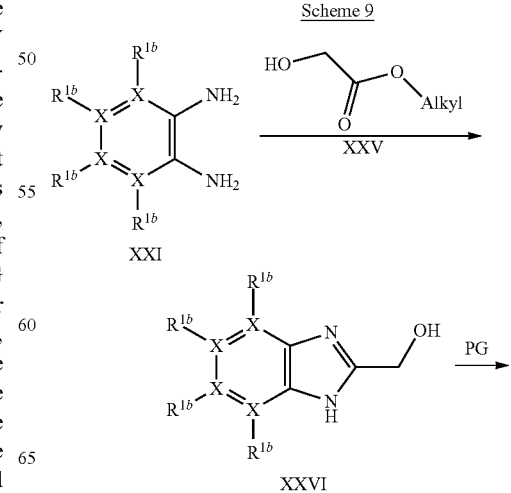

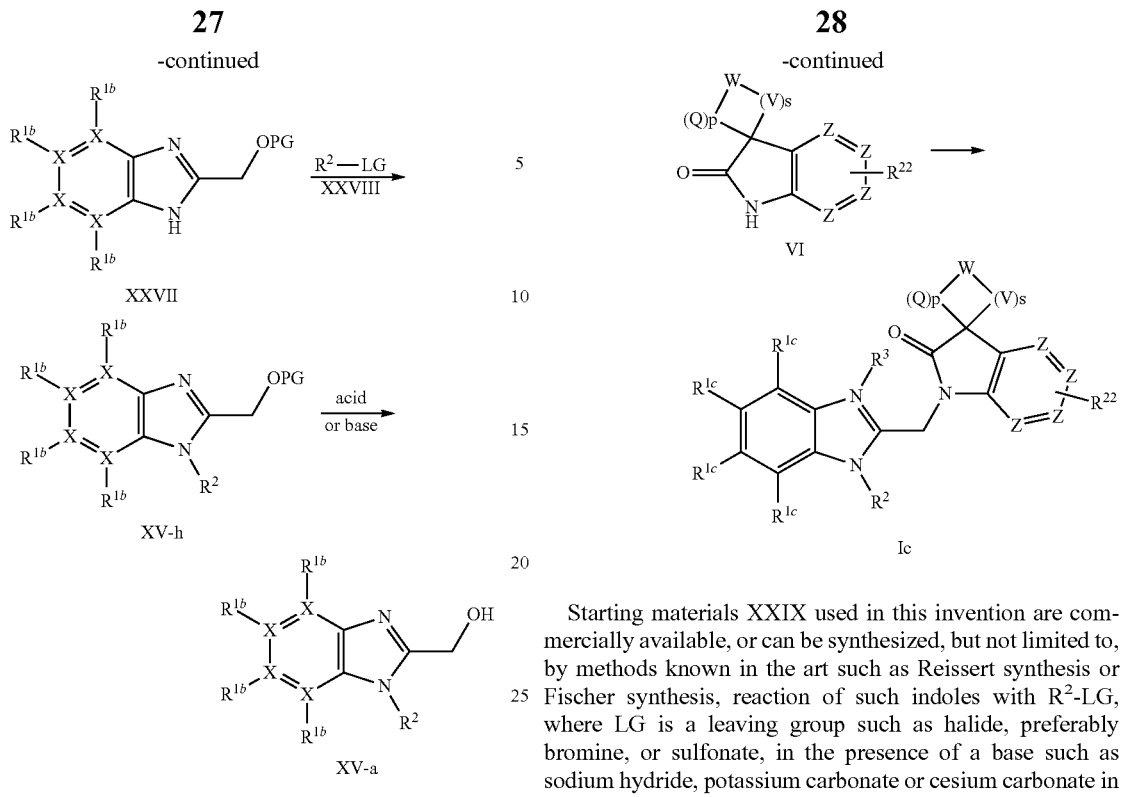

Compounds of formula Ic, or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

Referring to scheme 10, a compound of formula Ic, where $R^{1c}$, $R^2$, $R^3$, $R^{22}$, Q, V, W and Z are defined as above, can be synthesized by coupling 2-hydroxymethylene indole (XV-i) with (VI) with a method known in the art method such as a Mitsunobu reaction which uses azadiisopropyldicarboxylate and triphenyl phosphine in a suitable solvent such as DMF or THF. Alternatively, compound of formula Ic may be prepared by displacement of LG (leaving group), which is a halide, preferably chlorine (XV-j), or a sulfonate such as mesylate (XV-k) in the presence of a base such as sodium hydride, potassium carbonate or cesium carbonate in a suitable solvent such as DMF or THF.

Starting materials XXIX used in this invention are commercially available, or can be synthesized, but not limited to, by methods known in the art such as Reissert synthesis or Fischer synthesis, reaction of such indoles with $R^2$-LG, where LG is a leaving group such as halide, preferably bromine, or sulfonate, in the presence of a base such as sodium hydride, potassium carbonate or cesium carbonate in a suitable solvent such as DMF or THF, gives compound XXX (scheme 11). The conversion of the alkyl ester of compound XXX to the alcohol XV-i can be carried out with metal hydride such as lithium aluminum hydride or sodium borohydride in a suitable solvent such as THF, methanol or ethanol.

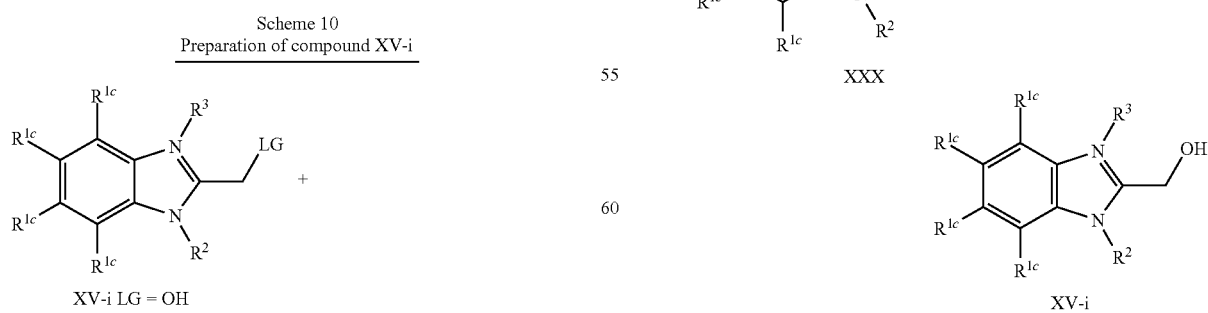

Treatment of the alcohol XV-i with thionyl chloride provides 2-chloromethyl indole XV-j. Alternatively, alcohol XV-i may be transformed to the intermediate XV-k by a reaction with methane sulfonyl chloride in the presence of an organic base such as triethyl amine or diisopropyl ethyl amine in a suitable solvent such dichloromethane (scheme 12).

Scheme 12

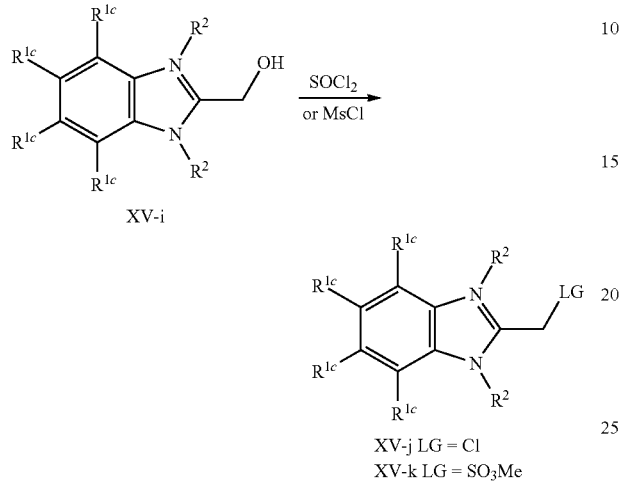

Scheme 13 illustrates a method for the preparation of compounds of formula (Id), where $R^{1d}$, $R^2$, $R^3$, $R^{22}$, Q, V, W, X and Z are defined as above.

Scheme 13: General synthesis of compounds of formula (Id)

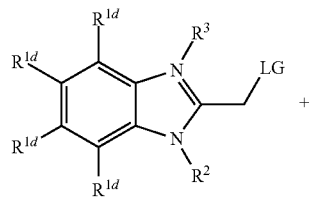

XV-l LG = OH
XV-m LG = Cl, Br
XV-n LG = OMesyl, OTosyl

-continued

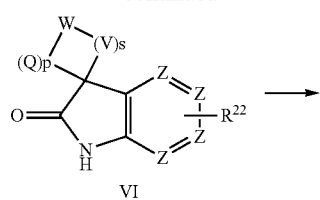

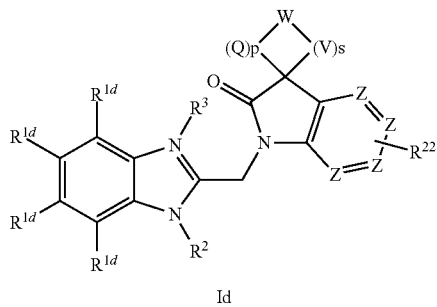

A compound of formula Id can be synthesized by coupling 2-hydroxymethylene azaindole XV-l with a spiro oxoindole or spiro oxo-azaindole VI in a known in the art method such as Mitsunobu reaction which uses azadiisopropyldicarboxylate (DIAD) and triphenylphosphine in a suitable solvent such as DMF or THF. Alternatively, compounds of formula Id may be prepared by displacement of LG, where LG is a leaving group, which is a halide, preferably chlorine XV-m or sulfonate such as mesylate XV-n in the presence of a base such as, but not limited to, sodium hydride, potassium carbonate or cesium carbonate in a suitable solvent such as DMF or THF.

Scheme 14: General synthesis of XV-l type compounds

Method 1

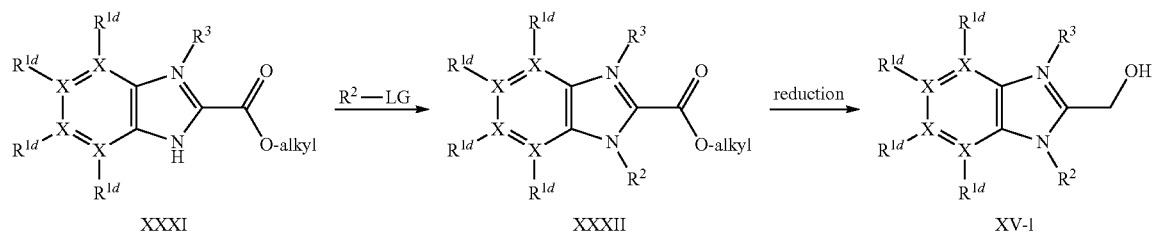

Method 2

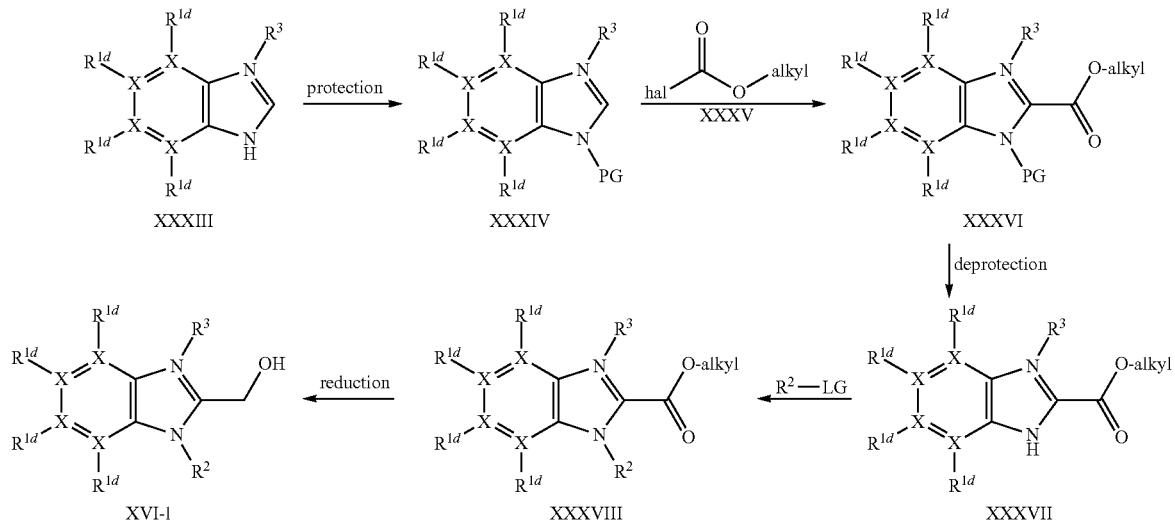

Compound XV-l is prepared according to the methods as depicted in scheme 14.

Starting materials XXXI used in this invention, according to method 1, are commercially available, or can be synthesized, but not limited to, by methods known in the art such as Reissert synthesis or Fischer synthesis. Reaction of such a compound with $R^2$-LG, where LG is a leaving group such as halide, preferably bromine, or sulfonate, in the presence of a base such as sodium hydride, potassium carbonate or cesium carbonate in a suitable solvent such as DMF or THF, gives compound XXXII. The conversion of the alkyl ester of compound XXXII to the alcohol XV-1 can be done with a metal hydride such as lithium aluminum hydride or sodium borohydride in a suitable solvent such as THF or methanol.

Alternatively a XV-1 type compound can also be synthesized as shown in scheme 14, method 2. The commercially available starting material XXXIII is protected by a PG, where PG is a protecting group such as, but not limited to, a tosyl, which consequently results in compound XXXIV. A suitable solvent for this kind of reactions can be, but not limiting to, toluene. The metallation of compound XXXIV followed by treatment with compound XXXV, wherein the halide is preferably chlorine, in a suitable solvent such as, but not limited to, THF, yields compound XXXVI. The removal of the PG in compound XXXVI may be done in the presence of a base such as potassium carbonate or cesium carbonate in a suitable solvent such as THF and methanol to obtain indole XXXVII. Reaction of indoles XXXVII with $R^2$-LG, where LG is a leaving group such as a halide, preferably bromine, or sulfonate, in the presence of a base such as sodium hydride, potassium carbonate or cesium carbonate in a suitable solvent such as DMF or THF, gives compound XXXVIII. The conversion of the alkyl ester of compound XXXVIII to the alcohol XV-1 can be carried out with a metal hydride such as lithium aluminum hydride or sodium borohydride in a suitable solvent such as THF or ethanol.

Scheme 15: General synthesis of XV-m and XV-n type compounds

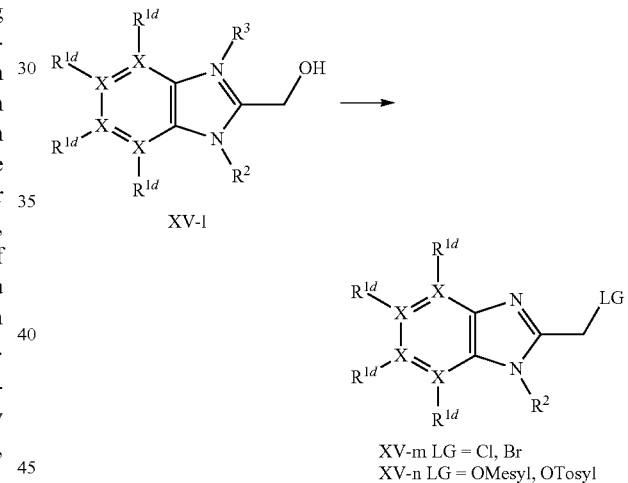

XV-m LG = Cl, Br
XV-n LG = OMesyl, OTosyl

Treatment of the alcohol XV-l with reagents like, but not limited to, $SOCl_2$, $PBr_3$, p-TsCl, MsCl provides 2-chloromethyl indole XV-m or compounds like XV-n.

The compounds of Formula (RI) may be converted to the corresponding N-oxide forms following art-known procedures for converting a trivalent nitrogen into its N-oxide form. Said N-oxidation reaction may generally be carried out by reacting the starting material of Formula (RI) with appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

All starting materials can be obtained commercially or can be prepared by those skilled in the art.

Pure stereochemically isomeric forms of the compounds of Formula (RI) may be obtained by the application of art-known procedures. Diastereomers may be separated by physical methods such as selective crystallization and chromatographic techniques, e.g., counter-current distribution, liquid chromatography and the like. Appropriate physical separation methods that may advantageously be employed are, for example, selective crystallization and chromatography, e.g. column chromatography.

The compounds of Formula (RI) as prepared in the hereinabove described processes are generally racemic mixtures of enantiomers which can be separated from one another following art-known resolution procedures. The racemic compounds of Formula (RI) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of Formula (RI) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of Formula (RI) as specified herein, or a compound of any of the embodiments of compounds of Formula (RI) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of Formula (RI), as specified herein, or of a compound of any of the embodiments of compounds of Formula (RI) as specified herein.

Therefore, the compounds of the present invention or any embodiment thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. Preferred is oral administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of Formula (RI) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (RI) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of Formula (RI) or any embodiment thereof, tautomers and stereoisomeric forms thereof, and the pharmaceutically acceptable addition salts, and the solvates thereof, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of Formula (RI), as specified herein, or of a compound of any of the embodiments of compounds of Formula (RI), as specified herein.

The exact dosage and frequency of administration depends on the particular compound of Formula (RI) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of Formula (RI) can be used as a medicine. Thus, the present invention also relates to a product containing (a) a compound of Formula (RI), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Experimental Part

Synthesis of Intermediates

Intermediate 1b: Synthesis of 2',3',5',6'-tetrahydrospiro[indoline-3,4'-pyran]-2-one Method 1

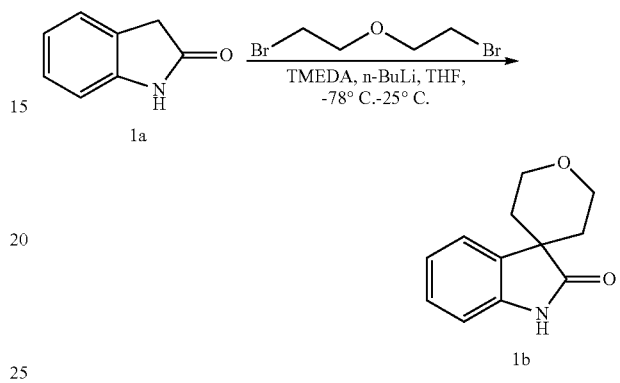

n-BuLi (108 ml, 216 mmol, 2 M in THF) was added to a solution of oxindole 1a (CAS number: 59-48-3, 11 g, 82.6 mmol) at −78° C. in THF (1000 ml). After complete addition, TMEDA (25 g, 214.76 mmol) was added, maintaining the internal temperature ←70° C. After 1 h at −78° C., bis(2-bromomethyl)ether (CAS number: 5414-19-7, 57.5 g, 247.8 mmol) was added and the reaction warmed to ambient temperature. After 48 h the reaction was quenched with $H_2O$ and the mixture was partitioned between EtOAc and $H_2O$. The aqueous solution was extracted with EtOAc and the combined organic layers were washed with brine, dried over $Na_2SO_4$, filtered, and concentrated in vacuum. The residue was purified by silica gel chromatography, eluting with a gradient of $CH_2Cl_2$: MeOH=100:0 to 97:3 to give 8% of 2',3',5',6'-tetrahydrospiro[indoline-3,4'-pyran]-2-one 1b.

Method 2

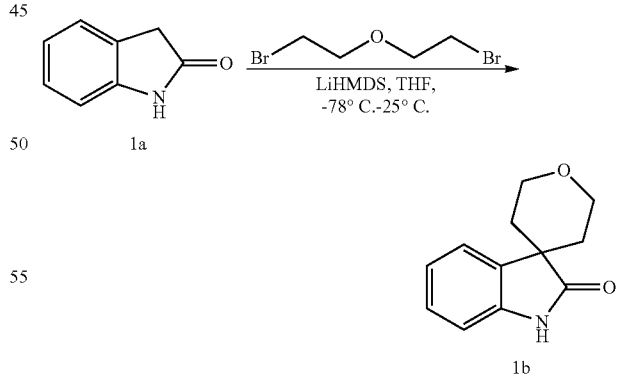

Oxindole 1a (CAS number: 59-48-3, 40 g, 264.659 mmol) was added to a solution of LiHMDS (800 ml, 800 mmol) at −78° C. The mixture was stirred 1 hour at −78° C. Bis(2-bromomethyl)ether (CAS number: 5414-19-7, 61.378 g, 264.659 mmol) was then added, maintaining the internal temperature ←50° C. The reaction was warmed to ambient temperature. After 18 hours the reaction was quenched with H₂O and the mixture was partitioned between EtOAc and H₂O. The aqueous solution was extracted with EtOAc and the combined organic layers were washed with brine, dried over Na₂SO₄, filtered, and concentrated in vacuum. The residue was purified by silica gel chromatography, eluting with a gradient of petroleum ether: ethyl acetate=3:1 to give 10.187 g (17%) of 2',3',5',6'-tetrahydrospiro[indoline-3,4'-pyran]-2-one 1b.

Intermediate 2c: Synthesis of tert-butyl 2-oxospiro[indoline-3,4'-piperidine]-1'-carboxylate

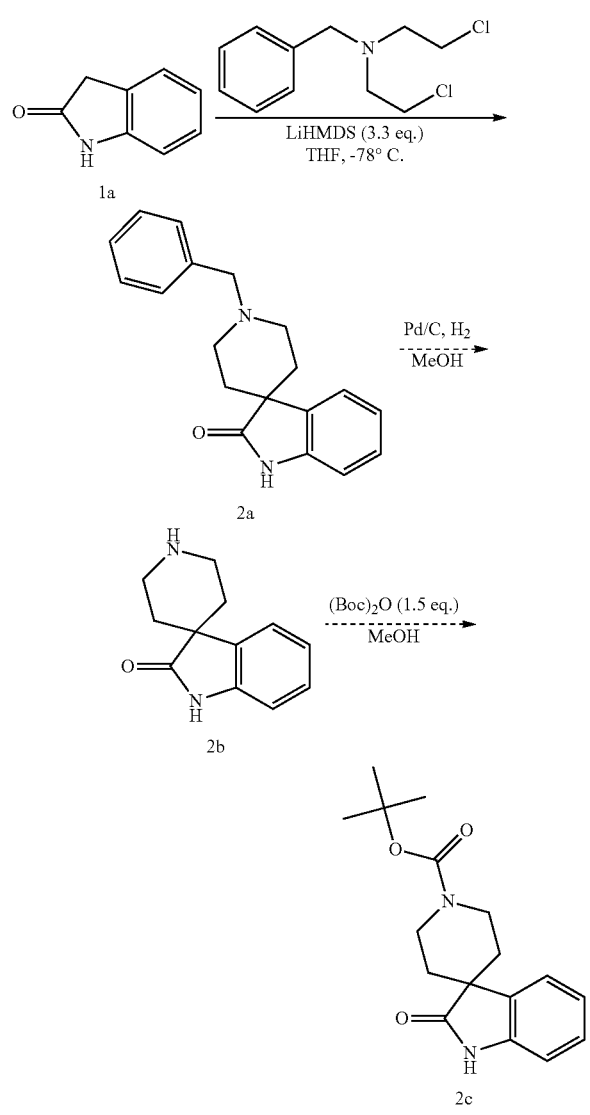

Step 1

1'-benzylspiro[indoline-3,4'-piperidin]-2-one 2a was synthetized with a yield of 59% (52 g) following the method 2 used for the synthesis of 2',3',5',6'-tetrahydrospiro[indoline-3,4'-pyran]-2-one 1b, using N,N-bis(2-chloroethyl)benzenemethanamine (CAS number: 55-51-6, 70 g, 302 mmoles) instead of bis(2-bromomethyl)ether.

Step 2

A solution of 1'-benzylspiro[indoline-3,4'-piperidin]-2-one 2a (5 g, 17.10 mmol, 1 eq.) in methanol (100 ml) was hydrogenated at RT with 10% Pd/C (0.18 g) as a catalyst for 15 h. The catalyst was filtered off and the solvent was evaporated under vacuum. The residue was then recrystallized from DIPE/acetonitrile to give 2.7 g (78% yield) of spiro[indoline-3,4'-piperidin]-2-one 2b.

Step 3

To a solution of spiro[indoline-3,4'-piperidin]-2-one 2b (2.73 g, 11.42 mmol, 1 eq.) in THF (100 ml) were added Boc₂O (2.74 g, 12.57 mmol) and triethylamine (2.38 mL, 17.135 mmoles) at RT. The mixture was stirred at room temperature for 4 h. The solvent was then evaporated under vacuum and the residue was treated with a mixture of water and DCM. The aqueous layer was extracted with DCM (3×) and the organic layers were combined, dried over Na₂SO₄, filtered and concentrated to give tert-butyl-2-oxospiro[indoline-3,4'-piperidine]-1'-carboxylate 2c (4.02 g, quantitative yield) as a white foam. 1H NMR (400 MHz, DMSO-d6) δ ppm 1.44 (s, 9H) 1.56-1.73 (m, 4H) 3.55-3.79 (m, 4H) 6.86 (dd, J=7.70, 0.40 Hz, 1H) 6.95 (td, J=7.59, 1.10 Hz, 1H) 7.19 (td, J=7.70, 1.10 Hz, 1H) 7.43 (dd, J=6.80, 0.70 Hz, 1H) 10.41 (br. s., 1H); m/z=303.05 (M+H)⁺.

Intermediate 3f: Synthesis of tert-butyl 2'-oxospiro[azetidine-3,3'-indoline]-1-carboxylate

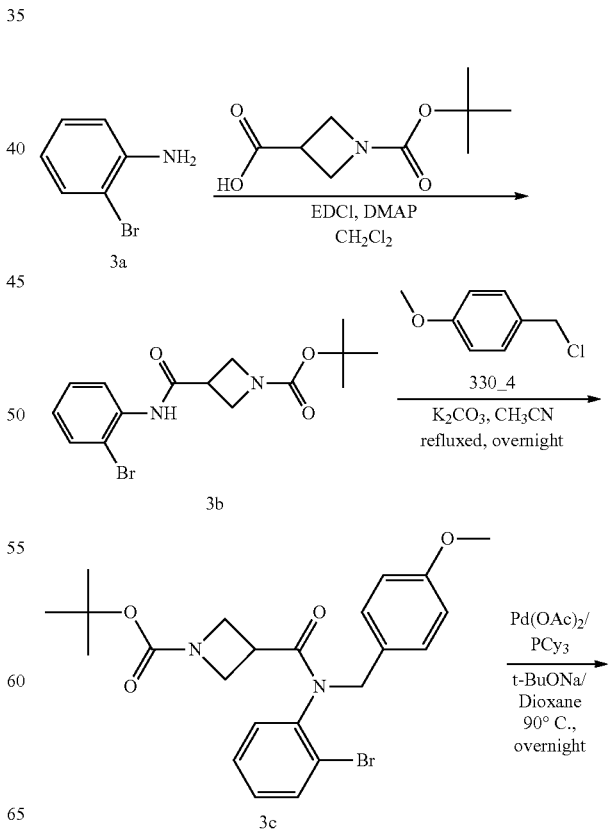

-continued

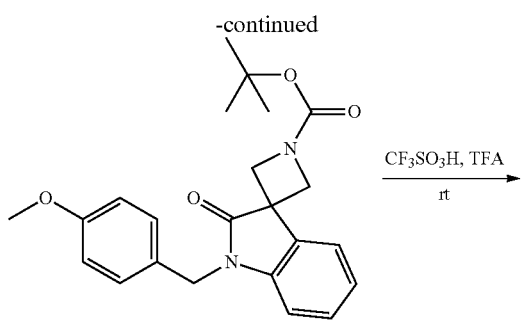

3d

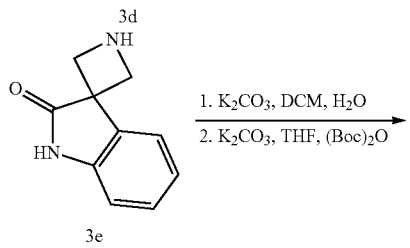

3e

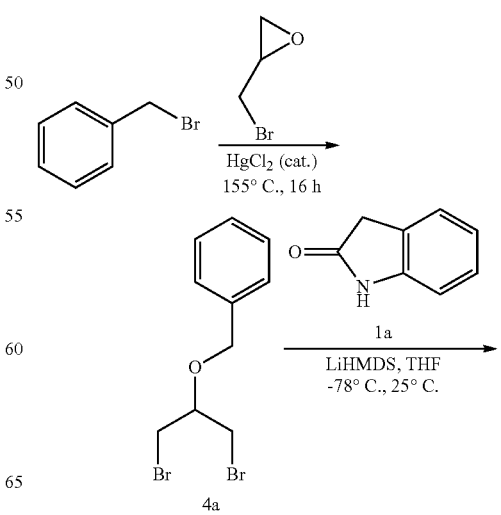

Step 1

To a stirred solution of 2-bromoaniline (150 g, 872 mmol, 1 eq.) and DMAP (138.5 g, 1133 mmol, 1.3 eq.) in CH$_2$Cl$_2$ (2500 ml) was added N-(tert-butoxycarbonyl)azetidine-3-carboxylic acid (CAS number: 142253-55-2, 176 g, 872 mmoles, 1 eq) in one portion followed by the addition of EDCI (217 g, 1133 mmol, 1.3 eq.) in one portion at room temperature. The resulting mixture was stirred at room temperature overnight. It was then successively washed with 10% citric acid aqueous solution, water, saturated Na$_2$CO$_3$ aqueous solution, and brine, and dried over Na$_2$SO$_4$. After filtration, the solvent was removed under vacuum to give tert-butyl 3-((2-bromophenyl)carbamoyl)azetidine-1-carboxylate 3b (328 g, 85% yield).

Step 2

A mixture of tert-butyl 3-((2-bromophenyl)carbamoyl) azetidine-1-carboxylate 3b (307 g, 864 mmol, 1 eq.), 4-methoxybenzylchloride (203 g, 1296 mmol, 1.5 eq.) and K$_2$CO$_3$ (358 g, 2593 mmol, 3 eq.) in CH$_3$CN (3000 ml) was refluxed overnight. The solution was then filtered, and the solid was washed with CH$_3$CN (1000 ml). The filtrate was concentrated under vacuum and the crude product was triturated in petroleum ether/ethyl acetate (30:1) to give tert-butyl 3-((2-bromophenyl)(4-methoxybenzyl)carbamoyl)azetidine-1-carboxylate 3c (380 g, 90% yield).

Step 3

Pd(OAc)$_2$ (2.25 g, 10 mmol, 0.025 eq.) and PCy$_3$ (2.8 g, 10 mmol, 0.025 eq.) were added to the solution of tert-butyl 3-((2-bromophenyl)(4-methoxybenzyl)carbamoyl)azetidine-1-carboxylate 3c (190 g, 400 mmol, 1 eq.) and t-BuONa (57.6 g, 600 mmol, 1.5 eq.) in dioxane (960 ml) under N$_2$ atmosphere. The reaction was stirred at 90° C. overnight under N$_2$ atmosphere. The solution was then filtered and concentrated under vacuum. The residue was dissolved in CH$_2$Cl$_2$, washed with NH$_4$Cl, brine and dried over Na$_2$SO$_4$. The solvent was removed under vacuum to give 158 g (quantitative yield) of tert-butyl 1'-(4-methoxybenzyl)-2'-oxospiro[azetidine-3,3'-indoline]-1-carboxylate 3d.

Step 4

CF$_3$SO$_3$H (119 ml, 1350 mmol, 3 eq.) was added to a mixture of tert-butyl 1'-(4-methoxybenzyl)-2'-oxospiro[azetidine-3,3'-indoline]-1-carboxylate 3d (178 g, 450 mmol, 1 eq. crude) in TFA (750 ml). The mixture was stirred overnight at 25° C. The solvent was then removed under vacuum and the residue (78.4 g) was used directly in the next step.

Step 5

A solution of spiro[azetidine-3,3'-indolin]-2'-one 3e (78.4 g, 450 mmol, 1 eq. crude) in CH$_2$Cl$_2$ (1500 ml) was poured into a mixture of K$_2$CO$_3$ (186.6 g, 1350 mmol, 3 eq.) in ice water (1500 ml). The aqueous layer was separated and washed with CH$_2$Cl$_2$ (3*500 mL). The aqueous layer was diluted in THF (1500 ml) and (Boc)$_2$O (98.2 g, 450 mmol, 1 eq.) was added. The solution was stirred overnight. 500 mL of a solution of ammonia in MeOH (7M) was then added dropwise to the above solution. The organic solvent was evaporated under vacuum. The aqueous solution was extracted with CH$_2$Cl$_2$ (800 ml*3), washed with brine, dried over Na$_2$SO$_4$, filtered and then concentrated under vacuum. The resulting residue was washed with t-butyl methyl ether to give the pure product tert-butyl 2'-oxospiro[azetidine-3,3'-indoline]-1-carboxylate 3f (44 g, 37% yield).

Intermediates 4c and 4d: Synthesis of (3S) and (3R)-hydroxyspiro[cyclobutane-1,3'-indolin]-2'-one -continued

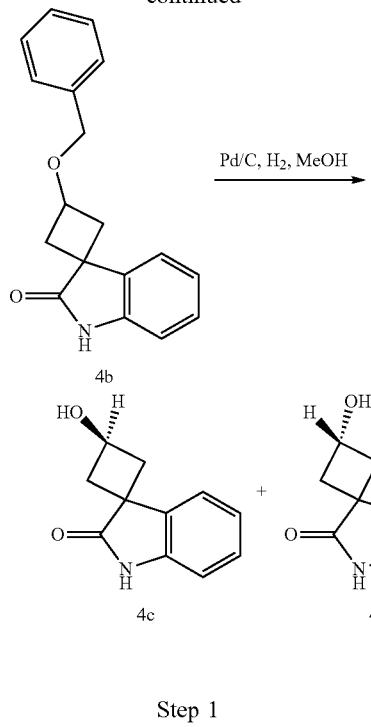

Step 1

In a flask fitted with a condenser, a mixture consisting of benzylbromide (62.43 g, 365.03 mmol, 1 eq.), 2-(bromomethyl)oxirane (50 g, 365.03 mmol, 1 eq.) and HgCl₂ (100 mg) was heated with stirring at 155° C. during 16 hours. The product was isolated via vacuum distillation through a 30 cm Vigreux condenser (110-115, 0.5 mm Hg) to provide a colorless liquid. The residue was purified by column chromatography over silica gel (eluent: dichloromethane) to give 65 g of (((1,3-dibromopropan-2-yl)oxy)methyl)benzene 4a.

Step 2

Oxindole 1a (20 g, 150.210 mmol, 1 eq.) was dissolved in THF (400 ml) and HMPA (40 ml). The reaction mixture was cooled to −78° C., then n-BuLi (132.185 ml, 330.462 mmol, 2.2 eq.) was added. The reaction mixture was stirred at −78° C. for 1 hour. Then (((1,3-dibromopropan-2-yl)oxy)methyl)benzene 4a (46.27 g, 150.210 mmol, 1 eq.) was added. The mixture was successively stirred at room temperature for 14 hours, quenched with water and extracted with dichloromethane. The residue was purified by column chromatography over silica gel (eluent:petrolumn ether:ethyl acetate 10:1). The product fractions were collected and the solvent was evaporated to give 15 g of the desired product 3-(benzyloxy)spiro[cyclobutane-1,3'-indolin]-2'-one 4b.

Step 3

A mixture of 3-(benzyloxy)spiro[cyclobutane-1,3'-indolin]-2'-one 4b (15 g, 53.699 mmol, 1 eq) and Pd/C (1.5 g) in methanol (150 ml) was hydrogenated under a 30 psi pressure for 15 hours. The reaction mixture was filtered on a celite pad which was washed several times with CH₃OH. The combined filtrates were evaporated till dryness. The residue was purified by column chromatography over silica gel (eluent:petroleum ether:ethyl acetate=3:1) to provide the racemic mixture of (3)-hydroxyspiro[cyclobutane-1,3'-indolin]-2'-one, whose enantiomers 4c and 4d were separated by high performance liquid chromatography (HPLC condition: Column: SYNERGI 250*50 10 um, Flow rate: 80 ml/min, Mobile Phase A: Purified water (containing 0.075% TFA), Mobile Phase B: Acetonitrile, Gradient: 5-30%(% B)). The desired fractions were collected, evaporated to remove off CH₃CN in vacuum and made alkaline with a saturated NaHCO₃ solution. The aqueous solution was extracted with CH₂Cl₂. The organic layers were dried, filtered and the solvent was evaporated to give 4.59 g of (3S)-hydroxyspiro[cyclobutane-1,3'-indolin]-2'-one 4c and 0.89 g of (3R)-hydroxyspiro[cyclobutane-1,3'-indolin]-2'-one 4d.

Intermediate 5c: Synthesis of tert-butyl 5-fluoro-2-oxospiro[indoline-3,4'-piperidine]-1'-carboxylate

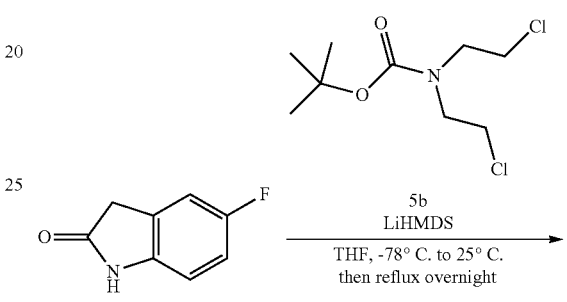

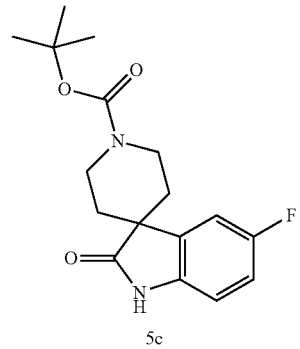

5-fluoroindolin-2-one 5a (35 g, 231.576 mmol, 1 eq.) was added to a solution of LiHMDS (700 ml, 700 mmol, 3 eq) at −78° C. The mixture was stirred 1 hour at −78° C., then tert-butyl bis(2-chloroethyl)carbamate 5b (56.075 g, 231.576 mmol, 1 eq) was added, maintaining the internal temperature ←50° C. The reaction was then warmed to ambient temperature during 2 hours, and the reaction was refluxed overnight. The mixture was quenched with H₂O and the mixture was partitioned between EtOAc and H₂O. The aqueous solution was extracted with EtOAc and the combined organic layers were washed with brine, dried over Na₂SO₄, filtered, and concentrated in vacuum. The resulting residue was purified by high performance liquid chromatography (HPLC condition: Column: Synergi-10 μm, 250× 50 mm I.D, Flow rate: 80 ml/min, Mobile Phase A: Purified water (containing 0.1% TFA), Mobile Phase B: Acetonitrile, Gradient: 35-65%(% B)) to give 5.003 g (7% yield) of tert-butyl 5-fluoro-2-oxospiro[indoline-3,4'-piperidine]-1'-carboxylate 5c.

Intermediate 6a: Synthesis of 5-fluoro-2',3',5',6'-tetrahydrospiro[indoline-3,4'-pyran]-2-one

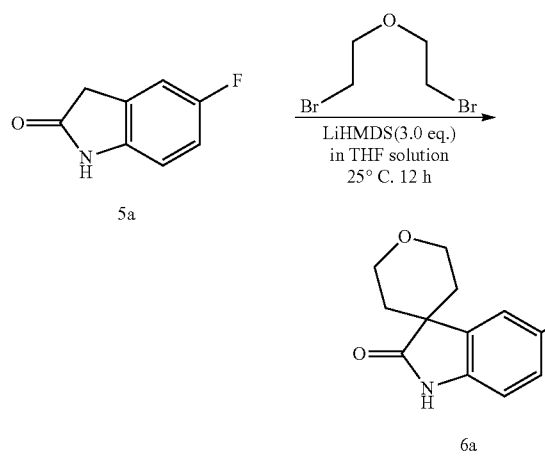

5-fluoroindolin-2-one 5a (30 g, 198.49 mmol, 1.0 eq.) was added to LiHMDS (1M in THF, 595.48 ml, 595.48 mmol, 3.0 eq.) at −78° C. The mixture was stirred at −78° C. for 10 minutes and warmed to 0° C. The mixture was stirred at 0° C. for 30 minutes, then bis(2-bromomethyl)ether (CAS number: 5414-19-7, 46.03 g, 198.49 mmol, 1.0 eq.) was added. The mixture was stirred at room temperature overnight. Water (300 ml) was added to the reaction mixture. The resulting precipitate was filtered off and washed with water to give 5-fluoro-2',3',5',6'-tetrahydrospiro[indoline-3,4'-pyran]-2-one 6a (12 g, 13% yield).

Intermediate 7b: Synthesis of 4-fluoro-2',3',5',6'-tetrahydrospiro[indoline-3,4'-pyran]-2-one

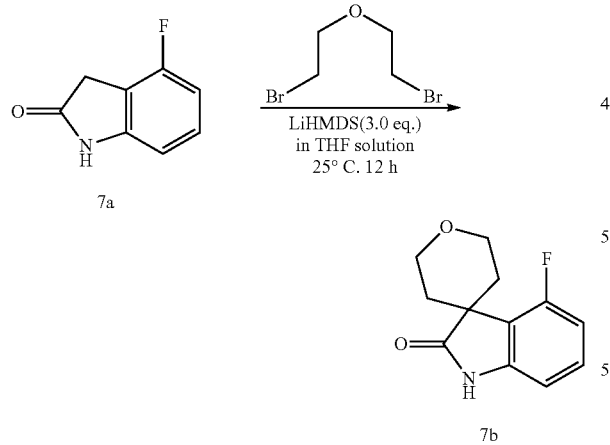

4-fluoroindolin-2-one 7a (9.5 g, 62.856 mmol, 1.0 eq.) was added to LiHMDS (1M in THF, 188.568 ml, 188.568 mmol, 3.0 eq.) at −78° C. The mixture was stirred at −78° C. for 10 minutes and warmed to 0° C. The mixture was stirred at 0° C. for 30 minutes, then bis(2-bromomethyl) ether (14.577 g, 62.856 mmol, 1.0 eq.) was added. The mixture was stirred at room temperature overnight. Water (300 ml) was added to the reaction mixture. The resulting solid was filtered off and washed with water to give 4-fluoro-2',3',5',6'-tetrahydrospiro[indoline-3,4'-pyran]-2-one 7b (1.61 g, 12% yield).

Intermediate 8d: Synthesis of spiro[cyclopentane-1,3'-pyrrolo[2,3-c]pyridin]-2'(1'H)-one

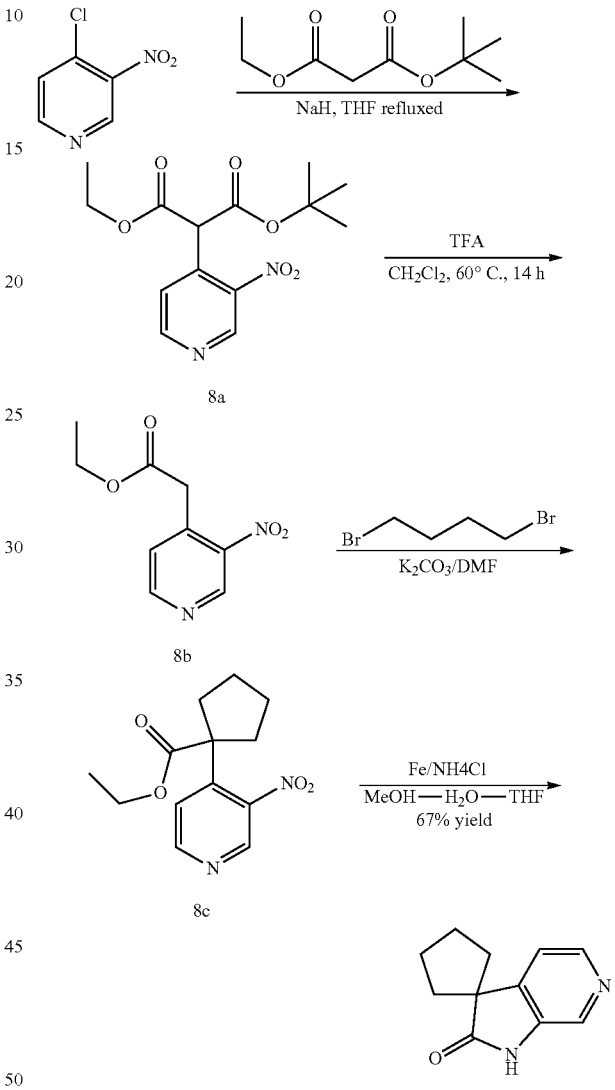

Step 1

To a solution of tert-butyl ethyl malonate (160 g, 850 mmol) in THF (1600 ml) was added NaH (80 g, 2118 mmol) portionwise at 0° C. The mixture was stirred for 1 h at 15° C., then 4-chloro-3-nitropyridine (112 g, 706 mmol) was added portionwise at 0° C. The mixture was stirred for 1 h at 15° C. The reaction was quenched with water and 1N HCl was added until pH=5. The mixture was extracted with ethyl acetate twice. The organic layers were washed with brine, dried and evaporated under vacuum to give 1-(tert-butyl) 3-ethyl 2-(3-nitropyridin-4-yl)malonate 8a (250 g), which was used without further purification in the next step.

Step 2

To a solution of 1-(tert-butyl) 3-ethyl 2-(3-nitropyridin-4-yl)malonate 8a (crude, 250 g, 706 mmol) in CH$_2$Cl$_2$ (1500 ml) was added TFA (250 mL). After 14 h of stirring at 60° C., the mixture was evaporated. A 10% NaHCO$_3$ aqueous solution was then added and the mixture was extracted with ethyl acetate twice. The organic layers were washed with brine, dried and evaporated under vacuum to give ethyl 2-(3-nitropyridin-4-yl)acetate 8b (180 g), which was used without further purification in the next step.

Step 3

Ethyl 2-(3-nitropyridin-4-yl)acetate 8b (50 g, 238 mmol), 1,4-dibromobutane (50 g, 238 mmol), K$_2$CO$_3$ (100 g, 714 mmol) and 4A molecular sieve (50 g) in DMF (500 ml) were stirred for 14 h at 80° C. 1N HCl was then added and the mixture was extracted with CH$_2$Cl$_2$ twice. The organic layers were washed with a 10% NaHCO$_3$ aqueous solution (2×), brine (2×), dried and evaporated under vacuum. The residue was purified by column chromatography over silica gel (eluent: CH$_2$Cl$_2$/ethyl acetate=10/1) to give 8.4 g (15% yield in total for the three steps) of ethyl 1-(3-nitropyridin-4-yl)cyclopentane-1-carboxylate 8c.

Step 4

Ethyl 1-(3-nitropyridin-4-yl)cyclopentane-1-carboxylate 8c (8.4 g, 31.8 mmol), Fe (7 g, 127 mmol) and NH$_4$Cl (7 g, 127 mmol) in CH$_3$OH (80 ml), THF (80 ml) and H$_2$O (80 ml) were stirred and refluxed for 3 h. The mixture was then filtered off and the solvent was evaporated under vacuum. A 10% NaHCO$_3$ aqueous solution was added and the mixture was extracted with ethyl acetate (3×). The combined organic layers were washed with brine, dried and evaporated under vacuum. The residue was washed with CH$_3$CN (2×) and the solid was collected and dried to give 4 g (67% yield) of spiro[cyclopentane-1,3'-pyrrolo[2,3-c]pyridin]-2'(1'H)-one 8d.

Intermediate 9c Synthesis of 2,3,5,6-tetrahydrospiro[pyran-4,3'-pyrrolo[2,3-c]-pyridin]-2'(1'H)-one

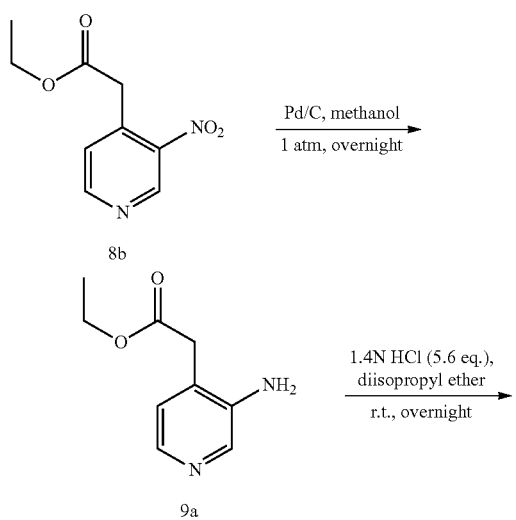

Step 1: synthesis of ethyl 2-(3-aminopyridin-4-yl)acetate (intermediate 9a)

A mixture of ethyl 2-(3-nitropyridin-4-yl)acetate 8b (65 g, 309 mmol, 90% purity, 1 eq.) in methanol (1500 ml) was hydrogenated at 20° C. (atmospheric pressure) with 10% Pd/C (6.5 g) as a catalyst for 16 h. After uptake of H$_2$ (3 equiv), the catalyst was filtered off and the filtrate was evaporated under vacuum to give 50 g (Yield: 90%) of ethyl 2-(3-aminopyridin-4-yl)acetate 9a, which was used without further purification in the next step.

Step 2: synthesis of 1,3-dihydro-2H-pyrrolo[2,3-c]pyridin-2-one (intermediate 9b)

Ethyl 2-(3-aminopyridin-4-yl)acetate 9a (34 g, 189 mmol, 1 eq.) was dissolved in 1.4 N HCl (1000 ml) and diisopropyl ether (1000 ml). The mixture was stirred at room temperature overnight. The separated organic layer was separated and washed with H$_2$O. The combined aqueous layers were washed with CH$_2$Cl$_2$ and evaporated to almost dryness. The resulting precipitate was filtered off and dried (vacuum, 60° C., 2 hours) to give 26 g (Yield: 94%) of 1,3-dihydro-2H-pyrrolo[2,3-c]pyridin-2-one 9b as a hydrochloric acid salt.

Step 3: synthesis of 2,3,5,6-tetrahydrospiro[pyran-4,3'-pyrrolo[2,3-c]pyridin]-2'(1'H)-one (intermediate 9c)

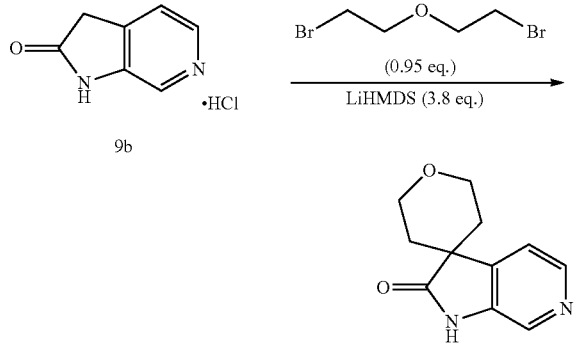

1,3-dihydro-2H-pyrrolo[2,3-c]pyridin-2-one 9b (12 g, 70.34 mmol, 1.05 eq.) was added to 1M LiHMDS solution in THF (281 ml, 281 mmol, 4 eq.) at −78° C. The mixture was stirred at −78° C. for 10 min. and warmed to 0° C. naturally. After stirring at 0° C. for 0.5 h, 1-bromo-2-(2-bromoethoxyl)ethane (15.54 g, 66.99 mmol, 1 eq.) was added. The mixture was warmed to 20° C. and stirred at 20° C. for 0.5 h, then refluxed overnight. After cooling down to room temperature, the reaction mixture was successively quenched with a 10% NH$_4$Cl solution (300 ml) and extracted with ethyl acetate (2*300 ml). The combined organic layers were washed with brine, dried (Na$_2$SO$_4$), filtered and the solvent was evaporated under vacuum. The residue was purified by column chromatography over silica gel (eluent: CH$_2$Cl$_2$: methanol from 1:0 to 20:1) to give 1.735 g (12% yield) of 2,3,5,6-tetrahydrospiro[pyran-4,3'-pyrrolo[2,3-c]pyridin]-2'(1'H)-one 9c.

Intermediate 10c Synthesis of tert-butyl 2'-oxo-1',2'-dihydrospiro[piperidine-4,3'-pyrrolo[2,3-c]pyridine]-1-carboxylate

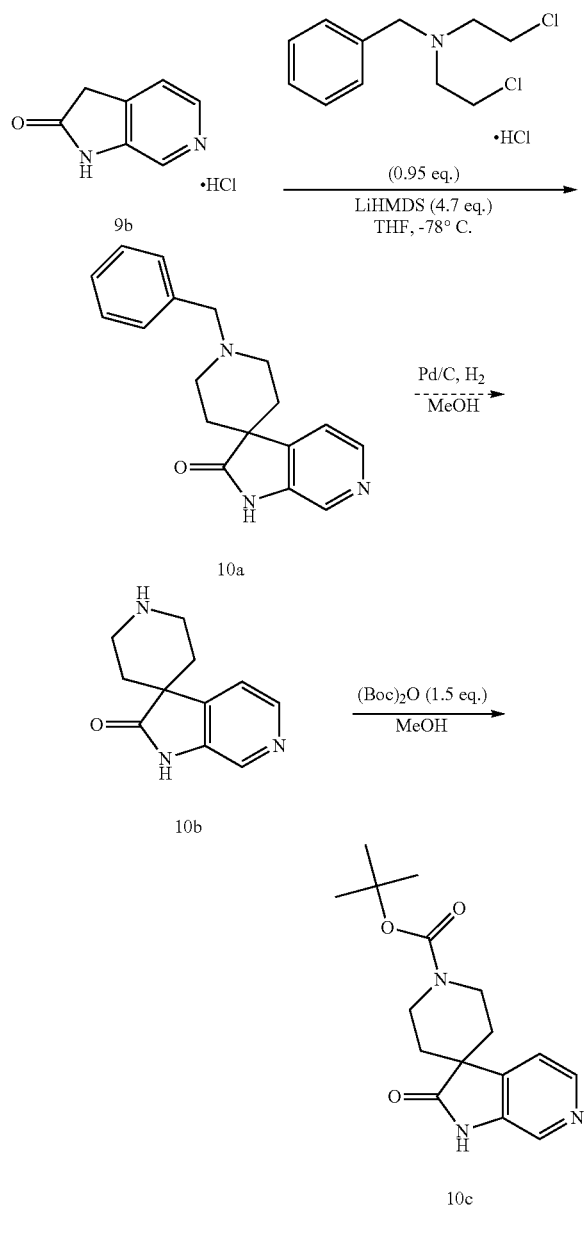

Step 1: synthesis of 1-benzylspiro[piperidine-4,3'-pyrrolo[2,3-c]pyridin]-2'(1H)-one (intermediate 10a)

The hydrochloric acid salt 1,3-dihydro-2H-pyrrolo[2,3-c]pyridin-2-one 9b (160 g, 938 mmol, 1 eq.) was added to 1M LiHMDS solution in THF (3751 ml, 3751 mmol, 4 eq.) at −78° C. After warming up to 0° C., N-benzyl-2-chloro-N-(2-chloroethyl)ethan-1-amine hydrochloride (218 g, 938 mmol, 1 eq.) was added. The mixture was warmed to 20° C., then refluxed overnight. After cooling down to room temperature, the reaction mixture was successively quenched with a 10% NH$_4$Cl solution (300 ml) and extracted with ethyl acetate (2*300 ml). The combined organic layers were washed with brine, dried (Na$_2$SO$_4$), filtered and the solvent was evaporated under vacuum. The residue was purified by column chromatography over silica gel (eluent: CH$_2$Cl$_2$: methanol from 1:0 to 10:1) to give 70 g (23% yield) of 1-benzylspiro[piperidine-4,3'-pyrrolo[2,3-c]pyridin]-2'(1'H)-one 10a.

Step 2: synthesis of spiro[piperidine-4,3'-pyrrolo[2,3-c]pyridin]-2'(1'H)-one (intermediate 10b)

A mixture of 1-benzylspiro[piperidine-4,3'-pyrrolo[2,3-c]pyridin]-2'(1'H)-one 10a (70 g, 238.61 mmol, 1 eq.) in methanol (1000 ml) was hydrogenated at 50° C. (50 psi) with 10% Pd/C (50 g) as a catalyst for 15 h. The catalyst was filtered off and the solvent was evaporated under vacuum. The residue was purified by flash column chromatography over silica gel (eluent: CH$_2$Cl$_2$/ethyl acetate from 1/0 to 0/1) to give 50 g (93% yield) of spiro[piperidine-4,3'-pyrrolo[2,3-c]pyridin]-2'(1'H)-one 10b.

Step 3: synthesis of tert-butyl 2'-oxo-1',2'-dihydrospiro[piperidine-4,3'-pyrrolo[2,3-c]pyridine]-1-carboxylate (intermediate 10c)

To a solution of spiro[piperidine-4,3'-pyrrolo[2,3-c]pyridin]-2'(1'H)-one 10b (50 g, 246.05 mmol, 1 eq.) in MeOH (1000 ml) was added Boc$_2$O (64.43 g, 295.22 mmol, 1.2 eq.). The mixture was stirred at room temperature overnight, then evaporated till dryness. The residue was purified by column chromatography over silica gel (eluent:dichloromethane:ethyl acetate from 1:0 to 0:1) to give 43.32 g (58% yield) of ten-butyl 2'-$_{oxo}$-1',2'-dihydrospiro[piperidine-4,3'-pyrrolo[2,3-c]pyridine]-1-carboxylate 10c.

Intermediate 11c Synthesis of 2,3,5,6-tetrahydrospiro[pyran-4,3'-pyrrolo[3,2-c]pyridin]-2'(1'H)-one

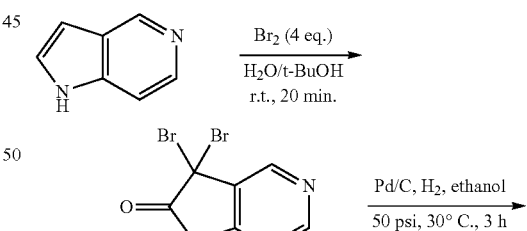

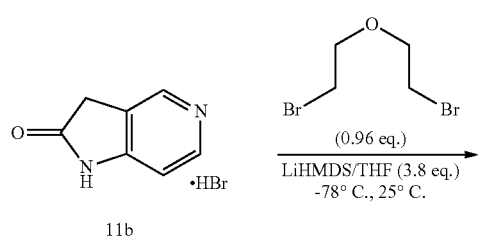

Intermediate 12d Synthesis of 2,6-dimethyl-2,3,5,6-tetrahydrospiro[pyran-4,3'-pyrrolo[2,3-c]pyridin]-2'(1'H)-one

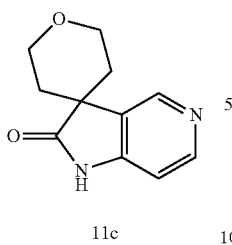

11c

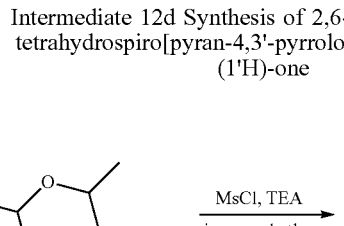

12a

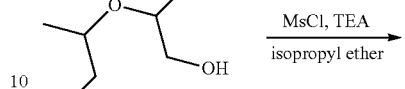

12b

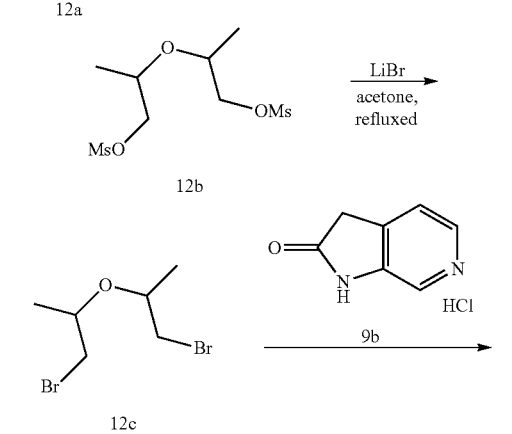

12c

12d

Step 1: synthesis of 3,3,7-tribromo-1,3-dihydro-2H-pyrrolo[3,2-c]pyridin-2-one (intermediate 11a)

Br$_2$ (26 ml, 507 mmol, 4 eq.) was added dropwise to a solution of 1H-pyrrolo[3,2-c]pyridine (15 g, 127 mmol, 1 eq.) in H$_2$O (500 ml) and t-BuOH (500 ml) at room temperature over a period of 20 min. Following addition of Br$_2$, the pH of the mixture was approximately 1. Saturated NaHCO$_3$ solution (800 ml) was added slowly and carefully over 30 min, and the pH of the mixture was adjusted to 6.5-7. The mixture was stirred for 1 h, then filtered off. The resulting solid was further washed with water and co-evaporated with ethanol to give 28.5 g (61% yield) of 3,3,7-tribromo-1,3-dihydro-2H-pyrrolo[3,2-c]pyridin-2-one 11a.

Step 2: synthesis of 1,3-dihydro-2H-pyrrolo[3,2-c]pyridin-2-one hydrobromide (intermediate 11b)

The reaction was carried out in three parallel reactors. A mixture of 3,3,7-tribromo-1,3-dihydro-2H-pyrrolo[3,2-c]pyridin-2-one 11a (28.5 g, 76.9 mmol, 1 eq.) in ethanol (2850 ml) was hydrogenated at 30° C. (50 psi) with Pd/C (14 g) as a catalyst for 3 h. After uptake of H$_2$ (3 eq.), the catalyst was filtered off and the filtrate was evaporated under vacuum to give 14 g (85% yield) of 1,3-dihydro-2H-pyrrolo[3,2-c]pyridin-2-one hydrobromide 11b.

Step 3: synthesis of 2,3,5,6-tetrahydrospiro[pyran-4,3'-pyrrolo[3,2-c]pyridin]-2'(1'H)-one (intermediate 11c)

1,3-dihydro-2H-pyrrolo[3,2-c]pyridin-2-one hydrobromide 11b (11.7 g, 54.4 mmol, 1.04 eq.) was added to 1M LiHMDS solution in THF (210 ml, 210 mmol, 4 eq.) at −78° C. The mixture was stirred at −78° C. for 10 min and warmed to 0° C. naturally. After stirring at 0° C. for 0.5 h, 1-bromo-2-(2-bromoethoxyl)ethane (12.1 g, 52.2 mmol, 1 eq.) was added. The mixture was warmed to 20° C., then refluxed overnight. The mixture was then cooled to room temperature, quenched with a saturated NH$_4$Cl solution (200 ml), filtered over a celite pad and the filtrate was extracted with ethyl acetate (2*200 ml). The combined organic layers were washed with brine, dried (Na$_2$SO$_4$), filtered and the solvent was evaporated under vacuum. The residue was dissolved in CH$_2$Cl$_2$: methanol (5:1) and purified by column chromatography over silica gel (eluent: CH$_2$Cl$_2$: methanol from 1:0 to 10:1) to give a residue which was further washed with CH$_3$CN to give 812 mg (7% yield) of 2,3,5,6-tetrahydrospiro[pyran-4,3'-pyrrolo[3,2-c]pyridin]-2'(11-1)-one 11c.

Step 1: synthesis of oxybis(propane-2,1-diyl)dimethanesulfonate (intermediate 12b)

2,2'-oxybis(propan-1-ol) 12a (obtained from the reduction of diethyl 2,2'-oxydipropionate with LiAlH$_4$ as described in Journal of the Chemical Society, Perkin Transactions 1: Organic and Bio-Organic Chemistry (1972-1999), (3), 245-50; 1975) was mesylated using mesylchloride and triethylamine in isopropylether, to give oxybis(propane-2,1-diyl) dimethanesulfonate 12b. Diethyl 2,2'-oxydipropionate was obtained following the procedure reported in Supramolecular Chemistry, 22(11 & 12), 827-837; 2010, by mixing the commercially available ethyl 2-hydroxypropanoate and ethyl 2-bromopropanoate in the presence of NaH in THF.

Step 2: synthesis of 1-bromo-2-((1-bromopropan-2-yl)oxy)propane (intermediate 12c)

To a solution of oxybis(propane-2,1-diyl)dimethanesulfonate 12b in acetone was added LiBr and the reaction mixture was stirred under reflux until completion, to give 1-bromo-2-((1-bromopropan-2-yl)oxy)propane 12c.

Step 3: synthesis of 2,6-dimethyl-2,3,5,6-tetrahydrospiro[pyran-4,3'-pyrrolo[2,3-c]pyridin]-2'(1'H)-one (intermediate 12d)

2,6-dimethyl-2,3,5,6-tetrahydrospiro[pyran-4,3'-pyrrolo[2,3-c]pyridin]-2'(1'H)-one 12d was synthetized following the protocol used for the synthesis of 2,3,5,6-tetrahydrospiro [pyran-4,3'-pyrrolo[2,3-c]pyridin]-2'(1'H)-one 9c, using 1-bromo-2-((1-bromopropan-2-yl)oxy)propane 12c instead of 1-bromo-2-(2-bromoethoxyl)ethane, and NaH in DMF instead of LiHMDS.

Intermediate 13c Synthesis of 2',3',5',6'-tetrahydrospiro[pyrrolo[2,3-c]pyridine-3,4'-thiopyran]-2(1H)-one 1',1'-dioxide

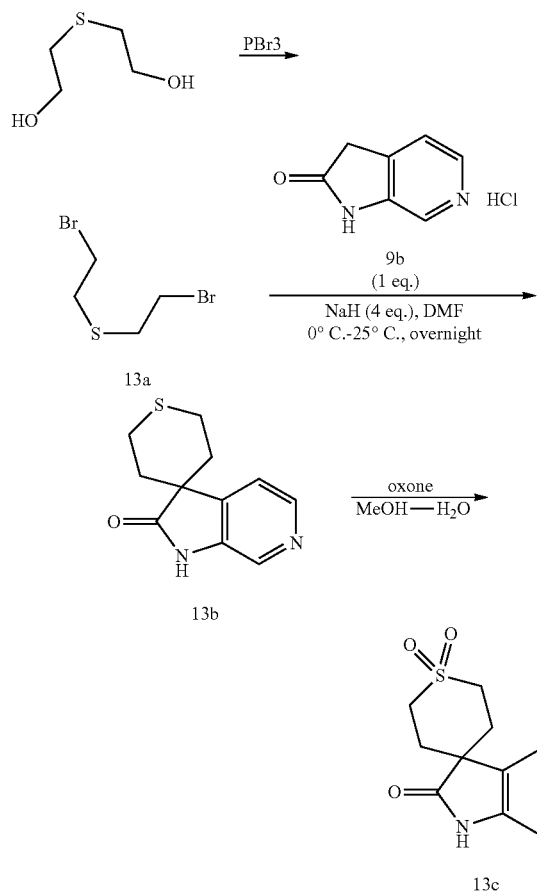

Step 1: synthesis of bis(2-bromoethyl)sulfane (intermediate 13a)

To a solution of 2,2'-thiodiethanol (5 g, 40.9 mmoles) in dry THF was added phosphorous tribromide (7.75 g, 0.7 eq.) at −15° C., under $N_2$. After stirring for 30 minutes at −15° C., the reaction mixture was allowed to warm up and stirred for 12 hours at room temperature. It was then diluted with a $NaHCO_3$ aq. solution at 0° C. The organic layer was separated, concentrated and purified by column chromatography over silica gel (eluent:petroleum ether/ethyl acetate=10/1, v/v) to give 2.5 g (22% yield) of bis(2-bromoethyl)sulfane 13a.

Step 2: synthesis of 2',3',5',6'-tetrahydrospiro[pyrrolo[2,3-c]pyridine-3,4'-thiopyran]-2(1H)-one (intermediate 13b)

2',3',5',6'-tetrahydrospiro[pyrrolo[2,3-c]pyridine-3,4'-thiopyran]-2(1H)-one 13b was synthetized following the protocol used for the synthesis of 2,3,5,6-tetrahydrospiro [pyran-4,3'-pyrrolo[2,3-c]pyridin]-2'(1'H)-one 9c, using bis (2-bromoethyl)sulfane 13a instead of 1-bromo-2-(2-bromoethoxyl)ethane, and NaH (4 eq.) in DMF at 0° C. instead of LiHMDS.

Step 3: synthesis of 2',3',5',6'-tetrahydrospiro[pyrrolo[2,3-c]pyridine-3,4'-thiopyran]-2(1H)-one (intermediate 13c)

A solution of 2',3',5',6'-tetrahydrospiro[pyrrolo[2,3-c] pyridine-3,4'-thiopyran]-2(1H)-one 13b in MeOH/$H_2O$ was oxidized with oxone to give 2',3',5',6'-tetrahydrospiro[pyrrolo[2,3-c]pyridine-3,4'-thiopyran]-2(1H)-one 13c.

Intermediate 14d Synthesis of 3-(methylsulfonyl)propan-1-amine hydrochloride

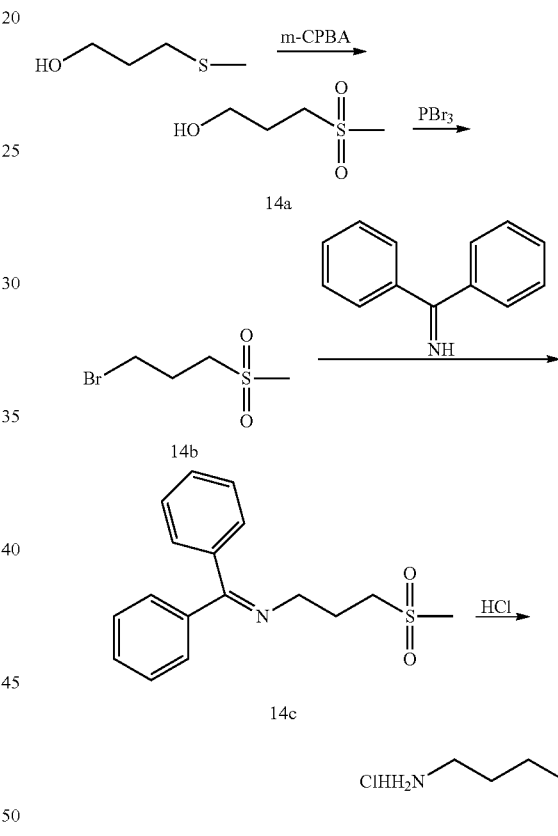

Step 1: synthesis of 3-(methylsulfonyl)propan-1-ol (intermediate 14a)

3-(methylthio)propan-1-ol (200 g, 1900 mmol, CAS 505-10-2) was dissolved in $CH_2Cl_2$ (2000 mL). The mixture was cooled to 0° C., then m-CPBA 85% in water (970 g, 5700 mmol, CAS 937-14-4) was added portion wise keeping the temperature between 0 and 5° C. After addition, the mixture was allowed to warm to 25° C. and stirred for 15 h. The mixture was filtered through a celite pad and the filtrate was purified by flash column (Eluent:petroleum ether:ethyl acetate=3:1 and then ethyl acetate: methanol=10:1) to yield the intermediate 14a (75 g, 29%).

Step 2: synthesis of 1-bromo-3-(methylsulfonyl)propane (intermediate 14b)

To a solution of the intermediate 14a (75 g, 543 mmol) in CH$_2$Cl$_2$ (750 mL), at 0° C., was added dropwise phosphorus tribromide (53.6 mL, 570 mmol), keeping the temperature between 0 and 5° C. After addition, the mixture was allowed to warm to 25° C. and stirred for 15 h. The mixture was poured into ice-water, the organic layer was then separated, washed with brine (2×500 mL), dried over Na$_2$SO$_4$, filtered and evaporated under vacuum to yield the title compound 14b (77 g, 71%). $^1$H NMR (400 MHz, CHLOROFORM-d) δ ppm 2.25-2.40 (m, 2H) 2.91 (s, 3H) 3.1-3.2 (m, 2H) 3.5-3.6 (m, 2H).

Step 3: synthesis of N-(diphenylmethylene)-3-(methylsulfonyl)propan-amines (intermediate 14c)

To a solution of the intermediate 14b (27 g, 134 mmol) in CH$_3$CN (60 mL) were added diphenylmethanimine (27 g, 148 mmol) and DIEA (19.6 g, 152 mmol). The mixture was refluxed for 4 h and then cooled to room temperature. The mixture was then neutralized with 50% aqueous acetic acid at 25° C. Water (80 mL) was added and the mixture was extracted with ethyl acetate (2×300 mL). The combined organic layers were washed with brine, dried over Na$_2$SO$_4$, filtered and evaporated under vacuum. The residue was washed with petroleum ether (4×100 mL). The mixture was treated with methyl tert-butyl ether. The solid was collected and washed with petroleum ether. The filtrate was dried under vacuum and the resulting residue was purified by column chromatography (Eluent: CH$_2$Cl$_2$: ethyl acetate from 1:0 to 10:1) to give the title compound 14c (34 g, 85%) as a white solid.

Step 4: synthesis of 3-(methylsulfonyl)propan-1-amine hydrochloride (intermediate 14d)

To a solution of the intermediate 14c (34 g, 113 mmol) in dioxane (600 mL) was added a solution of 4N HCl/dioxane (120 mL, 480 mmol) dropwise at 0° C. After addition, the mixture was allowed to warm to 25° C. and stirred for 15 h. The mixture was filtered. The solid was collected and washed with dioxane to give the title product 14d (11.5 g, 50%) as a yellow powder.

Intermediate 15e Synthesis of 5-chloro-2-(chloromethyl)-1-(3-(methylsulfonyl)-propyl)-1H-benzo[d]imidazole hydrochloride

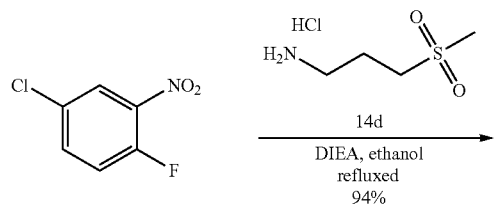

Step 1: Synthesis of 4-chloro-N-(3-(methylsulfonyl)propyl)-2-nitroaniline

A solution of 1-chloro-4-chloro-3-nitrobenzene (7.6 g, 35 mmol), 3-(methylsulfonyl)-propan-1-amine hydrochloride 14d (6 g, 35 mmol) and diisopropylethylamine (DIEA) (13.5 g, 105 mmol) in ethanol (70 mL) was refluxed for 14 h. The mixture was then cooled to 20° C. and the resulting precipitate was filtered and washed with ethanol. 11 g (94%) of intermediate 15a was obtained as an orange powder.

Step 2: Synthesis of 4-chloro-N1-(3-(methylsulfonyl)propyl)benzene-1,2-diamine Intermediate 15a (10 g, 29.7 mmol) in methanol (200 mL), EtOAc (200 mL) and THF (200 mL) was hydrogenated with Raney Ni (10 g) as a catalyst at 20° C. (1 atm) for 3 h. After uptake of $H_2$ (3 eq), the catalyst was filtered off and the filtrate was evaporated. 10 g (90%) of intermediate 15b was obtained as a black solid.

Step 3: Synthesis of 5-chloro-2-(diethoxymethyl)-1-(3-(methylsulfonyl)propyl)-1H-benzo[d]imidazole Intermediate 15b (10 g, 29.7 mmol) and methyl dimethoxyacetate (9.2 g, 68.31 mmol) in 24 wt % KOEt in ethanol (13.5 g, 38.5 mmol) were stirred and refluxed overnight. The mixture was evaporated under vacuum. Water (200 mL) was then added, followed by acetic acid to neutralize the mixture. The mixture was extracted with ethyl acetate (2×100 mL). The combined organic layers were washed with saturated $NaHCO_3$, brine and dried over $Na_2SO_4$. The solvent was removed under vacuum to yield 12.3 g (90%) of intermediate 15c as a dark oil.

Step 4: Synthesis of (5-chloro-1-(3-(methylsulfonyl)propyl)-1H-benzo[d]imidazol-2-yl)methanol Intermediate 15c (12.3 g, 29.3 mmol) in THF (100 mL) was stirred for 0.5 h at 20° C. until complete dissolution. Conc. HCl (21 mL) and $H_2O$ (42 mL) were then added. The mixture was refluxed for 6 h and then cooled to −10° C. $CH_3OH$ (50 mL) were added, followed by careful addition of $NaBH_4$ (24 g, 629 mmol). The mixture was stirred for 0.5 h at 10° C. and concentrated under vacuum. Water (200 mL) was added. The mixture was extracted with ethyl acetate (2×100 mL). The combined organic layers were washed with brine and dried over $Na_2SO_4$. The solvent was removed under vacuum. The resulting solid was washed with ethyl acetate (2×5 mL) and dried under vacuum. 6.8 g (60%) of intermediate 15d was obtained as an off-white solid.

$^1$H NMR (400 MHz, DMSO-$d_6$) δ ppm 2.20 (dq, J=7.8, 7.5 Hz, 2H), 2.98 (s, 3H), 3.16-3.24 (m, 2H), 4.42 (t, J=7.4 Hz, 2H), 4.73 (d, J=6.0 Hz, 2H), 5.73 (t, J=5.8 Hz, 1H), 7.42 (dd, J=8.7, 1.9 Hz, 1H), 7.63 (d, J=8.5 Hz, 1H), 7.79-7.83 (m, 1H).

Step 5

To a solution of alcohol 15d (363 mg, 1.414 mmole) in 30 mL of dichloromethane was added dropwise a solution of thionyl chloride (336 mg, 2 eq) in 10 mL of dichloromethane. The reaction mixture was stirred for one hour at 45° C. It was then concentrated under vacuum to give the desired intermediate 15e (440 mg, 99%) as an HCl salt, which was used as such in the next step.

Intermediate 16a Synthesis of (5-bromo-1-(3-(methylsulfonyl)propyl)-1H-benzo[d]imidazol-2-yl)methanol

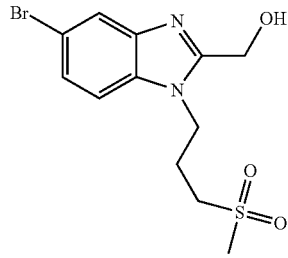 [SMILES: CS(=O)(=O)CCCn1c(CO)nc2cc(Br)ccc21]

(5-bromo-1-(3-(methylsulfonyl)propyl)-1H-benzo[d]imidazol-2-yl)methanol 16a was synthetized following the chemical pathway used for the synthesis of (5-chloro-1-(3-(methylsulfonyl)propyl)-1H-benzo[d]imidazol-2-yl)methanol 15d, using 1-bromo-4-fluoro-3-nitrobenzene (7.6 g, 35 mmol) instead of 1-chloro-4-fluoro-3-nitrobenzene in the first step. 6.8 g of the desired product 16a were obtained as an off-white solid. $^1$H NMR (400 MHz, DMSO-$d_6$) δ ppm 2.20 (dq, J=7.8, 7.5 Hz, 2H), 2.98 (s, 3H), 3.16-3.24 (m, 2H), 4.42 (t, J=7.4 Hz, 2H), 4.73 (d, J=6.0 Hz, 2H), 5.73 (t, J=5.8 Hz, 1H), 7.42 (dd, J=8.7, 1.9 Hz, 1H), 7.63 (d, J=8.5 Hz, 1H), 7.79-7.83 (m, 1H); m/z=347 & 349 (M+H)+Br pattern.

Intermediate 17b Synthesis of (5-chloro-1-(3-(methylsulfonyl)propyl)-1H-indol-2-yl)methanol

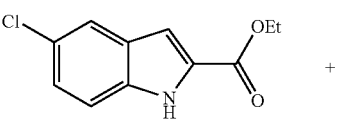

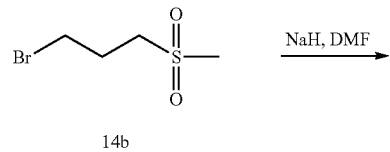

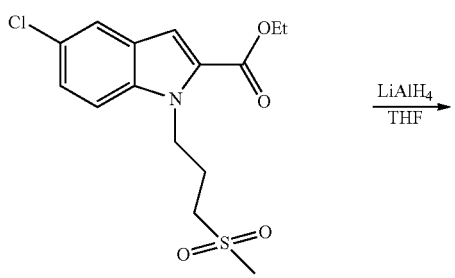

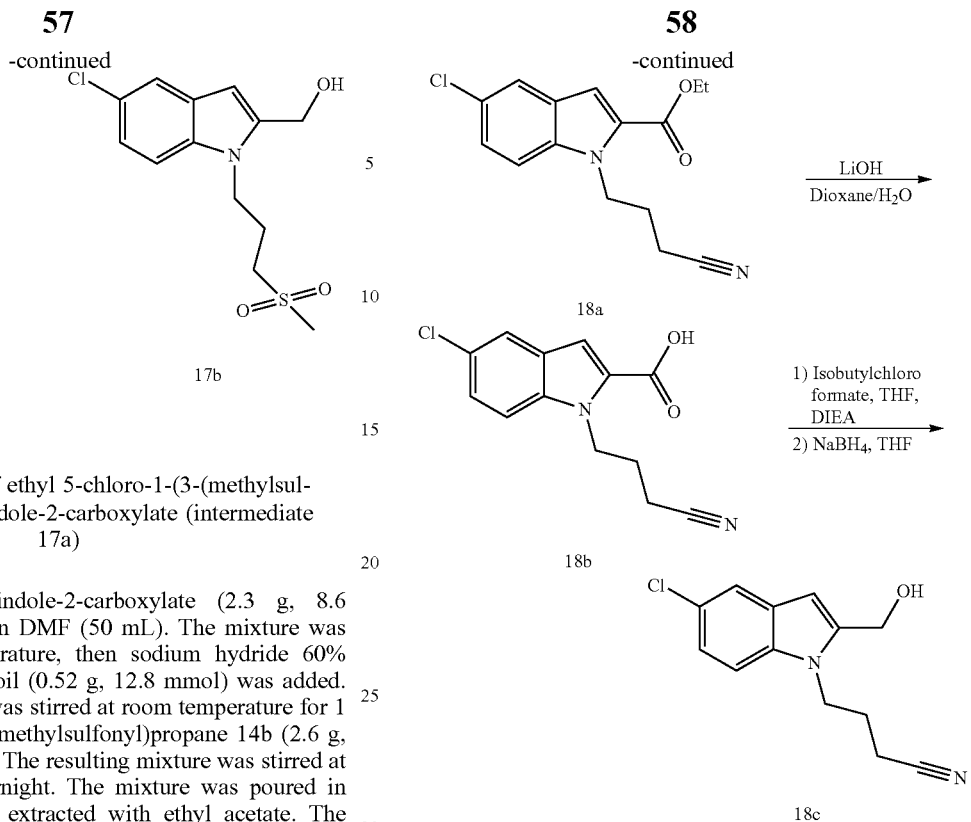

Step 1: synthesis of ethyl 5-chloro-1-(3-(methylsulfonyl)propyl)-1H-indole-2-carboxylate (intermediate 17a)

Ethyl 5-bromo-1H-indole-2-carboxylate (2.3 g, 8.6 mmol) was dissolved in DMF (50 mL). The mixture was stirred at room temperature, then sodium hydride 60% suspension in mineral oil (0.52 g, 12.8 mmol) was added. The resulting mixture was stirred at room temperature for 1 hour, then 1-bromo-3-(methylsulfonyl)propane 14b (2.6 g, 12.8 mmol) was added. The resulting mixture was stirred at room temperature overnight. The mixture was poured in ice/water solution and extracted with ethyl acetate. The organic layer was dried over MgSO$_4$ and concentrated to yield a brown crude oil. The crude was purified by column chromatography using dichloro-methane/methanol to yield the title compound ethyl 5-chloro-1-(3-(methylsulfonyl)propyl)-1H-indole-2-carboxylate 17a (3.2 g, 96%) as a white solid. m/z=344 (M+H)$^+$.

Step 2: synthesis of (5-chloro-1-(3-(methylsulfonyl)propyl)-1H-indol-2-yl)methanol (intermediate 17b)

To a solution of intermediate 17a (3.2 g, 8.24 mmol) in THF (100 mL) was added at room temperature lithium aluminum hydride (2 M solution in THF, 5.2 mL, 10.4 mmol). The resulting mixture was stirred at room temperature overnight. The reaction mixture was quenched by addition of ethyl acetate and ethanol. The resulting mixture was poured in ice/water solution then filtered on celite. The aqueous layer was extracted with ethyl acetate (3×50 mL). The combined organic extracts were washed with brine (100 mL), dried over MgSO$_4$, filtered and concentrated under reduced pressure. The residue was purified by column chromatography using dichloromethane/methanol as the eluent to give the desired product (5-chloro-1-(3-(methylsulfonyl)propyl)-1H-indol-2-yl)methanol 17b (2.5 g, 88%) as a white solid. m/z=302 (M+H)$^+$.

Intermediate 18c Synthesis of 4-(5-chloro-2-(hydroxymethyl)-1H-indol-1-yl)-butanenitrile

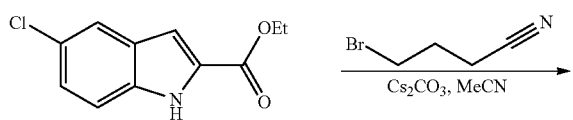

Step 1: synthesis of ethyl 5-chloro-1-(3-cyanopropyl)-1H-indole-2-carboxylate (intermediate 18a)

Ethyl-5-chloroindol-2-carboxylate (33.55 g, 150 mmol) was dissolved in acetonitrile (600 mL) and stirred at room temperature. Then cesiumcarbonate (73.31 g, 225 mmol) was added and stirring was continued for 30 minutes. 4-Bromobutyronitrile (18.83 mL, 180 mmol) was added in small portions over a period of one hour and stirring was continued overnight at ambient temperature. The reaction mixture was filtered and the filtrate was evaporated to dryness. The residue was dissolved in dichloromethane and washed with water. The organic layer was dried over MgSO$_4$, filtered and evaporated to give 43.5 g (99% yield) of ethyl 5-chloro-1-(3-cyanopropyl)-1H-indole-2-carboxylate 18a, which was used as such in the next step. m/z=290 (M+H)$^+$.

Step 2: synthesis of 5-chloro-1-(3-cyanopropyl)-1H-indole-2-carboxylic acid (intermediate 18b)

Ethyl 5-chloro-1-(3-cyanopropyl)indol-2-carboxylate 18a (43.61 g, 149.97 mmol) was dissolved in 1,4-dioxane (850 mL) and stirred at room temperature. Then a solution of lithiumhydroxide (10.78 g, 450 mmol) in distilled water (150 mL) was added. After stirring overnight at RT, the reaction mixture was evaporated to dryness. The residue was dissolved in 500 mL water and neutralised with aqueous hydrochloric acid 1 N (450 mL). The white precipitate was filtered off and dried in vacuo to yield 39.8 g (quantitative yield) of 5-chloro-1-(3-cyanopropyl)-1H-indole-2-carboxylic acid 18b. m/z=262 (M+H)$^+$.

Step 3: synthesis of 4-(5-chloro-2-(hydroxymethyl)-1H-indol-1-yl)butanenitrile (intermediate 18c)

5-chloro-1-(3-cyanopropyl)indol-2-carboxylic acid 18b (39.4 g, 149.98 mmol) and Hunigs base (51.69 mL, 300 mmol) were dissolved in tetrahydrofuran (550 mL) and stirred at −10° C. under a nitrogen atmosphere. Then a solution of isobutylchloroformate in tetrahydrofuran (50 ml) was added dropwise and the stirring was continued for one hour at −10° C. and one hour at ambient temperature. Then sodiumborohydride (17.02 g, 450 mmol) was added portionwise at −10° C. and stirred for one hour, afterwards distilled water (200 mL) was added cautiously to the reaction mixture and stirring was continued for another hour at room temperature under a nitrogen atmosphere. The mixture was neutralised with 10% citric acid in water and then extracted with ethyl acetate. The organic layer was dried over $MgSO_4$, filtered and evaporated. The residue was purified over silica with heptane/dichloromethane/methanol 50/50/0→0/100/0→0/99/1 as gradient. The corresponding fractions were evaporated to yield 23.9 g (64% yield) of 4-(5-chloro-2-(hydroxymethyl)-1H-indol-1-yl)butanenitrile 18c as a white powder. m/z=248 (M+H)⁺.

Intermediate 19b Synthesis of (5-chloro-1-(4,4,4-trifluorobutyl)-1H-imidazo[4,5-b]pyridin-2-yl)methanol

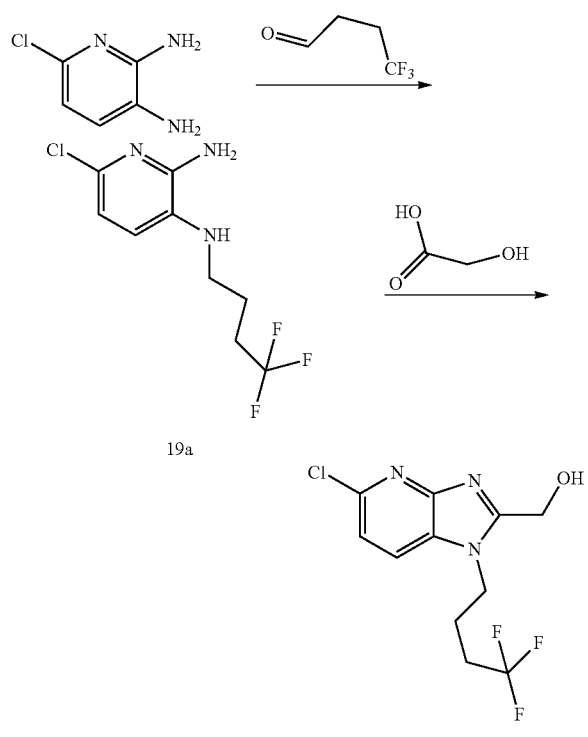

Step 1: 6-chloro-N³-(4,4,4-trifluorobutyl)-pyridine-2,3-diamine (intermediate 19a)

6-chloropyridine-2,3-diamine (5 g, 34.82 mmol) was dissolved in dichloromethane (200 mL), acetic acid (20 drops) and 4,4,4-trifluorobutanal (4.38 g, 34.8 mmol) were added. The resulting mixture was stirred for 30 minutes and then sodium triacetoxyhydroborate (22.14 g, 104.5 mmol) was added. The reaction mixture was stirred at room temperature overnight and a solution of 50% $Na_2CO_3$ was added dropwise until gas evolution stopped. The organic layer was separated, dried on $MgSO_4$, filtrated and evaporated to dryness. The residue was purified by column chromatography using heptane/EtOAc 7/3 to pure EtOAc. Intermediate 6-chloro-N³-(4,4,4-trifluorobutyl)-pyridine-2,3-diamine 19a was recovered as a white solid and dried in vacuo overnight (6.16 g, 70%). m/z=254 (M+H)⁺.

Step 2: synthesis of (5-chloro-1-(4,4,4-trifluorobutyl)-1H-imidazo[4,5-b]pyridin-2-yl)methanol (intermediate 19b)

A mixture of intermediate 19a (5.68 g, 22.46 mmol) and 2-hydroxyacetic acid (4.27 g, 56.2 mmol) was stirred at 150° C. for 4 hours. The mixture was allowed to cool down to room temperature and treated carefully with 3N hydrochloric acid. The resulting mixture was made basic with aqueous ammonia and extracted with $CH_2Cl_2$ (300 mL). The organic layer was dried over $MgSO_4$ and evaporated to dryness. The residue was purified by column chromatography on silica using $CH_2Cl_2$ to EtOAc to give 4.27 g (65%) of (5-chloro-1-(4,4,4-trifluorobutyl)-1H-imidazo[4,5-b]pyridin-2-yl)methanol 19b as a brown solid. m/z=294 (M+H)⁺. ¹H NMR (400 MHz, CHLOROFORM-d) δ ppm 1.00 (s, 2H), 1.12-1.23 (m, 2H), 1.83-1.99 (m, 2H), 2.12-2.31 (m, 2H), 2.91 (spt, J=3.50 Hz, 1H), 4.38-4.54 (m, 2H), 5.38 (s, 2H), 7.13 (dd, J=5.27, 0.50 Hz, 1H), 7.27 (d, J=8.28 Hz, 1H), 7.61 (d, J=8.53 Hz, 1H), 8.36 (d, J=5.27 Hz, 1H), 8.77 (s, 1H).

Intermediate 20e Synthesis of (5-chloro-1-(4-fluorobutyl)-1H-pyrrolo[3,2-b]pyridin-2-yl)methanol

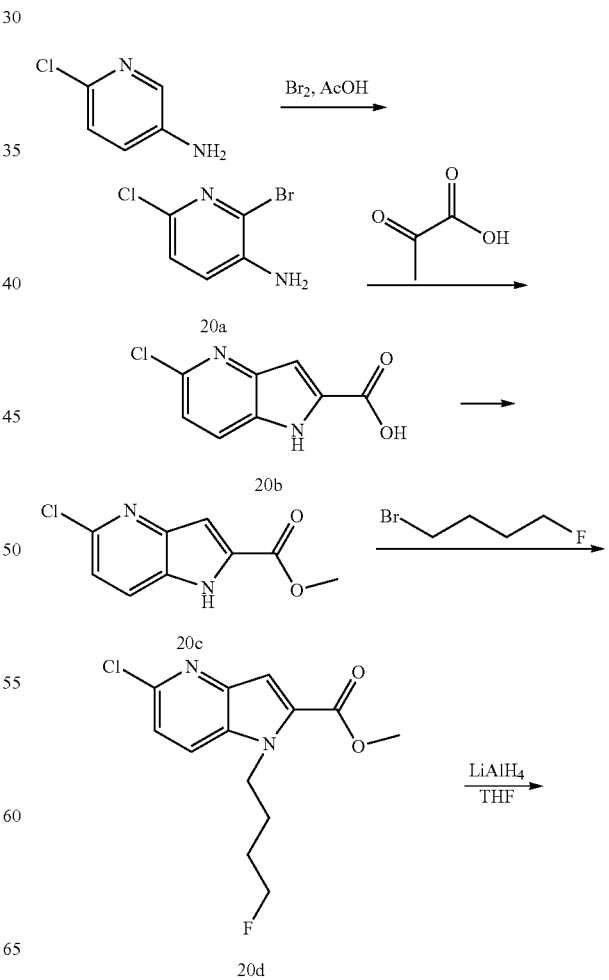

-continued

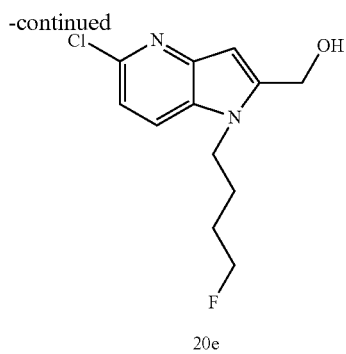

20e

Step 1: synthesis of 2-bromo-6-chloropyridin-3-amine (intermediate 20a)

Bromine (24.86 g, 155.57 mmol) was added to a solution of 6-chloropyridin-3-amine (20.00 g, 155.57 mmol) and sodium acetate (25.52 g, 311.14 mmol) in acetic acid (383 ml). The reaction mixture was stirred at room temperature for 1 hour. Acetic acid was then evaporated. The residue was dissolved in EtOAc, washed with saturated aqueous Na$_2$CO$_3$, water and brine. The organic layer was dried over MgSO$_4$, filtered and evaporated, yielding 32.20 g of the desired product 20a (99.8%). m/z=206.96 (M+H)$^+$, Cl+Br pattern.

Step 2: synthesis of 5-chloro-1H-pyrrolo[3,2-b]pyridine-2-carboxylic acid (intermediate 20b)

2-oxopropanoic acid (36.22 g, 411.31 mmol), palladium (II)acetate (7.74 g, 34.15 mmol) and Et$_3$N (69.11 g, 682.94 mmol) were added to a solution of 2-bromo-6-chloropyridin-3-amine 20a (32.20 g, 155.21 mmol) and TPP (35.83 g, 136.59 mmol) in dry DMF (300 ml). The reaction mixture was stirred at 100° C. overnight. The solvent was then evaporated, water was added and the water layer was washed with EtOAc. The water layer was acidified with conc. HCl. The precipitate was filtered off and dried, yielding 25.21 g of the wanted product 20b (82.6%). m/z=197.1 (M+H)$^+$, Cl pattern.

Step 3: synthesis of methyl 5-chloro-1H-pyrrolo[3,2-b]pyridine-2-carboxylate (intermediate 20c)

5-chloro-1H-pyrrolo[3,2-b]pyridine-2-carboxylic acid 20b (25.20 g, 128.18 mmol) was added to a refluxing mixture of sulfuric acid (20 ml) and methanol (400 ml). The mixture was refluxed overnight. The mixture was then evaporated and a cold NaHCO$_3$ solution was added until basic pH. The precipitate was filtered off and dried, yielding 16.15 g of the desired product 20c (59.8%). m/z=211.17 (M+H)$^+$, Cl pattern.

Step 4: synthesis of methyl 5-chloro-1-(4-fluorobutyl)-1H-pyrrolo[3,2-b]pyridine-2-carboxylate (intermediate 20d)

To a solution of methyl 5-chloro-1H-pyrrolo[3,2-b]pyridine-2-carboxylate 20c (2.9 g, 12.2 mmol) in DMF (50 mL) were added successively cesium carbonate (4 g, 12.2 mmol) and 1-bromo-4-fluorobutane (1.3 mL, 12.2 mmol). The resulting mixture was heated at 60° C. overnight. The reaction mixture was allowed to cool down to room temperature then poured into iced water and the product was extracted 3 times with DCM. The combined organic layers were dried over Na$_2$SO$_4$, filtered and evaporated to give the targeted product 20d as a yellowish solid. The product was used as such in the next step. m/z=313 (M+H)$^+$, Cl pattern.

Step 5: synthesis of (5-chloro-1-(4-fluorobutyl)-1H-pyrrolo[3,2-b]pyridin-2-yl)-methanol (intermediate 20e)

To a solution of methyl 5-chloro-1-(4-fluorobutyl)-1H-pyrrolo[3,2-b]pyridine-2-carboxylate 20d (3.82 g, 10.8 mmol) in dry THF (100 mL) was added a 1M solution of lithium aluminumhydride (11.96 mL, 11.96 mmol) at −75° C. The cooling bath was then removed and the reaction mixture was kept at room temperature for 3 hours. EtOAc was added, followed by a saturated NH$_4$Cl solution. The mixture was stirred for 30 min. The organic layer was dried over Na$_2$SO$_4$, filtered and evaporated to give a yellow oil, which was purified by column chromatography to yield the targeted product (5-chloro-1-(4-fluorobutyl)-1H-pyrrolo[3,2-b]pyridin-2-yl)methanol 20e (2.8 g, 98%). m/z=257 (M+H)$^+$, Cl pattern.

Intermediates 21 b and 21c Synthesis of 4-(5-chloro-2-(hydroxymethyl)-1H-benzo[d]imidazol-1-yl)butanenitrile (intermediate 21b) and 4-(6-chloro-2-(hydroxymethyl)-1H-benzo[d]imidazol-1-yl)butanenitrile (intermediate 21c)

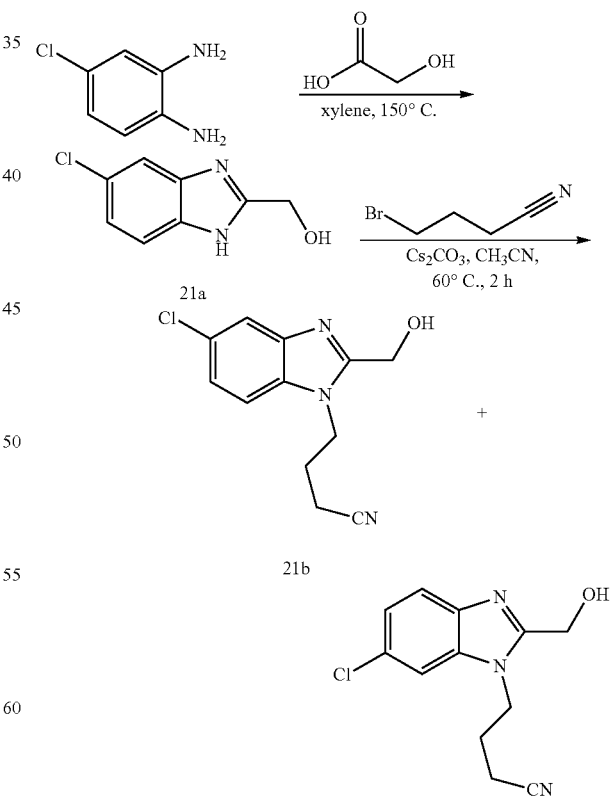

Step 1: synthesis of (5-chloro-1H-benzo[d]imidazol-2-yl)methanol (intermediate 21a)

A mixture of 4-chlorobenzene-1,2-diamine (105 g, 736 mmoles, 1 eq.) and hydroxyacetic acid (112 g, 2 eq.) in xylene (1500 mL) was stirred at 150° C. for 4 hours. The mixture was then cooled to 60° C. and treated with 3N HCl (480 ml), then basified to pH=7-8 by the addition of aqueous ammonia. The mixture was filtered and the solid was collected, washed with H₂O and tert-butyl methyl ether to give 123 g (82% yield) of (5-chloro-1H-benzo[d]imidazol-2-yl)methanol 21a.

Step 2: synthesis of 4-(5-chloro-2-(hydroxymethyl)-1H-benzo[d]imidazol-1-yl)butanenitrile (intermediate 21b) and 4-(6-chloro-2-(hydroxymethyl)-1H-benzo[d]imidazol-1-yl)butanenitrile (intermediate 21c)

A mixture of (5-chloro-1H-benzo[d]imidazol-2-yl)methanol 21a (500 mg, 2.738 mmoles, 1 eq.), 4-bromobutyronitrile (466 mg, 1.15 eq.), cesium carbonate (1.338 g, 1.5 eq.) and potassium iodide (45 mg, 0.1 eq.) in acetonitrile (5 mL) was refluxed overnight. The mixture was then cooled and filtered. The filtrate was evaporated under vacuum and the residue was treated with ethyl acetate (30 ml) and brine (20 ml). The separated organic layer was dried (Na₂SO₄), filtered and the solvent was evaporated under vacuum. The residue was purified by column chromatography (eluent: CH₂Cl₂: methanol from 1:0 to 15:1) to yield 732 mg (54%) of a mixture containing the two regio-isomers 21b and 21c in a 1/1 ratio. This mixture was further separated by SFC to provide the pure regio-isomer 21b.

Intermediate 22c Synthesis of 3-aminospiro[cyclobutane-1,3'-indolin]-2'-one

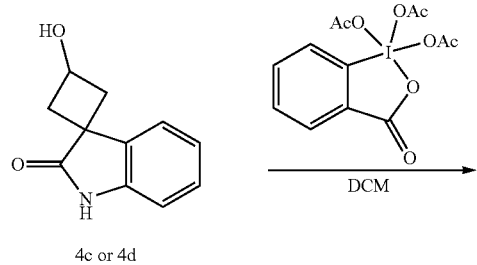

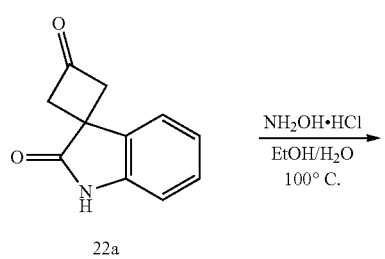

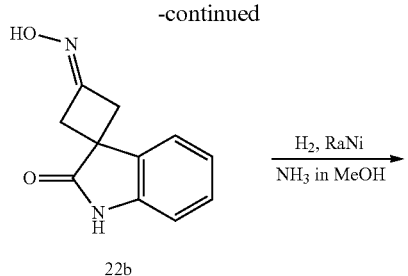

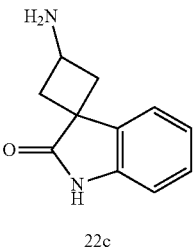

Step 1

To alcohol 4c or 4d (5 g, 26.425 mmoles) in DCM was added Dess-martin periodinane (16.8 g, 1.5 eq) at 0° C. After 16 h at RT, the RM was filtered off and a saturated solution of NaHCO₃ (50 mL) and a NaS₂O₃ solution (50 mL) were added. After stirring for 30 minutes, the organic layer was separated, dried over Na₂SO₄, and concentrated in vacuo to provide the desired spiro[cyclobutane-1,3'-indoline]-2',3-dione 22a as a racemic mixture, which was used without further purification in the next step.

Step 2

A mixture of ketone 22a (2 g, 10.68 mmoles), sodium carbonate (3.397 g, 3 eq) and hydroxylamine hydrochloride (1.485 g, 2 eq) in EtOH/H₂O (1/1, 100 mL) was heated at 100° C. during 1 h. The RM was then concentrated in vacuo and the resulting precipitate was filtered off, washed with water and dried in the vacuum oven to give 3-(hydroxyimino)spiro[cyclobutane-1,3'-indolin]-2'-one 22b (1.5 g, 69% yield).

Step 3

The oxime 22b was hydrogenated over RaNi (435 mg, 1 eq) in NH₃ 7 N in MeOH (50 mL) overnight. The solution was then filtered over decalite and concentrated in vacuo. The crude was then triturated in Et₂O, and the resulting solid was filtered off and dried in the oven to give aminospiro[cyclobutane-1,3'-indolin]-2'-one 22c (1.3 g, 85% yield) as a mixture of two isomers.

Synthesis of Final Compounds

Compound 1 Synthesis of tert-butyl 1'-({5-chloro-1-[3-(methylsulfonyf)propyl]-1H-indol-2-yl}methyl)-2'-oxo-1',2'-dihydro-1H-spiro[piperidine-4,3'-pyrrolo[2,3-c]-pyridine]-1-carboxylate compound 1

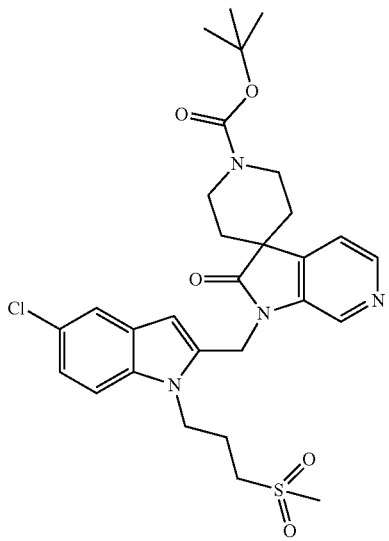

Compound 2 Synthesis of 1'-({5-chloro-1-[3-(methylsulfonyl)propyl]-1H-indol-2-yl}methyl)spiro[piperidine-4,3'-pyrrolo[2,3-c]pyridin]-2'(1'H)-one Compound 2

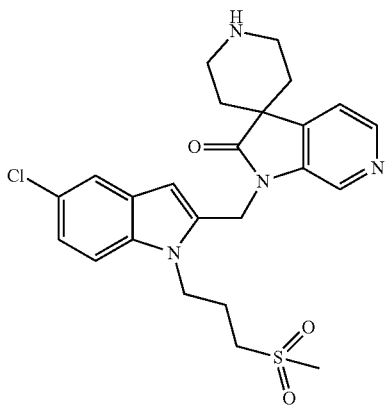

To a suspension of {5-chloro-1-[3-(methylsulfonyl)propyl]-1H-indol-2-yl}methanol 17b (4000 mg, 13.25 mmols), tert-butyl 2'-oxo-1',2'-dihydro-1H-spiro[piperidine-4,3'-pyrrolo[2,3-c]pyridine]-1-carboxylate 10c (4423 mg, 14.58 mmols) and TPP (4172 mg, 15.91 mmols) in dry THF (92 ml) was added DIAD (3.869 ml, 19.88 mmols) at room temperature and the reaction mixture was stirred overnight. THF was evaporated and the crude was purified by column chromatography. After evaporation of the relevant fractions, the residue was recrystallized in water. The formed crystals were filtered off and washed with some water and heptane to get the title product 1 as a beige powder (1231 mg, Y=15.8%). $^1$H NMR (400 MHz, DMSO-$d_6$) δ ppm 1.45 (s, 9H) 1.80 (t, J=5.50 Hz, 4H) 2.03-2.16 (m, 2H) 3.01 (s, 3H) 3.14-3.25 (m, 2H) 3.60-3.83 (m, 4H) 4.37 (t, J=7.48 Hz, 2H) 5.20 (s, 2H) 6.37 (s, 1H) 7.16 (dd, J=8.69, 2.09 Hz, 1H) 7.53 (d, J=1.98 Hz, 1H) 7.55 (d, J=8.80 Hz, 1H) 7.69 (d, J=4.62 Hz, 1H) 8.33 (d, J=4.84 Hz, 1H) 8.39 (s, 1H); m/z=587.23 (M+H)$^+$+Cl pattern.

To a solution of tert-butyl 1'-({5-chloro-1-[3-(methylsulfonyl)propyl]-1H-indol-2-yl}-methyl)2'-oxo-1',2'-dihydro-1H-spiro[piperidine-4,3'-pyrrolo[2,3-c]pyridine]-1-carboxylate 1 (3.39 g, 3.75 mmols) in DCM (20 ml) was added TFA (2.872 ml, 37.53 mmols) and the mixture was stirred overnight at room temperature. Then water was added and the reaction mixture was basified with Na$_2$CO$_3$-solution. DCM was evaporated and the remaining aqueous suspension was stirred for 3 hours. The solid was filtered off, washed with water and then purified by column chromatography to obtain a pink glassy oil. The product was triturated in diethyl ether to give the desired product 2 as a pink powder which was dried in the vacuum oven (466 mg, 23.7%); $^1$H NMR (400 MHz, DMSO-$d_6$) δ ppm 1.62-1.88 (m, 4H) 2.02-2.18 (m, 2H) 2.93-3.07 (m, 5H) 3.11-3.24 (m, 4H) 4.38 (t, J=7.48 Hz, 2H) 5.19 (s, 2H) 6.33 (s, 1H) 7.16 (dd, J=8.69, 2.09 Hz, 1H) 7.50-7.58 (m, 2H) 7.64 (d, J=4.84 Hz, 1H) 8.29-8.42 (m, 2H); m/z=487.27 (M+H)$^+$+Cl pattern.

Compound 3 Synthesis of 1'-({5-chloro-1-[3-(methylsulfonyl)propyl]-1H-indol-2-yl}methyl)-1-(methylsulfonyl)spiro[piperidine-4,3'-pyrrolo[2,3-c]pyridin]-2'(1'H)-one Compound 4 Synthesis of tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate

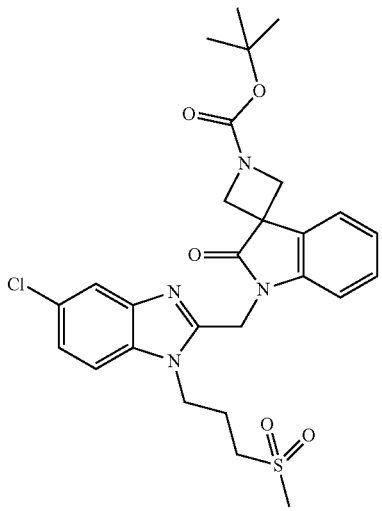

Compound 4

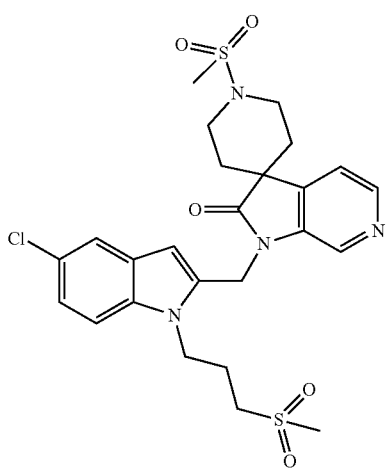

Compound 3

Tert-butyl 2'-oxo-1',2'-dihydro-1H-spiro[azetidine-3,3'-indole]-1-carboxylate 3f (1000 mg, 3.65 mmols) was dissolved in dry DMF (23 ml), then 5-chloro-2-(chloromethyl)-1-[3-(methylsulfonyl)propyl]-1H-benzimidazole hydrochloric acid 15e (1304 mg, 3.64 mmols) and cesium carbonate (3563 mg, 3.56 mmols) were added. The reaction mixture was stirred at room temperature overnight. Iced water was added and the mixture was stirred overnight. The formed solid was filtered off and washed with water and a little ether. After drying in the vacuum oven the desired product 4 was obtained as a pink solid (1695 mg, Y=81.5%). $^1$H NMR (400 MHz, DMSO-$d_6$) δ ppm 1.44 (s, 9H) 2.10-2.21 (m, 2H) 3.00 (s, 3H) 3.19-3.25 (m, 2H) 4.03-4.19 (m, 4H) 4.47 (t, J=7.48 Hz, 2H) 5.22 (s, 2H) 7.13 (td, J=7.48, 0.88 Hz, 1H) 7.19 (d, J=7.70 Hz, 1H) 7.27-7.34 (m, 2H) 7.65-7.69 (m, 3H); m/z=559.21 (M+H)$^+$+Cl pattern.

Compound 5 Synthesis of 1'-({5-chloro-1-[3-(methylsulfonyl)propyl]-1H-benzimidazol-2-yl}methyl)spiro[azetidine-3,3'-indol]-2'(1'H)-one 1'-({5-chloro-1-[3-(methylsulfonyl)propyl]-1H-indol-2-yl}methyl)spiro[piperidine-4,3'-pyrrolo[2,3-c]pyridin]-2'(1'H)-one 2 (500 mg, 0.72 mmols) was dissolved in DCM (5 ml), then methanesulfonyl chloride (0.11 ml, 1.44 mmols) and Et$_3$N (0.30 ml, 2.16 mmols) were added. The mixture was stirred at room temperature for 30 minutes. Water was added and the reaction mixture was basified with NaHCO$_3$-solution. The product was extracted with DCM (2 times). The organic layers were dried over MgSO$_4$, filtered and evaporated. The residue was purified by preparative column chromatography to give the desired product 3 (172 mg, Y=42.4%). $^1$H NMR (400 MHz, DMSO-$d_6$) δ ppm 1.88-2.16 (m, 6H) 3.00 (s, 3H) 3.01 (s, 3H) 3.17-3.26 (m, 2H) 3.41-3.51 (m, 2H) 3.52-3.64 (m, 2H) 4.38 (t, J=7.48 Hz, 2H) 5.20 (s, 2H) 6.38 (s, 1H) 7.16 (dd, J=8.69, 2.09 Hz, 1H) 7.53 (d, J=1.98 Hz, 1H) 7.56 (d, J=8.80 Hz, 1H) 7.70 (d, J=4.84 Hz, 1H) 8.36 (d, J=4.84 Hz, 1H) 8.41 (s, 1H); m/z=565.03 (M+H)$^+$+Cl pattern.

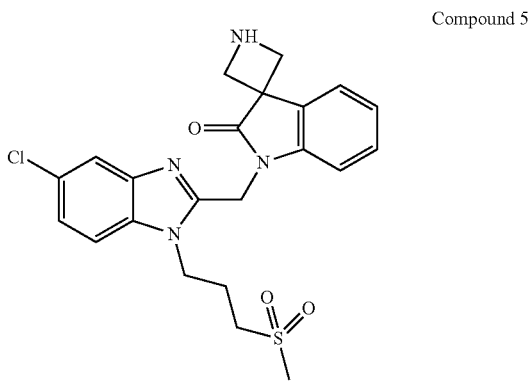 [SMILES: CS(=O)(=O)CCCn1c(CN2C(=O)C3(CNC3)c3ccccc32)nc2cc(Cl)ccc21]

Compound 5

To a solution of tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate 4 (1.5 g, 2.63 mmoles) in DCM (20 mL) was added TFA (1 mL, 5 eq.) at RT. After 12 h, more TFA (2 mL) was added and the mixture was stirred for 24 h. The reaction was then neutralized by a Na₂CO₃-solution. DCM was evaporated and the formed solid was filtered off and washed with water and ether to give the TFA salt of the desired product 5 as a grey powder (1.303 g, Y=86.5%). ¹H NMR (400 MHz, DMSO-d₆) δ ppm 2.11-2.26 (m, 2H) 3.01 (s, 3H) 3.19-3.28 (m, 2H) 4.16-4.35 (m, 4H) 4.48 (t, J=7.48 Hz, 2H) 5.22 (s, 2H) 7.18-7.28 (m, 2H) 7.32 (dd, J=8.80, 1.98 Hz, 1H) 7.36 (td, J=7.90, 0.88 Hz, 1H) 7.66 (d, J=1.98 Hz, 1H) 7.69 (d, J=8.80 Hz, 1H) 7.85 (d, J=6.82 Hz, 1H) 9.27 (br. s., 2H); m/z=459.18 (M+H)⁺+Cl pattern.

Compound 6 Synthesis of 1'-({5-chloro-1-[3-(methylsulfonyl)propyl]-1H-benzimidazol-2-yl}methyl)-1-(2-hydroxy-2-methylpropanoyl)spiro[azetidine-3,3'-indol]-2'(1'H)-one

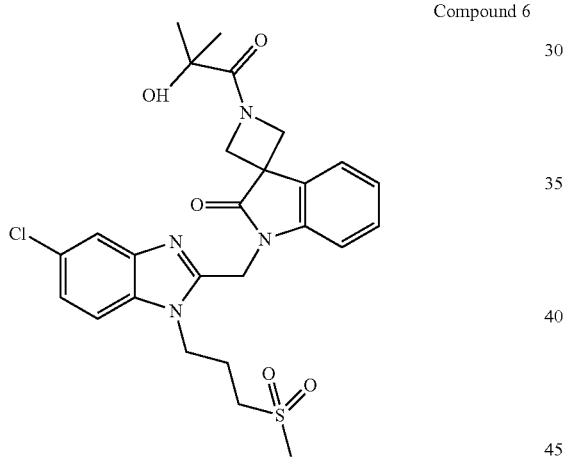

Compound 6

1'-({5-chloro-1-[3-(methylsulfonyl)propyl]-1H-benzimidazol-2-yl}methyl)spiro[azetidine-3,3'-indol]-2'(1'H)-one 5 (300 mg, 0.50 mmols), 2-hydroxy-2-methylpropanoic acid (117 mg, 1.12 mmols) and Et₃N (0.482 ml, 2.80 mmoles) were stirred vigorously at room temperature in dry DMF (4 ml), while DECP (0.188 ml, 1.12 mmols) was added dropwise. Stirring was continued for 1 hour at ambient temperature in a closed vessel. Some ice was added followed by a saturated sodium bicarbonate solution. The resulting suspension was stirred for 2 hours and the solid was filtered off and further purified by column chromatography eluting with a gradient of DCM and MeOH. All pure fractions were evaporated to give a yellowish foam which was further triturated in ether and filtered off to give the title product 6 (121 mg, Y=42.0%). ¹H NMR (400 MHz, DMSO-d₆) δ ppm 1.31 (s, 3H) 1.33 (s, 3H) 2.11-2.24 (m, 2H) 3.00 (s, 3H) 3.18-3.27 (m, 2H) 4.02-4.20 (m, 2H) 4.47 (t, J=7.37 Hz, 2H) 4.55-4.75 (m, 2H) 5.23 (s, 2H) 5.25 (s, 1H) 7.11-7.23 (m, 2H) 7.27-7.35 (m, 2H) 7.60-7.65 (m, 1H) 7.65-7.71 (m, 2H); m/z=545.41 (M+H)⁺+Cl pattern.

Compound 7 Synthesis of 1'-({5-chloro-1-[3-(methylsulfonyl)propyl]-1H-benzimidazol-2-yl}methyl)-1-(pyridin-3-yl)spiro[azetidine-3,3'-indol]-2'(1'H)-one

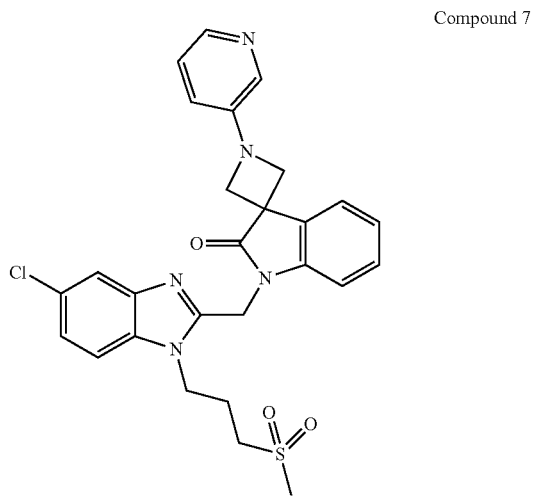 [SMILES: CS(=O)(=O)CCCn1c(CN2C(=O)C3(CN(c4cccnc4)C3)c3ccccc32)nc2cc(Cl)ccc21]

Compound 7

A mixture of 1'-({5-chloro-1-[3-(methylsulfonyl)propyl]-1H-benzimidazol-2-yl}methyl)spiro[azetidine-3,3'-indol]-2'(1'H)-one 5 (259 mg, 0.43 mmols) and 3-bromopyridine (0.084 ml, 0.87 mmols) in toluene (1.5 ml) was degassed with nitrogen gas during 5 minutes. Then Pd₂(dba)₃ (10 mg, 0.01 mmols), NaOtBu (52 mg, 0.54 mmols) and BINAP (20 mg, 0.03 mmols) were added. The mixture was degassed again and then heated in a μ-wave oven for 2 hours at 125° C. The reaction mixture was evaporated, taken up in water and extracted with DCM. Some insolubles were filtered off. The two phases were separated and the organic layer was dried over Na₂SO₄, filtered and evaporated to dry. The crude was purified by preparative column chromatography to give the title product 7 (35 mg, Y=15.0%). ¹H NMR (400 MHz, DMSO-d₆) δ ppm 2.09-2.21 (m, 2H) 3.00 (s, 3H) 3.19-3.27 (m, 2H) 4.13-4.27 (m, 4H) 4.47 (t, J=7.48 Hz, 2H) 5.26 (s, 2H) 6.99 (ddd, J=8.25, 2.75, 1.32 Hz, 1H) 7.12-7.17 (m, 1H) 7.20 (d, J=7.70 Hz, 1H) 7.25 (dd, J=8.14, 4.62 Hz, 1H) 7.28-7.36 (m, 3H) 7.64-7.71 (m, 3H) 7.98 (d, J=2.64 Hz, 1H) 8.02 (dd, J=4.62, 1.32 Hz, 1H); m/z=536.07 (M+H)⁺+Cl pattern.

Compound 8 Synthesis of 1'-({5-chloro-1-[3-(methylsulfonyl)propyl]-1H-benzimidazol-2-yl}methyl)-1-(2-hydroxy-2-methylpropyl)spiro[azetidine-3,3'-indol]-2'(1'H)-one

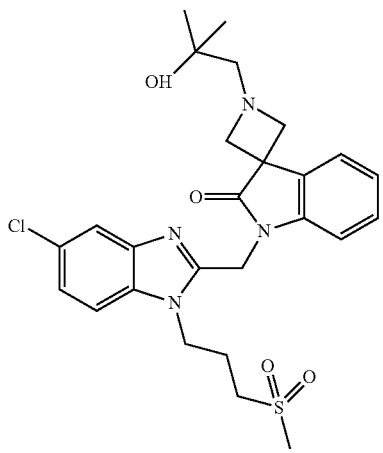

Compound 8

To a solution of 1'-({5-chloro-1-[3-(methylsulfonyl)propyl]-1H-benzimidazol-2-yl}-methyl)spiro[azetidine-3,3'-indol]-2'(1'H)-one 5 (150 mg, 0.33 mmols) in EtOH (20 ml) and DMF (5 ml) was added Et$_3$N (0.227 ml, 1.63 mmols) and 2,2-dimethyloxirane (0.087 ml, 0.98 mmols). The reaction mixture was heated at 60° C. for 40 hours. Heating was stopped and iced water was added. EtOH was evaporated. The formed solid was filtered and washed with water and ether to get a grey powder. The crude was purified by column chromatography to get the title product 8 as a white solid after drying in the vacuum oven (74 mg, Y=39.2%). $^1$H NMR (400 MHz, DMSO-d$_6$) δ ppm 1.12 (s, 6H) 2.06-2.17 (m, 2H) 2.46 (s, 2H) 2.99 (s, 3H) 3.17-3.25 (m, 2H) 3.54 (q, J=7.04 Hz, 4H) 4.12 (s, 1H) 4.45 (t, J=7.37 Hz, 2H) 5.21 (s, 2H) 7.10-7.17 (m, 2H) 7.23-7.28 (m, 1H) 7.30 (dd, J=8.58, 1.98 Hz, 1H) 7.64-7.68 (m, 2H) 7.73-7.77 (m, 1H); m/z=531.09 (M+H)$^+$+Cl pattern.

Compound 9 Synthesis of 1'-[[5-chloro-1-(3-methylsulfonylpropyl)benzimidazol-2-yl]methyl]-1-(2,2,2-trifluoroethyl)spiro[azetidine-3,3'-indoline]-2'-one

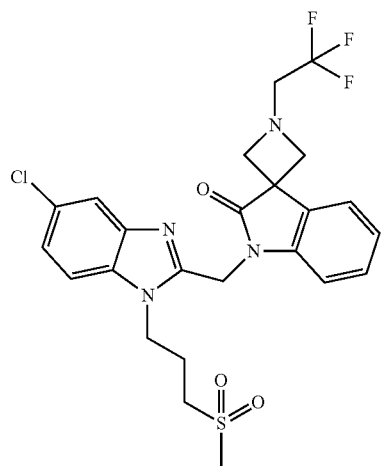

compound 9

A solution of 1'-[[5-chloro-1-(3-methylsulfonylpropyl)benzimidazol-2-yl]methyl]spiro-[azetidine-3,3'-indoline]-2'-one 5 (573 mg, 1 mmol), 2,2,2-trifluoroethyl 1,1,2,2,3,3,4,4,4-nonafluorobutane-1-sulfonate (382 mg, 1 mmol) and N-ethyl-N-isopropyl-propan-2-amine (0.52 mL, 3 mmol) were stirred in dioxane (10 mL) at 50° C. over weekend. The reaction mixture was then allowed to cool to ambient temperature. The mixture was evaporated to dryness and the residue was crystallised in ethanol/acetonitrile 100/1. The off-white crystals were collected by filtration and dried in vacuo to give the title product 9 (420 mg, 77%). $^1$H NMR (360 MHz, DMSO-d$_6$) δ ppm 2.13 (m, J=8.1 Hz, 2H), 3.00 (s, 3H), 3.22 (m, J=15.4 Hz, 2H), 3.42 (q, J=10.0 Hz, 2H), 3.64 (d, J=7.0 Hz, 2H), 3.75 (d, J=7.0 Hz, 2H), 4.46 (t, J=7.1 Hz, 2H), 5.22 (s, 2H), 7.07-7.22 (m, 2H), 7.31 (d, J=8.8 Hz, 1H), 7.27 (d, J=7.3 Hz, 1H), 7.62-7.79 (m, 3H); m/z=540.99 (M+H)$^+$+Cl pattern; melting point: 200.68° C.

Compound 12 synthesis of (1R,3R)-1'-((5-chloro-1-(3-(methylsulfonyl)propyl)-1H-benzo[d]imidazol-2-yl)methyl)-3-hydroxyspiro[cyclobutane-1,3'-indolin]-2'-one

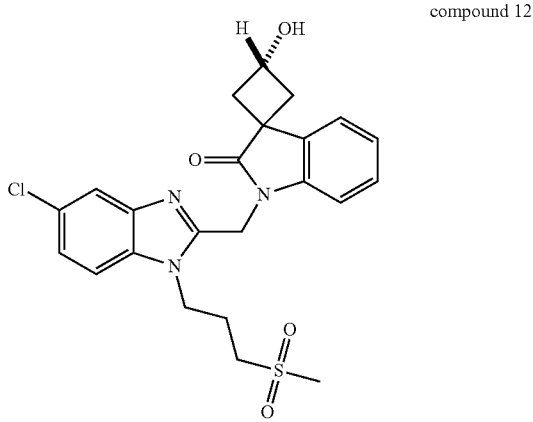

compound 12

(3R)-1'-({5-chloro-1-[3-(methylsulfonyl)propyl]-1H-benzimidazol-2-yl}methyl)-3-hydroxyspiro[cyclobutane-1,3'-indol]-2'(1'H)-one 12 was synthetized following the reaction conditions used for the synthesis of compound 4, using (3R)-hydroxyspiro-[cyclobutane-1,3'-indolin]-2'-one 4d instead of tert-butyl 2'-oxo-1',2'-dihydro-1H-spiro[azetidine-3,3'-indole]-1-carboxylate 3f and was obtained as a slightly pink solid, with a yield of 82%. $^1$H NMR (400 MHz, DMSO-d$_6$) δ ppm 2.08-2.21 (m, 2H) 2.27-2.38 (m, 2H) 2.60-2.72 (m, 2H) 2.99 (s, 3H) 3.19-3.27 (m, 2H) 4.46 (t, J=7.48 Hz, 2H) 4.50-4.62 (m, 1H) 5.20 (s, 2H) 5.45 (d, J=6.82 Hz, 1H) 7.05-7.14 (m, 2H) 7.18-7.25 (m, 1H) 7.30 (dd, J=8.80, 1.98 Hz, 1H) 7.45-7.55 (m, 1H) 7.63-7.71 (m, 2H); m/z=474.05 (M+H)+; MP=209.84° C.

Compound 104 synthesis of (1R,3R)-1'-((5-chloro-1-(3-(methylsulfonyl)propyl)-1H-benzo[d]imidazol-2-yl)methyl)-2'-oxospiro[cyclobutane-1,3'-indoline]-3-yl methylcarbamate

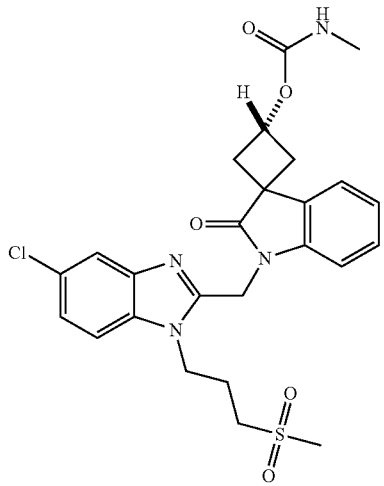

compound 104

A solution of (3R)-1'-({5-chloro-1-[3-(methylsulfonyl)propyl]-1H-benzimidazol-2-yl}-methyl)-3-hydroxyspiro[cyclobutane-1,3'-indol]-2'(1'H)-one 12 (100 mg, 0.205 mmole), triethylamine (0.142 mL, 1.023 mmole) and N,N'-disuccinimidyl carbonate (210 mg, 0.82 mmole) in DCM (1.5 mL) was stirred at RT for 2 h. A 2M solution of methyl amine (1.54 mL, 3.07 mmoles) was then added and the RM was further stirred for 30 minutes. It was then concentrated and the residue was purified by chromatography on silica gel using a gradient of MeOH (0 to 5%) in DCM to give 110 mg (99% yield) of 1'-({5-Chloro-1-[3-(methylsulfonyl)propyl]-1H-benzimidazol-2-yl}methyl)-2'-oxo-1',2'-dihydrospiro[cyclobutane-1,3'-indol]-3-yl methylcarbamate 104 as a slightly pink solid. 1H NMR (400 MHz, DMSO-$d_6$) δ ppm 2.16 (quin, J=7.59 Hz, 2H) 2.45-2.52 (m, 2H) 2.59 (d, J=4.62 Hz, 3H) 2.73-2.82 (m, 2H) 3.00 (s, 3H) 3.20-3.27 (m, 2H) 4.47 (t, J=7.37 Hz, 2H) 5.22 (s, 2H) 5.25-5.35 (m, 1H) 7.07-7.16 (m, 3H) 7.22-7.28 (m, 1H) 7.28-7.33 (m, 1H) 7.48-7.54 (m, 1H) 7.64-7.70 (m, 2H); m/z=531.15 (M+H)+.

Compound 117 synthesis of N-[(1'-{[5-Chloro-1-(3-cyanopropyl)-1H-indol-2-yl]methyl}-2'-oxo-1',2'-dihydro-1H-spiro[azetidine-3,3'-indol]-1-yl)sulfonyl] acetamide

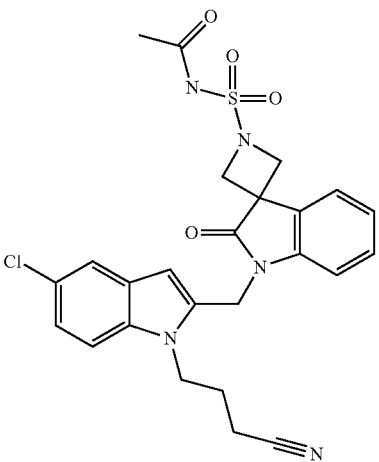

compound 117

A mixture of 4-{5-chloro-2-[(2'-oxospiro[azetidine-3,3'-indol]-1'(2'H)-yl)methyl]-1H-indol-1-yl}butanenitrile 59 (588 mg, 1.133 mmole) and sulfamide (326 mg, 3.4 mmoles) in dioxane (20 mL) was heated in a microwave oven at 160° C. during 40 minutes. After cooling, the RM was concentrated in vacuo and the residue was recrystallized from methanol. This crude material (212 mg, 0.438 mmole) was then redissolved in DCM (30 mL) and acetic anhydride (82 µL, 0.876 mmole), N-methylmorpholine (96 µL, 0.876 mmole) and DMAP (3.7 mg, 0.03 mmole) were added. After 3 h at RT, two more equivalents of acetic anhydride and N-methylmorpholine were added and the RM was stirred overnight. It was then quenched with MeOH (1 mL) and concentrated in vacuo. The resulting residue was purified by chromatography on silica gel using a gradient of MeOH (0 to 5%) in DCM to give 140 mg (58% yield) of N-[(1'-{[5-Chloro-1-(3-cyanopropyl)-1H-indol-2-yl]methyl}-2'-oxo-1',2'-dihydro-1H-spiro[azetidine-3,3'-indol]-1-yl)sulfonyl] acetamide 117 as a white solid. 1H NMR (400 MHz, DMSO-$d_6$) δ ppm 1.93-2.04 (m, 1H), 2.16 (s, 3H), 2.58 (t, J=7.4 Hz, 2H), 4.25 (d, J=8.1 Hz, 2H), 4.27-4.35 (m, 2H), 4.40 (d, J=8.4 Hz, 2H), 5.12 (s, 2H), 6.38 (s, 1H), 7.08 (d, J=7.9 Hz, 1H), 7.11-7.21 (m, 2H), 7.26-7.35 (m, 1H), 7.48-7.55 (m, 2H), 7.58 (d, J=7.0 Hz, 1H), 10.84-10.85 (m, 0H), 11.75 (br. s., 2H); m/z=524 (M−H)−; MP=182.85° C.

Compound 115 synthesis of Diethyl (1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl)phosphonate compound 115

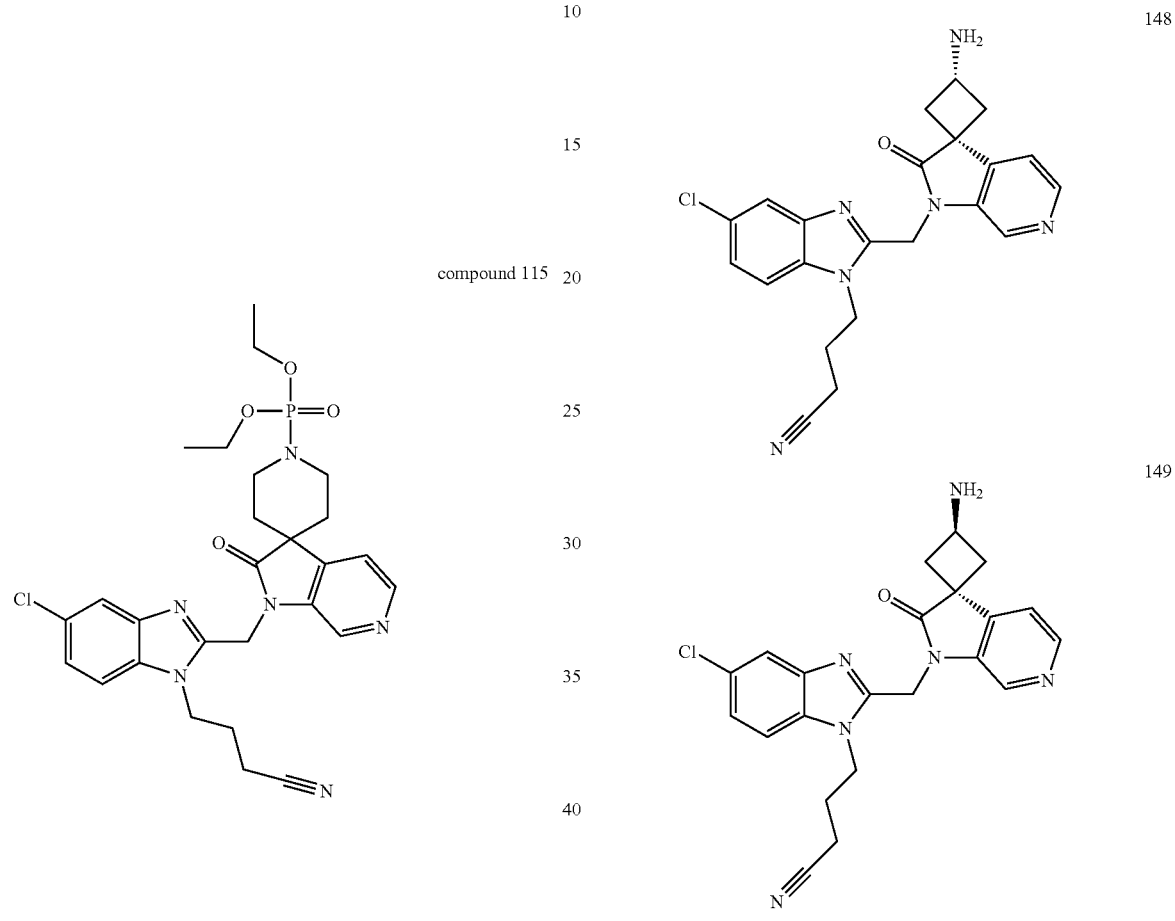

A mixture of 4-(5-chloro-2-((2'-oxospiro[piperidine-4,3'-pyrrolo[2,3-c]pyridin]-1'(2'H)-yl)methyl)-1H-benzo[d]imidazol-1-yl)butanenitrile hydrochloride 84 (500 mg, 0.985 mmole), diethoxycyanophosphonate (0.448 mL, 3 eq) and triethylamine (0.411 mL, 3 eq) in DMF (10 mL) was stirred at RT for 2 hours. The mixture was then extracted with DCM and washed with water. The organics were then dried over MgSO$_4$, concentrated in vacuo and purified by chromatography on silica gel using a gradient of MeOH (0 to 10%) in DCM, followed by a purification by Prep HPLC (Stationary phase: RP Vydac Denali C18—10 μm, 200 g, 5 cm), Mobile phase: 0.25% NH$_4$HCO$_3$ solution in water, CH$_3$CN), to give 320 mg (56% yield) of Diethyl (1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl) phosphonate 115. m/z=571 (M+H)$^+$.

Compounds 148 and 149 Synthesis of 4-(2-(((1r,3r)-3-amino-2'-oxospiro[cyclobutane-1,3'-indolin]-1'-yl)methyl)-5-chloro-1H-benzo[d]imidazol-1-yl)butanenitrile and 4-(2-(((1s,3s)-3-amino-2'-oxospiro[cyclobutane-1,3'-indolin]-1'-yl)methyl)-5-chloro-1H-benzo[d]imidazol-1-yl)butanenitrile To a solution of amine 22c (194 mg, 1.035 mmole) in dry DMF (10 mL) was added sodium hydride (79 mg, 2 eq) at RT. After 30 minutes, 4-(5-chloro-2-(chloromethyl)-1H-benzo[d]imidazol-1-yl)butanenitrile hydrochloric acid (332 mg, 1 eq) was added and the RM was stirred at RT for 2 h. The crude was then filtered off and the filtrate was concentrated in vacuo. The resulting crude was further purified by preparative SFC (Stationary phase: Chiralcel Diacel OJ 20×250 mm, Mobile phase: CO$_2$, iPrOH with 0.2% iPrNH$_2$), to give the pure isomers 148 (85 mg, 19% yield) and 149 (158 mg, 35% yield).

For 148: $^1$H NMR (400 MHz, DMSO-d$_6$) δ ppm 1.91-2.10 (m, 2H) 2.13-2.27 (m, 2H) 2.55-2.71 (m, 4H) 3.78 (quin, J=8.03 Hz, 1H) 4.38 (t, J=7.59 Hz, 2H) 5.20 (s, 2H) 7.08 (td, J=8.10, 1.54 Hz, 2H) 7.20 (td, J=7.70, 1.32 Hz, 1H) 7.29 (dd, J=8.58, 1.98 Hz, 1H) 7.53-7.70 (m, 3H); m/z=420 [M+H]$^+$. For 149: $^1$H NMR (400 MHz, DMSO-d$_6$) δ ppm 1.80-2.20 (m, 4H) 2.20-2.34 (m, 2H) 2.36-2.47 (m, 2H) 2.59 (t, J=7.48 Hz, 2H) 3.77-3.95 (m, 1H) 4.36 (t, J=7.50 Hz, 2H) 5.21 (s, 2H) 7.00-7.14 (m, 2H) 7.16-7.25 (m, 1H) 7.29 (dd, J=8.58, 1.98 Hz, 1H) 7.55 (d, J=6.82 Hz, 1H) 7.64 (d, J=8.80 Hz, 1H) 7.66 (d, J=1.76 Hz, 1H).

Compounds 143 and 144 Synthesis of 1-((1s,3s)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea and 1-((1r,3r)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea

143

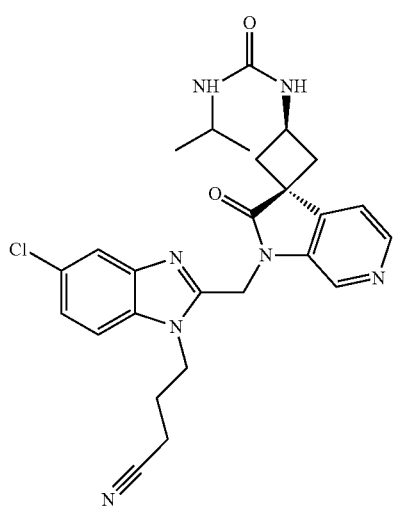

144

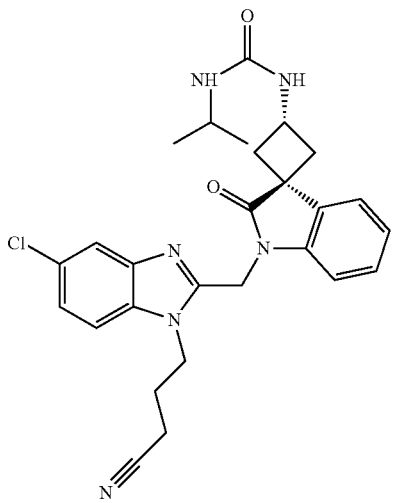

A mixture of 4-(2-(3-amino-2'-oxospiro[cyclobutane-1,3'-indolin]-1'-yl)methyl)-5-chloro-1H-benzo[d]imidazol-1-yl)butanenitrile (racemic mixture, 500 mg, 1.191 mmole), 2-isocyanatopropane (0.14 mL, 1.2 eq) and DIPEA (3.175 mL, 2 eq) was stirred at RT for 1 h. The RM was then concentrated in vacuo and purified by preparative HPLC (Stationary phase: RP Vydac Denali C18—10 μm, 200 g, 5 cm), Mobile phase: 0.25% $NH_4HCO_3$ solution in water, $CH_3CN$) to give the pure mixture of enantiomers, which were subsequently separated by preparative SFC (Stationary phase: Chiralpak Diacel AD 30×250 mm), Mobile phase: $CO_2$, MeOH with 0.2% $iPrNH_2$), yielding 240 mg (40% yield) of 143 and 122 mg (20% yield) of 144.

The compounds in the following table were synthetized according to the protocols described above, and to methods known in the art by the skilled chemist.

| No | structure | Name/analytical details |
|---|---|---|
| 1 | 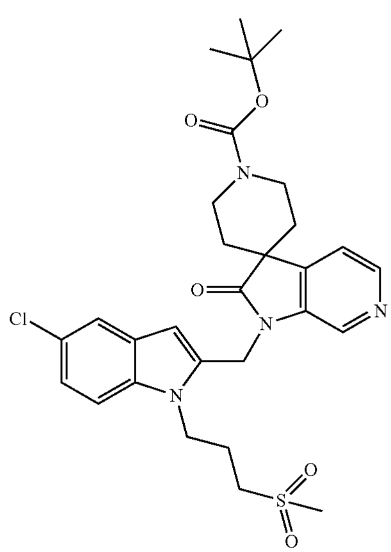 [SMILES: CC(C)(C)OC(=O)N1CCC2(CC1)C(=O)N(Cc1cc3cc(Cl)ccc3n1CCCS(C)(=O)=O)c1cnccc12] | tert-butyl 1'-({5-chloro-1-[3-(methylsulfonyl)propyl]-1H-indol-2-yl}methyl)-2'-oxo-1',2'-dihydro-1H-spiro[piperidine-4,3'-pyrrolo[2,3-c]pyridine]-1-carboxylate<br>$^1$H NMR (400 MHz, DMSO-$d_6$) δ ppm 1.45 (s, 9 H) 1.80 (t, J = 5.50 Hz, 4 H) 2.03-2.16 (m, 2 H) 3.01 (s, 3 H) 3.14-3.25 (m, 2 H) 3.60-3.83 (m, 4 H) 4.37 (t, J = 7.48 Hz, 2 H) 5.20 (s, 2 H) 6.37 (s, 1 H) 7.16 (dd, J = 8.69, 2.09 Hz, 1 H) 7.53 (d, J = 1.98 Hz, 1 H) 7.55 (d, J = 8.80 Hz, 1 H) 7.69 (d, J = 4.62 Hz, 1 H) 8.33 (d, J = 4.84 Hz, 1 H) 8.39 (s, 1 H); m/z = 587.23 (M + H)$^+$ + Cl pattern. |

| No | structure | Name/analytical details |
|---|---|---|
| 2 | 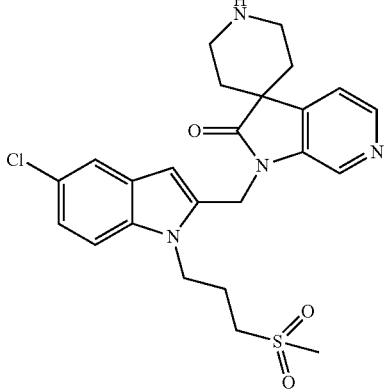 | 1'-({5-chloro-1-[3-(methylsulfonyl)propyl]-1H-indol-2-yl}-methyl)spiro[piperidine-4,3'-pyrrolo[2,3-c]pyridin]-2'(1'H)-one<br>$^1$H NMR (400 MHz, DMSO-d$_6$) δ ppm 1.62-1.88 (m, 4 H) 2.02-2.18 (m, 2 H) 2.93-3.07 (m, 5 H) 3.11-3.24 (m, 4 H) 4.38 (t, J = 7.48 Hz, 2 H) 5.19 (s, 2 H) 6.33 (s, 1 H) 7.16 (dd, J = 8.69, 2.09 Hz, 1 H) 7.50-7.58 (m, 2 H) 7.64 (d, J = 4.84 Hz, 1 H) 8.29-8.42 (m, 2 H); m/z = 487.27 (M + H)$^+$ + Cl pattern. |
| 3 | 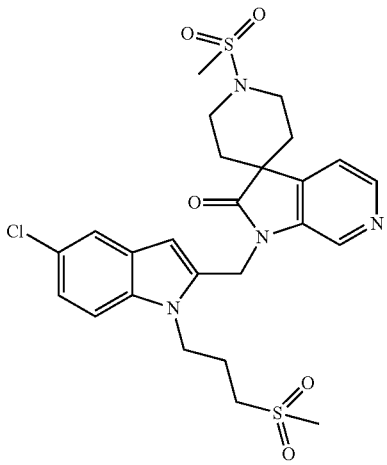 [SMILES: CS(=O)(=O)CCCn1c(CN2C(=O)C3(CCN(S(C)(=O)=O)CC3)c3ccncc32)cc2cc(Cl)ccc21] | 1'-({5-chloro-1-[3-(methylsulfonyl)propyl]-1H-indol-2-yl}-methyl)spiro[piperidine-4,3'-pyrrolo[2,3-c]pyridin]-2'(1'H)-one<br>$^1$H NMR (400 MHz, DMSO-d$_6$) δ ppm 1.88-2.16 (m, 6 H) 3.00 (s, 3 H) 3.01 (s, 3 H) 3.17-3.26 (m, 2 H) 3.41-3.51 (m, 2 H) 3.52-3.64 (m, 2 H) 4.38 (t, J = 7.48 Hz, 2 H) 5.20 (s, 2H) 6.38 (s, 1 H) 7.16 (dd, J = 8.69, 2.09 Hz, 1 H) 7.53 (d, J = 1.98 Hz, 1 H) 7.56 (d, J = 8.80 Hz, 1 H) 7.70 (d, J = 4.84 Hz, 1 H) 8.36 (d, J = 4.84 Hz, 1 H) 8.41 (s, 1 H); m/z = 565.03 (M + H)$^+$ + Cl pattern. |
| 4 | 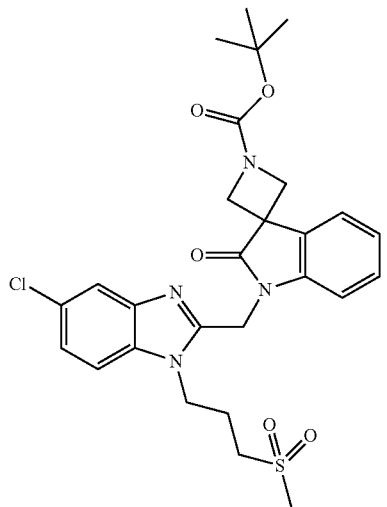 [SMILES: CC(C)(C)OC(=O)N1CC2(C1)C(=O)N(Cc1nc3cc(Cl)ccc3n1CCCS(C)(=O)=O)c1ccccc12] | tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate<br>$^1$H NMR (400 MHz, DMSO-d$_6$) δ ppm 1.44 (s, 9 H) 2.10-2.21 (m, 2 H) 3.00 (s, 3 H) 3.19-3.25 (m, 2 H) 4.03-4.19 (m, 4 H) 4.47 (t, J = 7.48 Hz, 2 H) 5.22 (s, 2 H) 7.13 (td, J = 7.48, 0.88 Hz, 1 H) 7.19 (d, J = 7.70 Hz, 1 H) 7.27-7.34 (m, 2 H) 7.65-7.69 (m, 3 H); m/z = 559.21 (M + H)$^+$ + Cl pattern. |

| No | structure | Name/analytical details |
|---|---|---|
| 5 | 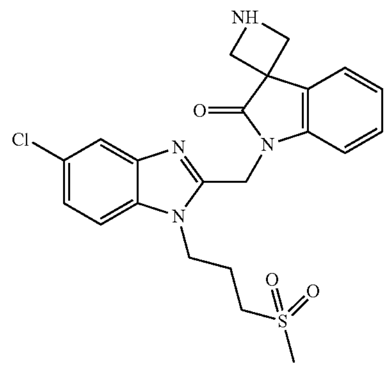 [SMILES: CS(=O)(=O)CCCn1c(CN2C(=O)C3(CNC3)c3ccccc32)nc2cc(Cl)ccc21] | 1'-({5-chloro-1-[3-(methylsulfonyl)propyl]-1H-benzimidazol-2-yl}methyl)spiro[azetidine-3,3'-indol]-2'(1'H)-one<br>¹H NMR (400 MHz, DMSO-d$_6$) δ ppm 2.11-2.26 (m, 2 H) 3.01 (s, 3 H) 3.19-3.28 (m, 2 H) 4.16-4.35 (m, 4 H) 4.48 (t, J = 7.48 Hz, 2 H) 5.22 (s, 2 H) 7.18-7.28 (m, 2 H) 7.32 (dd, J = 8.80, 1.98 Hz, 1 H) 7.36 (td, J = 7.90, 0.88 Hz, 1 H) 7.66 (d, J = 1.98 Hz, 1 H) 7.69 (d, J = 8.80) Hz, 1 H) 7.85 (d, J = 6.82 Hz, 1 H) 9.27 (br. s., 2 H); m/z = 459.18 (M + H)⁺ + Cl pattern. |
| 6 | 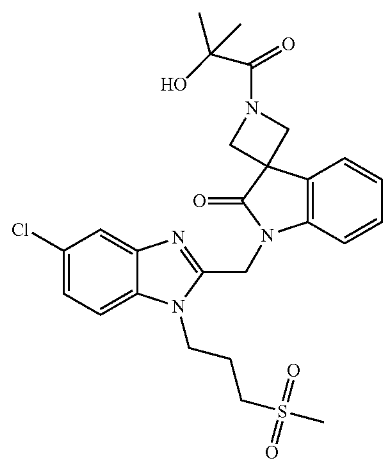 [SMILES: CC(C)(O)C(=O)N1CC2(C1)C(=O)N(Cc1nc3cc(Cl)ccc3n1CCCS(C)(=O)=O)c1ccccc12] | 1'-({5-chloro-1-[3-(methylsulfonyl)propyl]-1H-benzimidazol-2-yl}methyl)-1-(2-hydroxy-2-methyl-propanoyl)spiro[azetidine-3,3'-indol]-2'(1'H)-one<br>¹H NMR (400 MHz, DMSO-d$_6$) δ ppm 1.31 (s, 3 H) 1.33 (s, 3 H) 2.11-2.24 (m, 2 H) 3.00 (s, 3 H) 3.18-3.27 (m, 2 H) 4.02-4.20 (m, 2 H) 4.47 (t, J = 7.37 Hz, 2 H) 4.55-4.75 (m, 2 H) 5.23 (s, 2 H) 5.25 (s, 1 H) 7.11-7.23 (m, 2 H) 7.27-7.35 (m, 2 H) 7.60-7.65 (m, 1 H) 7.65-7.71 (m, 2 H); m/z = 545.41 (M + H)⁺ + Cl pattern |
| 7 | 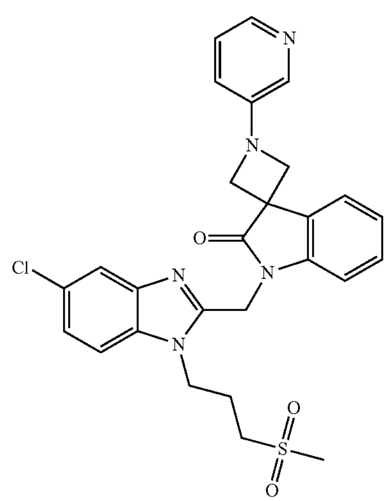 [SMILES: CS(=O)(=O)CCCn1c(CN2C(=O)C3(CN(c4cccnc4)C3)c3ccccc32)nc2cc(Cl)ccc21] | 1'-({5-chloro-1-[3-(methylsulfonyl)propyl]-1H-benzimidazol-2-yl}methyl)-1-(pyridin-3-yl)spiro[azetidine-3,3'-indol]-2'(1'H)-one<br>¹H NMR (400 MHz, DMSO-d$_6$) δ ppm 2.09-2.21 (m, 2 H) 3.00 (s, 3 H) 3.19-3.27 (m, 2 H) 4.13-4.27 (m, 4 H) 4.47 (t, J = 7.48 Hz, 2 H) 5.26 (s, 2 H) 6.99 (ddd, J = 8.25, 2.75, 1.32 Hz, 1 H) 7.12-7.17 (m, 1 H) 7.20 (d, J = 7.70 Hz, 1 H) 7.25 (dd, J = 8.14, 4.62 Hz, 1 H) 7.28-7.36 (m, 2 H) 7.64-7.71 (m, 3 H) 7.98 (d, J = 2.64 Hz, 1 H) 8.02 (dd, J = 4.62, 1.32 Hz, 1 H); m/z = 536.07 (M + H)⁺ + Cl pattern |

| No | structure | Name/analytical details |
|---|---|---|
| 8 | 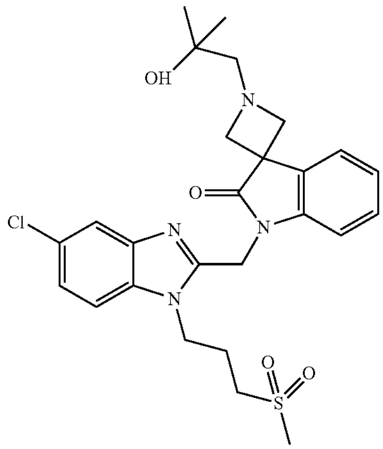 [SMILES: CC(C)(O)CN1CC2(C1)C(=O)N(Cc1nc3cc(Cl)ccc3n1CCCS(C)(=O)=O)c1ccccc12] | 1'-({5-chloro-1-[3-(methylsulfonyl)propyl]-1H-benzimidazol-2-yl}methyl)-1-(2-hydroxy-2-methyl-propyl)spiro[azetidine-3,3'-indol]-2'(1'H)-one<br>$^1$H NMR (400 MHz, DMSO-d$_6$) δ ppm 1.12 (s, 6 H) 2.06-2.17 (m, 2 H) 2.46 (s, 2 H) 2.99 (s, 3 H) 3.17-3.25 (m, 2 H) 3.54 (q, J = 7.04 Hz, 4 H) 4.12 (s, 1 H) 4.45 (t, J = 7.37 Hz, 2 H) 5.21 (s, 2 H) 7.10-7.17 (m, 2 H) 7.23-7.28 (m, 1 H) 7.30 (dd, J = 8.58, 1.98 Hz, 1 H) 7.64-7.68 (m, 2 H) 7.73-7.77 (m, 1 H); m/z = 531.09 (M + H)$^+$ + Cl pattern |
| 9 | 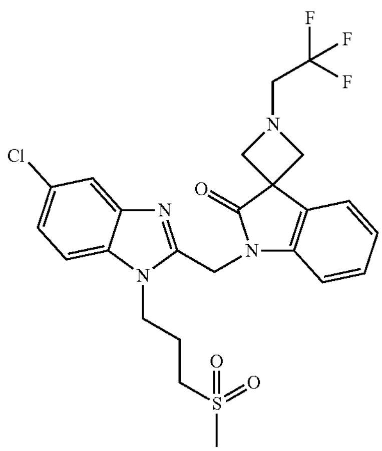 [SMILES: CS(=O)(=O)CCCn1c(CN2C(=O)C3(CN(CC(F)(F)F)C3)c3ccccc32)nc2cc(Cl)ccc21] | 1'-[[5-chloro-1-(3-methylsulfonylpropyl)benzimidazol-2-yl]-methyl]-1-(2,2,2-trifluoroethyl)spiro[azetidine-3,3'-indoline]-2'-one<br>$^1$H NMR (360 MHz, DMSO-d$_6$) δ ppm 2.13 (m, J = 8.1, 2 H), 3.00 (s, 3 H), 3.22 (m, J = 15.4 Hz, 2 H), 3.42 (q, J = 10.0 Hz, 2 H), 3.64 (d, J = 7.0 Hz, 2 H), 3.75 (d, J = 7.0 Hz, 2 H), 4.46 (t, J = 7.1 Hz, 2 H), 5.22 (s, 2 H), 7.07-7.22 (m, 2 H), 7.31 (d, J = 8.8 Hz, 1 H), 7.27 (d, J = 7.3 Hz, 1 H), 7.62-7.79 (m, 3 H); m/z = 540.99 (M + H)$^+$ + Cl pattern; melting point: 200.68° C. |
| 10 | 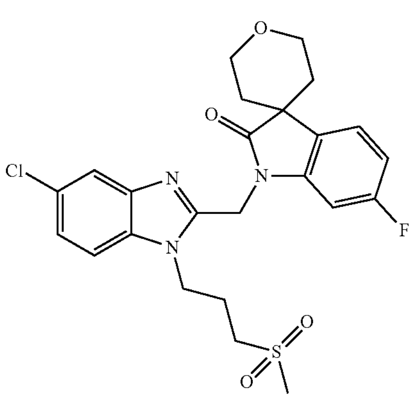 [SMILES: CS(=O)(=O)CCCn1c(CN2C(=O)C3(CCOCC3)c3ccc(F)cc32)nc2cc(Cl)ccc21] | 1-((5-chloro-1-(3-(methylsulfonyl)propyl)-1H-benzo[d]-imidazol-2-yl)methyl)-6-fluoro-2',3',5',6'-tetrahydro-spiro[indoline-3,4'-pyran]-2-one<br>$^1$H NMR (400 MHz, DMSO-d$_6$) δ ppm 1.63-1.92 (m, 4 H) 2.12-2.26 (m, 2 H) 3.01 (s, 3 H) 3.21-3.28 (m, 2 H) 3.76-3.90 (m, 2 H) 3.98-4.13 (m, 2 H) 4.46 (t, J = 6.93 Hz, 2 H) 5.24 (s, 2 H) 6.82-6.91 (m, 1 H) 7.14 (dd, J = 9.57, 1.65 Hz, 1 H) 7.31 (dd, J = 8.36, 1.32 Hz, 1 H) 7.60 (dd, J = 7.92, 5.72 Hz, 1 H) 7.65 (d, J = 1.32 Hz, 1 H) 7.67 (d, J = 8.80 Hz, 1 H);<br>m/z = 506.13 (M + H) + Cl pattern<br>MP = 207.14° C. |

| No | structure | Name/analytical details |
|---|---|---|
| 11 | 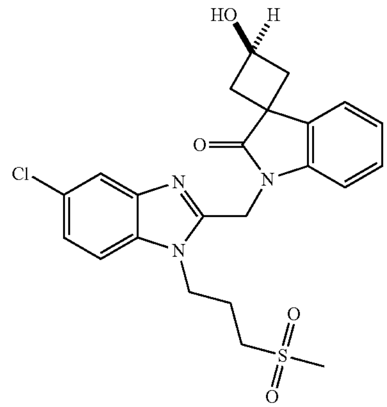 | (3S)-1'-({5-chloro-1-[3-(methylsulfonyl)propyl]-1H-benzimidazol-2-yl}methyl)-3-hydroxyspiro[cyclobutane-1,3'-indol]-2'(1'H)-one<br>$^1$H NMR (400 MHz, DMSO-$d_6$) δ ppm 2.00-2.17 (m, 2 H) 2.38-2.48 (m, 4 H) 2.99 (s, 3 H) 3.15-3.25 (m, 2 H) 4.45 (t, J = 7.26 Hz, 2 H) 4.63-4.79 (m, 1 H) 5.23 (s, 2 H) 5.57 (br. s., 1 H) 7.00-7.16 (m, 2 H) 7.17-7.26 (m, 1 H) 7.30 (dd, J = 8.69, 1.87 Hz, 1 H) 7.50 (d, J = 7.26 Hz, 1 H) 7.62-7.71 (m, 2H)<br>m/z = 474.05 (M + H)$^+$ + Cl pattern; MP = 232.91° C. |
| 12 | 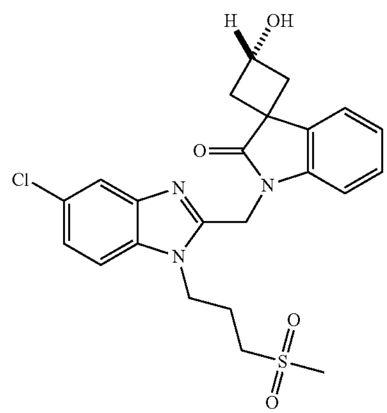 | (3R)-1'-({5-chloro-1-[3-(methylsulfonyl)propyl]-1H-benzimidazol-2-yl}methyl)-3-hydroxyspiro[cyclobutane-1,3'-indol]-2'(1'H)-one<br>$^1$H NMR (400 MHz, DMSO-$d_6$) δ ppm 2.08-2.21 (m, 2 H) 2.27-2.38 (m, 2 H) 2.60-2.72 (m, 2 H) 2.99 (s, 3 H) 3.19-3.27 (m, 2 H) 4.46 (t, J = 7.48 Hz, 2 H) 4.50-4.62 (m, 1 H) 5.20 (s, 2 H) 5.45 (d, J = 6.82 Hz, 1 H) 7.05-7.14 (m, 2 H) 7.18-7.25 (m, 1 H) 7.30 (dd, J = 8.80, 1.98 Hz, 1 H) 7.45-7.55 (m, 1 H) 7.63-7.71 (m, 2 H); m/z = 474.05 (M + H)$^+$ + Cl pattern; MP = 209.84° C. |
| 13 | 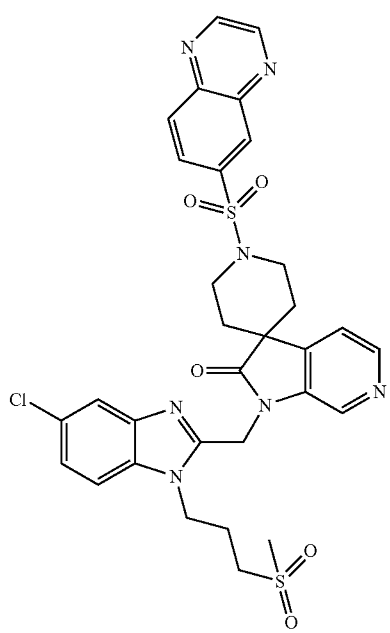 [SMILES: CS(=O)(=O)CCCn1c(CN2C(=O)C3(CCN(S(=O)(=O)c4ccc5nccnc5c4)CC3)c3ccncc32)nc2cc(Cl)ccc21] | 1'-((5-chloro-1-(3-(methylsulfonyl)propyl)-1H-benzo[d]-imidazol-2-yl)methyl)-1-(quinoxalin-6-ylsulfonyl)spiro-[piperidine-4,3'-pyrrolo[2,3-c]pyridin]-2'(1'H)-one<br>$^1$H NMR (400 MHz, CHLOROFORM-d) δ ppm 1.91-2.02 (m, 2 H), 2.04-2.16 (m, 2 H), 2.21-2.35 (m, 2 H), 2.89 (s, 3 H), 3.00 (t, J = 7.2 Hz, 2 H), 3.44-3.56 (m, 2 H), 3.70-3.81 (m, 2 H), 4.36-4.47 (m, 2 H), 5.11 (s, 2 H), 7.10 (d, J = 4.4 Hz, 1 H), 7.24 (m, J = 1.8 Hz, 2 H), 7.69 (d, J = 1.1 Hz, 1 H), 8.15 (dd, J = 8.8, 2.0 Hz, 1 H), 8.33 (d, J = 8.8 Hz, 1 H), 8.40 (d, J = 4.8 Hz, 1 H), 8.66 (d, J = 1.8 Hz, 1 H), 8.70 (s, 1 H), 8.99-9.07 (m, 2 H); m/z = 681 (M + H)$^+$ + Cl pattern |

| No | structure | Name/analytical details |
|---|---|---|
| 14 | 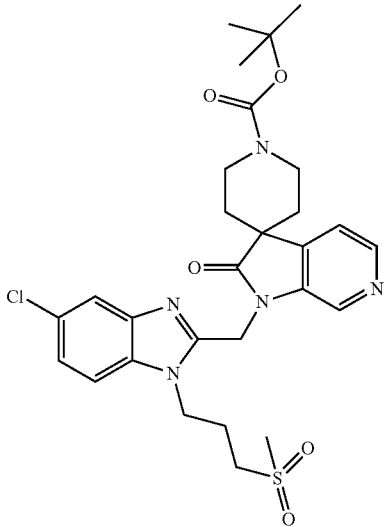 [SMILES: CC(C)(C)OC(=O)N1CCC2(CC1)C(=O)N(Cc1nc3cc(Cl)ccc3n1CCCS(C)(=O)=O)c1cnccc12] | tert-butyl 1'-((5-chloro-1-(3-(methylsulfonyl)propyl)-1H-benzo[d] imidazol-2-yl)methyl)-2'-oxo-1',2'-dihydrospiro-[piperidine-4,3'-pyrrolo[2,3-c]pyridine]-1-carboxylate<br>$^1$H NMR (400 MHz, DMSO-$d_6$) δ ppm 1.44 (s, 9 H), 1.79 (m, J = 5.6, 5.6 Hz, 4 H), 2.18 (m, J = 7.6, 7.6 Hz, 2 H), 3.01 (s, 3 H), 3.20-3.29 (m, 2 H), 3.61-3.81 (m, 4 H), 4.47 (t, J = 7.4 Hz, 2 H), 5.30 (s, 2 H), 7.31 (dd, J = 8.6, 2.0 Hz, 1 H),<br>7.62-7.72 (m, 3 H), 8.33 (d, J = 4.8 Hz, 1 H), 8.48 (s, 1 H);<br>m/z = 589 (M + H)$^+$ + Cl pattern |
| 15 | 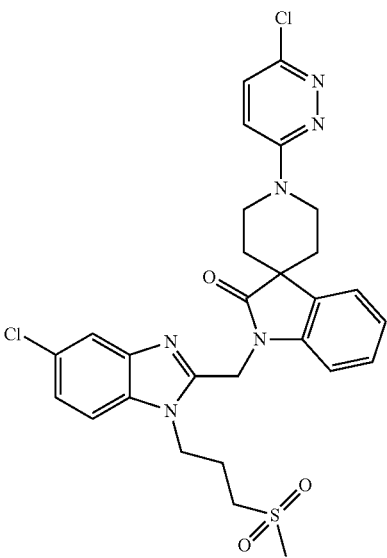 [SMILES: CS(=O)(=O)CCCn1c(CN2C(=O)C3(CCN(c4ccc(Cl)nn4)CC3)c3ccccc32)nc2cc(Cl)ccc21] | 1-((5-chloro-1-(3-(methylsulfonyl)propyl)-1H-benzo[d]-imidazol-2-yl)methyl)-1'-(6-chloropyridazin-3-yl)spiro-[indoline-3,4'-piperidin]-2-one<br>$^1$H NMR (400 MHz, DMSO-$d_6$) δ ppm 1.83-1.98 (m, 4 H), 2.13-2.25 (m, 2 H), 3.01 (s, 3 H), 3.20-3.29 (m, 2 H), 3.92-4.13 (m, 4 H), 4.48 (t, J = 7.4 Hz, 2 H), 5.26 (s, 2 H), 7.05 (t, J = 7.4 Hz, 1 H), 7.17-7.23 (m, 1 H), 7.23-7.35 (m, 2 H), 7.43-7.51 (m, 1 H), 7.51-7.59 (m, 2 H), 7.63-7.72 (m, 2 H)<br>m/z = 600 (M + H) + Cl pattern |

| No | structure | Name/analytical details |
|---|---|---|
| 16 | 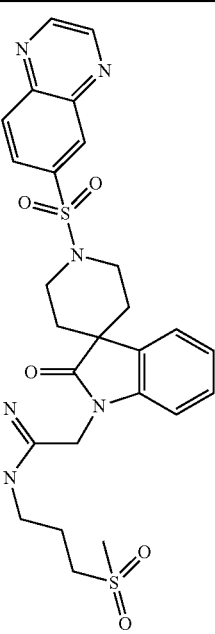 | 1-((5-chloro-1-(3-(methylsulfonyl)propyl)-1H-benzo[d]-imidazol-2-yl)methyl)-1'-(quinoxalin-6-ylsulfonyl)spiro-[indoline-3,4'-piperidin]-2-one<br>$^1$H NMR(400 MHz, DMSO-$d_6$) δ ppm 1.85 (m, J = 14.1 Hz, 2 H), 2.03-2.15 (m, 4 H), 2.93 (s, 3 H), 3.11-3.19 (m, 2 H), 3.28 (td, J = 1.6, 2.9 Hz, 2 H), 3.62-3.74 (m, 2 H), 4.36 (t, J = 7.5 Hz, 2 H), 5.12 (s, 2 H), 5.75 (s, 1 H), 7.02 (td, J = 7.5, 0.9 Hz, 1 H), 7.12 (d, J = 7.5 Hz, 1 H), 7.19-7.25 (m, 1 H), 7.27 (dd, J = 8.6, 2.0 Hz, 1 H), 7.36 (d, J = 7.3 Hz, 1 H),<br>7.59 (d, J = 1.8 Hz, 1 H), 7.62 (d, J = 8.6 Hz, 1 H), 8.20 (dd, J = 8.8, 2.0 Hz, 1 H), 8.39 (d, J = 8.8 Hz, 1 H), 8.51 (d, J = 2.0 Hz, 1 H), 9.10-9.19 (m, 2 H); m/z = 680 (M + H) + Cl pattern |
| 17 | 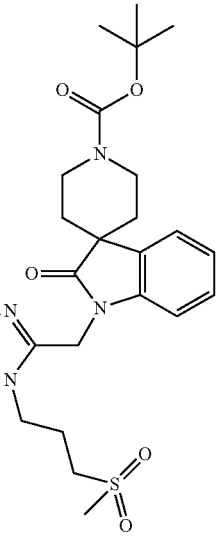 | tert-butyl 1-((5-bromo-1-(3-(methylsulfonyl)propyl)-1H-benzo[d] imidazol-2-yl)methyl)-2-oxospiro[indoline-3,4'-piperidine]-1'-carboxylate<br>$^1$H NMR (400 MHz, CHLOROFORM-d) δ ppm 1.51 (s, 9 H), 1.73-1.91 (m, 4 H), 2.23-2.35 (m, 2 H), 2.96 (s, 3 H), 3.11 (t, J = 7.2 Hz, 2 H), 3.72-3.91 (m, 4 H), 4.49 (t, J = 7.8 Hz, 2 H), 5.19 (s, 2 H), 7.05-7.11 (m, 1 H), 7.26 (s, 1 H), 7.29 (m, J = 8.5 Hz, 2 H), 7.28-7.28 (m, 1 H), 7.41 (dd, J = 8.7, 1.6 Hz, 1 H), 7.49 (d, J = 7.8 Hz, 1 H), 7.92 (d, J = 1.5 Hz, 1 H); m/z = 632 (M + H) + Br pattern |

| No | structure | Name/analytical details |
|---|---|---|
| 18 | 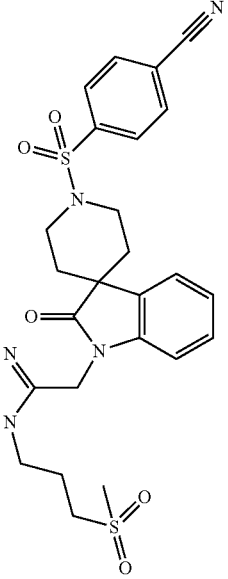 | 4-(1-((5-chloro-1-(3-(methylsulfonyl)propyl)-1H-benzo[d]-imidazol-2-yl)methyl)-2-oxospiro[indoline-3,4'-piperidine]-1'-ylsulfonyl) benzonitrile<br>$^1$H NMR (400 MHz, DMSO-d$_6$) δ ppm 1.83 (d, J = 14.1 Hz, 2 H), 1.98-2.22 (m, 4 H), 2.97 (s, 3 H), 3.13-3.28 (m, 4 H), 3.53-3.63 (m, 2 H), 4.40 (t, J = 7.5 Hz, 1 H), 5.15 (s, 2 H), 6.99-7.08 (m, 1 H), 7.13 (d, J = 7.8 Hz, 1 H), 7.20-7.26 (m, 1 H), 7.28 (dd, J = 8.7, 1.9 Hz, 1 H), 7.36 (d, J = 7.3 Hz, 1 H), 7.60 (d, J = 1.5 Hz, 1 H), 7.62-7.67 (m, 1 H), 7.99 (d, J = 8.5 Hz, 1 H), 8.15 (d, J = 8.3 Hz, 1 H); m/z = 653 (M + H) + Cl pattern |
| 19 | 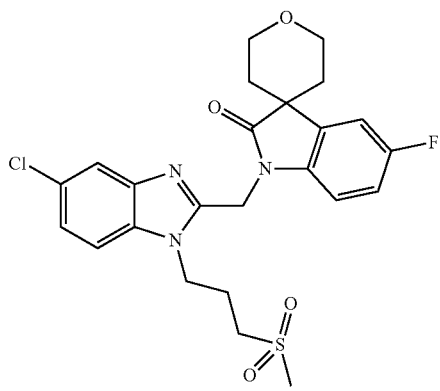 [SMILES: CS(=O)(=O)CCCn1c(CN2C(=O)C3(CCOCC3)c3cc(F)ccc32)nc2cc(Cl)ccc21] | 1-((5-chloro-1-(3-(methylsulfonyl)propyl)-1H-benzo)[d]-imidazol-2-yl) methyl)-5-fluoro-2',3',5',6'-tetrahydrospiro-[indoline-3,4'-pyran]-2-one<br>$^1$H NMR (400 MHz, DMSO-d$_6$) δ ppm 1.72-1.82 (m, 2 H), 1.89 (m, J = 18.2, 4.2, 4.2 Hz, 1 H), 2.17 (m, J = 7.6, 7.6, 7.6, 7.6 Hz, 1 H), 3.01 (s, 3 H), 3.20-3.28 (m, 2 H), 3.78-3.90 (m, 2 H), 4.07 (ddd, J = 11.7, 8.9, 3.2 Hz, 2 H), 4.46 (t, J = 7.5 Hz, 2 H), 5.23 (s, 2 H), 7.06-7.14 (m, 1 H), 7.17-7.22 (m, 1 H), 7.31 (dd, J = 8.6, 2.0 Hz, 1 H), 7.53 (dd, J = 8.7, 2.5 Hz, 1 H), 7.64 (d, J = 2.0 Hz, 1 H), 7.67 (d, J = 8.6 Hz, 1 H); m/z = 506 (M + H) + Cl pattern |
| 20 | 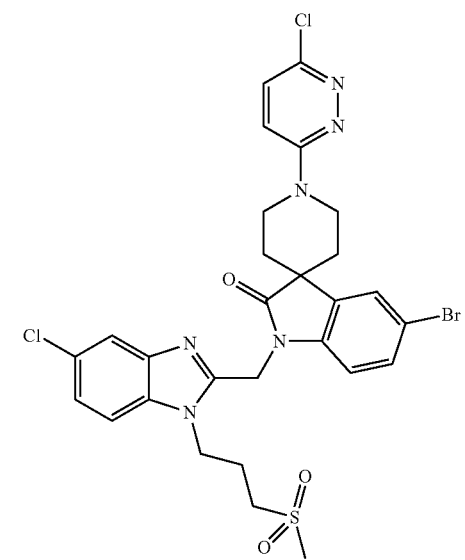 [SMILES: CS(=O)(=O)CCCn1c(CN2C(=O)C3(CCN(c4ccc(Cl)nn4)CC3)c3cc(Br)ccc32)nc2cc(Cl)ccc21] | 5-bromo-1-((5-chloro-1-(3-(methylsulfonyl)propyl)-1H-benzo[d] imidazol-2-yl)methyl)-1'-(6-chloropyridazin-3-yl)spiro[indoline-3,4'-piperidin]-2-one<br>$^1$H NMR (400 MHz, DMSO-d$_6$) δ ppm 1.81-1.90 (m, 2 H), 1.94-2.04 (m, 2 H), 2.18 (m, J = 7.3, 7.3 Hz, 2 H), 3.01 (s, 3 H), 3.21-3.28 (m, 2 H), 3.87-3.99 (m, 2 H), 4.06-4.17 (m, 2 H), 4.47 (t, J = 7.5 Hz, 2 H), 5.26 (s, 2 H), 7.16 (d, J = 8.4 Hz, 1 H), 7.31 (dd, J = 8.6, 2.0 Hz, 1 H), 7.42-7.49 (m, 2 H), 7.52-7.57 (m, 1 H), 7.64 (d, J = 2.0 Hz, 1 H), 7.67 (d, J = 8.6 Hz, 1 H), 7.77 (d, J = 2.0 Hz, 1 H); m/z = 679 (M + H) + Cl/Br pattern |

| No | structure | Name/analytical details |
|---|---|---|
| 21 | 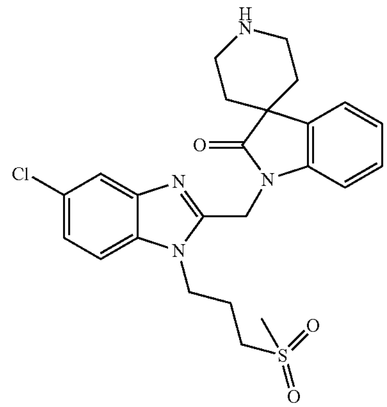 [SMILES: CS(=O)(=O)CCCn1c(CN2C(=O)C3(CCNCC3)c3ccccc32)nc2cc(Cl)ccc21] | 1-((5-chloro-1-(3-(methylsulfonyl)propyl)-1H-benzo[d]-imidazol-2-yl)methyl)spiro[indoline-3,4'-piperidin]-2-one<br>$^1$H NMR (400 MHz, DMSO-$d_6$) δ ppm 1.91-2.10 (m, 4 H), 2.21-2.32 (m, 2 H), 2.97 (s, 3 H), 3.17 (br. s., 2 H), 3.20-3.28 (m, 2 H), 3.41 (br. s., 2 H), 4.49 (t, J = 7.3 Hz, 2 H), 5.22 (s, 2 H), 7.04-7.13 (m, 1 H), 7.16-7.22 (m, 1 H), 7.23-7.30 (m, 2 H), 7.44 (d, J = 6.9 Hz, 1 H), 7.58 (s, 1 H), 7.61 (d, J = 8.5 Hz, 1 H); m/z = 488 (M + H) + Cl/Br pattern |
| 22 | 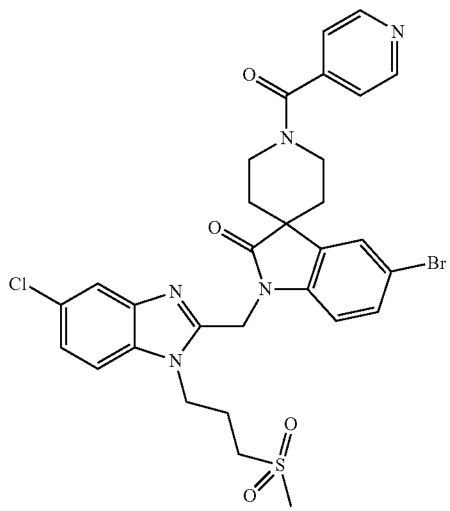 [SMILES: CS(=O)(=O)CCCn1c(CN2C(=O)C3(CCN(C(=O)c4ccncc4)CC3)c3cc(Br)ccc32)nc2cc(Cl)ccc21] | 5-bromo-1-((5-chloro-1-(3-(methylsulfonyl)propyl)-1H-benzo[d] imidazol-2-yl)methyl)-1'-isonicotinoylspiro-[indoline-3,4'-piperidin]-2-one<br>$^1$H NMR (400 MHz, DMSO-$d_6$) δ ppm 1.72 (d, J = 13.2 Hz, 1 H), 1.86 (d, J = 13.9 Hz, 1 H), 2.02 (m, J = 13.9 Hz, 2 H), 2.12-2.24 (m, 2 H), 3.01 (s, 3 H), 3.20-3.28 (m, 2 H), 3.45 (d, J = 13.6 Hz, 1 H), 3.74 (m, J = 10.3 Hz, 1 H), 4.28 (d, J = 13.4 Hz, 1 H), 4.46 (t, J = 7.5 Hz, 2 H), 5.24 (s, 2 H), 7.15 (d, J = 8.4 Hz, 1 H), 7.30 (dd, J = 8.7, 2.1 Hz, 1 H), 7.46 (dd, J = 8.4, 2.0 Hz, 1 H), 7.49-7.54 (m, 2 H), 7.62 (d, J = 2.0 Hz, 1 H), 7.67 (d, J = 8.6 Hz, 1 H), 7.88 (d, J = 2.0 Hz, 1 H), 8.66-8.73 (m, 2 H); m/z = 672 (M + H) + Cl pattern |
| 23 | 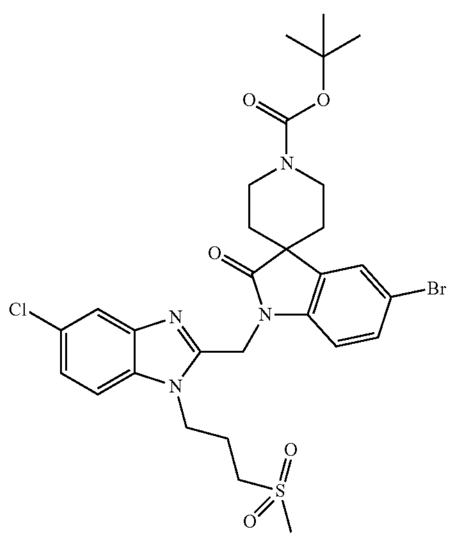 [SMILES: CC(C)(C)OC(=O)N1CCC2(CC1)C(=O)N(Cc1nc3cc(Cl)ccc3n1CCCS(C)(=O)=O)c1ccc(Br)cc12] | tert-butyl 5-bromo-1-((5-chloro-1-(3-(methyl-sulfonyl)propyl)-1H-benzo[d]imidazol-2-yl)methyl)-2-oxospiro[indoline-3,4'-piperidine]-1'-carboxylate<br>$^1$H NMR (400 MHz, DMSO-$d_6$) δ ppm 1.45 (s, 9 H), 1.69-1.79 (m, 2 H), 1.80-1.90 (m, 2 H), 2.17 (t, J = 7.4 Hz, 2 H), 3.01 (s, 3 H), 3.21-3.28 (m, 2 H), 3.63 (br. s., 2 H), 3.70-3.79 (m, 2 H), 4.45 (t, J = 7.5 Hz, 2 H), 5.24 (s, 2 H), 7.15 (d, J = 8.6 Hz, 1 H), 7.31 (dd, J = 8.6, 2.0 Hz, 1 H), 7.45 (dd, J = 8.4, 2.0 Hz, 1 H), 7.63 (d, J = 1.8 Hz, 1 H), 7.67 (d, J = 8.6 Hz, 1 H), 7.75 (d, J = 2.0 Hz, 1 H); m/z = 667 (M + H) + Cl pattern |

| No | structure | Name/analytical details |
|---|---|---|
| 24 | 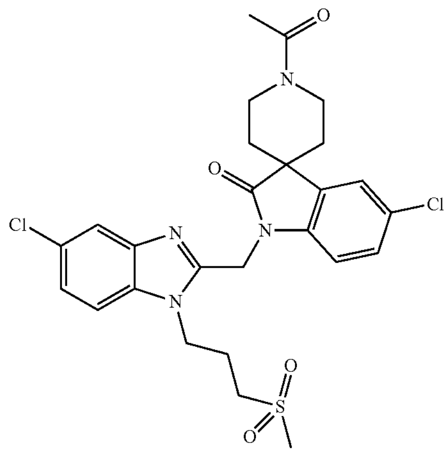 [SMILES: CC(=O)N1CCC2(CC1)C(=O)N(Cc1nc3cc(Cl)ccc3n1CCCS(C)(=O)=O)c1ccc(Cl)cc12] | 1-acetyl-5-chloro-1-((5-chloro-1-(3-(methylsulfonyl)-propyl)-1H-benzo[d]imidazol-2-yl)methyl)spiro[indoline-3,4'-piperidin]-2-one<br>$^1$H NMR (400 MHz, DMSO-$d_6$) δ ppm 1.68-1.87 (m, 3 H), 1.91-2.02 (m, 1 H), 2.07 (s, 3 H), 2.18 (quin, J = 7.6 Hz, 2 H), 3.01 (s, 3 H), 3.21-3.29 (m, 2 H), 3.53-3.64 (m, 1 H), 3.69-3.77 (m, 1 H), 3.80 (dd, J = 9.7, 3.3 Hz, 1 H), 3.99-4.08 (m, 1 H), 4.46 (t, J = 7.5 Hz, 2 H), 5.25 (s, 2 H), 7.19 (d, J = 8.6 Hz, 1 H), 7.28-7.35 (m, 1 H), 7.64 (dd, J = 4.3, 2.1 Hz, 1 H), 7.67 (d, J = 8.6 Hz, 1 H); m/z = 564 (M + H) + Cl pattern |
| 25 | 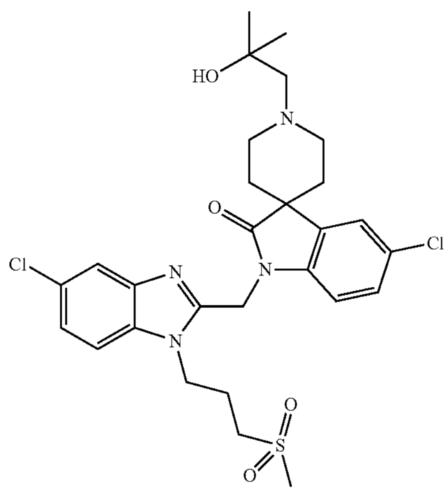 [SMILES: CC(C)(O)CN1CCC2(CC1)C(=O)N(Cc1nc3cc(Cl)ccc3n1CCCS(C)(=O)=O)c1ccc(Cl)cc12] | 5-chloro-1-((5-chloro-1-(3-(methylsulfonyl)propyl)-1H-benzo[d] imidazol-2-yl)methyl)-1-(2-hydroxy-2-methylpropyl)spiro[indoline-3,4'-piperidin]-2-one<br>$^1$H NMR (400 MHz, DMSO-$d_6$) δ ppm 1.13 (s, 6 H), 1.74-1.90 (m, 4 H), 2.16 (m, J = 7.3, 7.3 Hz, 2 H), 2.35 (s, 2 H), 2.69-2.78 (m, 2 H), 2.94-3.00 (m, 2 H), 3.01 (s, 3 H), 3.20-3.28 (m, 2 H), 4.08 (s, 1 H), 4.45 (t, J = 7.5 Hz, 2 H), 5.23 (s, 2 H), 7.18 (d, J = 8.4 Hz, 1 H), 7.31 (ddd, J = 8.5, 6.5, 2.1 Hz, 1 H), 7.59 (d, J = 2.0 Hz, 1 H), 7.63 (d, J = 1.8 Hz, 1 H), 7.66 (d, J = 8.6 Hz, 1 H); m/z = 594 (M + H) + Cl pattern |
| 26 | 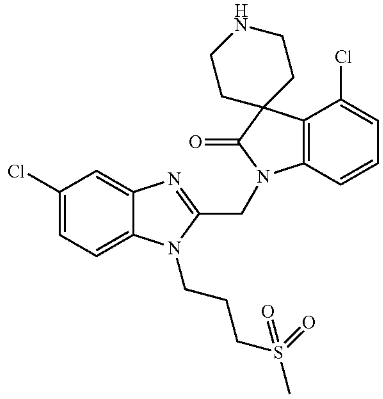 [SMILES: CS(=O)(=O)CCCn1c(CN2C(=O)C3(CCNCC3)c3c(Cl)cccc32)nc2cc(Cl)ccc21] | 4-chloro-1-({5-chloro-1-[3-(methylsulfonyl)propyl]-1H-benzimidazol-2-yl}methyl)spiro[indole-3,4'-piperidin]-2(1H)-one<br>$^1$H NMR (400 MHz, DMSO-$d_6$) δ ppm 1.51 (br. s. 2 H) 2.11-2.26 (m, 2 H) 2.42-2.54 (m, 2 H) 2.73-2.86 (m, 2 H) 3.02 (s, 3 H) 3.21-3.28 (m, 2 H) 3.28-3.39 (m, 2 H) 4.47 (t, J = 7.37 Hz, 2 H) 5.23 (s, 2 H) 7.04 (d, J = 8.14 Hz, 1 H) 7.12 (d, J = 7.48 Hz, 1 H) 7.25 (t, J = 7.92 Hz, 1 H) 7.30 (dd, J = 8.69, 1.87 Hz, 1 H) 7.63 (d, J = 1.98 Hz, 1 H) 7.67 (d, J = 8.80 Hz, 1 H); m/z = 521.01 (M + H) + 2*Cl pattern |

| No | structure | Name/analytical details |
|---|---|---|
| 27 | 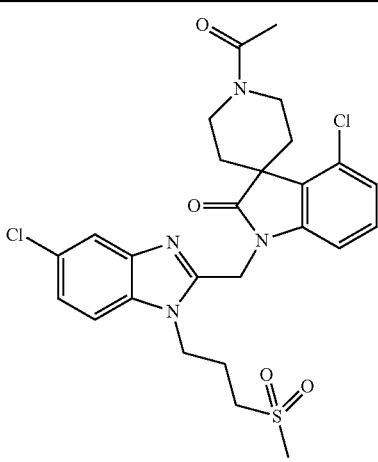 | 1'-acetyl-4-chloro-1-({5-chloro-1-[3-(methylsulfonyl)propyl]-1H-benzimidazol-2-yl}methyl)spiro[indole-3,4'-piperidin]-2(1H)-one<br>$^1$H NMR (400 MHz, DMSO-d$_6$) δ ppm 1.61-1.79 (m, 2 H) 2.07 (s, 3 H) 2.14-2.26 (m, 2 H) 2.37-2.64 (m, 2 H) 3.02 (s, 3 H) 3.21-3.29 (m, 2 H) 3.31-3.39 (m, 1 H) 3.77-3.88 (m, 2 H) 4.35-4.43 (m, 1 H) 4.47 (t, J = 7.37 Hz, 2 H) 5.26 (s, 2 H) 7.07 (d, J = 8.14 Hz, 1 H) 7.18 (d, J = 7.70 Hz, 1 H) 7.25-7.34 (m, 2 H) 7.64 (d, J = 1.76 Hz, 1 H) 7.68 (d, J = 8.80 Hz, 1 H); m/z = 563.05 (M + H) + 2*Cl pattern |
| 28 | 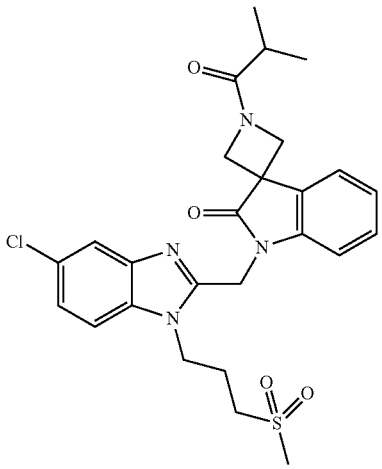 [SMILES: CC(C)C(=O)N1CC2(C1)C(=O)N(Cc1nc3cc(Cl)ccc3n1CCCS(C)(=O)=O)c1ccccc12] | 1'-({5-chloro-1-[3-(methylsulfonyl)propyl]-1H-benzimidazol-2-yl}methyl)-1-(2-methylpropanoyl)-spiro[azetidine-3,3'-indol]-2'(1'H)-one<br>$^1$H NMR (400 MHz, DMSO-d$_6$) δ ppm 1.00-1.10 (m, 6 H) 2.08-2.22 (m, 2 H) 2.52-2.60 (m, 1 H) 3.00 (s, 3 H) 3.19-3.26 (m, 2 H) 4.01-4.20 (m, 2 H) 4.37-4.55 (m, 4 H) 5.17-5.31 (m, 2 H) 7.10-7.24 (m, 2 H) 7.27-7.36 (m, 2 H) 7.62-7.74 (m, 3 H); m/z = 529.11 (M + H) + Cl pattern; MP = 133.12° C. and 226.64° C. |
| 29 | 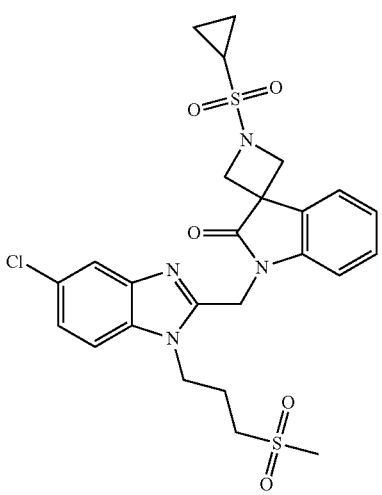 [SMILES: CS(=O)(=O)CCCn1c(CN2C(=O)C3(CN(S(=O)(=O)C4CC4)C3)c3ccccc32)nc2cc(Cl)ccc21] | 1'-({5-chloro-1-[3-(methylsulfonyl)propyl]-1H-benzimidazol-2-yl}methyl)-1-(cyclopropylsulfonyl)-spiro[azetidine-3,3'-indol]-2'(1'H)-one<br>$^1$H NMR (400 MHz, DMSO-d$_6$) δ ppm 1.00-1.19 (m, 4 H) 2.09-2.21 (m, 2 H) 2.93-3.03 (m, 4 H) 3.20-3.27 (m, 2 H) 4.12-4.34 (m, 4 H) 4.47 (t, J = 7.37 Hz, 2 H) 5.23 (s, 2 H) 7.14-7.25 (m, 2 H) 7.28-7.37 (m, 2 H) 7.63-7.71 (m, 3 H); m/z = 563.05 (M + H) + Cl pattern; MP = 191.15° C. |

-continued

| No | structure | Name/analytical details |
|---|---|---|
| 30 | 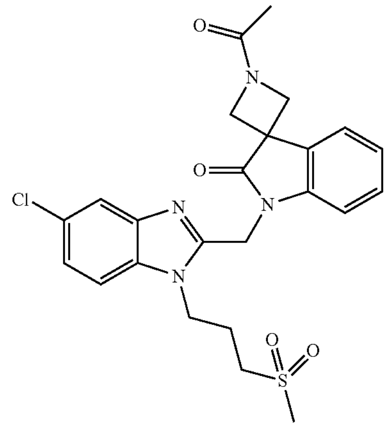 [SMILES: CC(=O)N1CC2(C1)C(=O)N(Cc1nc3cc(Cl)ccc3n1CCCS(C)(=O)=O)c1ccccc12] | 1-acetyl-1'-({5-chloro-1-[3-(methylsulfonyl)propyl]-1H-benzimidazol-2-yl}methyl)spiro[azetidine-3,3'-indol]-2'(1'H)-one<br>$^1$H NMR (400 MHz, DMSO-d$_6$) δ ppm 1.87 (s, 3 H) 2.10-2.22 (m, 2 H) 3.00 (s, 3 H) 3.19-3.27 (m, 2 H) 4.02-4.17 (m, 2 H) 4.36-4.44 (m, 2 H) 4.47 (t, J = 7.59 Hz, 2 H) 5.16-5.31 (m, 2 H) 7.10-7.17 (m, 1 H) 7.18-7.23 (m, 1 H) 7.27-7.36 (m, 2 H) 7.64-7.73 (m, 3 H); m/z = 501.11 (M + H) + Cl pattern; MP = 221.24° C. |
| 31 | 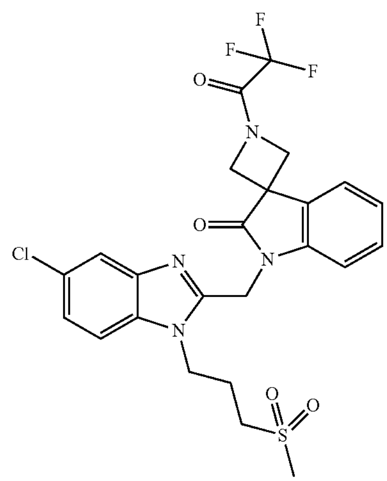 [SMILES: CS(=O)(=O)CCCn1c(CN2C(=O)C3(CN(C(=O)C(F)(F)F)C3)c3ccccc32)nc2cc(Cl)ccc21] | 1-({5-chloro-1-[3-(methylsulfonyl)propyl]-1H-benzimidazol-2-yl} methyl)-1-(trifluoroacetyl)spiro-[azetidine-3,3'-indol]-2'(1'H)-one<br>$^1$H NMR (400 MHz, DMSO-d$_6$) δ ppm 2.10-2.22 (m, 2 H) 3.00 (s, 3 H) 3.20-3.27 (m, 2 H) 4.29-4.36 (m, 1 H) 4.36-4.41 (m, 1 H) 4.48 (t, J = 7.37 Hz, 2 H) 4.61-4.68 (m, 1 H) 4.70-4.77 (m, 1 H) 5.23 (s, 2 H) 7.11-7.19 (m, 1 H) 7.22-7.27 (m, 1 H) 7.29-7.37 (m, 2 H) 7.64-7.72 (m, 2 H) 7.82-7.88 (m, 1 H); m/z = 554.99 (M + H) + Cl pattern; MP = 249.58° C. |
| 32 | 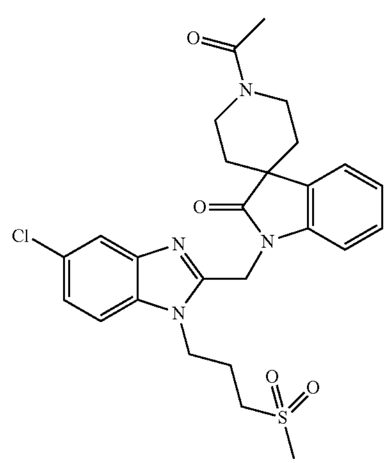 [SMILES: CC(=O)N1CCC2(CC1)C(=O)N(Cc1nc3cc(Cl)ccc3n1CCCS(C)(=O)=O)c1ccccc12] | 1'-acetyl-1-({5-chloro-1-[3-(methylsulfonyl)propyl]-1H-benzimidazol-2-yl}methyl)spiro[indole-3,4'-piperidin]-2(1H)-one<br>$^1$H NMR (400 MHz, DMSO-d$_6$) δ ppm 1.67-1.94 (m, 4 H) 2.08 (s, 3 H) 2.12-2.24 (m, 2 H) 3.01 (s, 3 H) 3.20-3.28 (m, 2 H) 3.62-4.04 (m, 4 H) 4.47 (t, J = 7.48 Hz, 2 H) 5.24 (s, 2 H) 7.06 (t, J = 7.50 Hz, 1 H) 7.19 (d, J = 7.48 Hz, 1 H) 7.26 (t, J = 7.50 Hz, 1 H) 7.31 (dd, J = 8.58, 1.98 Hz, 1 H) 7.51 (d, J = 7.26 Hz, 1 H) 7.65 (d, J = 1.76 Hz, 1 H) 7.67 (d, J = 8.80 Hz, 1 H); m/z = 529.11 (M + H) + Cl pattern; MP = 247.98° C. |

| No | structure | Name/analytical details |
|---|---|---|
| 33 | 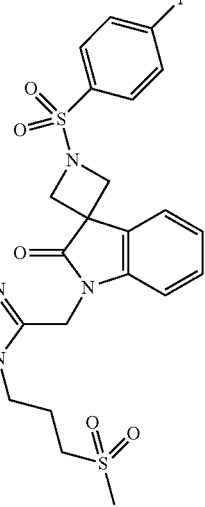 | 1'-({5-chloro-1-[3-(methylsulfonyl)propyl]-1H-benzimidazol-2-yl}methyl)-1-[(4-fluorophenyl)-sulfonyl]spiro[azetidine-3,3'-indol]-2'(1'H)-one<br>$^1$H NMR (400 MHz, DMSO-d$_6$) δ ppm 2.02-2.17 (m, 2 H) 2.99 (s, 3 H) 3.12-3.24 (m, 2 H) 3.91-4.12 (m, 4 H) 4.40 (t, J = 7.37 Hz, 2 H) 5.13 (s, 2 H) 6.98 (d, J = 7.26 Hz, 1 H) 7.06 (t, J = 7.30 Hz, 1 H) 7.16 (d, J = 7.70 Hz, 1 H) 7.23-7.35 (m, 2 H) 7.56-7.72 (m, 4 H) 7.97-8.07 (m, 2 H); m/z = 617.40 (M + H) + Cl pattern |
| 34 | 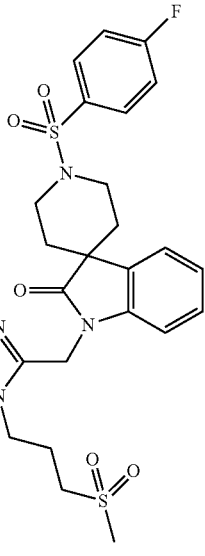 | 1-({5-chloro-1-[3-(methylsulfonyl)propyl]-1H-benzimidazol-2-yl}methyl)-1'-[(4-fluorophenyl)-sulfonyl]spiro[indole-3,4'-piperidin]-2(1H)-one<br>$^1$H NMR (400 MHz, DMSO-d$_6$) δ ppm 1.77-1.90 (m, 2 H) 1.99-2.18 (m, 4 H) 2.97 (s, 3 H) 3.08-3.23 (m, 4 H) 3.46-3.59 (m, 2 H) 4.40 (t, J = 7.37 Hz, 2 H) 5.15 (s, 2 H) 6.99-7.08 (m, 1 H) 7.14 (d, J = 7.70 Hz, 1 H) 7.20-7.26 (m, 1 H) 7.29 (dd, J = 8.58, 1.98 Hz, 1 H) 7.35 (d, J = 7.26 Hz, 1 H) 7.48-7.57 (m, 2 H) 7.61 (d, J = 1.76 Hz, 1 H) 7.65 (d, J = 8.80 Hz, 1 H) 7.83-7.94 (m, 2 H); m/z = 645.47 (M + H) + Cl pattern; MP = 183.97° C. |
| 35 | 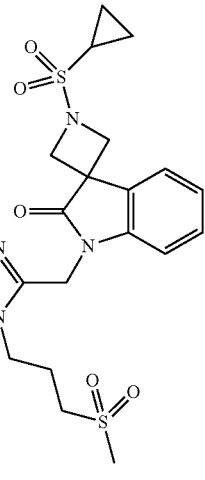 | 1-({5-chloro-1-[3-(methylsulfonyl)propyl]-1H-benzimidazol-2-yl}methyl)-1'-(cyclopropylsulfonyl)-spiro[indole-3,4'-piperidin]-2(1H)-one<br>$^1$H NMR (400 MHz, DMSO-d$_6$) δ ppm 0.93-1.10 (m, 4 H) 1.84-2.04 (m, 4 H) 2.10-2.24 (m, 2 H) 2.68-2.81 (m, 1 H) 3.01 (s, 3 H) 3.19-3.28 (m, 2 H) 3.49-3.73 (m, 4 H) 4.47 (t, J = 7.04 Hz, 2 H) 5.24 (s, 2 H) 7.03-7.12 (m, 1 H) 7.17-7.35 (m, 3 H) 7.50 (d, J = 7.48 Hz, 1 H) 7.60-7.73 (m, 2 H); m/z = 591.04 (M + H) + Cl pattern; MP = 194.85° C. |

| No | structure | Name/analytical details |
|---|---|---|
| 36 | 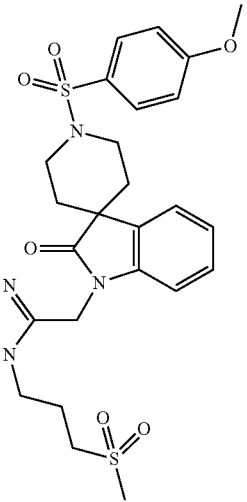 | 1-({5-chloro-1-[3-(methylsulfonyl)propyl]-1H-benzimidazol-2-yl}methyl)-1'-[(4-methoxyphenyl)-sulfonyl]spiro[indole-3,4'-piperidin]-2(1H)-one<br>$^1$H NMR (400 MHz, DMSO-d$_6$) δ ppm 1.74-1.87 (m, 2 H) 1.98-2.18 (m, 4 H) 2.96 (s, 3 H) 3.06-3.23 (m, 4 H) 3.43-3.55 (m, 2 H) 3.87 (s, 3 H) 4.40 (t, J = 7.48 Hz, 2 H) 5.15 (s, 2 H) 7.03 (t, J = 7.37 Hz, 1 H) 7.13 (d, J = 7.92 Hz, 1 H) 7.15-7.20 (m, 2 H) 7.20-7.26 (m, 1 H) 7.29 (dd, J = 8.58, 1.76 Hz, 1 H) 7.33 (d, J = 7.48 Hz, 1 H) 7.61 (d, J = 1.98 Hz, 1 H) 7.65 (d, J = 8.80 Hz, 1 H) 7.70-7.77 (m, 2 H); m/z = 657.05 (M + H) + Cl pattern; MP = 237.33° C. |
| 37 | 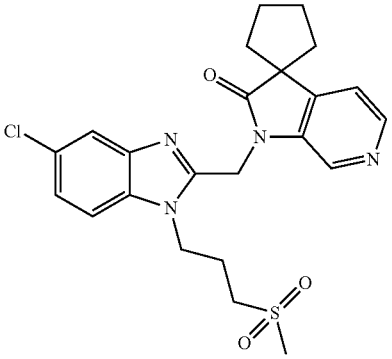 [SMILES: CS(=O)(=O)CCCn1c(CN2C(=O)C3(CCCC3)c3ccncc32)nc2cc(Cl)ccc21] | 1'-((5-chloro-1-(3-(methylsulfonyl)propyl)-1H-benzo[d]-imidazol-2-yl)methyl)spiro[cyclopentane-1,3'-pyrrolo[2,3-c]pyridin]-2'(1'H)-one<br>$^1$H NMR (400 MHz, CHLOROFORM-d) δ ppm 1.79-2.30 (m, 10 H) 2.91 (s, 3 H) 3.10 (t, J = 7.15 Hz, 2 H) 4.38-4.51 (m, 2 H) 5.18 (s, 2 H) 7.10 (dd, J = 4.77, 0.75 Hz, 1 H) 7.17-7.23 (m, 1 H) 7.27-7.32 (m, 1 H) 7.68 (d, J = 1.76 Hz, 1 H) 8.32 (d, J = 4.77 Hz, 1 H) 8.68 (s, 1 H); m/z = 473 (M + H)$^+$ |
| 38 | 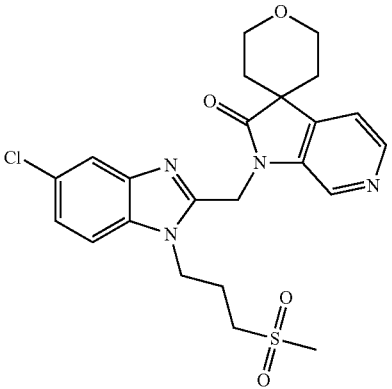 [SMILES: CS(=O)(=O)CCCn1c(CN2C(=O)C3(CCOCC3)c3ccncc32)nc2cc(Cl)ccc21] | 1'-((5-chloro-1-(3-(methylsulfonyl)propyl)-1H-benzo[d]-imidazol-2-yl)methyl)-2,3,5,6-tetrahydrospiro[pyran-4,3'-pyrrolo[2,3-c]pyridin]-2'(1'H)-one<br>$^1$H NMR (400 MHz, DMSO-d$_6$) δ ppm 1.83 (t, J = 5.39 Hz, 4 H) 2.19 (quin, J = 7.65 Hz, 2 H) 3.02 (s, 3 H) 3.21-3.29 (m, 2 H) 3.78-3.91 (m, 2 H) 4.04 (dt, J = 11.72, 5.69 Hz, 2 H) 4.48 (t, J = 7.48 Hz, 2 H) 5.30 (s, 2 H) 7.31 (dd, J = 8.58, 1.98 Hz, 1 H) 7.65 (d, J = 1.76 Hz, 1 H) 7.68 (d, J = 8.58 Hz, 1 H) 7.70 (d, J = 4.84 Hz, 1 H) 8.35 (d, J = 4.84 Hz, 1 H) 8.48 (s, 1 H); m/z = 489 (M + H)$^+$ |

| No | structure | Name/analytical details |
|---|---|---|
| 39 | 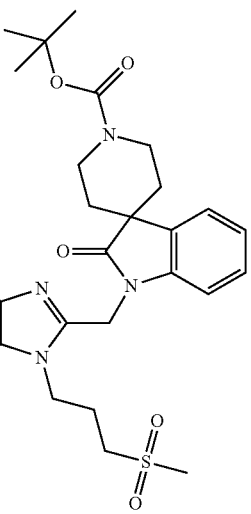 | tert-butyl 1-((5-chloro-1-(3-(methylsulfonyl)propyl)-1H-benzo[d]imidazol-2-yl)methyl)-2-oxospiro[indoline-3,4'-piperidine]-1'-carboxylate<br>$^1$H NMR (400 MHz, CHLOROFORM-d) δ ppm 1.51 (s, 9 H), 1.73-1.91 (m, 4 H), 2.22-2.36 (m, 2 H), 2.96 (d, J = 0.75 Hz, 3 H), 3.11 (t, J = 7.15 Hz, 2 H), 3.72-3.92 (m, 4 H), 4.49 (t, J = 7.78 Hz, 2 H), 5.19 (s, 2 H), 7.05-7.11 (m, 1 H), 7.30 (s, 4 H), 7.49 (d, J = 7.78 Hz, 1 H), 7.75 (d, J = 2.01 Hz, 1 H)<br>m/z = 587 (M + H)$^+$, Cl pattern |
| 40 | 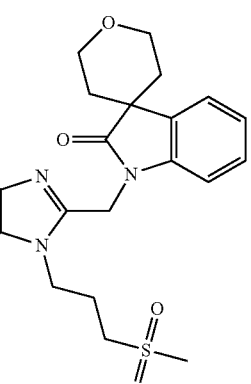 | 1-((5-chloro-1-(3-(methylsulfonyl)propyl)-1H-benzo[d]-imidazol-2-yl)methyl)-2',3',5',6'-tetrahydrospiro[indoline-3,4'-pyran]-2-one<br>$^1$H NMR (400 MHz, CHLOROFORM-d) δ ppm 1.80-1.96 (m, 4 H), 2.29 (quin, J = 7.47 Hz, 2 H), 2.95 (s, 3 H), 3.12 (t, J = 7.28 Hz, 2 H), 3.88-4.02 (m, 2 H), 4.23 (ddd, J = 11.80, 7.28, 4.52 Hz, 2 H), 4.44-4.56 (m, 2 H), 5.19 (s, 2 H), 7.05-7.13 (m, 1 H), 7.27-7.36 (m, 3 H), 7.39 (d, J = 7.28 Hz, 1 H), 7.50 (d, J = 7.78 Hz, 1 H), 7.76 (d, J = 7.76 Hz, 1 H); m/z = 488 (M + H)$^+$, Cl pattern |
| 41 | 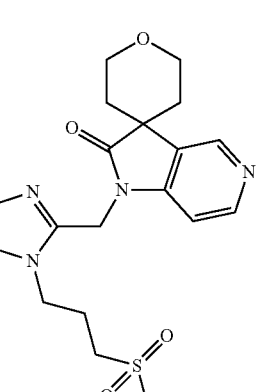 | 1-((5-chloro-1-(3-(methylsulfonyl)propyl)-1H-benzo[d]-imidazol-2-yl)methyl)-2,3,5,6-tetrahydrospiro[pyran-4,3'-pyrrolo[3,2-c]pyridin]-2'(1'H)-one<br>$^1$H NMR (400 MHz, CHLOROFORM-d) δ ppm 1.76-1.89 (m, 2 H), 2.01 (ddd, J = 13.64, 7.37, 3.63 Hz, 2 H), 2.27-2.39 (m, 2 H), 2.99 (s, 3 H), 3.14 (d, J = 14.30 Hz, 2 H), 3.94 (ddd, J = 11.72, 7.54, 3.63 Hz, 2 H), 4.19 (ddd, J = 11.66, 7.37, 3.85 Hz, 2 H), 4.45-4.57 (m, 2 H), 5.17 (s, 2 H), 7.27-7.31 (m, 1 H), 7.31-7.36 (m, 1 H), 7.46 (d, J = 5.28 Hz, 1 H), 7.73 (d, J = 1.76 Hz, 1 H), 8.51 (d, J = 5.28 Hz, 1 H), 8.63 (s, 1 H); m/z = 489 (M + H)$^+$, Cl pattern |

-continued

| No | structure | Name/analytical details |
|---|---|---|
| 42 | 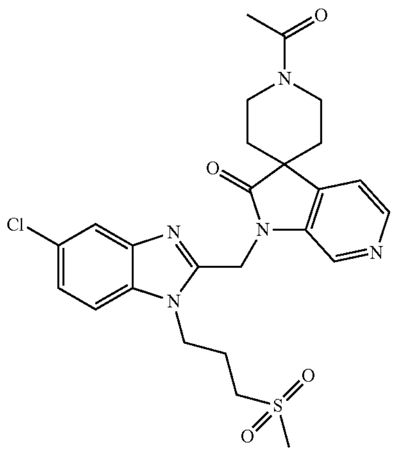 [SMILES: CC(=O)N1CCC2(CC1)C(=O)N(Cc1nc3cc(Cl)ccc3n1CCCS(C)(=O)=O)c1cnccc12] | 1-acetyl-1'-((5-chloro-1-(3-(methylsulfonyl)propyl)-1H-benzo[d]imidazol-2-yl)methyl)spiro[piperidine-4,3'-pyrrolo-[2,3-c]pyridin]-2'(1'H)-one<br>$^1$H NMR (400 MHz, DMSO-d$_6$) δ ppm 1.72-1.82 (m, 2 H), 1.83-1.92 (m, 2 H), 2.08 (s, 3 H), 2.19 (m, J = 7.4, 7.4 Hz, 2 H), 3.02 (s, 3 H), 3.22-3.29 (m, 2 H), 3.66-3.79 (m, 2 H), 3.80-3.93 (m, 2 H), 4.48 (t, J = 7.5 Hz, 2 H), 5.31 (s, 2 H), 7.31 (dd, J = 8.7, 1.9 Hz, 1 H), 7.65 (d, J = 2.0 Hz, 2 H), 7.68 (d, J = 8.6 Hz, 1 H), 8.34 (d, J = 4.8 Hz, 1 H), 8.49 (s, 1 H) |
| 43 | 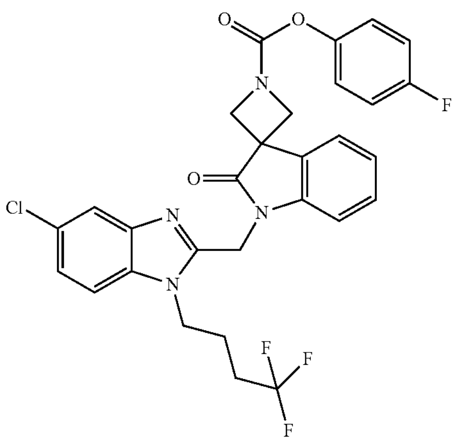 [SMILES: O=C(Oc1ccc(F)cc1)N1CC2(C1)C(=O)N(Cc1nc3cc(Cl)ccc3n1CCCC(F)(F)F)c1ccccc12] | 4-fluorophenyl 1'-((5-chloro-1-(4,4,4-trifluorobutyl)-1H-benzo[d]imidazol-2-yl)methyl)-2'-oxospiro[azetidine-3,3'-indoline]-1-carboxytale<br>$^1$H NMR (400 MHz, DMSO-d$_6$) δ ppm 1.89-2.04 (m, 2 H), 2.33-2.48 (m, 2 H), 4.27 (br. s., 2 H), 4.44 (t, J = 7.5 Hz, 3 H), 5.25 (s, 2 H), 7.17 (td, J = 7.5, 0.8 Hz, 1 H), 7.21-7.28 (m, 5 H), 7.28-7.38 (m, 2 H), 7.65-7.73 (m, 2 H), 7.80-7.86 (m, 1 H); m/z = 587 (M + H)$^+$, Cl pattern |
| 44 | 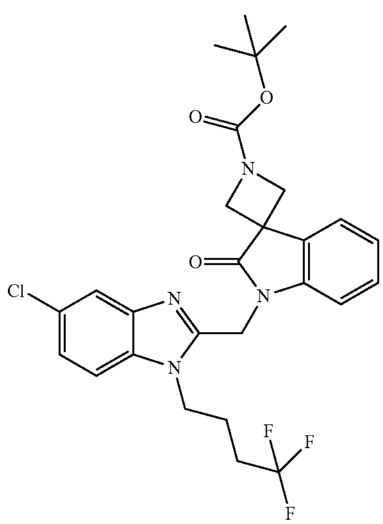 | tert-butyl 1'-((5-chloro-1-(4,4,4-trifluorobutyl)-1H-benzo[d]imidazol-2-yl)methyl)-2'-oxospiro[azetidine-3,3'-indoline]-1-carboxylate<br>$^1$H NMR (400 MHz, CHLOROFORM-d) δ ppm 1.47-1.53 (m, 9 H), 1.95 (m, J = 7.8, 7.8 Hz, 2 H), 2.14-2.29 (m, 2 H), 4.08 (d, J = 8.3 Hz, 2 H), 4.33-4.41 (m, 4 H), 5.19 (s, 2 H), 7.13-7.19 (m, 1 H), 7.20-7.29 (m, 2 H), 7.29-7.35 (m, 1 H), 7.51 (d, J = 7.8 Hz, 1 H), 7.54 (d, J = 7.3 Hz, 1 H), 7.76 (d, J = 1.8 Hz, 1 H); m/z = 587 (M + H)$^+$, Cl pattern |

| No | structure | Name/analytical details |
|---|---|---|
| 45 | 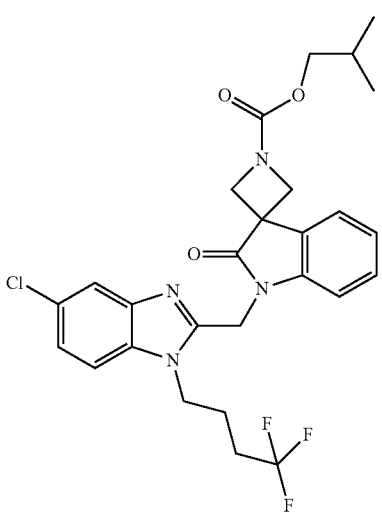 [SMILES: CC(C)COC(=O)N1CC2(C1)C(=O)N(Cc1nc3cc(Cl)ccc3n1CCCC(F)(F)F)c1ccccc12] | isobutyl 1'-((5-chloro-1-(4,4,4-trifluorobutyl)-1H-benzo[d]-imidazol-2-yl)methyl)-2'-oxospiro[azetidine-3,3'-indoline]-1-carboxylate<br>$^1$H NMR (400 MHz, CHLOROFORM-d) δ ppm 0.95 (d, J = 6.5 Hz, 6 H), 1.88-2.03 (m, 3 H), 2.14-2.29 (m, 2 H), 3.92 (d, J = 6.8 Hz, 2 H), 4.14 (d, J = 8.3 Hz, 2 H), 4.37 (t, J = 7.8 Hz, 2 H), 4.42 (d, J = 8.3 Hz, 2 H), 5.19 (s, 2 H), 7.12-7.20 (m, 1 H), 7.21-7.30 (m, 2 H), 7.33 (td, J = 7.8, 1.3 Hz, 1 H), 7.53 (t, J = 7.2 Hz, 2 H), 7.76 (d, J = 1.5 Hz, 1 H); m/z = 549 (M + H)$^+$, Cl pattern |
| 46 | 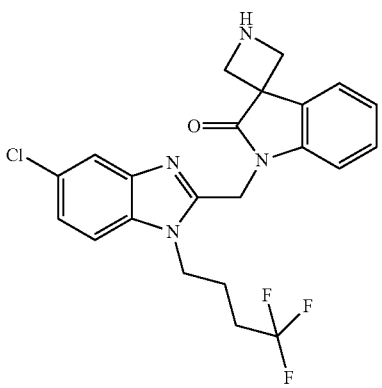 [SMILES: O=C1N(Cc2nc3cc(Cl)ccc3n2CCCC(F)(F)F)c2ccccc2C12CNC2] | 1'-((5-chloro-1-(4,4,4-trifluorobutyl)-1H-benzo[d]imidazol-2-yl) methyl)spiro[azetidine-3,3-indolin]-2'-one<br>$^1$H NMR (400 MHz, DMSO-d$_6$) δ ppm 1.92-2.05 (m, 2 H), 2.35-2.46 (m, 2 H), 4.19-4.26 (m, 2 H), 4.26-4.33 (m, 2 H), 4.43 (t, J = 7.7 Hz, 2 H), 5.21 (s, 2 H), 7.20 (t, J = 7.4 Hz, 1 H), 7.26 (d, J = 7.8 Hz, 1 H), 7.31 (dd, J = 8.8, 2.0 Hz, 1 H), 7.33-7.40 (m, 1 H), 7.65 (d, J = 2.0 Hz, 1 H), 7.70 (d, J = 8.5 Hz, 1 H), 7.85 (d, J = 7.3 Hz, 1 H), 9.39 (br. s., 1 H); m/z = 449 (M + H)$^+$, Cl pattern |
| 47 | 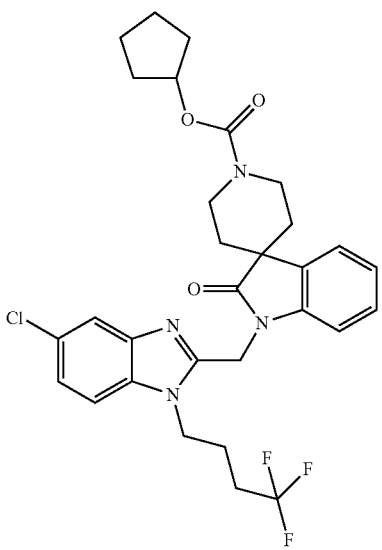 [SMILES: O=C(OC1CCCC1)N1CCC2(CC1)C(=O)N(Cc1nc3cc(Cl)ccc3n1CCCC(F)(F)F)c1ccccc12] | Cyclopentyl 1-((5-chloro-1-(4,4,4-trifluorobutyl)-1H-benzo[d]imidazol-2-yl)methyl)-2-oxospiro[indoline-3,4'-piperidine]-1'-carboxylate<br>$^1$H NMR (400 MHz, CHLOROFORM-d) δ ppm 1.54-1.67 (m, 2 H), 1.68-2.06 (m, 12 H), 2.22 (m, J = 10.2, 8.1, 8.1 Hz, 2 H), 3.75-3.96 (m, 4 H), 4.32-4.41 (m, 2 H), 5.14-5.23 (m, 3 H), 7.05-7.11 (m, 1 H), 7.19-7.25 (m, 1 H), 7.27-7.32 (m, 2 H), 7.52-7.61 (m, 1 H), 7.77 (d, J = 1.8 Hz, 1 H) m/z = 590 (M + H)$^+$ Cl pattern |

| No | structure | Name/analytical details |
|---|---|---|
| 48 | 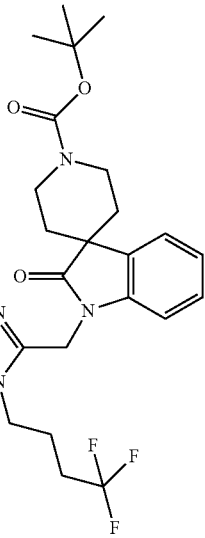 | tert-butyl 1-((5-chloro)-1-(4,4,4-trifluorobutyl)-1H-benzo[d]-imidazol-2-yl)methyl)-2-oxospiro[indoline-3,4'-piperidine]-1'-carboxylate<br>$^1$H NMR (400 MHz, CHLOROFORM-d) δ ppm 1.51 (s, 10 H), 1.73-1.89 (m, 4 H), 1.91-2.02 (m, 2 H), 2.15-2.30 (m, 2 H), 3.74-3.91 (m, 4 H), 4.32-4.40 (m, 2 H), 5.19 (s, 2 H), 7.05-7.11 (m, 1 H), 7.20-7.24 (m, 1 H), 7.26-7.31 (m, 2 H), 7.55 (d, J = 7.5 Hz, 1 H), 7.77 (d, J = 1.8 Hz, 1 H)<br>m/z = 577 (M + H)$^+$, Cl patient |
| 49 | 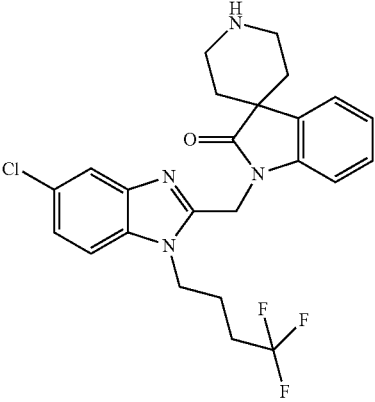 [SMILES: O=C1N(Cc2nc3cc(Cl)ccc3n2CCCC(F)(F)F)c2ccccc2C12CCNCC2] | 1-((5-chloro-1-(4,4,4-trifluorobutyl)-1H-benzo[d]imidazol-2-yl)methyl) spiro[indoline-3,4'-piperidin]-2-one<br>$^1$H NMR (400 MHz, DMSO-d$_6$) δ ppm 1.89-2.03 (m, 4 H), 2.04-2.17 (m, 2 H), 2.34-2.47 (m, 2 H), 3.35-3.41 (m, 2 H), 3.52 (br. s., 2 H), 4.42 (t, J = 7.7 Hz, 2 H), 5.24 (s, 2 H), 7.13 (t, J = 7.5 Hz, 1 H), 7.21-7.27 (m, 1 H), 7.27-7.35 (m, 1 H), 7.41 (d, J = 7.3 Hz, 1 H), 7.63 (d, J = 2.0 Hz, 1 H), 7.69<br>(d, J = 8.8 Hz, 1 H), 8.76 (br. s., 1 H); m/z = 477 (M + H)$^+$, Cl<br>pattern |
| 50 | 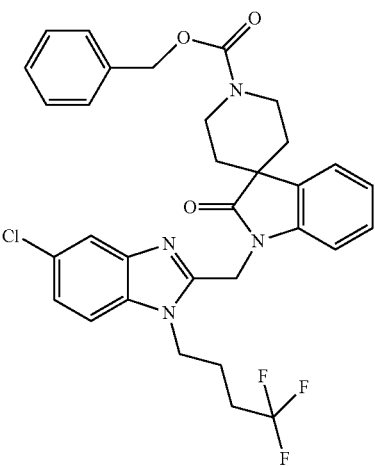 [SMILES: O=C(OCc1ccccc1)N1CCC2(CC1)C(=O)N(Cc1nc3cc(Cl)ccc3n1CCCC(F)(F)F)c1ccccc12] | benzyl 1-((5-chloro-1-(4,4,4-trifluorobutyl)-1H-benzo[d]-imidazol-2-yl)methyl)-2-oxospiro[indoline-3,4'-piperidine]-1'-carboxylate<br>$^1$H NMR(400 MHz, CHLOROFORM-d) δ ppm 1.75-1.91 (m, 4 H), 1.91-2.03 (m, 2 H), 2.21 (m, J = 10.4, 8.0, 8.0 Hz, 2 H), 3.84-4.01 (m, 4 H), 4.31-4.42 (m, 2 H), 5.15-5.25 (m, 4 H), 7.04-7.11 (m, 1 H), 7.20-7.30 (m, 4 H), 7.30-7.37 (m, 2 H), 7.37-7.43 (m, 3 H), 7.55 (d, J = 8.0 Hz, 1 H), 7.77 (d, J = 1.8 Hz, 1 H)<br>m/z = 612 (M + H)$^+$, Cl pattern |

| No | structure | Name/analytical details |
|---|---|---|
| 51 | 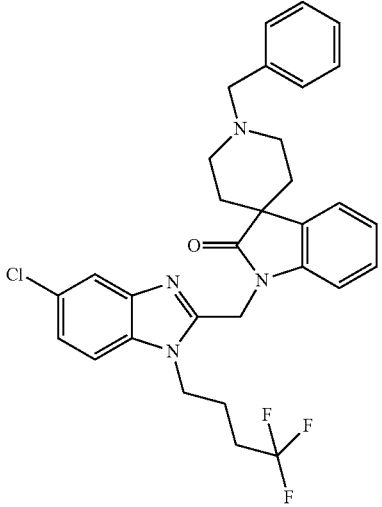 [SMILES: O=C1N(Cc2nc3cc(Cl)ccc3n2CCCC(F)(F)F)c2ccccc2C12CCN(Cc1ccccc1)CC2] | 1'-benzyl-1-((5-chloro-1-(4,4,4-trifluorobutyl)-1H-benzo[d]-imidazol-2-yl)methyl)spiro[indoline-3,4'-piperidin]-2-one<br>$^1$H NMR (400 MHz, DMSO-d$_6$) δ ppm 1.71-1.80 (m, 2 H), 1.81-1.89 (m, 2 H), 1.93 (t, J = 7.7 Hz, 2 H), 2.31-2.47 (m, 3 H), 2.58-2.69 (m, 2 H), 2.83 (m, J = 7.7, 7.7, 3.8, 3.8 Hz, 2 H), 3.63 (s, 2 H), 4.40 (t, J = 7.7 Hz, 2 H), 5.22 (s, 2 H), 7.01-7.08 (m, 1 H), 7.17-7.41 (m. 8 H), 7.53 (d, J = 1.5 Hz, 1 H), 7.65 (d, J = 2.0 Hz, 1 H), 7.67 (d, J = 8.8 Hz, 1 H); m/z = 568 (M + H)$^+$, Cl pattern |
| 52 | 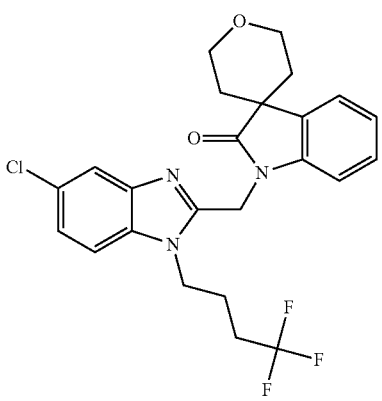 | 1-((5-chloro-1-(4,4,4-trifluorobutyl)-1H-benzo[d]imidazol-2-yl)methyl)-2',3',5',6'-tetrahydrospiro[indoline-3,4'-pyran]-2-one<br>$^1$H NMR (400 MHz, CHLOROFORM-d) δ ppm 1.87 (t, J = 5.52 Hz, 4 H), 1.91-2.02 (m, 2 H), 2.14-2.33 (m, 2 H), 3.95 (dt, J = 11.73, 4.93 Hz, 2 H), 4.24 (dt, J = 11.86, 5.99 Hz, 2 H), 4.32-4.43 (m, 2 H), 5.19 (s, 2 H), 7.04-7.14 (m, 1 H), 7.19-7.25 (m, 1 H), 7.25-7.32 (m, 2 H), 7.37 (d, J = 7.28 Hz, 1 H), 7.55 (d, J = 7.78 Hz, 1 H), 7.77 (d, J = 1.76 Hz, 1 H); m/z = 478 (M + H)$^+$,Cl pattern |
| 53 | 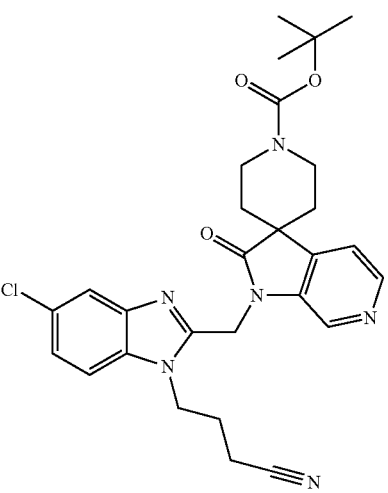 [SMILES: CC(C)(C)OC(=O)N1CCC2(CC1)C(=O)N(Cc1nc3cc(Cl)ccc3n1CCCC#N)c1cnccc12] | tert-butyl 1'-((5-chloro-1-(3-cyanopropyl)-1H-benzo[d]-imidazol-2-yl)methyl)-2'-oxo-1',2'-dihydrospiro[piperidine-4,3'-pyrrolo[2,3-c]pyridine]-1-carboxylate<br>$^1$H NMR (400 MHz, DMSO-d$_6$) δ ppm 1.44 (s, 9 H), 1.79 (m, J = 5.7, 5.7 Hz, 4 H), 2.02-2.16 (m, 2 H), 2.63 (t, J = 7.4 Hz, 2 H), 3.61-3.78 (m, 2 H), 4.39 (t, J = 7.5 Hz, 1 H), 5.30 (s, 1 H), 7.30 (dd, J = 8.6, 2.0 Hz, 1 H), 7.64 (d, J = 2.0 Hz, 1 H), 7.65 (d, J = 5.5 Hz, 1 H), 7.67 (s, 1 H), 8.32 (d, J = 4.6 Hz, 1 H), 8.47 (s, 1 H) |

| No | structure | Name/analytical details |
|---|---|---|
| 54 | 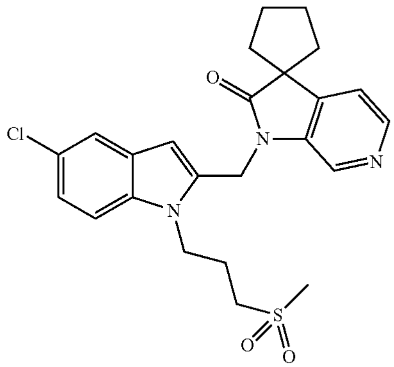 [SMILES: CS(=O)(=O)CCCn1c(CN2C(=O)C3(CCCC3)c3ccncc32)cc2cc(Cl)ccc21] | 1'-({5-chloro-1-[3-(methylsulfonyl)propyl]-1H-indol-2-yl}methyl)spiro [cyclopentane-1,3'-pyrrolo[2,3-c]pyridin]-2'(1'H)-one<br>$^1$H NMR (400 MHz, DMSO-d$_6$) δ ppm 1.81-2.16 (m, 10 H) 3.00 (s, 3 H) 3.14-3.24 (m, 2 H) 4.37 (t, J = 7.40 Hz, 2 H) 5.19 (s, 2 H) 6.37 (s, 1 H) 7.16 (dd, J = 8.78, 2.01 Hz, 1 H) 7.43 (d, J = 4.77 Hz, 1 H) 7.55 (m, J = 5.40, 3.40 Hz, 2 H) 8.31 (d, J = 4.77 Hz, 1 H) 8.34 (s, 1 H); m/z = 472.44 (M + H)$^+$ Cl pattern |
| 55 | 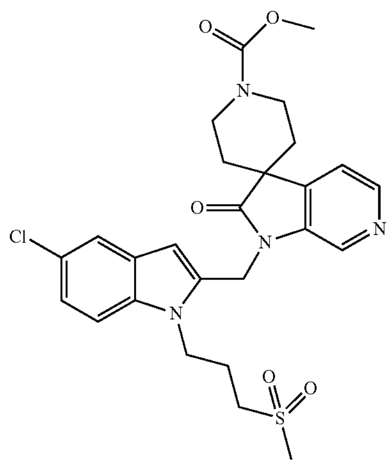 [SMILES: COC(=O)N1CCC2(CC1)C(=O)N(Cc1cc3cc(Cl)ccc3n1CCCS(C)(=O)=O)c1cnccc12] | 1'-({5-chloro-1-[3-(methylsulfonyl)propyl]-1H-indol-2-yl}-methyl)-2'-oxo-1',2'-dihydro-1H-spiro[piperidine-4,3'-pyrrolo[2,3-c]pyridine]-1-carboxylate<br>$^1$H NMR (400 MHz, DMSO-d$_6$) δ ppm 1.73-1.92 (m, 4 H) 2.03-2.15 (m, 2 H) 3.01 (s, 3 H) 3.16-3.24 (m, 2 H) 3.66 (s, 3 H) 3.70-3.85 (m, 4 H) 4.38 (t, J = 7.59 Hz, 2 H) 5.20 (s, 2 H) 6.37 (s, 1 H) 7.16 (dd, J = 8.69, 2.09 Hz, 1 H) 7.53 (d, J = 2.20 Hz, 1 H) 7.55 (d, J = 8.80 Hz, 1 H) 7.68-7.71 (m, 1 H) 8.34 (d, J = 4.84 Hz, 1 H) 8.39 (s, 1 H); m/z = 545.04 (M + H)$^+$, Cl pattern; MP = 234.28° C. |
| 56 | 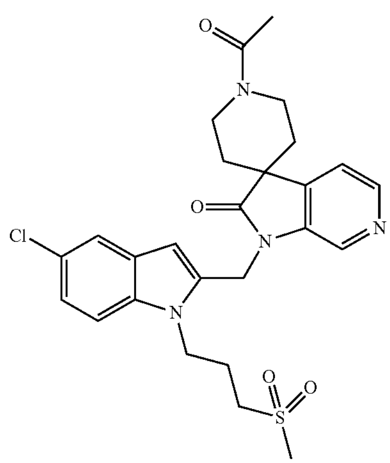 [SMILES: CC(=O)N1CCC2(CC1)C(=O)N(Cc1cc3cc(Cl)ccc3n1CCCS(C)(=O)=O)c1cnccc12] | 1-acetyl-1'-({5-chloro-1-[3-(methylsulfonyl)propyl]-1H-indol-2-yl}methyl)spiro[piperidine-4,3'-pyrrolo[2,3-c]pyridin]-2'(1'H)-one<br>$^1$H NMR (400 MHz, DMSO-d$_6$) δ ppm 1.75-1.82 (m, 2 H) 1.84-1.96 (m, 2 H) 2.04-2.17 (m, 5 H) 3.01 (s, 3 H) 3.17-3.24 (m, 2 H) 3.64-3.95 (m, 4 H) 4.38 (t, J = 7.59 Hz, 2 H) 5.21 (s, 2 H) 6.38 (s, 1 H) 7.16 (dd, J = 8.69, 2.09 Hz, 1 H) 7.53 (d, J = 1.98 Hz, 1 H) 7.56 (d, J = 8.80 Hz, 1 H) 7.68 (d, J = 4.62 Hz, 1 H) 8.34 (d, J = 4.62 Hz, 1 H) 8.39 (s, 1 H); m/z = 529.07 (M + H)$^+$, Cl pattern; MP = 258.32° C. |

-continued

| No | structure | Name/analytical details |
|---|---|---|
| 57 | 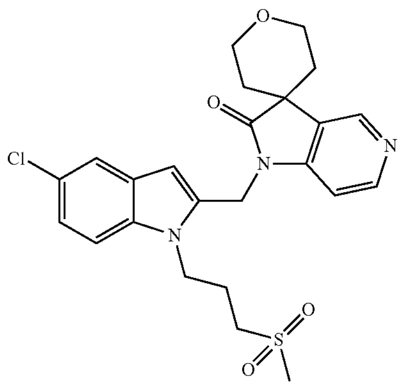 [SMILES: CS(=O)(=O)CCCn1c(CN2C(=O)C3(CCOCC3)c3cnccc32)cc2cc(Cl)ccc21] | 1'-((5-chloro)-1-(3-(methylsulfonyl)propyl)-1H-indol-2-yl)-methyl)-2,3,5,6-tetrahydrospiro[pyran-4,3'-pyrrolo[3,2-c]-pyridin]-2'(1'H)-one<br>$^1$H NMR (400 MHz, CHLOROFORM-d) δ ppm 1.85 (ddd, J = 13.64, 7.15, 3.63 Hz, 2 H), 2.01 (ddd, J = 13.59, 7.10, 3.74 Hz, 2 H), 2.31 (quin, J = 7.26 Hz, 2 H), 2.96 (s, 3 H), 3.07 (t, J = 7.15 Hz, 2 H), 3.95 (ddd, J = 11.72, 7.43, 3.74 Hz, 2 H), 4.16-4.26 (m, 2 H), 4.40 (t, J = 7.37 Hz, 2 H), 5.07 (s, 2 H), 6.37 (s, 1 H), 6.99 (d, J = 5.28 Hz, 1 H), 7.14-7.21 (m, 1 H), 7.23-7.29 (m, 1 H), 7.50 (d, J = 1.76 Hz, 1 H), 8.47 (d, J = 5.28 Hz, 1 H), 8.64 (s, 1 H); m/z = 488 (M + H)$^+$, Cl pattern |
| 58 | 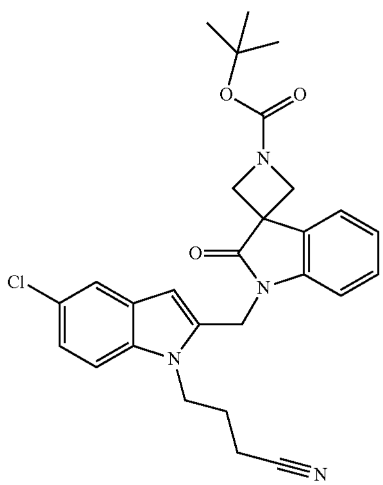 [SMILES: CC(C)(C)OC(=O)N1CC2(C1)C(=O)N(Cc1cc3cc(Cl)ccc3n1CCCC#N)c1ccccc12] | tert-butyl 1'-{[5-chloro-1-(3-cyanopropyl)-1H-indol-2-yl]-methyl}-2'-oxo-1',2'-dihydro-1H-spiro[azetidine-3,3'-indole]-1-carboxylate<br>$^1$H NMR (400 MHz, DMSO-d$_6$) δ ppm 1.45 (s, 9 H) 1.87-2.03 (m, 2 H) 2.57 (t, J = 7.37 Hz, 2 H) 4.03-4.21 (m, 4 H) 4.30 (t, J = 7.59 Hz, 2 H) 5.13 (s, 2 H) 6.36 (s, 1 H) 7.08 (d, J = 7.92 Hz, 1 H) 7.11-7.18 (m, 2 H) 7.25-7.31 (m, 1 H) 7.49-7.55 (m, 2 H) 7.68 (d, J = 6.82 Hz, 1 H); m/z = 505.42 (M + H)$^+$ Cl pattern |
| 59 | 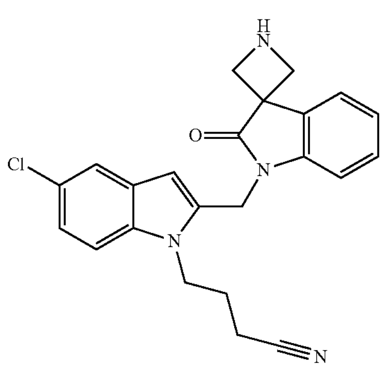 [SMILES: N#CCCCn1c(CN2C(=O)C3(CNC3)c3ccccc32)cc2cc(Cl)ccc21] | 4-{5-chloro-2-[(2'-oxospiro[azetidine-3,3'-indol]-1'(2'H )-yl)-methyl]-1H-indol-1-yl}butanenitrile<br>$^1$H NMR (400 MHz, DMSO-d$_6$) δ ppm 1.83-2.00 (m, 2 H) 2.53-2.65 (m, 2 H) 3.45 (s, 1 H) 3.51-3.85 (m, 4 H) 4.21-4.39 (m, 2 H) 5.13 (s, 2 H) 6.25-6.45 (m, 1 H) 6.99-7.20 (m, 3 H) 7.21-7.32 (m, 1 H) 7.44-7.61 (m, 2 H) 7.78 (d, J = 6.82 Hz, 1 H); m/z = 405.03 (M + H)$^+$, Cl pattern |

| No | structure | Name/analytical details |
|---|---|---|
| 60 | 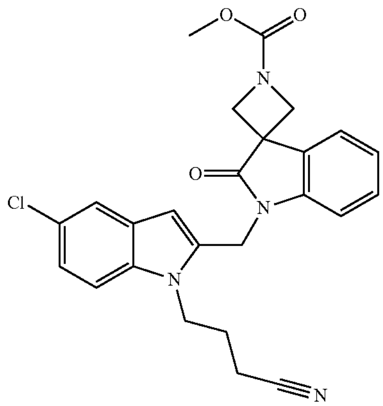 [SMILES: COC(=O)N1CC2(C1)C(=O)N(Cc1cc3cc(Cl)ccc3n1CCCC#N)c1ccccc12] | 1'-{[5-chloro-1-(3-cyanopropyl)-1H-indol-2-yl]methyl}-2'-oxo-1',2'-dihydro-1H-spiro[azetidine-3,3'-indole]-1-carboxylate<br>$^1$H NMR (400 MHz, DMSO-d6) δ ppm 1.97 (quin, J = 7.48 Hz, 2 H) 2.57 (t, J = 7.37 Hz, 2 H) 3.65 (s, 3 H) 4.11-4.36 (m, 6 H) 5.13 (s, 2 H) 6.37 (s, 1 H) 7.08 (d, J = 7.92 Hz, 1 H) 7.11-7.18 (m, 2 H) 7.29 (td, J = 7.81, 1.10 Hz, 1 H) 7.48-7.55 (m, 2 H) 7.70-7.76 (m, 1 H); m/z = 463.09 (M + H)$^+$, Cl pattern |
| 61 | 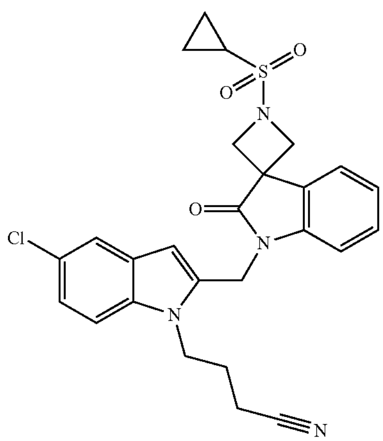 [SMILES: N#CCCCn1c(CN2C(=O)C3(CN(S(=O)(=O)C4CC4)C3)c3ccccc32)cc2cc(Cl)ccc21] | 4-(5-chloro-2-{[1-(cyclopropylsulfonyl)-2'-oxospiro-[azetidine-3,3'-indol]-1'(2'H)-yl]methyl}-1H-indol-1-yl)-butanenitrile<br>$^1$H NMR (400 MHz, DMSO-d$_6$) δ ppm 0.99-1.08 (m, 2 H) 1.12-1.20 (m, 2 H) 1.90-2.02 (m, 2 H) 2.58 (t, J = 7.26 Hz, 2 H) 2.93-3.04 (m, 1 H) 4.13-4.37 (m, 6 H) 5.13 (s, 2 H) 6.38 (s, 1 H) 7.07-7.21 (m, 3 H) 7.27-7.35 (m, 1 H) 7.48-7.55 (m, 2 H) 7.67 (d, J = 7.04 Hz, 1 H); m/z = 509.07 (M + H)$^+$, Cl pattern |
| 62 | 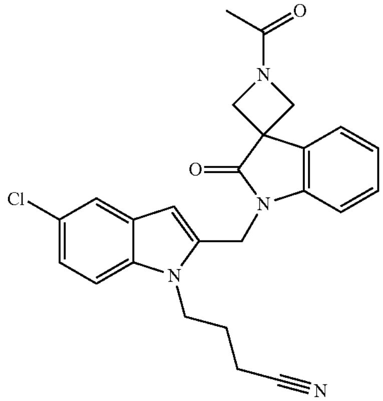 [SMILES: CC(=O)N1CC2(C1)C(=O)N(Cc1cc3cc(Cl)ccc3n1CCCC#N)c1ccccc12] | 4-{2-[(1-acetyl-2'-oxospiro[azetidine-3,3'-indol]-1'(2'H)-yl)-methyl]-5-chloro-1H-indol-l-yl}butanenitrile<br>$^1$H NMR (400 MHz, DMSO-d$_6$) δ ppm 1.88 (s, 3 H) 1.91-2.03 (m, 2 H) 2.58 (t, J = 7.48 Hz, 2 H) 4.03-4.19 (m, 2 H) 4.31 (t, J = 7.59 Hz, 2 H) 4.37-4.47 (m, 2 H) 5.14 (s, 2 H) 6.37 (s, 1 H) 7.05-7.19 (m, 3 H) 7.29 (td, J = 7.70, 1.10 Hz, 1 H) 7.48-7.56 (m, 2 H) 7.71 (dd, J = 6.82, 0.70 Hz, 1 H); m/z = 447.42 (M + H)$^+$, Cl pattern; MP = 195.25° C. |

-continued

| No | structure | Name/analytical details |
|---|---|---|
| 63 | 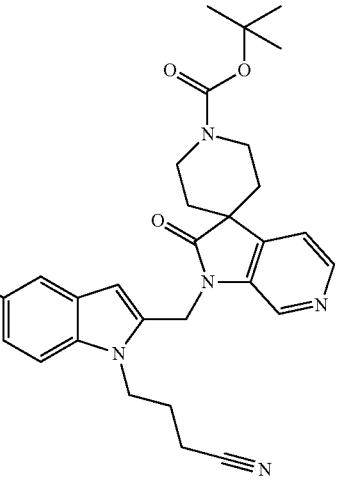 | tert-butyl 1'-((5-chloro-1-(3-cyanopropyl)-1H-indol-2-yl)-methyl)-2'-oxo-1',2'-dihydrospiro[piperidine-4,3'-pyrrolo-[2,3-c]pyridine]-1-carboxylate<br>$^1$H NMR (400 MHz, DMSO-$d_6$) δ ppm 1.45 (s, 9 H) 1.80 (t, J = 5.61 Hz, 4H) 1.92-2.04 (m, 2 H) 2.58 (t, J = 7.26 Hz, 2 H) 3.58-3.82 (m, 4 H) 4.29 (t, J = 7.59 Hz, 2 H) 5.20 (s, 2 H) 6.36 (s, 1 H) 7.10-7.18 (m, 1 H) 7.48-7.57 (m, 2 H) 7.69 (d, J = 4.62 Hz, 1 H) 8.33 (d, J = 4.84 Hz, 1 H) 8.39 (s, 1 H); m/z = 534 (M + H)$^+$ |
| 64 | 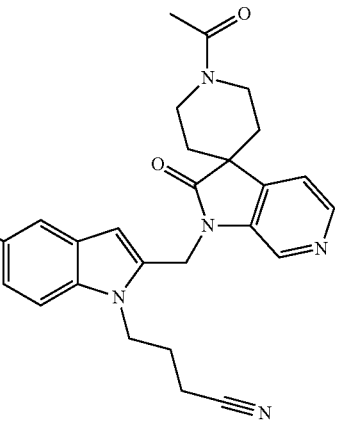 | 4-(2-((1-acetyl-2'-oxospiro[piperidine-4,3'-pyrrolo[2,3-c]-pyridin]-1'(2'H)-yl)methyl)-5-chloro-1H-indol-1-yl)butane-nitrile<br>$^1$H NMR (400 MHz, DMSO-$d_6$) δ ppm 1.71-1.82 (m, 2 H) 1.83-1.93 (m, 2 H) 1.99 (t, J = 7.48 Hz, 2 H) 2.09 (s, 3 H) 2.59 (t, J = 7.37 Hz, 2 H) 3.60-3.96 (m, 4 H) 4.20-4.37 (m, 2 H) 5.20 (s, 2 H) 6.36 (s, 1 H) 7.09-7.19 (m, 1 H) 7.46-7.57 (m, 2 H) 7.68 (d, J = 4.62 Hz, 1 H) 8.34 (d, J = 4.62 Hz, 1 H) 8.39 (s, 1 H)<br>m/z = 476 (M + H)$^+$ |
| 65 | 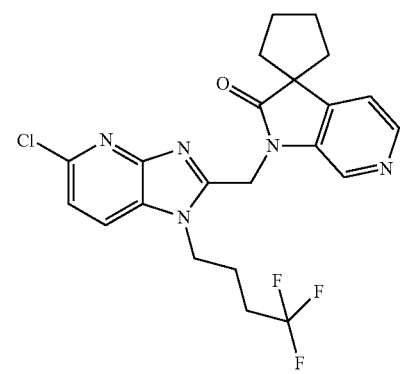 [SMILES: O=C1N(Cc2nc3nc(Cl)ccc3n2CCCC(F)(F)F)c2cnccc2C12CCCC2] | 1'-((5-chloro-1-(4,4,4-trifluorobutyl)-1H-imidazo[4,5-b]-pyridin-2-yl)methyl)spiro[cyclopentane-1,3'-pyrrolo[2,3-c]-pyridin]-2'(1'H)-one<br>$^1$H NMR (400 MHz, CHLOROFORM-d) δ ppm 1.81-1.92 (m, 2 H), 1.94-2.06 (m, 4 H), 2.07-2.32 (m, 7 H), 4.39-4.47 (m, 2 H), 5.26 (s, 2 H), 7.12 (dd, J = 4.8, 1.0 Hz, 1 H), 7.27 (d, J = 8.5 Hz, 1 H), 7.62 (d, J = 8.3 Hz, 1 H), 8.40 (d, J = 4.8 Hz, 1 H), 8.83 (d, J = 0.5 Hz, 1 H); m/z = 464 (M + H)$^+$ |

| No | structure | Name/analytical details |
|---|---|---|
| 66 | 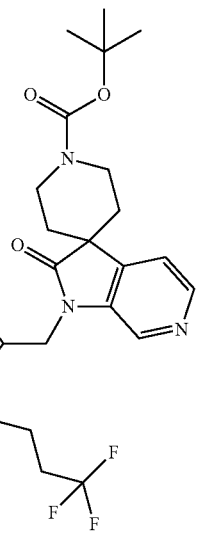 | tert-butyl-2'-oxo-1'-((1-(4,4,4-trifluorobutyl)-1H-imidazo-[4,5-b]pyridine-2-yl)methyl)-1',2'-dihydrospiro[piperidine-4,3'-pyrrolo[2,3-c]pyridine]-1-carboxylate<br>$^1$H NMR (400 MHz, DMSO-d$_6$) δ ppm 1.44 (s, 9 H) 1.79 (t, J = 5.61 Hz, 4 H) 1.94-2.11 (m, 2 H) 2.34-2.46 (m, 2 H) 3.51-3.83 (m, 4 H) 4.45 (t, J = 7.59 Hz, 2 H) 5.35 (s, 2 H) 7.28 (dd, J = 8.03, 4.73 Hz, 1 H) 7.69 (d, J = 4.84 Hz, 1 H) 8.11 (dd, J = 8.14, 1.32 Hz, 1 H) 8.34 (d, J = 4.84 Hz, 1 H) 8.37 (dd, J = 4.62, 1.32 Hz, 1 H) 8.52 (s, 1 H); m/z = 476 (M + H)$^+$ |
| 67 | 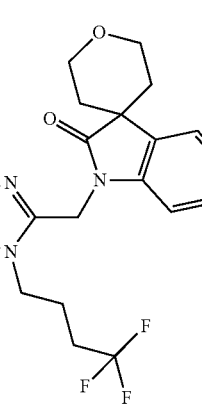 | 1'-((5-chloro-1-(4,4,4-trifluorobutyl)-1H-imidazo[4,5-b]-pyridin-2-yl)methyl)-2,3,5,6-tetrahydrospiro[pyran-4,3'-pyrrolo[2,3-c]pyridine]-2'(1'H)-one<br>$^1$H NMR (400 MHz, DMSO-d$_6$) δ ppm 1.69-1.89 (m, 4 H) 1.92-2.08 (m, 2 H) 2.28-2.45 (m, 2 H) 3.75-3.91 (m, 2 H) 3.96-4.09 (m, 2 H) 4.45 (t, J = 7.59 Hz, 2 H) 5.34 (s, 2 H) 7.36 (d, J = 8.36 Hz, 1 H) 7.70 (dd, J = 4.73, 0.55 Hz, 1 H) 8.19 (d, J = 8.36 Hz, 1 H) 8.35 (d, J = 4.84 Hz, 1 H) 8.46 (s, 1 H); m/z = 480 (M + H)$^+$ |
| 68 | 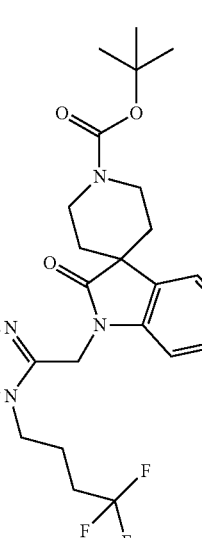 | tert-butyl-1'-((5-chloro-1-(4,4,4-trifluorobutyl)-1H-imidazo-[4,5-b]pyridine-2-yl)methyl)-2'-oxo-1',2'-dihydrospiro-[piperidine-4,3'-pyrrolo[2,3-c]pyridine]-1-carboxylate<br>$^1$H NMR(400 MHz, CHLOROFORM-d) δ ppm 1.51 (s, 9 H), 1.72-1.82 (m, 2 H), 1.82-1.92 (m, 2 H), 1.97-2.10 (m, 2 H), 2.19-2.36 (m, 2 H), 3.67-3.80 (m, 2 H), 3.80-3.91 (m, 2 H), 4.44 (t, J = 7.90 Hz, 2 H), 5.24 (s, 2 H), 7.24 (dd, J = 4.84, 0.66 Hz, 1 H), 7.27 (d, J = 8.36 Hz, 1 H), 7.63 (d, J = 8.58 Hz, 1 H), 8.42 (d, J = 4.84 Hz, 1 H), 8.84 (s, 1 H); m/z = 480 (M + H)$^+$, Cl pattern |

| No | structure | Name/analytical details |
|---|---|---|
| 69 | 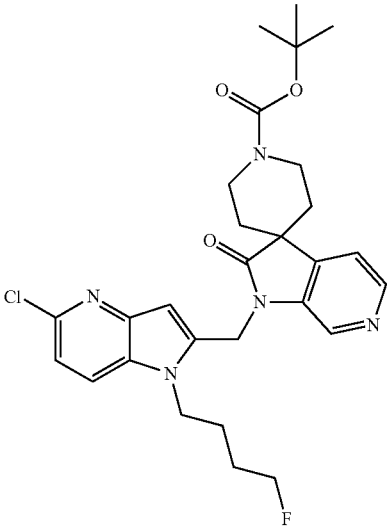 [SMILES: CC(C)(C)OC(=O)N1CCC2(CC1)C(=O)N(Cc1cc3nc(Cl)ccc3n1CCCCF)c1cnccc12] | tert-butyl 1'-((5-chloro-1-(4-fluorobutyl)-1H-pyrrolo[3,2-b]-pyridin-2-yl)methy)-2'-oxo-1',2'-dihydrospiro[piperidine-4,3'-pyrrolo[2,3-c]pyridine]-1-carboxylate<br>$^1$H NMR (400 MHz, CHLOROFORM-d) δ ppm 1.51 (s, 9 H), 1.68-1.95 (m, 8 H), 3.69-3.82 (m, 2 H), 3.83-3.93 (m, 2 H), 4.20-4.29 (m, 2 H), 4.43 (t, J = 5.61 Hz, 1 H), 4.55 (t, J = 5.50 Hz, 1 H), 5.13 (s, 2 H), 6.61 (s, 1 H), 7.12 (d, J = 8.58 Hz, 1 H), 7.27 (d, J = 0.66 Hz, 1 H), 7.55 (dd, J = 8.58, 0.66 Hz, 1 H), 8.33 (s, 1 H), 8.40 (d, J = 4.84 Hz, 1 H); m/z = 542 (M + H)$^+$, Cl pattern |
| 70 | 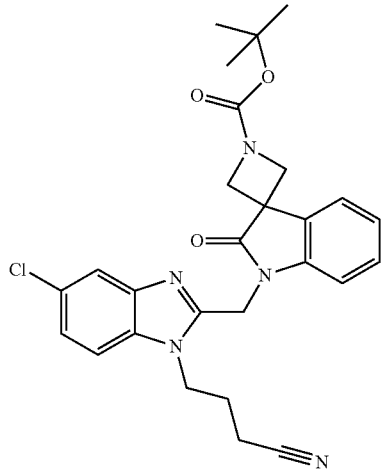 [SMILES: CC(C)(C)OC(=O)N1CC2(C1)C(=O)N(Cc1nc3cc(Cl)ccc3n1CCCC#N)c1ccccc12] | tert-butyl 1'-((5-chloro-1-(3-cyanopropyl)-1H-benzo[d]-imidazol-2-yl)methyl)-2'-oxospiro[azetidine-3,3'-indoline]-1-carboxylate<br>1H NMR (400 MHz, DMSO-d$_6$) δ ppm 1.44 (s, 9 H) 2.06 (quin, J = 7.48 Hz, 2 H) 2.62 (t, J = 7.37 Hz, 2 H) 3.97-4.23 (m, 4 H) 4.39 (t, J = 7.48 Hz, 2 H) 5.22 (s, 2 H) 7.08-7.22 (m, 2 H) 7.26-7.36 (m, 2 H) 7.60-7.73 (m, 3 H)<br>m/z = 506.14 (M + H) + Cl pattern; MP: 144.10° C. |
| 71 | 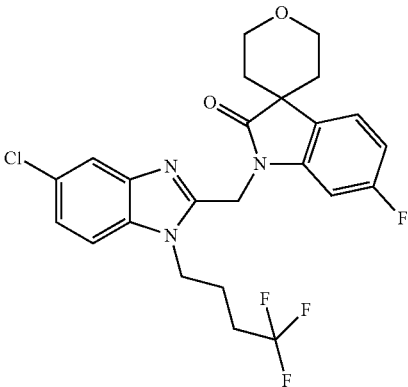 [SMILES: O=C1N(Cc2nc3cc(Cl)ccc3n2CCCC(F)(F)F)c2cc(F)ccc2C12CCOCC2] | 1-((5-chloro-1-(4,4,4-trifluorobutyl)-1H-benzo[d]imidazol-2-yl)methyl)-6-fluoro-2',3',5',6'-tetrahydrospiro[indoline-3,4'-pyran]-2-one<br>1H NMR(400 MHz, DMSO-d$_6$) δ ppm 1.68-1.89 (m, 4 H) 1.90-2.04 (m, 2 H) 2.34-2.47 (m, 2 H) 3.78-3.87 (m, 2 H) 3.99-4.13 (m, 2 H) 4.41 (t, J = 7.48 Hz 2 H) 5.23 (s, 2 H) 6.80-6.91 (m, 1 H) 7.16 (dd, J = 9.46, 2.20 Hz, 1 H) 7.30 (dd, J = 8.58, 1.76 Hz, 1 H) 7.59 (dd, J = 8.14, 5.50 Hz, 1 H) 7.66 (d, J = 1.76 Hz, 1 H) 7.68 (d, J = 8.58 Hz, 1 H); m/z = 496.11 (M + H) + Cl pattern; MP = 172.70° C. |

| No | structure | Name/analytical details |
|---|---|---|
| 72 | 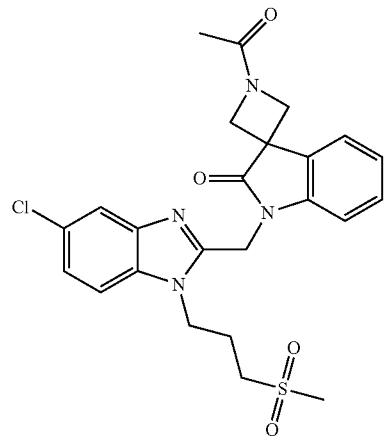 [SMILES: CC(=O)N1CC2(C1)C(=O)N(Cc1nc3cc(Cl)ccc3n1CCCS(C)(=O)=O)c1ccccc12] | 1-acetyl-1'-((5-chloro-1-(3-(methylsulfonyl)propyl)-1H-benzo[d]imidazol-2-yl)methyl)spiro[azetidine-3,3'-indolin]-2'-one<br>1H NMR (400 MHz, DMSO-$d_6$) δ ppm 1.87 (s, 3 H) 2.08-2.23 (m, 2 H) 3.00 (s, 3 H) 3.19-3.27 (m, 2 H) 4.03-4.18 (m, 2 H) 4.36-4.44 (m, 2 H) 4.47 (t, J = 7.48 Hz, 2 H) 5.13-5.35 (m, 2 H) 7.09-7.17 (m, 1 H) 7.20 (d, J = 7.48 Hz, 1 H) 7.25-7.36 (m, 2 H) 7.64-7.74 (m, 3 H); m/z = 501.03 (M + H) + Cl pattern;<br>MP = 226.51° C. |
| 73 | 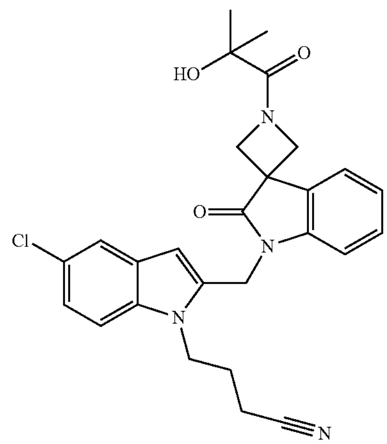 [SMILES: CC(C)(O)C(=O)N1CC2(C1)C(=O)N(Cc1cc3cc(Cl)ccc3n1CCCC#N)c1ccccc12] | 4-(5-chloro-2-((1-(2-hydroxy-2-methylpropanoyl)-2'-oxospiro[azetidine-3,3'-indolin]-1'-yl)methyl)-1H-indol-1-yl)butanenitrile<br>1H NMR (400 MHz, DMSO-$d_6$) δ ppm 1.32 (s, 3 H) 1.34 (s, 3 H) 1.98 (quin, J = 7.21 Hz, 2 H) 2.57 (t, J = 7.26 Hz, 2 H) 4.07 (d, J = 9.46 Hz, 1 H) 4.18 (d, J = 9.46 Hz, 1 H) 4.31 (t, J = 7.37 Hz, 2 H) 4.60 (d, J = 9.68 Hz, 1 H), 4.73 (d, J = 9.68 Hz, 1 H) 5.14 (s, 2 H) 5.27 (s, 1 H) 6.34 (s, 1 H) 7.08 (d, J = 7.70 Hz, 1 H) 7.11-7.20 (m, 2 H) 7.24-7.34 (m, 1 H) 7.46-7.56 (m, 2 H) 7.64 (d, J = 7.26 Hz, 1 H); m/z = 491.13 (M + H) + Cl pattern; MP = 89.86° C. |
| 74 | 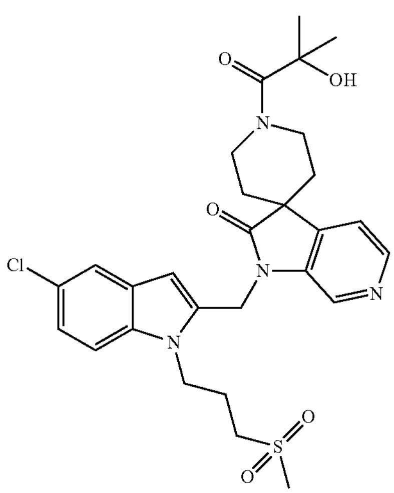 [SMILES: CC(C)(O)C(=O)N1CCC2(CC1)C(=O)N(Cc1cc3cc(Cl)ccc3n1CCCS(C)(=O)=O)c1cnccc12] | 1'-((5-chloro-1-(3-(methylsulfonyl)propyl)-1H-indol-2-yl)methyl)-1-(2-hydroxy-2-methylpropanoyl)spiro[piperidine-4,3'-pyrrolo[2,3-c]pyridin]-2'(1'H)-one<br>1H NMR (400 MHz, DMSO-$d_6$ δ ppm 1.38 (s, 6 H) 1.72-1.97 (m, 4 H) 2.03-2.16 (m, 2 H) 3.01 (s, 3 H) 3.15-3.25 (m, 2 H) 3.69-4.04 (m, 2 H) 4.07-4.33 (m, 2 H) 4.38 (t, J = 7.59 Hz, 2H) 5.21 (s, 2 H) 5.49 (s, 1 H) 6.37 (s, 1 H) 7.16 (dd, J = 8.69, 2.09 Hz, 1 H) 7.53 (d, J = 1.98 Hz, 1 H) 7.56 (d,<br>J = 8.80 Hz, 1 H) 7.68 (d, J = 4.62 Hz, 1 H) 8.35 (d, J = 4.84 Hz,<br>1 H) 8.40 (s, 1 H); m/z = 573.08 (M + H) + Cl pattern |

| No | structure | Name/analytical details |
|---|---|---|
| 75 | 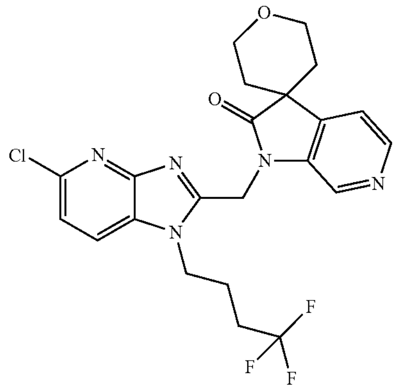 [SMILES: O=C1N(Cc2nc3nc(Cl)ccc3n2CCCC(F)(F)F)c2cnccc2C12CCOCC2] | 1'-((5-chloro-1-(4,4,4-trifluorobutyl)-1H-imidazo[4,5-b]-pyridin-2-yl)methyl)-2,3,5,6-tetrahydrospiro[pyran-4,3'-pyrrolo[2,3-c]pyridin]-2'(1'H)-one<br>$^1$H NMR (400 MHz, DMSO-d$_6$) δ ppm 1.69-1.89 (m, 4 H) 1.92-2.08 (m, 2 H) 2.28-2.45 (m, 2 H) 3.75-3.91 (m, 2 H) 3.96-4.09 (m, 2 H) 4.45 (t, J = 7.59 Hz, 2 H) 5.34 (s, 2 H) 7.36 (d, J = 8.36 Hz, 1 H) 7.70 (dd, J = 4.73, 0.55 Hz, 1 H) 8.19 (d, J = 8.36 Hz, 1 H) 8.35 (d, J = 4.84 Hz, 1 H) 8.46 (s, 1 H); m/z = 480 (M + H) + Cl pattern: MP = 188.67° C. |
| 76 | 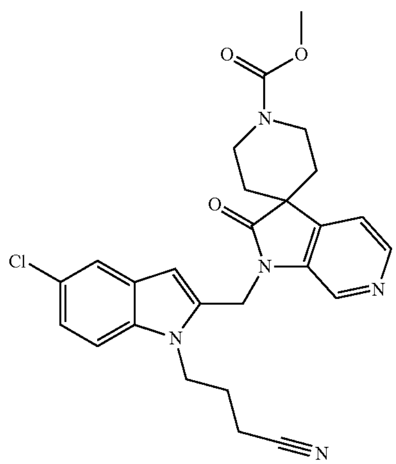 [SMILES: COC(=O)N1CCC2(CC1)C(=O)N(Cc1cc3cc(Cl)ccc3n1CCCC#N)c1cnccc12] | methyl 1'-(5-chloro-1-(3-cyanopropyl)-1H-indol-2-yl)-methy)-2'-oxo-1',2'-dihydrospiro[piperidine-4,3'-pyrrolo-[2,3-c]pyridine]-1-carboxylate<br>$^1$H NMR (400 MHz, DMSO-d$_6$) δ ppm 1.71-1.90 (m, 4 H) 1.98 (dt, J = 14.96, 7.48 Hz, 2 H) 2.58 (t, J = 7.37 Hz, 2 H) 3.66 (s, 3 H) 3.69-3.84 (m, 4 H) 4.21-4.34 (m, 2 H) 5.19 (s, 2 H) 6.36 (s, 1 H) 7.08-7.18 (m, 1 H) 7.48-7.57 (m, 2 H) 7.70 (d, J = 4.18 Hz, 1 H) 8.34 (d, J = 4.84 Hz, 1 H) 8.39 (s, 1 H); m/z = 492 (M + H) + Cl pattern |
| 77 | 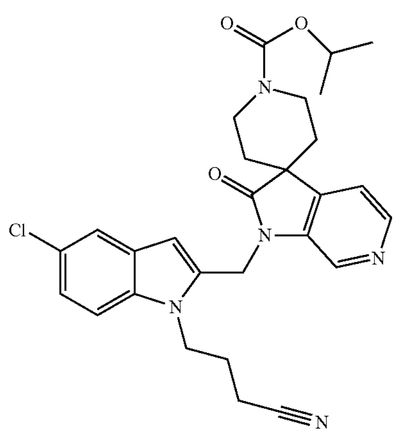 [SMILES: CC(C)OC(=O)N1CCC2(CC1)C(=O)N(Cc1cc3cc(Cl)ccc3n1CCCC#N)c1cnccc12] | isopropyl 1'-((5-chloro-1-(3-cyanopropyl)-1H-indol-2-yl)-methyl)-2'-oxo-1',2'-dihydrospiro[piperidine-4,3'-pyrrolo-[2,3-c]pyridine]-1-carboxylate<br>$^1$H NMR (400 MHz, DMSO-d$_6$) δ ppm 1.23 (d, J = 6.38 Hz, 6 H) 1.69-1.90 (m, 4 H) 1.92-2.05 (m, 2 H) 2.58 (t, J = 7.90 Hz, 2 H) 3.57-3.90 (m, 4 H) 4.15-4.40 (m, 2 H) 4.72-4.91 (m, 1 H) 5.20 (s, 2 H) 6.36 (s, 1 H) 7.09-7.20 (m, 1 H) 7.49-7.57 (m, 2 H) 7.71 (d, J = 5.06 Hz, 1 H) 8.34 (d, J = 4.84 Hz, 1 H) 8.39 (s, 1 H); m/z = 520 (M + H) + Cl pattern |

| No | structure | Name/analytical details |
|----|-----------|------------------------|
| 78 | 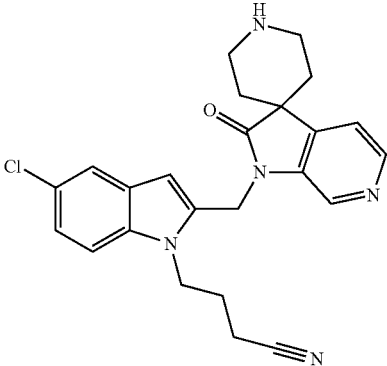 [SMILES: N#CCCCn1c(CN2C(=O)C3(CCNCC3)c3ccncc32)cc2cc(Cl)ccc21] | 4-(5-chloro-2-((2'-oxospiro[piperidine-4,3'-pyrrolo[2,3-c]-pyridin]-1'(2'H)-yl)methyl)-1H-indol-1-yl)butanenitrile hydrochloride<br>$^1$H NMR (400 MHz, DMSO-d$_6$) δ ppm 1.97-2.12 (m, 4 H) 2.16-2.30 (m, 2 H) 2.52-2.58 (m, 2 H) 3.27-3.42 (m, 2 H) 3.47-3.64 (m, 2 H) 4.29 (t, J = 7.70 Hz, 2 H) 5.19 (s, 2 H) 6.17-6.51 (m, 1 H) 7.13 (dd, J = 8.58, 2.20 Hz, 1 H) 7.38-7.63 (m, 3 H) 8.38 (s, 1 H) 8.42 (d, J = 5.06 Hz, 1 H) 9.08 (br. s, 2 H); m/z = 434 (M + H) + Cl pattern; MP = 82.02° C. |
| 79 | 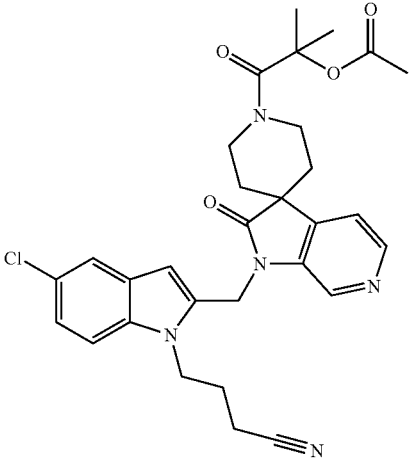 [SMILES: CC(=O)OC(C)(C)C(=O)N1CCC2(CC1)C(=O)N(Cc1cc3cc(Cl)ccc3n1CCCC#N)c1cnccc12] | 1-(1'-((5-chloro-1-(3-cyanopropyl)-1H-indol-2-yl)methyl)-2'-oxo-1',2'-dihydrospiro[piperidine-4,3'-pyrrolo[2,3-c]pyridin]-1-yl)-2-methyl-1-oxopropan-2-yl acetate<br>$^1$H NMR (360 MHz, DMSO-d$_6$) δ ppm 1.55 (s, 6 H), 1.80 (br. s., 4 H), 1.91-2.04 (m, 2 H), 2.08 (s, 3 H), 2.59 (t, J = 7.3 Hz, 2 H), 3.93 (br. s., 4 H), 4.29 (t, J = 7.7 Hz, 2 H), 5.20 (s, 2 H), 6.37 (s, 1 H), 7.16 (dd, J = 8.6, 2.0 Hz, 1 H), 7.47-7.60 (m, 2 H), 7.65 (d, J = 4.8 Hz, 1 H), 8.23-8.50 (m, 2 H); m/z = 562 (M + H) + Cl patten |
| 80 | 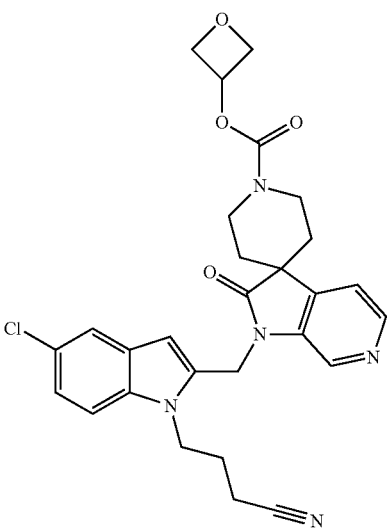 [SMILES: N#CCCCn1c(CN2C(=O)C3(CCN(C(=O)OC4COC4)CC3)c3ccncc32)cc2cc(Cl)ccc21] | oxetan-3-yl 1'-((5-chloro-1-(3-cyanopropyl)-1H-indol-2-yl)-methyl)-2'-oxo-1',2'-dihydro[spiropiperidine-4,3'-pyrrolo-[2,3-c]pyridine]-1-carboxylate<br>$^1$H NMR (400 MHz, DMSO-d$_6$) δ ppm 1.84 (br. s., 4H) 1.99 (quin, J = 7.54 Hz, 2 H) 2.59 (t, J = 7.37 Hz, 2 H) 3.60-3.97 (m, 4 H) 4.21-4.35 (m, 2 H) 4.48-4.60 (m, 2 H) 4.80 (t, J = 7.04 Hz, 2 H) 5.20 (s, 2 H) 5.31-5.40 (m, 1 H) 6.37 (s, 1 H) 7.15 (dd, J = 8.80, 2.42 Hz, 1 H) 7.48-7.56 (m, 2 H) 7.71 (d, J = 4.84 Hz, 1 H) 8.34 (d, J = 4.84 Hz, 1 H) 8.39 (s, 1 H); m/z = 534 (M + H) + Cl pattern; MP = 208.24° C. |

| No | structure | Name/analytical details |
|---|---|---|
| 81 | 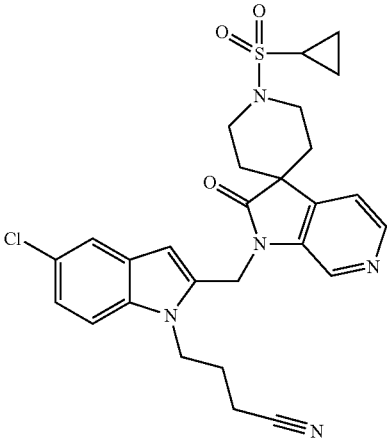 [SMILES: N#CCCCn1c(CN2C(=O)C3(CCN(S(=O)(=O)C4CC4)CC3)c3ccncc32)cc2cc(Cl)ccc21] | 4-(5-chloro-2-((1-(cyclopropylsulfonyl)-2'-oxospiro-[piperidine-4,3'-pyrrolo[2,3-c]pyridin]-1'(2'H)-yl)methyl)-1H-indol-1-yl)butanenitrile<br>$^1$H NMR (360 MHz, DMSO-d$_6$) δ ppm 0.94-1.11 (m, 4 H), 1.86-2.11 (m, 6 H), 2.59 (t, J = 1.1 Hz, 2 H), 2.69-2.82 (m, 1 H), 3.46-3.60 (m, 2 H), 3.61-3.76 (m, 2 H), 4.20-4.39 (m, 2 H), 5.20 (s, 2 H), 6.37 (s, 1 H), 7.10-7.20 (m, 1 H), 7.49-7.58 (m, 2 H), 7.66 (d, J = 4.4 Hz, 1 H), 8.31-8.44 (m, 2 H); m/z = 538 (M + H) + Cl pattern; MP = 93.04° C. |
| 82 | 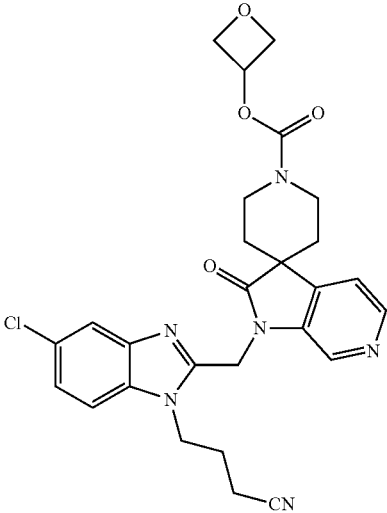 [SMILES: N#CCCCn1c(CN2C(=O)C3(CCN(C(=O)OC4COC4)CC3)c3ccncc32)nc2cc(Cl)ccc21] | oxetan-3-yl 1'-((5-chloro-1-(3-cyanopropyl)-1H-benzo[d]-imidazol-2-yl)methyl)-2'-oxo-1',2'-dihydrospiro[piperidine-4,3'-pyrrolo[2,3-c]pyridine]-1-carboxylate<br>$^1$H NMR (400 MHz, DMSO-d$_6$) δ ppm 1.84 (d, J = 13.4 Hz, 4 H), 2.02-2.19 (m, 2 H), 2.63 (t, J = 7.4 Hz, 2 H), 3.65-3.93 (m, 4 H), 4.39 (t, J = 7.5 Hz, 2 H), 4.48-4.60 (m, 2 H), 4.79 (t, J = 7.0 Hz, 2 H), 5.30 (s, 2 H), 5.32-5.40 (m, 1 H), 7.30 (dd, J = 8.6, 2.0 Hz, 1 H), 7.59-7.73 (m, 3 H), 8.34 (d, J = 4.6 Hz, 1 H), 8.47 (s, 1 H); m/z = 535 (M + H) + Cl pattern; MP = 203.41° C. |
| 83 | 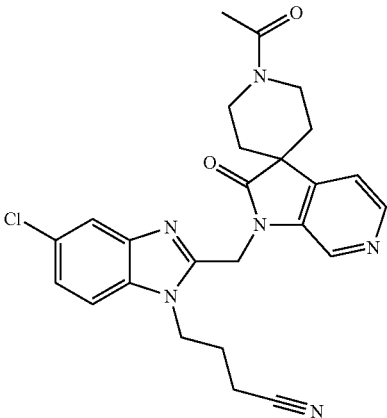 [SMILES: CC(=O)N1CCC2(CC1)C(=O)N(Cc1nc3cc(Cl)ccc3n1CCCC#N)c1cnccc12] | 4-(2-((1-acetyl-2'-oxospiro[piperidine-4,3'-pyrrolo[2,3-c]-pyridin]-1'(2'H)-yl)methyl)-5-chloro-1H-benzo[d]imidazol-1-yl)butanenitrile<br>$^1$H NMR (400 MHz, DMSO-d$_6$) δ ppm 1.71-1.82 (m, 2 H), 1.82-1.95 (m, 2 H), 2.08 (s, 3 H), 2.09-2.15 (m, 2 H), 2.63 (t, J = 7.4 Hz, 2 H), 3.67-3.79 (m, 2 H), 3.80-3.94 (m, 2 H), 4.39 (t, J = 7.6 Hz, 2 H), 5.30 (s, 2 H), 7.30 (dd, J = 8.6, 2.0 Hz, 1 H), 7.62-7.69 (m, 3 H), 8.33 (d, J = 4.6 Hz, 1 H), 8.47 (s, 1 H); m/z = 477 (M + H) + Cl pattern; MP = 223.53° C. |

| No | structure | Name/analytical details |
|---|---|---|
| 84 | 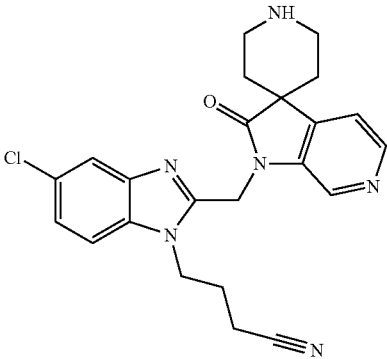 [SMILES: N#CCCCn1c(CN2C(=O)C3(CCNCC3)c3ccncc32)nc2cc(Cl)ccc21] | 4-(5-chloro)-2-((2'-oxospiro[piperidine-4,3'-pyrrolo[2,3-c]-pyridin]-1'(2'H)-yl)methyl)-1H-benzo[d]imidazol-1-yl)butanenitrile hydrochloride<br>$^1$H NMR (400 MHz, DMSO-d$_6$) δ ppm 2.15-2.35 (m, 4 H), 2.41-2.48 (m, 2 H), 2.74 (t, J = 7.3 Hz, 2 H), 3.41 (br. s., 4 H), 4.53 (t, J = 7.0 Hz, 2 H), 5.22 (br. s., 10 H), 5.62 (br. s., 3 H), 7.49 (dd, J = 8.6, 1.8 Hz, 1 H), 7.71 (d, J = 1.8 Hz, 1 H), 7.93 (d, J = 8.6 Hz, 1 H), 8.14 (d, J = 5.3 Hz, 1 H), 8.77 (d, J = 5.3 Hz, 1 H), 9.00 (s, 1 H), 9.67 (br. s., 2 H); m/z = 435 (M + H) + Cl pattern |
| 85 | 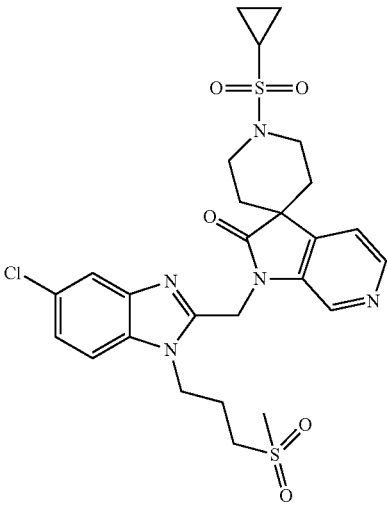 [SMILES: CS(=O)(=O)CCCn1c(CN2C(=O)C3(CCN(S(=O)(=O)C4CC4)CC3)c3ccncc32)nc2cc(Cl)ccc21] | 1'-((5-chloro-1-(3-(methylsulfonyl)propyl)-1H-benzo[d]-imidazol-2-yl)methyl)-1-(cyclopropylsulfonyl)spiro-[piperidine-4,3'-pyrrolo[2,3-c]pyridin]-2'(1'H)-one<br>$^1$H NMR (400 MHz, DMSO-d$_6$) δ ppm 0.93-1.01 (m, 2 H) 1.01-1.08 (m, 2 H) 1.86-1.95 (m, 2 H) 1.97-2.07 (m, 2 H) 2.13-2.26 (m, 2 H) 2.67-2.78 (m, 1 H) 3.02 (s, 3 H) 3.22-3.29 (m, 2 H) 3.47-3.58 (m, 2 H) 3.60-3.70 (m, 2 H) 4.48 (t, J = 7.48 Hz, 2 H) 5.30 (s, 2 H) 7.31 (dd, J = 8.58, 1.98 Hz, 1 H) 7.64 (d, J = 4.84 Hz, 1 H) 7.65 (d, J = 1.76 Hz, 1 H) 7.68 (d, J = 8.58 Hz, 1 H) 8.36 (d, J = 4.84 Hz, 1 H) 8.50 (s, 1 H); m/z = 592 (M + H) + Cl pattern; MP = 150.42° C. |
| 86 | 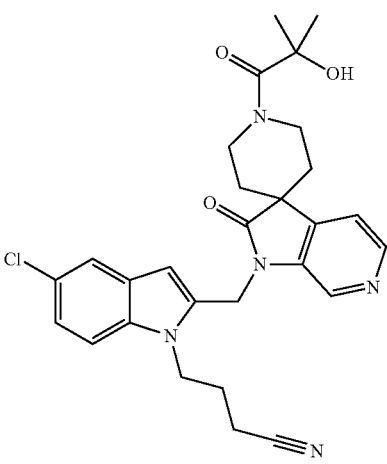 [SMILES: CC(C)(O)C(=O)N1CCC2(CC1)C(=O)N(Cc1cc3cc(Cl)ccc3n1CCCC#N)c1cnccc12] | 4-(5-chloro-2-((1-(2-hydroxy-2-methylpropanoyl)-2'-oxospiro[piperidine-4,3'-pyrrolo[2,3-c]pyridin]-1'(2'H)-yl)methyl)-1H-indol-1-yl)butanenitrile<br>$^1$H NMR (360 MHz, DMSO-d$_6$) δ ppm 1.37 (s, 6 H), 1.71-1.90 (m, 4 H), 1.90-2.08 (m, 2 H), 2.59 (t, J = 7.3 Hz, 2 H), 4.09-4.43 (m, 4 H), 5.21 (s, 2 H), 5.51 (s, 1 H), 6.36 (s, 1 H), 7.15 (m, J = 10.6 Hz, 1 H), 7.48-7.59 (m, 2 H), 7.69 (d, J = 4.8 Hz, 1 H), 8.35 (d, J = 4.8 Hz, 1 H), 8.41 (s, 1 H); m/z = 520 (M + H) + Cl pattern |

| No | structure | Name/analytical details |
|---|---|---|
| 87 | 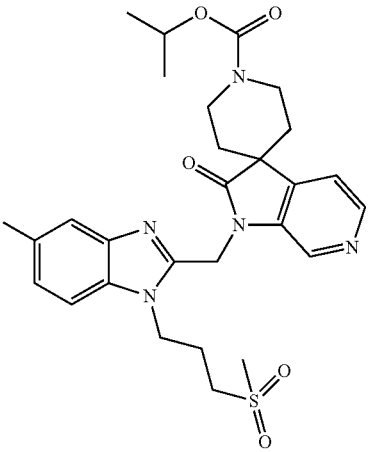 | isopropyl 1'-((5-chloro-1-(3-(methylsulfonyl)propyl)-1H-benzo[d]imidazol-2-yl)methyl)-2'-oxo-1',2'-dihydrospiro-[piperidine-4,3'-pyrrolo[2,3-c]pyridine]-1-carboxylate<br>¹H NMR (400 MHz, DMSO-d₆) δ ppm 1.23 (d, J = 6.16 Hz, 6 H) 1.65-1.90 (m, 4 H) 2.19 (quin, J = 7.59 Hz, 2 H) 3.02 (s, 3 H) 3.18-3.30 (m, 2 H) 3.62-3.83 (m, 4 H) 4.48 (t, J = 7.48 Hz, 2 H) 4.84 (quin, J = 6.22 Hz, 1 H) 5.31 (s, 2 H) 7.31 (dd, J = 8.58, 1.98 Hz, 1 H) 7.64-7.68 (m, 2 H) 7.69 (d, J = 2.42 Hz, 1 H) 8.33 (d, J = 4.84 Hz, 1 H) 8.49 (s, 1 H); m/z = 574 (M + H) + Cl pattern |
| 88 | 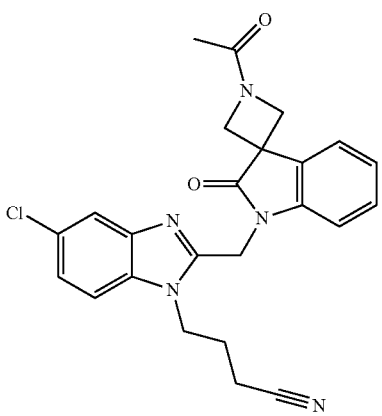 [SMILES: CC(=O)N1CC2(C1)C(=O)N(Cc1nc3cc(Cl)ccc3n1CCCC#N)c1ccccc12] | 4-(2-((1-acetyl-2'-oxospiro[azetidine-3,3'-indolin]-1'-yl)-methyl)-5-chloro-1H-benzo[d]imidazol-1-yl)butanenitrile<br>1H NMR (400 MHz, DMSO-d₆) δ ppm 1.87 (s, 3 H) 2.07 (quin, J = 7.59 Hz, 2 H) 2.63 (t, J = 7.37 Hz, 2 H) 3.98-4.18 (m, 2 H) 4.34-4.47 (m, 4 H) 5.16-5.31 (m, 2 H) 7.14 (td, J = 7.48, 0.88 Hz, 1 H) 7.18 (d, J = 7.70 Hz, 1 H) 7.27-7.34 (m, 2 H) 7.64-7.68 (m, 2 H) 7.68-7.72 (m, 1 H); m/z = 448.04 (M + H) + Cl pattern |
| 89 | 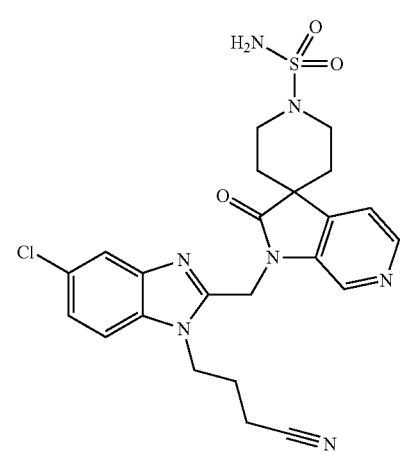 [SMILES: N#CCCCn1c(CN2C(=O)C3(CCN(S(N)(=O)=O)CC3)c3ccncc32)nc2cc(Cl)ccc21] | 1'-((5-chloro-1-(3-cyanopropyl)-1H-benzo[d]imidazol-2-yl)-methyl)-2'-oxo-1',2'-dihydrospiro[piperidine-4,3'-pyrrolo-[2,3-c]pyridine]-1-sulfonamide<br>1H NMR (400 MHz, DMSO-d₆) δ ppm 1.80-2.04 (m, 4 H), 2.10 (quin, J = 7.43 Hz, 2 H), 2.63 (t, J = 7.37 Hz, 2 H), 3.26-3.30 (m, 2 H), 3.38-3.50 (m, 2 H), 4.40 (t, J = 7.48 Hz, 2 H), 5.30 (s, 2 H), 6.88 (br. s, 2 H), 7.30 (dd, J = 8.58, 1.98 Hz, 1 H), 7.58 (d, J = 4.84 Hz, 1 H), 7.64 (d, J = 1.76 Hz, 1 H), 7.66 (d, J = 8.58 Hz, 1 H), 8.36 (d, J = 4.84 Hz, 1 H), 8.48 (s, 1 H):<br>m/z = 514 (M + H) + Cl pattern |

| No | structure | Name/analytical details |
|---|---|---|
| 90 | 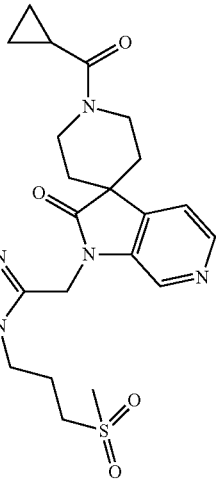 | 1'-({5-Chloro-1-[3-(methylsulfonyl)propyl]-1H-benzimidazol-2-yl}methyl)-1-(cyclopropylcarbonyl)spiro[piperidine-4,3'-pyrrolo[2,3-c]pyridin]-2'(1'H)-one<br>$^1$H NMR (400 MHz, DMSO-d$_6$) δ ppm 0.60-0.88 (m, 4 H) 1.67-1.96 (m, 4 H) 1.98-2.11 (m, 1 H) 2.14-2.25 (m, 2 H) 3.02 (s, 3 H) 3.22-3.28 (m, 2 H) 3.71-4.12 (m, 4 H) 4.48 (t, J = 7.26 Hz, 2 H) 5.31 (s, 2 H) 7.31 (dd, J = 8.58, 1.98 Hz, 1 H) 7.61-7.73 (m, 3 H) 8.34 (d, J = 4.84 Hz, 1 H) 8.49 (s, 1 H); m/z = 556 (M + H)+; MP = 208.64° C. |
| 91 | 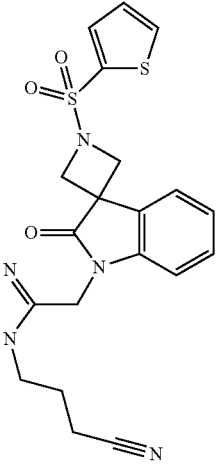 | 4-(5-Chloro)-2-{[2'-oxo-1-(thiophen-2-ylsulfonyl)spiro-[azetidine-3,3'-indol]-1'(2'H)-yl]methyl}-1H-benzimidazol-1-yl)butanenitrile<br>1H NMR (400 MHz, DMSO-d$_6$) δ ppm 2.03 (quin, J = 7.48 Hz, 2 H) 2.59 (t, J = 7.37 Hz, 2 H) 3.91-4.20 (m, 4 H) 4.35 (t, J = 7.59 Hz, 2 H) 5.15 (s, 2 H) 6.78-6.84 (m, 1 H) 7.03 (td, J = 7.54, 0.77 Hz, 1 H) 7.12-7.19 (m, 1 H) 7.23-7.32 (m, 2 H) 7.48 (dd, J = 4.95, 3.85 Hz, 1 H) 7.59-7.67 (m, 2 H) 7.92 (dd, J = 3.74, 1.10 Hz, 1 H) 8.27 (dd, J = 5.06, 1.32 Hz, 1 H); m/z = 552.04 (M + H)+ |
| 92 | 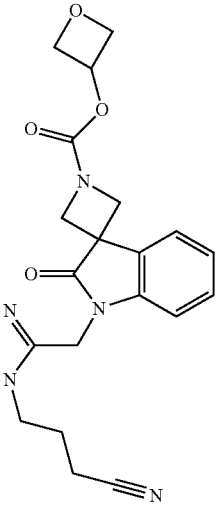 | Oxetan-3-yl 1'-{[5-chloro-1-(3-cyanopropyl)-1H-benzimidazol-2-yl]methyl}-2'-oxo-1',2'-dihydro-1H-spiro[azetidine-3,3'-indole]-1-carboxylate<br>1H NMR (400 MHz, DMSO-d$_6$) δ ppm 2.08 (quin, J = 7.48 Hz, 2 H) 2.62 (t, J = 7.37 Hz, 2 H) 4.09-4.35 (m, 4 H) 4.36-4.43 (m, 2 H) 4.50-4.57 (m, 2 H) 4.76-4.84 (m, 2 H) 5.23 (s, 2 H) 5.34-5.42 (m, 1 H) 7.11-7.23 (m, 2 H) 7.27-7.35 (m, 2 H) 7.63-7.69 (m, 2 H) 7.72-7.78 (m, 1 H); m/z = 506.09 (M + H)+ |

| No | structure | Name/analytical details |
|---|---|---|
| 93 | 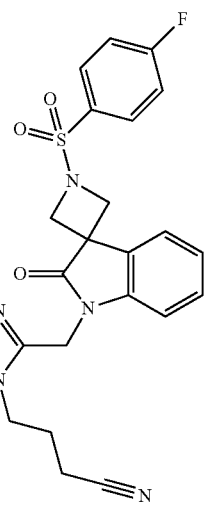 | 4-[5-Chroro-2-({1-[(4-fluorophenyl)sulfonyl]-2'-oxospiro-[azetidine-3,3'-indol]-1'(2'H)-yl}methyl)-1H-benzimidazol-1-yl]butanenitrile<br>1H NMR (400 MHz, DMSO-$d_6$) δ ppm 2.02 (quin, J = 7.48 Hz, 2 H) 2.57 (t, J = 7.37 Hz, 2 H) 3.92-4.09 (m, 4 H) 4.32 (t, J = 7.59 Hz, 2 H) 5.13 (s, 2 H) 6.95-7.01 (m, 1 H) 7.02-7.09 (m, 1 H) 7.11-7.16 (m, 1 H) 7.23-7.33 (m, 2 H) 7.58-7.67 (m, 4 H) 7.99-8.07 (m, 2 H); m/z = 564.06 (M + H)+ |
| 94 | 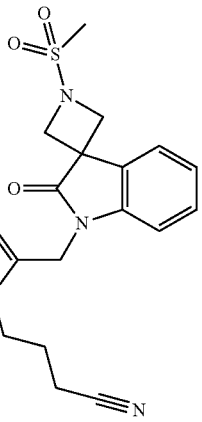 | 4-(5-Chloro-2-{[1-(methylsulfonyl)-2'-oxospiro[azetidine-3,3'-indol]-1'(2'H)-yl]methyl}-1H-benzimidazol-1-yl)-butanenitrile<br>1H NMR(400 MHz, DMSO-$d_6$) δ ppm 2.01-2.14 (m, 2 H) 2.63 (t, J = 7.37 Hz, 2 H) 3.21 (s, 3 H) 4.12-4.27 (m, 4 H) 4.40 (t, J = 7.59 Hz, 2 H) 5.23 (s, 2 H) 7.12-7.23 (m, 2 H) 7.27-7.37 (m, 2 H) 7.62-7.71 (m, 3 H); m/z = 484.04 (M + H)+; MP = 214.11° C. |
| 95 | 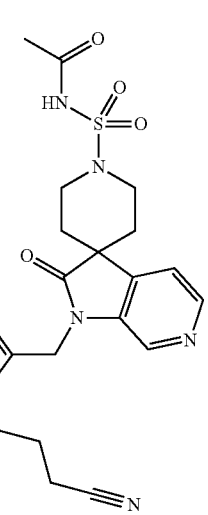 | N-[(1'-{[5-Chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl)sulfonyl]acetamide<br>1H NMR (400 MHz, CHLOROFORM-d) δ ppm 1.92-2.01 (m, 4 H), 2.09-2.17 (m, 2 H), 2.18 (s, 3 H), 2.38 (s, 6 H), 2.49 (s, 2 H), 2.55 (br. s., 8 H), 3.66-3.75 (m, 2 H), 3.75-3.81 (m, 8 H), 3.81-3.90 (m, 2 H), 4.38-4.47 (m, 2 H), 4.61-4.80 (m, 1 H), 5.21 (s, 2 H), 7.27 (s, 1 H), 7.28-7.32 (m, 2 H), 7.72 (d, J = 1.32 Hz, 1 H), 8.44 (d, J = 4.84 Hz, 1 H),<br>8.81 (s, 1 H); m/z = 556 (M + H)+ |

| No | structure | Name/analytical details |
|---|---|---|
| 96 | 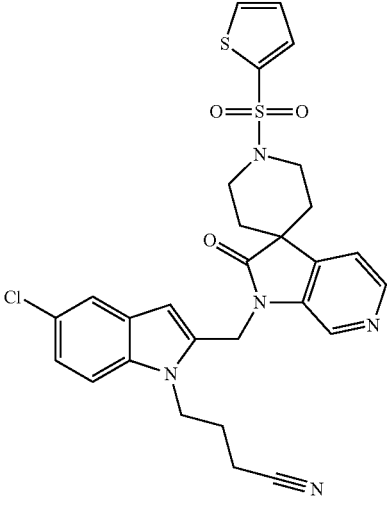 [SMILES: N#CCCCn1c(CN2C(=O)C3(CCN(S(=O)(=O)c4cccs4)CC3)c3ccncc32)cc2cc(Cl)ccc21] | 4-(5-Chloro-2-{[2'-oxo-1-(thiophen-2-ylsulfonyl)spiro-[piperidine-4,3'-pyrrolo[2,3-c]pyridin]-1'(2'H)-yl]methyl}-1H-indol-1-yl)butanenitrile<br>$^1$H NMR (400 MHz, DMSO-d$_6$) δ ppm 1.86-2.00 (m, 4 H) 2.10-2.21 (m, 2 H) 2.52-2.57 (m, 2 H) 3.20-3.29 (m, 2 H) 3.47-3.58 (m, 2 H) 4.13-4.31 (m, 2 H) 5.11 (s, 2 H) 6.28 (s, 1 H) 7.14 (dd, J = 8.69, 2.09 Hz, 1 H) 7.33 (dd, J = 5.06, 3.74 Hz, 1 H) 7.44-7.55 (m, 3 H) 7.71 (dd, J = 3.74, 1.32 Hz, 1 H) 8.09 (dd, J = 5.06, 1.32 Hz, 1 H) 8.31-8.36 (m, 2 H); m/z = 580 (M + H)+ |
| 97 | 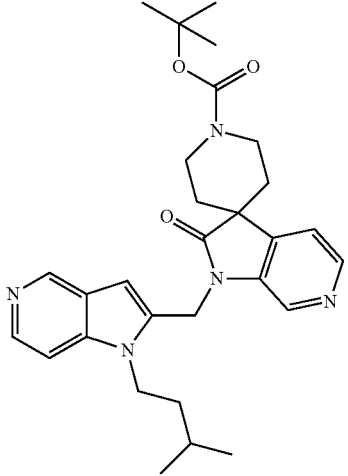 [SMILES: CC(C)CCn1c(CN2C(=O)C3(CCN(C(=O)OC(C)(C)C)CC3)c3ccncc32)cc2cnccc21] | tert-Butyl 1'-{[1-(3-methylbutyl)-1H-pyrrolo[3,2-c]pyridin-2-yl]methyl}-2'-oxo-1,2'-dihydro-1H-spiro[piperidine-4,3'-pyrrolo[2,3-c]pyridine]-1-carboxylate<br>$^1$H NMR (400 MHz CHLOROFORM-d) δ ppm 1.05 (d, J = 6.38 Hz, 6 H), 1.51 (s, 9 H), 1.63-1.84 (m, 3 H), 1.93 (t, J = 5.39 Hz, 4 H), 3.72-3.86 (m, 2 H), 3.86-3.99 (m, 2 H), 4.27-4.42 (m, 2 H), 5.20-5.38 (m, 2 H), 6.90 (s, 1 H), 7.63 (d, J = 6.60 Hz, 1 H), 7.69 (d, J = 4.84 Hz, 1 H), 8.38 (d, J = 6.60 Hz, 1 H), 8.54 (br. s., 1 H), 8.67 (br. s., 1 H), 9.01 (br. s., 1 H);<br>m/z = 504 (M + H)+ |
| 98 | 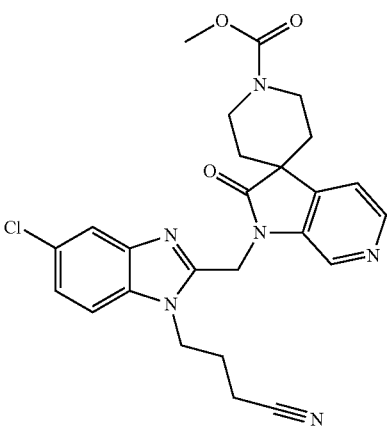 [SMILES: COC(=O)N1CCC2(CC1)C(=O)N(Cc1nc3cc(Cl)ccc3n1CCCC#N)c1cnccc12] | Methyl 1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridine]-1-carboxylate<br>1H NMR (400 MHz, DMSO-d$_6$) δ ppm 1.66-1.93 (m, 4 H), 2.09 (quin, J = 7.5 Hz, 2 H), 2.63 (t, J = 7.4 Hz, 2 H), 3.65 (s, 3 H), 3.71-3.84 (m, 4 H), 4.39 (t, J = 7.6 Hz, 2 H), 5.30 (s, 2 H), 7.30 (dd, J = 8.6, 2.0 Hz, 1 H), 7.56-7.75 (m, 2 H), 8.33 (d, J = 4.8 Hz, 1 H), 8.47 (s, 1 H); m/z = 493 (M + H)+ |

| No | structure | Name/analytical details |
|---|---|---|
| 99 | 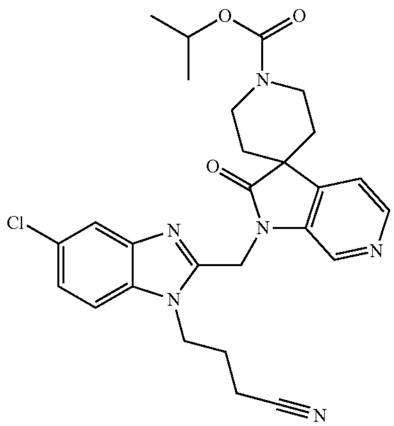 [SMILES: CC(C)OC(=O)N1CCC2(CC1)C(=O)N(Cc1nc3cc(Cl)ccc3n1CCCC#N)c1cnccc12] | 1-Methylethyl 1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridine]-1-carboxylate<br>1H NMR (400 MHz, DMSO-$d_6$) δ ppm 1.18-1.27 (m, 6 H), 1.72-1.89 (m, 4 H), 2.09 (quin, J = 7.4 Hz, 2 H), 2.63 (t, J = 7.4 Hz, 2 H), 3.65-3.83 (m, 4 H), 4.39 (t, J = 7.5 Hz, 2 H),<br>4.84 (dt, J = 12.5, 6.2 Hz, 1 H), 5.30 (s, 2 H), 7.30 (dd, J = 8.6,<br>2.0 Hz, 1 H), 7.62-7.72 (m, 3 H), 8.33 (d, J = 4.6 Hz, 1 H), 8.48 (s, 1 H); m/z = 521 (M + H)+ |
| 100 | 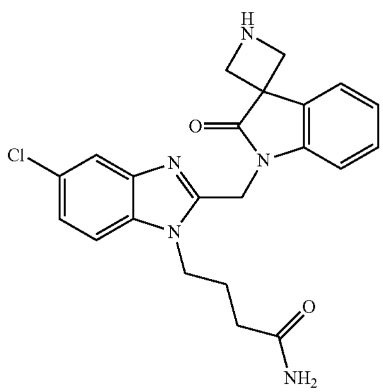 [SMILES: NC(=O)CCCn1c(CN2C(=O)C3(CNC3)c3ccccc32)nc2cc(Cl)ccc21] | 4-{5-Chloro-2-[(2'-oxospiro[azetidine-3,3'-indol]-1'(2'H)-yl)methyl]-1H-benzimidazol-1-yl}butanamide<br>1H NMR (400 MHz, DMSO-$d_6$) δ ppm 1.86-2.00 (m, 2 H) 2.34 (t, J = 7.26 Hz, 2 H) 4.15-4.32 (m, 4 H) 4.32-4.44 (m, 2 H) 5.21 (s, 2 H) 7.16-7.25 (m, 2 H) 7.27-7.32 (m, 1 H) 7.32-7.39 (m, 1 H) 7.61-7.69 (m, 2 H) 7.81-7.88 (m, 1 H); m/z = 425.02 (M + H)+ |
| 101 | 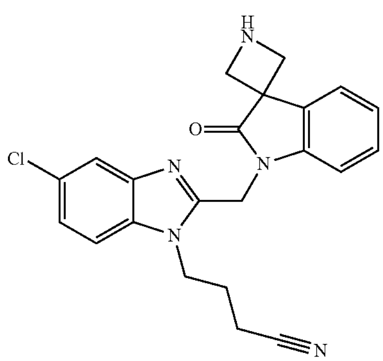 [SMILES: N#CCCCn1c(CN2C(=O)C3(CNC3)c3ccccc32)nc2cc(Cl)ccc21] | 4-{5-Chloro-2-[(2'-oxospiro[azetidine-3,3'-indol]-1'(2'H)-yl)methyl]-1H-benzimidazol-1-yl}butanenitrile<br>1H NMR (400 MHz, DMSO-$d_6$) δ ppm 2.00 (quin, J = 7.54 Hz, 2 H) 2.57-2.67 (m, 2 H) 3.56 (d, J = 7.26 Hz, 2 H) 4.00 (d, J = 7.48 Hz, 2 H) 4.38 (t, J = 7.59 Hz, 2 H) 5.21 (s, 2 H) 7.08-7.18 (m, 2 H) 7.21-7.32 (m, 2 H) 7.62-7.68 (m, 2 H) 7.73-7.82 (m, 1 H); m/z = 405.96 (M + H)+ |

| No | structure | Name/analytical details |
|---|---|---|
| 102 | 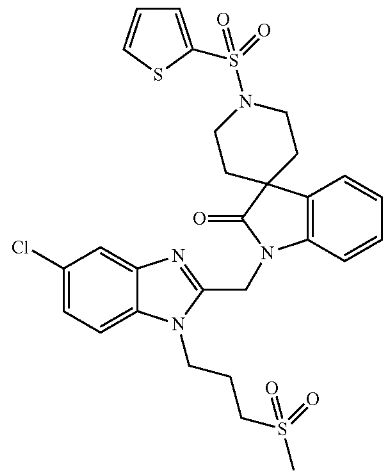 [SMILES: CS(=O)(=O)CCCn1c(CN2C(=O)C3(CCN(S(=O)(=O)c4cccs4)CC3)c3ccccc32)nc2cc(Cl)ccc21] | 1-({5-Chloro)-1-[3-(methylsulfonyl)propyl]-1H-benzimidazol-2-yl}methyl)-1'-(thiophen-2-ylsulfonyl)spiro[indole-3,4'-piperidin]-2(1H)-one<br>1H NMR (400 MHz, DMSO-$d_6$) δ ppm 1.79-1.94 (m, 2 H) 2.00-2.26 (m, 4 H) 2.98 (s, 3 H) 3.07-3.25 (m, 4 H) 3.42-3.78 (m, 2 H) 4.41 (t, J = 6.60 Hz, 2 H) 5.17 (s, 2 H) 6.98-7.09 (m, 1 H) 7.14 (d, J = 7.48 Hz, 1 H) 7.20-7.42 (m, 4 H) 7.54-7.78 (m, 3 H) 8.03-8.15 (m, 1 H); m/z = 632.94 (M + H)+; MP = 233.06° C. |
| 103 | 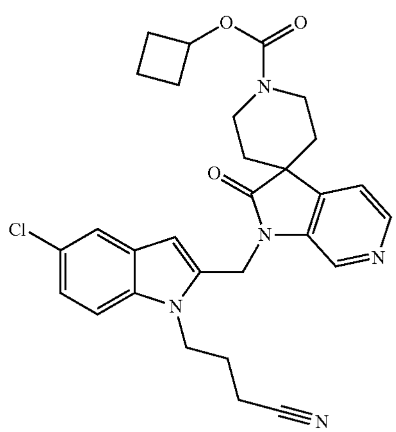 [SMILES: N#CCCCn1c(CN2C(=O)C3(CCN(C(=O)OC4CCC4)CC3)c3ccncc32)cc2cc(Cl)ccc21] | Cyclobutyl 1'-{[5-chloro-1-(3-cyanopropyl)-1H-indol-2-yl]-methyl}-2'-oxo-1',2'-dihydro-1H-spiro[piperidine-4,3'-pyrrolo[2,3-c]pyridine]-1-carboxylate<br>$^1$H NMR(400 MHz, DMSO-$d_6$) δ ppm 1.50-1.65 (m, 1 H) 1.66-1.90 (m, 5 H) 1.91-2.09 (m, 4 H) 2.20-2.36 (m, 2 H) 2.58 (t, J = 7.37 Hz, 2 H) 3.56-3.90 (m, 4 H) 4.16-4.38 (m, 2 H) 4.79-4.96 (m, 1 H) 5.20 (s, 2 H) 6.36 (s, 1 H) 7.15 (dd, J = 8.80, 1.98 Hz, 1 H) 7.48-7.57 (m, 2 H) 7.70 (d, J = 4.84 Hz, 1 H) 8.33 (d, J = 4.84 Hz, 1 H) 8.39 (s, 1 H); m/z = 532 (M + H)+ |
| 104 | 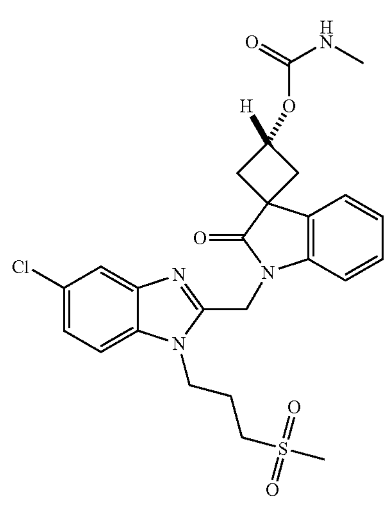 | (1R,3R)-1'-((5-chloro-1-(3-(methylsulfonyl)propyl)-1H-benzo[d]imidazol-2-yl)methyl)-2'-oxospiro[cyclobutane-1,3'-indoline]-3-yl methylcarbamate<br>1H NMR (400 MHz, DMSO-$d_6$) δ ppm 2.16 (quin, J = 7.59 Hz, 2 H) 2.45-2.52 (m, 2 H) 2.59 (d, J = 4.62 Hz, 3 H) 2.73-2.82 (m, 2 H) 3.00 (s, 3 H) 3.20-3.27 (m, 2 H) 4.47 (t, J = 7.37 Hz, 2 H) 5.22 (s, 2 H) 5.25-5.35 (m, 1 H) 7.07-7.16 (m, 3 H) 7.22-7.28 (m, 1 H) 7.28-7.33 (m, 1 H) 7.48-7.54 (m, 1 H) 7.64-7.70 (m, 2 H); m/z = 531.15 (M + H)+; MP = 204.17° C. |

| No | structure | Name/analytical details |
|---|---|---|
| 105 | 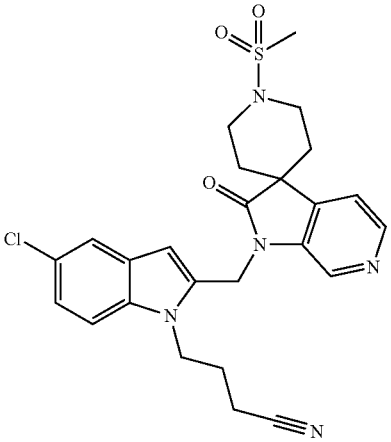 [SMILES: CS(=O)(=O)N1CCC2(CC1)C(=O)N(Cc1cc3cc(Cl)ccc3n1CCCC#N)c1cnccc12] | 4-(5-Chloro-2-{[1-(methylsulfonyl)-2'-oxospiro[piperidine-4,3'-pyrrolo[2,3-c]pyridin]-1'(2'H)-yl]methyl}-1H-indol-1-yl)butanenitrile<br>1H NMR (360 MHz, DMSO-d$_6$) δ ppm 1.85-2.12 (m, 6 H), 2.60 (t, J = 7.3 Hz, 2 H), 3.01 (s, 3 H), 3.40-3.51 (m, 2 H), 3.51-3.64 (m, 2 H), 4.30 (t, J = 7.7 Hz, 2 H), 5.20 (s, 2 H), 6.38 (s, 1 H), 7.09-7.21 (m, 1 H), 7.47-7.59 (m, 2 H), 7.71 (d, J = 4.8 Hz, 1 H), 8.36 (d, J = 4.8 Hz, 1 H), 8.41 (s, 1 H); m/z = 512 (M + H)+; MP = 145.30° C. |
| 106 | 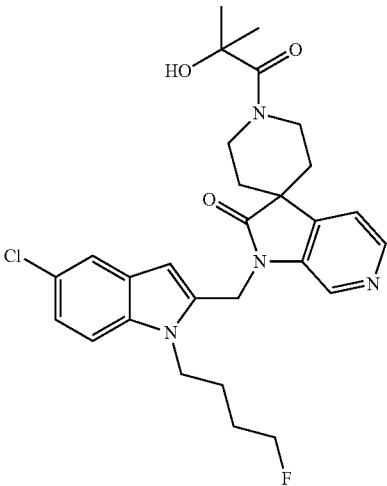 [SMILES: CC(C)(O)C(=O)N1CCC2(CC1)C(=O)N(Cc1cc3cc(Cl)ccc3n1CCCCF)c1cnccc12] | 1'-{[5-Chloro-1-(4-fluorobutyl)-1H-indol-2-yl]methyl}-1-(2-hydroxy-2-methylpropanoyl)spiro[piperidine-4,3'-pyrrolo-[2,3-c]pyridin]-2'(1'H)-one<br>$^1$H NMR(400 MHz, DMSO-d$_6$) δ ppm 1.40 (s, 6 H) 1.58-1.98 (m, 8 H) 3.99-4.16 (m, 4 H) 4.20-4.31 (m, 2 H) 4.33-4.42 (m, 1 H) 4.46-4.54 (m, 1 H) 5.07 (s, 1 H) 5.16 (s, 2 H) 6.37 (s, 1 H) 7.02-7.15 (m, 1 H) 7.41-7.47 (m, 1 H) 7.47-7.50 (m, 1 H) 7.53-7.57 (m, 1 H) 8.29-8.35 (m, 2 H); m/z = 527 (M + H)+ |
| 107 | 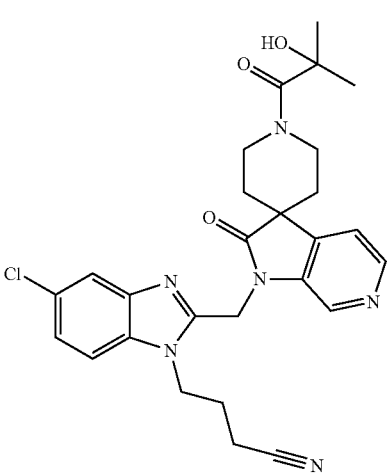 [SMILES: CC(C)(O)C(=O)N1CCC2(CC1)C(=O)N(Cc1nc3cc(Cl)ccc3n1CCCC#N)c1cnccc12] | 4-(5-Chloro-2-{[1-(2-hydroxy-2-methylpropanoyl)-2'-oxo-spiro[piperidine-4,3'-pyrrolo[2,3-c]pyridin]-1'(2'H)-yl]-methyl}-1H-benzimidazol-1-yl)butanenitrile<br>1H NMR(400 MHz, DMSO-d$_6$) δ ppm 1.37 (s, 6 H), 1.83 (br. s., 4 H), 2.04-2.15 (m, 2 H), 2.64 (t, J = 7.4 Hz, 2 H), 3.69-4.01 (m, 2 H), 4.12-4.34 (m, 2 H), 4.39 (t, J = 7.5 Hz, 2 H), 5.31 (s, 2 H), 7.30 (dd, J = 8.8, 2.0 Hz, 1 H), 7.63-7.69 (m, 3 H), 8.34 (d, J = 4.6 Hz, 1 H), 8.49 (s, 1 H); m/z = 521 (M + H)+ |

| No | structure | Name/analytical details |
|---|---|---|
| 108 | 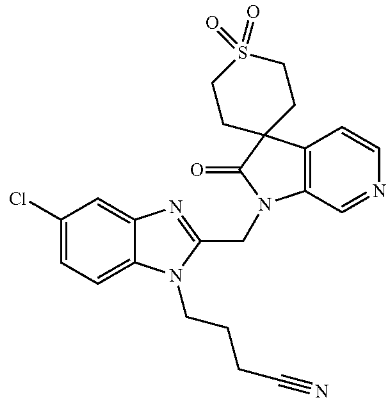 [SMILES: N#CCCCn1c(CN2C(=O)C3(CCS(=O)(=O)CC3)c3ccncc32)nc2cc(Cl)ccc21] | 4-{5-Chloro-2-[(1',1'-dioxido-2-oxo-2',3',5',6',-tetrahydro-spiro[pyrrolo[2,3-c]pyridine-3,4'-thiopyran]-1(2H)-yl)-methyl]-1H-benzimidazol-1-yl}butanenitrile<br>1H NMR (400 MHz, DMSO-d$_6$) δ ppm 2.12 (quin, J = 7.26 Hz, 2 H) 2.25 (m, J = 15.19 Hz, 2 H) 2.41-2.48 (m, 2 H) 2.65 (t, J = 7.37 Hz, 2 H) 3.16-3.28 (m, 2 H) 3.56-3.76 (m, 2 H) 4.40 (t, J = 7.37 Hz, 2 H) 5.32 (s, 2 H) 7.30 (dd, J = 8.69, 1.65 Hz, 1 H) 7.56-7.72 (m, 3 H) 8.37 (d, J = 4.84 Hz, 1 H) 8.50 (s, 1 H); m/z = 484.07 (M + H)+ |
| 109 | 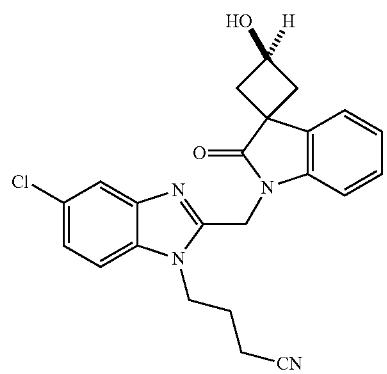 | 4-{5-Chloro-2-[(3-hydroxy-2'-oxospiro[cyclobutane-1,3'-indol]-1'(2'H)-yl)methyl]-1H-benzimidazol-1-yl}butanenitrile<br>1H NMR (400 MHz, DMSO-d$_6$) δ ppm 1.96 (quin. J = 7.65 Hz, 2 H) 2.38-2.48 (m, 4 H) 2.59 (t, J = 7.48 Hz, 2 H) 4.30-4.43 (m, 2 H) 4.65-4.79 (m, 1 H) 5.22 (s, 2 H) 5.58 (d, J = 6.60 Hz, 1 H) 7.07 (td, J = 7.48, 0.88 Hz, 1 H) 7.10-7.14 (m, 1 H) 7.22 (td, J = 7.70, 1.10 Hz, 1 H) 7.29 (dd, J = 8.58, 1.98 Hz, 1 H) 7.48-7.53 (m, 1 H) 7.65 (d, J = 8.58 Hz, 1 H) 7.66 (d, J = 1.98 Hz, 1 H); m/z = 421 (M + H)+ |
| 110 | 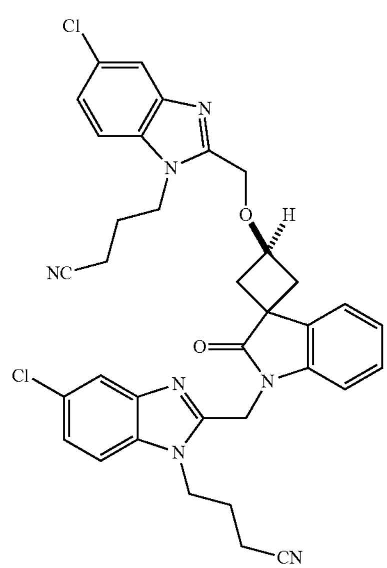 | 4-(5-chloro-2-(((1S,3S)-1'-((5-chloro-1-(3-cyanopropyl)-1H-benzo[d]imidazol-2-yl)methyl)-2'-oxospiro[cyclobutane-1,3'-indoline]-3-yloxy)methyl)-1H-benzo[d]imidazol-1-yl)butanenitrile<br>1H NMR (400 MHz, DMSO-d$_6$) δ ppm 1.97 (quin, J = 7.54 Hz, 2 H) 2.15 (quin, J = 7.37 Hz, 2 H) 2.44-2.56 (m, 4 H) 2.59 (t, J = 7.48 Hz, 2 H) 2.66 (t, J = 7.15 Hz, 2 H) 4.29-4.46 (m, 4 H) 4.75-4.87 (m, 3 H) 5.22 (s, 2 H) 7.06-7.15 (m, 2 H) 7.20-7.26 (m, 1 H) 7.29 (dd, J = 8.58, 1.98 Hz, 1 H) 7.33 (dd, J = 8.58, 1.98 Hz, 1 H) 7.48-7.53 (m, 1 H) 7.62-7.66 (m, 2 H) 7.69 (d, J = 8.80 Hz, 1 H) 7.72 (d, J = 1.76 Hz, 1 H);<br>m/z = 652 (M + H)+ |

| No | structure | Name/analytical details |
|---|---|---|
| 111 | 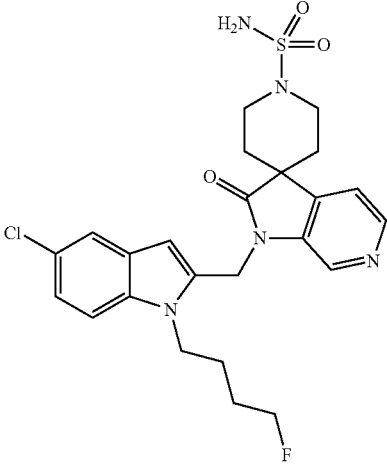 [SMILES: NS(=O)(=O)N1CCC2(CC1)C(=O)N(Cc1cc3cc(Cl)ccc3n1CCCCF)c1cnccc12] | 1'-{[5-Chloro-1-(4-fluorobutyl)-1H-indol-2-yl]methyl}-2'-oxo-1',2'-dihydro-1H-spiro[piperidine-4,3'-pyrrolo[2,3-c]-pyridine]-1-sulfonamide<br>$^1$H NMR (400 MHz, DMSO-$d_6$) δ ppm 1.60-1.81 (m, 4 H), 1.84-2.09 (m, 4 H), 3.31 (s, 2 H), 3.41-3.53 (m, 2 H), 4.27 (t, J = 7.04 Hz, 2 H), 4.40 (t, J = 5.83 Hz, 1 H), 4.47-4.57 (m, 1 H), 5.18 (s, 2 H), 6.38-6.47 (m, 1 H), 6.89 (s, 2 H), 7.13 (dd, J = 8.69, 2.09 Hz, 1 H), 7.51 (d, J = 8.80 Hz, 1 H), 7.53 (d, J = 1.98 Hz, 1 H), 7.59 (d, J = 5.28 Hz, 1 H), 8.35 (d, J = 4.62 Hz, 1 H), 8.38 (s, 1 H); m/z = 520 (M + H)$^+$; |
| 112 | 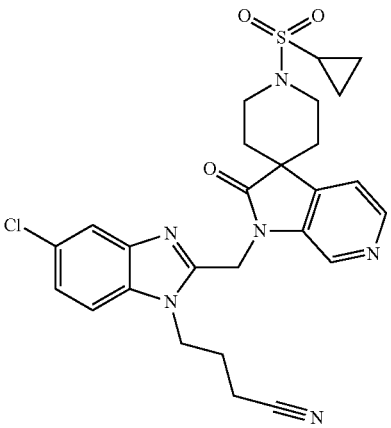 [SMILES: N#CCCCn1c(CN2C(=O)C3(CCN(S(=O)(=O)C4CC4)CC3)c3ccncc32)nc2cc(Cl)ccc21] | 4-(5-Chloro-2-{[1-(cyclopropylsulfonyl)-2'-oxospiro-[piperidine-4,3'-pyrrolo[2,3-c]pyridin]-1'(2'H)-yl]methyl}-1H-benzimidazol-1-yl)butanenitrile<br>1H NMR (400 MHz, DMSO-$d_6$) δ ppm 0.94-1.11 (m, 4 H), 1.86-1.97 (m, 2 H), 1.98-2.15 (m, 4 H), 2.64 (t, J = 7.3 Hz, 2 H), 2.68-2.78 (m, 1 H), 3.49-3.59 (m, 2 H), 3.60-3.72 (m, 2 H), 4.40 (t, J = 7.5 Hz, 2 H), 5.31 (s, 2 H), 7.30 (dd, J = 8.7, 1.9 Hz, 1 H), 7.61-7.71 (m, 3 H), 8.37 (d, J = 4.8 Hz, 1 H), 8.49 (s, 1 H); m/z = 539 (M + H)$^+$; |
| 113 | 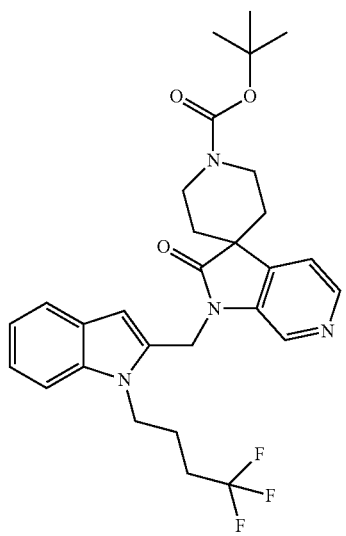 [SMILES: CC(C)(C)OC(=O)N1CCC2(CC1)C(=O)N(Cc1cc3ccccc3n1CCCC(F)(F)F)c1cnccc12] | tert-Butyl 2'-oxo-1'-{[1-(4,4,4-trifluorobutyl)-1H-indol-2-yl]methyl}-1',2'-dihydro-1H-spiro[piperidine-4,3'-pyrrolo[2,3-c]pyridine]-1-carboxylate<br>$^1$H NMR (400 MHz, CHLOROFORM-d) δ ppm 1.51 (s, 9 H), 1.71-1.82 (m, 2 H), 1.83-1.92 (m, 2 H), 1.93-2.04 (m, 2 H), 2.11-2.27 (m, 2 H), 3.70-3.81 (m, 2 H), 3.84-3.96 (m, 2 H), 4.23-4.32 (m, 2 H), 5.10 (s, 2 H), 6.62 (s, 1 H), 7.12 (ddd, J = 7.81, 6.60, 1.43 Hz, 1 H), 7.19-7.30 (m, 3 H), 7.58 (d, J = 7.92 Hz, 1 H), 8.38 (d, J = 4.62 Hz, 1 H), 8.48 (s, 1 H); m/z = 543 (M + H)$^+$; |

| No | structure | Name/analytical details |
|---|---|---|
| 114 | 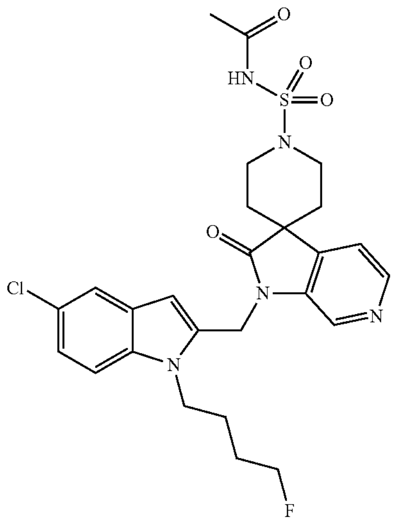 [SMILES: CC(=O)NS(=O)(=O)N1CCC2(CC1)C(=O)N(Cc1cc3cc(Cl)ccc3n1CCCCF)c1cnccc12] | N-[(1'-{[5-Chloro-1-(4-fluorobutyl)-1H-indol-2-yl]methyl}-2'-oxo-1',2'-dihydro-1H-spiro[piperidine-4,3'-pyrrolo[2,3-c]-pyridin]-1-yl)sulfonyl]acetamide<br>$^1$H NMR (400 MHz, DMSO-d$_6$) d ppm 1.60-1.78 (m, 4 H), 1.85-2.02 (m, 4 H), 2.04 (s, 3 H), 3.50-3.61 (m, 2 H), 3.68 (ddd, J = 12.71, 8.97, 3.63 Hz, 2 H), 4.27 (t, J = 7.04 Hz, 2 H),<br>4.40 (t, J = 5.72 Hz, 1 H), 4.52 (s, 1 H), 5.17 (s, 2 H), 6.41 (s, 1 H), 7.13 (dd, J = 8.69, 2.09 Hz, 1 H), 7.49-7.54 (m, 2 H), 7.56 (d, J = 4.84 Hz, 1 H), 8.35 (d, J = 4.84 Hz, 1 H), 8.38 (s, 1<br>H), 11.54 (s, 1 H); m/z = 562 (M + H)$^+$; MP = 236.92° C. |
| 115 | 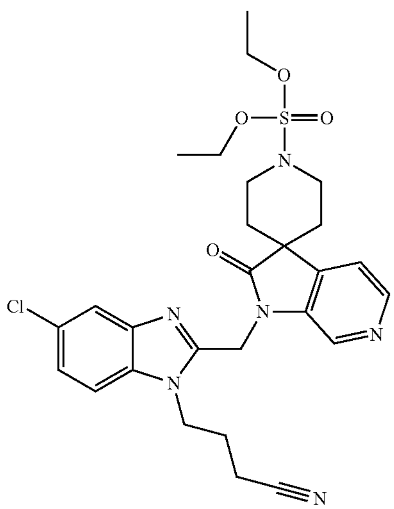 | Diethyl (1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl)phosphonate<br>$^1$H NMR (400 MHz, DMSO-d$_6$) δ ppm 1.28 (t, J = 7.70 Hz, 6 H) 1.66-1.89 (m, 4 H) 1.99-2.16 (m, 2 H) 2.63 (t, J = 7.30 Hz, 2 H) 3.26-3.38 (m, 2 H) 3.41-3.58 (m, 2 H) 3.89-4.07 (m, 4 H) 4.37 (t, J = 7.50 Hz, 2 H) 5.27 (s, 2 H) 7.30 (dd,<br>J = 8.80, 1.98 Hz, 1 H) 7.54-7.71 (m, 3 H) 8.34 (d, J = 6.16 Hz, 1 H) 8.47 (s, 1 H); m/z = 571 (M + H)$^+$ |
| 116 | 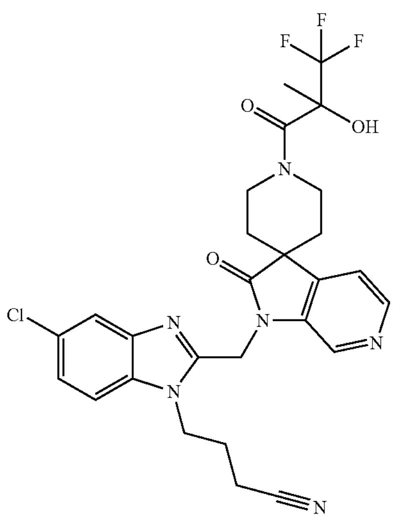 [SMILES: CC(O)(C(=O)N1CCC2(CC1)C(=O)N(Cc1nc3cc(Cl)ccc3n1CCCC#N)c1cnccc12)C(F)(F)F] | 4-(5-Chloro-2-{[2'-oxo-1-(3,3,3-trifluoro-2-hydroxy-2-methylpropanoyl)spiro[piperidine-4,3'-pyrrolo[2,3-c]pyridin]-1'(2'H)-yl]methyl}-1H-benzimidazol-1-yl)butanenitrile<br>$^1$H NMR (400 MHz, DMSO-d$_6$) δ ppm 1.55 (s, 3 H) 1.70-1.99 (m, 4 H) 2.02-2.17 (m, 2 H) 2.63 (t, J = 7.50 Hz, 2 H) 3.73-3.99 (m, 2 H) 4.15-4.29 (m, 2 H) 4.40 (t, J = 7.90 Hz, 2 H) 5.26 (s, 2 H) 7.17 (br. s, 1 H) 7.29 (dd, J = 8.58, 1.98 Hz,<br>1 H) 7.56-7.74 (m, 3 H) 8.32 (d, J = 5.06 Hz, 1 H) 8.47 (s, 1 H);<br>m/z = 575 (M + H)$^+$ |

| No | structure | Name/analytical details |
|---|---|---|
| 117 | 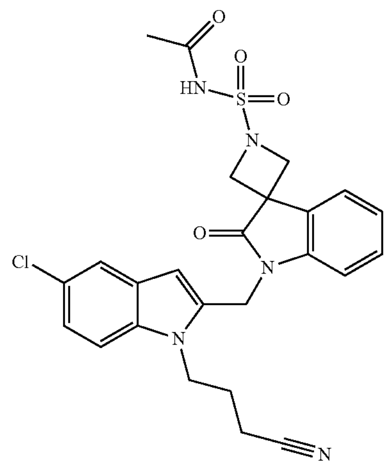 [SMILES: CC(=O)NS(=O)(=O)N1CC2(C1)C(=O)N(Cc1cc3cc(Cl)ccc3n1CCCC#N)c1ccccc12] | N-[(1'-{[5-Chloro-1-(3-cyanopropyl)-1H-indol-2-yl]methyl}-2'-oxo-1',2'-dihydro-1H-spiro[azetidine-3,3'-indol]-1-yl)sulfonyl]acetamide<br>$^1$H NMR (400 MHz, DMSO-d$_6$) δ ppm 1.93-2.04 (m, 1 H), 2.16 (s, 3 H), 2.58 (t, J = 7.4 Hz, 2 H), 4.25 (d, J = 8.1 Hz, 2 H), 4.27-4.35 (m, 2 H), 4.40 (d, J = 8.4 Hz, 2 H), 5.12 (s, 2 H), 6.38 (s, 1 H), 7.08 (d, J = 7.9 Hz, 1 H), 7.11-7.21 (m, 2 H), 7.26-7.35 (m, 1 H), 7.48-7.55 (m, 2 H), 7.58 (d, J = 7.0 Hz, 1 H), 10.84-10.85 (m, 0 H), 11.75 (br. s., 2 H); m/z = 524 (M − H)$^-$; MP= 182.85° C. |
| 120 | 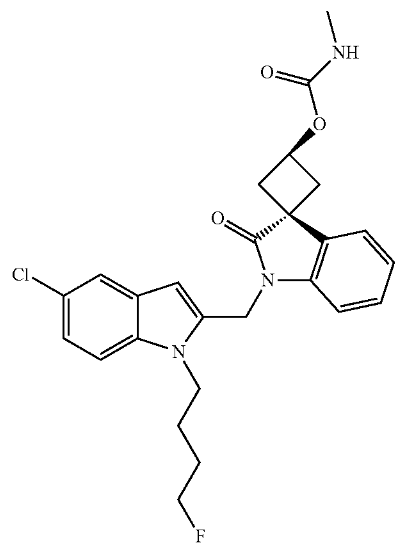 [SMILES: CNC(=O)O[C@H]1C[C@@]2(C1)C(=O)N(Cc1cc3cc(Cl)ccc3n1CCCCF)c1ccccc12] | (1r,3r)-1'-((5-chloro-1-(4-fluorobutyl)-1H-indol-2-yl)methyl)-2'-oxospiro[cyclobutane-1,3'-indolin]-3-yl methylcarbamate<br>$^1$H-NMR (400 MHz, DMSO-d$_6$) δ ppm 1.58-1.76 (m, 4 H) 2.59 (d, J = 4.62 Hz, 3 H) 2.78 (ddd, J = 9.96, 7.32, 2.53 Hz, 2 H) 4.28 (t, J = 6.82 Hz, 2 H) 4.38 (t, J = 5.61 Hz, 1 H) 4.50 (t, J = 5.39 Hz, 1 H) 5.08-5.14 (m, 2 H) 5.31 (quin. J = 7.32 Hz, 1 H) 6.33-6.37 (m, 1 H) 7.02 (d, J = 7.92 Hz, 1 H) 7.07-7.16 (m, 3 H) 7.19-7.26 (m, 1 H) 7.46-7.55 (m, 3 H); m/z = 484 (M + H)+ |
| 121 | 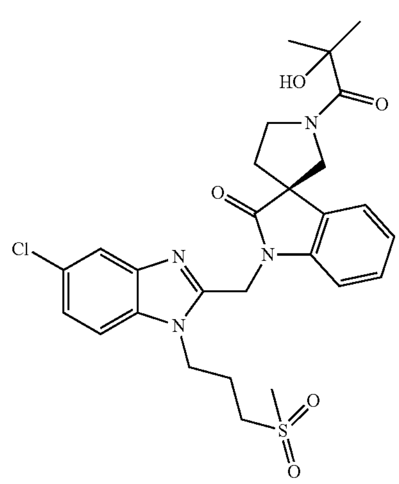 [SMILES: CC(C)(O)C(=O)N1CC[C@@]2(C1)C(=O)N(Cc1nc3cc(Cl)ccc3n1CCCS(C)(=O)=O)c1ccccc12] | (R)-1-({5-Chloro-1-[3-(methylsulfonyl)propyl]-1H-benzimidazol-2-yl}methyl)-1'-(2-hydroxy-2-methylpropanoyl)spiro[indole-3,3'-pyrrolidin]-2(1H)-one<br>$^1$H-NMR (400 MHz, DMSO-d$_6$) δ ppm 1.27 (d, J = 7.0 Hz, 3 H), 1.36 (d, J = 9.5 Hz, 3 H), 2.05-2.39 (m, 4 H), 3.01 (s, 3 H), 3.24 (t, J = 7.7 Hz, 2 H), 3.59-3.85 (m, 2 H), 4.04 (s, 1 H), 4.20 (br. s., 1 H), 4.47 (t, J = 7.5 Hz, 2 H), 5.17-5.35 (m, 3 H), 7.04-7.12 (m, 1 H), 7.17-7.41 (m, 4 H), 7.61-7.74 (m, 2 H); m/z = 559 (M + H)+ |

| No | structure | Name/analytical details |
|---|---|---|
| 122 | 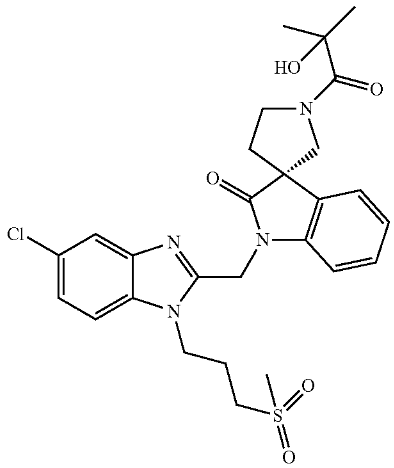 [SMILES: CC(C)(O)C(=O)N1CC[C@]2(C1)C(=O)N(Cc1nc3cc(Cl)ccc3n1CCCS(C)(=O)=O)c1ccccc12] | (S)-1-((5-chloro-1-(3-(methylsulfonyl)propyl)-1H-benzo[d]imidazol-2-yl)methyl)-1'-(2-hydroxy-2-methylpropanoyl)spiro[indoline-3,3'-pyrrolidin]-2-one<br>$^1$H-NMR (400 MHz, DMSO-d6) δ ppm 1.27 (d, J = 7.3 Hz, 3 H), 1.37 (d, J = 9.5 Hz, 3 H), 2.05-2.39 (m, 4 H), 3.01 (s, 3 H), 3.24 (t, J = 7.8 Hz, 2 H), 3.59-3.86 (m, 2 H), 4.05 (s, 1 H), 4.20 (br. s., 1 H), 4.48 (t, J = 7.5 Hz, 2 H), 5.18-5.35 (m, 3 H), 7.04-7.12 (m, 1 H), 7.17-7.42 (m, 4 H), 7.63-7.71 (m, 2 H); m/z = 559 (M + H)+ |
| 123 | 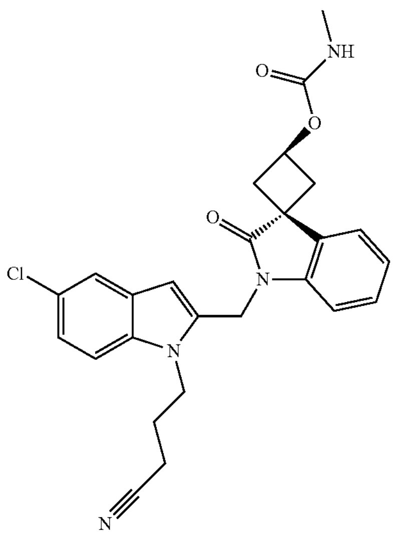 [SMILES: CNC(=O)O[C@H]1C[C@@]2(C1)C(=O)N(Cc1cc3cc(Cl)ccc3n1CCCC#N)c1ccccc12] | (1r,3r)-1'-((5-chloro)-1-(3-cyanopropyl)-1H-indol-2-yl)methyl)-2'-oxospiro[cyclobutane-1,3'-indolin]-3-yl methylcarbamate<br>$^1$H-NMR (400 MHz, DMSO-d6) δ ppm 1.92-2.02 (m, 2 H) 2.54-2.61 (m, 5 H) 2.79 (ddd, J = 9.96, 7.32, 2.75 Hz, 2 H) 4.31 (t, J = 7.48 Hz, 2 H) 5.13 (s, 2 H) 5.31 (quin, J = 7.37 Hz, 1 H) 6.27 (s, 1 H) 7.03 (d, J = 7.70 Hz, 1 H) 7.08-7.17 (m, 3 H) 7.20-7.28 (m, 1 H) 7.49-7.56 (m, 3 H); m/z = 478 (M + H)+ |
| 125 | 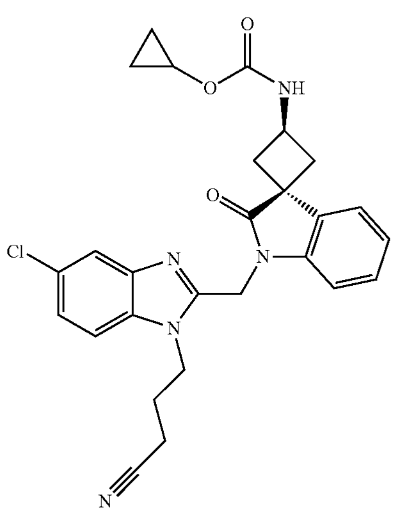 [SMILES: N#CCCCn1c(CN2c3ccccc3[C@]3(C[C@H](NC(=O)OC4CC4)C3)C2=O)nc2cc(Cl)ccc21] | cyclopropyl ((1s,3s)-1'-((5-chloro-1-(3-cyanopropyl)-1H-benzo[d]imidazol-2-yl)methyl)-2'-oxospiro[cyclobutane-1,3'-indolin]-3-yl)carbamate<br>$^1$H NMR (400 MHz, DMSO-d$_6$) δ ppm 0.46-0.73 (m, 4 H) 1.86-2.05 (m, 2 H) 2.52-2.63 (m, 6 H) 3.79-4.07 (m, 1 H) 4.34 (t, J = 7.70 Hz, 2 H) 4.49-4.65 (m, 1 H) 5.20 (s, 2 H) 7.07-7.15 (m, 2 H) 7.24 (td, J = 8.80, 1.10 Hz, 1 H) 7.29 (dd, J = 8.80, 2.20 Hz, 1 H) 7.59 (d, J = 7.26 Hz, 1 H) 7.62-7.67 (m, 2 H) 7.79 (d, J = 6.82 Hz, 1 H); m/z = 504 (M + H)+ |

| No | structure | Name/analytical details |
|---|---|---|
| 126 | 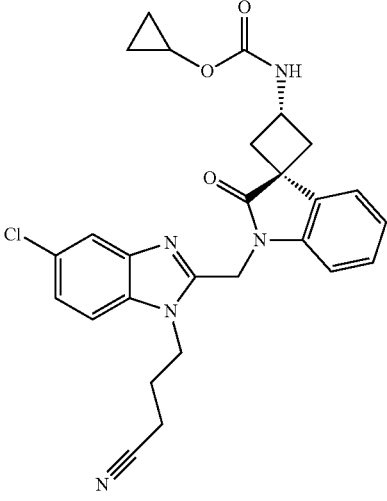 [SMILES: N#CCCCn1c(CN2c3ccccc3[C@]3(C[C@@H](NC(=O)OC4CC4)C3)C2=O)nc2cc(Cl)ccc21] | cyclopropyl ((1r,3r)-1-((5-chloro-1-(3-cyanopropyl)-1H-benzo[d]imidazol-2-yl)methyl)-2'-oxospiro[cyclobutane-1,3'-indolin]-3-yl)carbamate<br>¹H NMR (400 MHz, DMSO-d₆) δ ppm 0.50-0.69 (m, 4 H) 1.97-2.11 (m, 2 H) 2.51-2.56 (m, 2 H) 2.57-2.71 (m, 4 H) 3.89-4.02 (m, 1 H) 4.39 (t, J = 7.30 Hz, 2 H) 4.43-4.53 (m, 1 H) 5.21 (s, 2 H) 7.04-7.15 (m, 2 H) 7.23 (td, J = 7.70, 1.32 Hz, 1 H) 7.29 (dd, J = 8.69, 1.87 Hz, 1 H) 7.53 (d, J = 7.04 Hz, 1 H) 7.65 (dd, J = 5.28, 3.30 Hz, 2 H) 7.69 (br. d, J = 8.60 Hz, 1 H); m/z = 504 (M + H)+ |
| 129 | 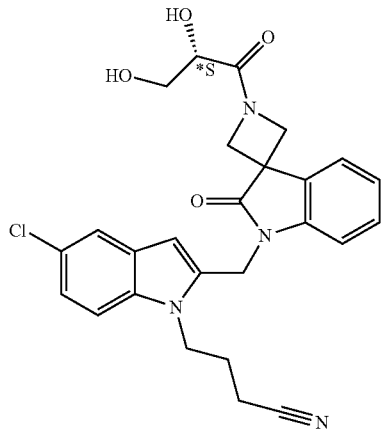 [SMILES: N#CCCCn1c(CN2C(=O)C3(CN(C(=O)[C@@H](O)CO)C3)c3ccccc32)cc2cc(Cl)ccc21] | (S)-4-(5-chloro-2-((1-(2,3-dihydroxypropanoyl)-2'-oxospiro[azetidine-3,3'-indolin]-1'-yl)methyl)-1H-indol-1-yl)butanenitrile<br>m/z = 493 (M + H)+ |
| 131 | 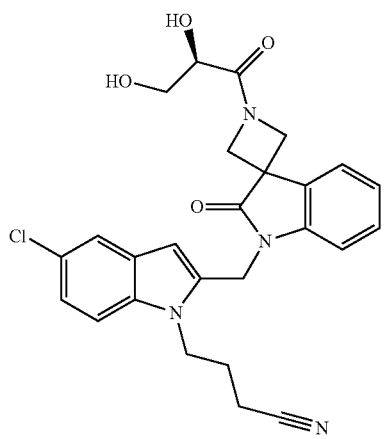 [SMILES: N#CCCCn1c(CN2C(=O)C3(CN(C(=O)[C@H](O)CO)C3)c3ccccc32)cc2cc(Cl)ccc21] | (R)-4-(5-chloro-2-((1-(2,3-dihydroxypropanoyl)-2'-oxospiro[azetidine-3,3'-indolin]-1'-yl)methyl)-1H-indol-1-yl)butanenitrile<br>m/z = 493 (M + H)+ |

| No | structure | Name/analytical details |
|---|---|---|
| 132 | 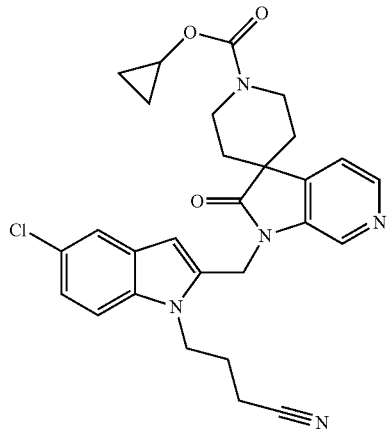 [SMILES: N#CCCCn1c(CN2C(=O)C3(CCN(C(=O)OC4CC4)CC3)c3ccncc32)cc2cc(Cl)ccc21] | Cyclopropyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate<br>$^1$H NMR (400 MHz, DMSO-d$_6$) δ ppm 0.49-0.74 (m, 4 H) 1.60-1.90 (m, 4 H) 1.92-2.05 (m, 2 H) 2.58 (t, J = 7.50 Hz, 2 H) 3.61-3.84 (m, 4 H) 3.99-4.11 (m, 1 H) 4.30 (t, J = 7.30 Hz, 2 H) 5.19 (s, 2 H) 6.36 (s, 1 H) 7.13 (dd, J = 8.80, 1.98 Hz, 1 H) 7.46-7.57 (m, 2 H) 7.70 (d, J = 4.84 Hz, 1 H) 8.33 (d, J = 4.84 Hz, 1 H) 8.39 (s, 1 H); m/z = 518 (M + H)+ |
| 133 | 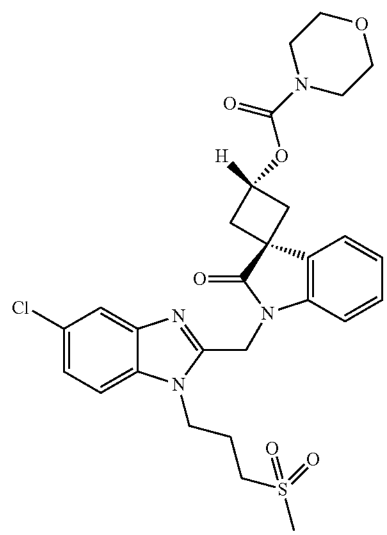 [SMILES: CS(=O)(=O)CCCn1c(CN2c3ccccc3[C@]3(C[C@@H](OC(=O)N4CCOCC4)C3)C2=O)nc2cc(Cl)ccc21] | (1r,3r)-1'-((5-chloro-1-(3-(methylsulfonyl)propyl)-1H-benzo[d]imidazol-2-yl)methyl)-2'-oxospiro[cyclobutane-1,3'-indolin]-3-yl morpholine-4-carboxylate<br>$^1$H-NMR (400 MHz, DMSO-d6) δ ppm 2.16 (dt, J = 15.24, 7.67 Hz, 2 H) 2.53-2.62 (m, 2 H) 2.72-2.84 (m, 2 H) 3.00 (s, 3 H) 3.19-3.27 (m, 2 H) 3.33-3.55 (m, 4 H) 3.55-3.66 (m, 4 H) 4.47 (t, J = 7.37 Hz, 2 H) 5.22 (s, 2 H) 5.33 (quin. J = 7.43 Hz, 1 H) 7.06-7.17 (m, 2 H) 7.22-7.28 (m, 1 H) 7.30 (dd, J = 8.58, 1.98 Hz, 1 H) 7.56 (d, J = 7.48 Hz, 1 H) 7.64-7.72 (m, 2 H); m/z = 587.17 (M + H)+ |
| 134 | 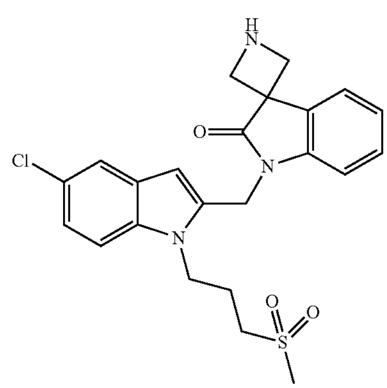 [SMILES: CS(=O)(=O)CCCn1c(CN2C(=O)C3(CNC3)c3ccccc32)cc2cc(Cl)ccc21] | 1'-({5-Chloro-1-[3-(methylsulfonyl)propyl]-1H-indol-2-yl}methyl)spiro[azetidine-3,3'-indol]-2'(1'H)-one<br>m/z = 458 (M + H)+ |

| No | structure | Name/analytical details |
|---|---|---|
| 135 | 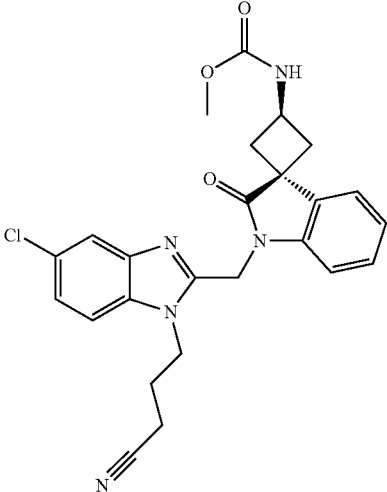 [SMILES: COC(=O)N[C@H]1C[C@]2(C1)C(=O)N(Cc1nc3cc(Cl)ccc3n1CCCC#N)c1ccccc12] | methyl ((1s,3s)-1'-((5-chloro-1-(3-cyanopropyl)-1H-benzo[d]imidazol-2-yl)methyl)-2'-oxospiro[cyclobutane-1,3'-indolin]-3-yl)carbamate<br>¹H NMR (400 MHz, DMSO-d₆) δ ppm 1.90-2.07 (m, 2 H) 2.36-2.49 (m, 2 H) 2.54-2.66 (m, 4 H) 3.55 (s, 3 H) 4.33 (t, J = 7.70 Hz, 2 H) 4.48-4.66 (m, 1 H) 5.22 (s, 2 H) 7.06-7.15 (m, 2 H) 7.20-7.27 (m, 1 H) 7.30 (dd, J = 8.58, 2.20 Hz, 1 H) 7.59 (d, J = 7.48 Hz, 1 H) 7.64 (d, J = 8.80 Hz, 1 H) 7.65 (d, J = 1.98 Hz, 1 H) 7.74-7.83 (m, 1 H); m/z = 478 (M + H)+ |
| 136 | 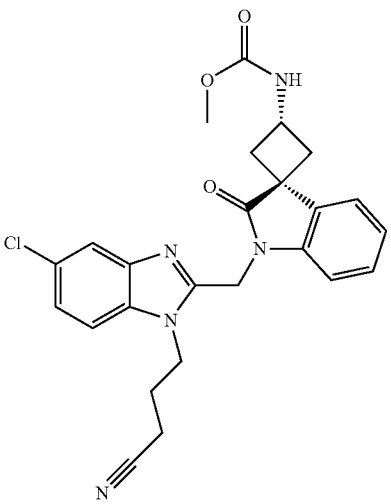 [SMILES: COC(=O)N[C@H]1C[C@@]2(C1)C(=O)N(Cc1nc3cc(Cl)ccc3n1CCCC#N)c1ccccc12] | methyl ((1r,3r)-1'-((5-chloro-1-(3-cyanopropyl)-1H-benzo[d]imidazol-2-yl)methyl)-2'-oxospiro[cyclobutane-1,3'-indolin]-3-yl)carbamate<br>¹H NMR (400 MHz, DMSO-d₆) δ ppm 1.94-2.12 (m, 2 H) 2.51-2.57 (m, 2 H) 2.58-2.69 (m, 4 H) 3.58 (s, 3 H) 4.35 (t, J = 7.50 Hz, 2 H) 4.43-4.54 (m, 1 H) 5.17 (s, 2 H) 7.06-7.16 (m, 2 H) 7.19-7.26 (m, 1 H) 7.19 (td, J = 7.70, 1.32 Hz, 1 H) 7.29 (dd, J = 8.80, 1.98 Hz, 1 H) 7.54 (d, J = 7.26 Hz, 1 H) 7.62-7.68 (m, 3 H); m/z = 478 (M + H)+ |
| 137 | 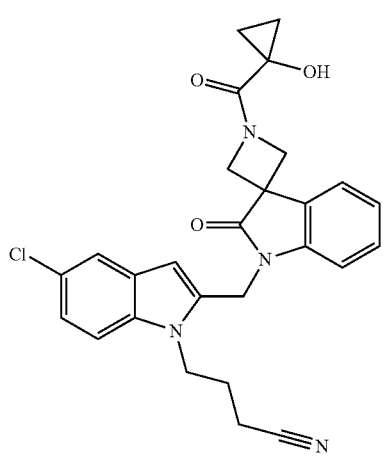 [SMILES: N#CCCCn1c(CN2C(=O)C3(CN(C(=O)C4(O)CC4)C3)c3ccccc32)cc2cc(Cl)ccc21] | 4-[5-Chloro-2-({1-hydroxycyclopropyl)carbonyl]-2'-oxospiro[azetidine-3,3'-indol]-1'(2'H)-yl}methyl)-1H-indol-1-yl]butanenitrile<br>¹H-NMR (360 MHz, DMSO-d6) δ ppm 0.87 (d, J = 3.7 Hz, 2 H), 1.04 (d, J = 6.2 Hz, 6 H), 1.12 (d, J = 5.5 Hz, 1 H), 1.98 (s,<br>1 H), 2.58 (t, J = 7.5 Hz, 1 H), 3.60 (t, J = 6.0 Hz, 1 H), 4.18 (s, 1 H), 4.31 (br. s., 1 H), 4.79 (s, 1 H), 5.15 (s, 1 H), 6.21 (br. s., 1 H), 6.35 (s, 1 H), 7.06-7.19 (m, 2 H), 7.29 (d, J = 1.1 Hz, 1 H), 7.49-7.56 (m, 1 H), 7.69 (d, J = 6.6 Hz, 1 H); m/z = 489 (M + H)+ |

| No | structure | Name/analytical details |
|---|---|---|
| 138 | 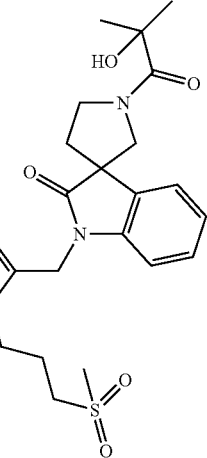 | 1-((5-chloro-1-(3-(methylsulfonyl)propyl)-1H-benzo[d]imidazol-2-yl)methyl)-1'-(2-hydroxy-2-methylpropanoyl)spiro[indoline-3,3'-pyrrolidlin]-2-one<br>$^1$H-NMR (400 MHz, DMSO-d6) δ ppm 1.27 (d, J = 7.3 Hz, 6 H), 2.06-2.28 (m, 4 H), 3.01 (s, 3 H), 3.24 (t, J = 7.7 Hz, 2 H), 3.59-3.86 (m, 2 H), 4.05 (s, 1 H), 4.20 (br. s., 1 H), 4.48 (t, J = 7.5 Hz, 2 H), 5.18-5.36 (m, 2 H), 7.04-7.12 (m, 1 H), 7.17-7.23 (m, 1 H), 7.25-7.33 (m, 2 H), 7.63-7.72 (m, 2 H); m/z = 559 (M + H)+ |
| 143 | 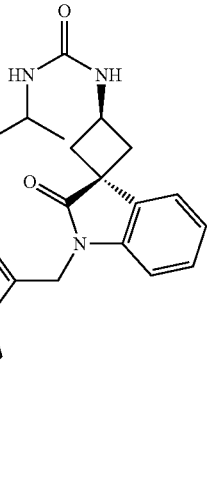 | 1-((1s,3s)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea<br>$^1$H NMR (400 MHz, DMSO-d$_6$) δ ppm 1.04 (d, J = 6.60 Hz, 6 H) 1.90-2.06 (m, 2 H) 2.32-2.46 (m, 2 H) 2.60 (1, J = 7.48 Hz, 2 H) 3.50-3.81 (m, 1 H) 4.24-4.48 (m, 2 H) 4.54-4.75 (m, 1 H) 5.23 (s, 2 H) 5.65 (d, J = 8.80 Hz, 1 H) 6.32 (d, J = 9.02 Hz, 1 H) 7.05-7.15 (m, 2 H) 7.23 (dd, J = 8.14, 1.32 Hz, 1 H) 7.29 (dd, J = 8.58, 1.98 Hz, 1 H) 7.58 (d, J = 8.36 Hz, 1 H) 7.62-7.68 (m, 2 H); m/z = 505 (M + H)+; MP = 242.49° C. |
| 144 | 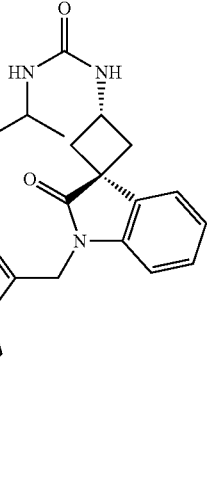 | 1-((1r,3r)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea<br>$^1$H NMR (400 MHz, DMSO-d$_6$) δ ppm 1.04 (d, J = 6.60 Hz, 6 H) 1.92-2.12 (m, 2 H) 2.37-2.48 (m, 2 H) 2.55-2.69 (m, 4 H) 3.52-3.79 (m, 1 H) 4.24-4.46 (m, 2 H) 4.48-4.65 (m, 1 H) 5.21 (s, 2 H) 5.75 (d, J = 7.70 Hz, 1 H) 6.26 (d, J = 8.58 Hz, 1 H) 7.09 (dd, J = 15.19, 7.92 Hz, 2 H) 7.22 (s, 1 H) 7.29 (dd, J = 8.80, 1.98 Hz, 1 H) 7.57 (d, J = 6.60 Hz, 1 H) 7.65 (dd, J = 5.17, 3.19 Hz, 2 H); m/z = 505 (M + H)+; MP = 219.90° C. |

-continued

| No | structure | Name/analytical details |
|---|---|---|
| 145 | 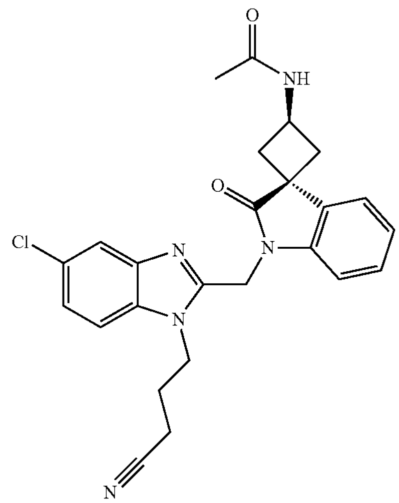 [SMILES: CC(=O)N[C@H]1C[C@]2(C1)C(=O)N(Cc1nc3cc(Cl)ccc3n1CCCC#N)c1ccccc12] | N-((1s,3s)-1'-((5-chloro-1-(3-cyanopropyl)-1H-benzo[d]imidazol-2-yl)methyl)-2'-oxospiro[cyclobutane-1,3'-indolin]-3-yl)acetamide<br>$^1$H NMR (400 MHz, DMSO-d$_6$) δ ppm 1.85 (s, 3 H) 1.93-2.07 (m, 2 H) 2.52-2.65 (m, 6 H) 4.17-4.48 (m, 2 H) 4.66-4.87 (m, 1 H) 5.24 (s, 2 H) 7.07-7.16 (m, 2 H) 7.20-7.27 (m, 1 H) 7.30 (dd, J = 8.80, 2.20 Hz, 1 H) 7.58-7.69 (m, 3 H) 8.45 (d, J = 7.92 Hz, 1 H); m/z = 462 (M + H)+; MP = 250.91° C. |
| 146 | 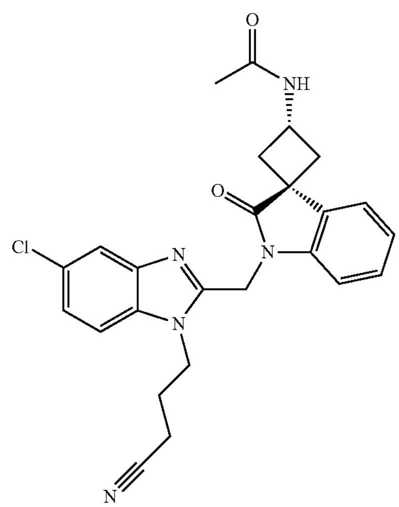 [SMILES: CC(=O)N[C@H]1C[C@@]2(C1)C(=O)N(Cc1nc3cc(Cl)ccc3n1CCCC#N)c1ccccc12] | N-((1r,3r)-1'-((5-chloro-1-(3-cyanopropyl)-1H-benzo[d]imidazol-2-yl)methyl)-2'-oxospiro[cyclobutane-1,3'-indolin]-3-yl)acetamide<br>$^1$H NMR (400 MHz, DMSO-d$_6$) δ ppm 1.84 (s, 3 H) 1.96-2.10 (m, 2 H) 2.41-2.47 (m, 1 H) 2.57-2.67 (m, 5 H) 4.37 (t, J = 7.30 Hz, 2 H) 4.61-4.75 (m, 1 H) 5.12 (s, 2 H) 7.04-7.15 (m, 2 H) 7.22 (td, J = 7.70, 1.10 Hz, 1 H) 7.28 (dd, J = 8.58, 1.76 Hz, 1 H) 7.53 (dd, J = 8.80, 0.88 Hz, 1 H) 7.61-7.68 (m, 2 H) 8.26 (d, J = 9.68 Hz, 1 H); m/z = 462 (M + H)+;<br>MP = 194.77° C. |
| 147 | 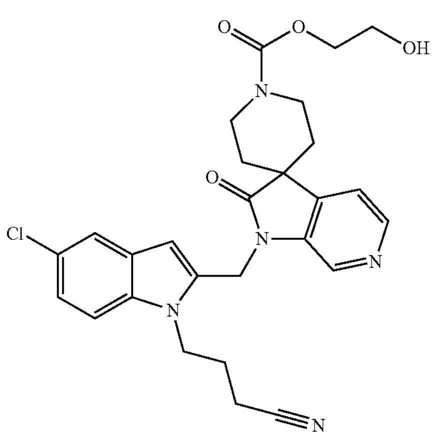 [SMILES: N#CCCCn1c(CN2C(=O)C3(CCN(C(=O)OCCO)CC3)c3ccncc32)cc2cc(Cl)ccc21] | 2-Hydroxyethyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate<br>$^1$H NMR (400 MHz, DMSO-d$_6$) δ ppm 1.75-1.91 (m, 4 H), 1.95-2.08 (m, 2 H), 2.56 (t, J = 7.4 Hz, 2 H), 3.61 (t, J = 5.1 Hz, 2 H), 3.69-3.89 (m, 4 H), 4.03-4.13 (m, 2 H), 4.25-4.35 (m, 2 H), 4.61 (br. s., 1 H), 5.18 (s, 2 H), 6.35 (s, 1 H), 7.13 (dd, J = 8.8, 2.0 Hz, 1 H), 7.50 (dd, J = 5.5, 3.3 Hz, 2 H),<br>7.63 (dd, J = 4.8, 0.7 Hz, 1 H), 8.33 (d, J = 4.8 Hz, 1 H), 8.36 (s, 1 H); m/z = 522 (M + H)+<br>MP = 144.55° C.; |

| No | structure | Name/analytical details |
|---|---|---|
| 148 | 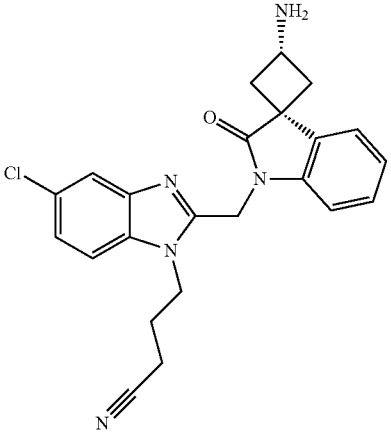 [SMILES: N#CCCCn1c(CN2c3ccccc3[C@]3(C[C@@H](N)C3)C2=O)nc2cc(Cl)ccc21] | 4-(2-(((1r,3r)-3-amino-2'-oxospiro[cyclobutane-1,3'-indolin]-1'-yl)methyl)-5-chloro-1H-benzo[d]imidazol-1-yl)butanenitrile<br>$^1$H NMR (400 MHz, DMSO-d$_6$) δ ppm 1.91-2.10 (m, 2 H) 2.13-2.27 (m, 2 H) 2.55-2.71 (m, 4 H) 3.78 (quin, J = 8.03 Hz, 1 H) 4.38 (t, J = 7.59 Hz, 2 H) 5.20 (s, 2 H) 7.08 (td, J = 8.10, 1.54 Hz, 2 H) 7.20 (td, J = 7.70, 1.32 Hz, 1 H) 7.29 (dd, J = 8.58, 1.98 Hz, 1 H) 7.53-7.70 (m, 3 H); m/z = 420 (M + H)+ |
| 149 | 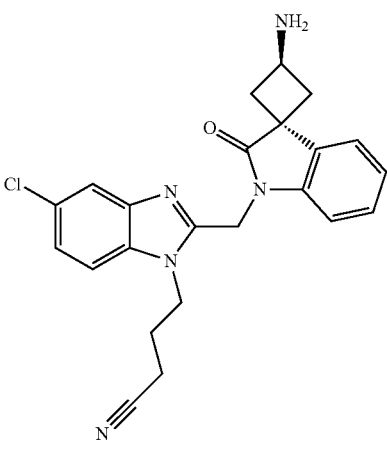 [SMILES: N#CCCCn1c(CN2c3ccccc3[C@]3(C[C@H](N)C3)C2=O)nc2cc(Cl)ccc21] | 4-(2-(((1s,3s)-3-amino-2'-oxospiro[cyclobutane-1,3'-indolin]-1'-yl)methyl)-5-chloro-1H-benzo[d]imidazol-1-yl)butanenitrile<br>$^1$H NMR (400 MHz, DMSO-d$_6$) δ ppm 1.80-2.20 (m, 4 H) 2.20-2.34 (m, 2 H) 2.36-2.47 (m, 2 H) 2.59 (t, J = 7.48 Hz, 2 H) 3.77-3.95 (m, 1 H) 4.36 (t, J = 7.50 Hz, 2 H) 5.21 (s, 2 H) 7.00-7.14 (m, 2 H) 7.16-7.25 (m, 1 H) 7.29 (dd, J = 8.58, 1.98 Hz, 1 H) 7.55 (d, J = 6.82 Hz, 1 H) 7.64 (d, J = 8.80 Hz, 1 H) 7.66 (d, J = 1.76 Hz, 1 H); m/z = 420 (M + H)+ |
| 150 | 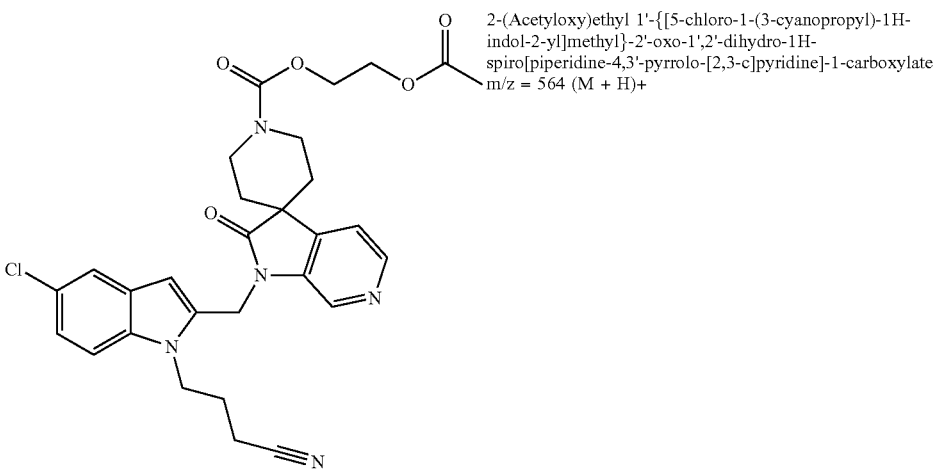 | 2-(Acetyloxy)ethyl 1'-{[5-chloro-1-(3-cyanopropyl)-1H-indol-2-yl]methyl}-2'-oxo-1',2'-dihydro-1H-spiro[piperidine-4,3'-pyrrolo-[2,3-c]pyridine]-1-carboxylate<br>m/z = 564 (M + H)+ |

-continued

| No | structure | Name/analytical details |
|---|---|---|
| 152 | 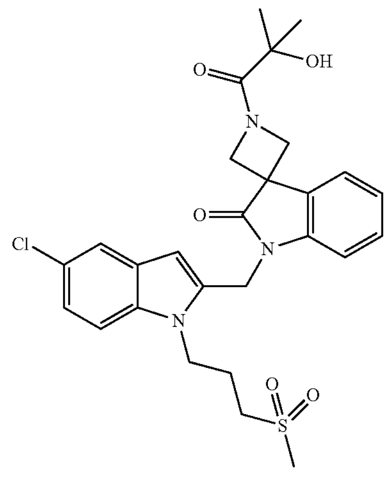 [SMILES: CC(C)(O)C(=O)N1CC2(C1)C(=O)N(Cc1cc3cc(Cl)ccc3n1CCCS(C)(=O)=O)c1ccccc12] | 1'-({5-Chloro-1-[3-(methylsulfonyl)propyl]-1H-indol-2-yl}methyl)-1-(2-hydroxy-2-methylpropanoyl)spiro[azetidine-3,3'-indol]-2'(1'H)-one<br>$^1$H-NMR (400 MHz, DMSO-d6) δ ppm 1.32 (s, 3 H) 1.34 (s, 3 H) 2.02-2.14 (m, 2 H) 2.99 (s, 3 H) 3.14-3.23 (m, 2 H) 4.03-4.23 (m, 2 H) 4.39 (t, J = 7.48 Hz, 2 H) 4.55-4.78 (m, 2 H) 5.14 (s, 2 H) 5.26 (s, 1 H) 6.38 (s, 1 H) 7.08 (d, J = 7.70 Hz, 1 H) 7.12-7.19 (m, 2 H) 7.25-7.32 (m, 1 H) 7.52 (d, J = 1.98 Hz, 1 H) 7.55 (d, J = 8.80 Hz, 1 H) 7.64 (dd, J = 7.37, 0.77 Hz, 1 H); m/z = 544.08 (M + H)+ |
| 153 | 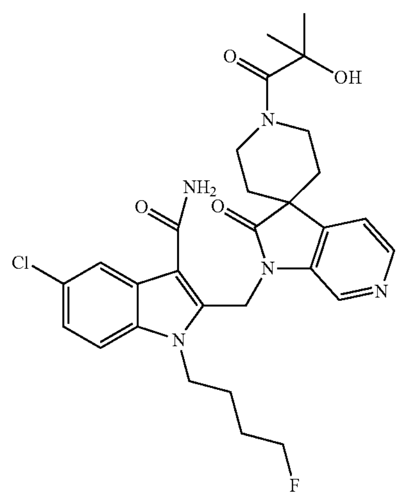 [SMILES: CC(C)(O)C(=O)N1CCC2(CC1)C(=O)N(Cc1c(C(N)=O)c3cc(Cl)ccc3n1CCCCF)c1cnccc12] | 5-Chloro-1-(4-fluorobutyl)-2-{[1-(2-hydroxy-2-methylpropanoyl)-2'-oxospiro[piperidine-4,3'-pyrrolo[2,3-c]pyridin]-1'(2'H)-yl]methyl}-1H-indole-3-carboxamide<br>$^1$H-NMR (400 MHz, DMSO-d6) δ ppm 1.37 (s, 6 H), 1.54-1.69 (m, 4 H), 1.71-1.91 (m, 4 H), 3.63-4.06 (m, 2 H), 4.13-4.31 (m, 2H), 4.14-4.23 (m, 2 H), 4.36 (br.s., 1 H), 4.47 (t, J = 5.6 Hz, 1 H), 5.48 (s, 1 H), 5.53 (s, 2 H), 7.26 (dd, J = 8.9, 2.1 Hz, 1 H), 7.58 (d, J = 9.0 Hz, 1 H), 7.61 (d, J = 4.8 Hz, 1 H), 7.63-7.73 (m, 2 H), 7.84 (d, J = 2.0 Hz, 1 H), 8.29 (d, J = 4.8 Hz, 1 H), 8.44 (s, 1 H); m/z = 570 (M + H)+ |
| 154 | 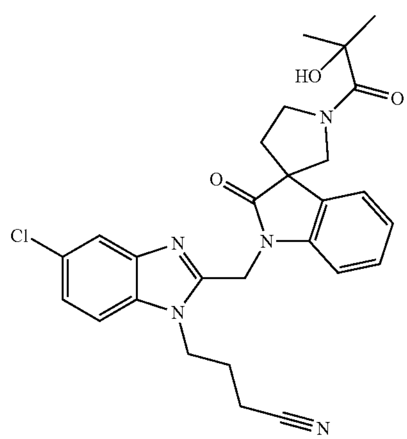 [SMILES: CC(C)(O)C(=O)N1CCC2(C1)C(=O)N(Cc1nc3cc(Cl)ccc3n1CCCC#N)c1ccccc12] | 4-(5-Chloro-2-{[1'-(2-hydroxy-2-methylpropanoyl)-2-oxospiro[indole-3,3'-pyrrolidin]-1(2H)-yl]methyl}-1H-benzimidazol-1-yl)butanenitrile<br>$^1$H-NMR (400 MHz, DMSO-d6) δ ppm 1.22-1.43 (m, 6 H), 2.00-2.15 (m, 2 H), 2.15-2.38 (m, 2 H), 2.62 (t, J = 7.4 Hz, 2 H), 3.59-3.86 (m, 2 H), 4.04 (s, 1 H), 4.20 (br. s., 1 H), 4.39 (t, J = 7.9 Hz, 2 H), 5.16-5.35 (m, 3 H), 7.04-7.12 (m, 1 H), 7.15-7.21 (m, 1 H), 7.22-7.40 (m, 3 H), 7.61-7.69 (m, 2 H); m/z = 506 (M + H)+ |

| No | structure | Name/analytical details |
|---|---|---|
| 155 | 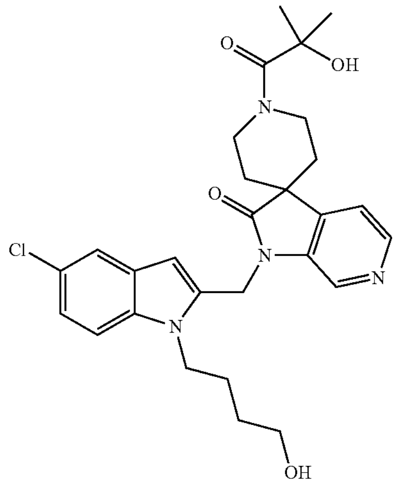 [SMILES: CC(C)(O)C(=O)N1CCC2(CC1)C(=O)N(Cc1cc3cc(Cl)ccc3n1CCCCO)c1cnccc12] | 1'-{[5-Chloro-1-(4-hydroxybutyl)-1H-indol-2-yl]methyl}-1-(2-hydroxy-2-methylpropanoyl)spiro[piperidine-4,3'-pyrrolo[2,3-c]pyridin]-2'(1'H)-one<br>¹H-NMR (360 MHz, DMSO-d6) δ ppm 1.37 (s, 6 H), 1.41-1.51 (m, 2 H), 1.65 (m, J = 6.6 Hz, 2 H), 1.83 (br. s., 4 H), 3.37-3.46 (m, 2 H), 3.73-4.41 (m, 4 H), 4.24 (t, J = 7.5 Hz, 2 H), 4.48 (t, J = 5.1 Hz, 1 H), 5.19 (s, 2 H), 5.52 (s, 1 H), 6.42 (s, 1 H), 7.13 (dd, J = 8.8, 1.8 Hz, 1 H), 7.43-7.57 (m, 2 H), 7.68 (d, J = 4.8 Hz, 1 H), 8.33 (d, J = 4.8 Hz, 1 H), 8.38 (s, 1 H); m/z = 525 (M + H)+ |
| 156 | 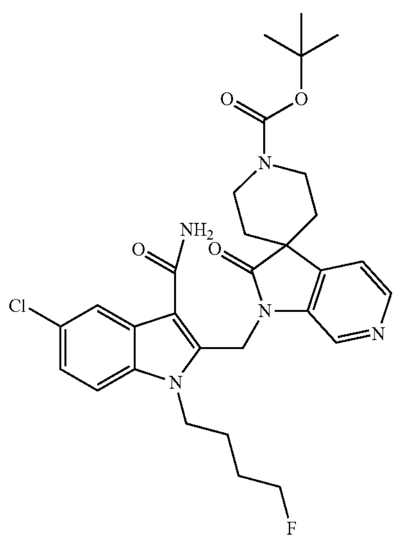 [SMILES: CC(C)(C)OC(=O)N1CCC2(CC1)C(=O)N(Cc1c(C(N)=O)c3cc(Cl)ccc3n1CCCCF)c1cnccc12] | tert-Butyl 1'-{[3-carbamoyl-5-chloro-1-(4-fluorobutyl)-1H-indol-2-yl]methyl}-2'-oxo-1',2'-dihydro-1H-spiro[piperidine-4,3'-pyrrolo[2,3-c]pyridine]-1-carboxylate<br>¹H-NMR (400 MHz, DMSO-d6) δ ppm 1.45 (s, 9 H), 1.54-1.70 (m, 4 H), 1.77 (t, J = 5.6 Hz, 4 H), 3.59-3.69 (m, 2 H), 3.70-3.80 (m, 2 H), 4.18 (t, J = 7.0 Hz, 2 H), 4.33-4.39 (m, 1 H), 4.48 (t, J = 5.6 Hz, 1 H), 5.52 (s, 2 H), 7.26 (dd, J = 8.8, 2.0 Hz, 1 H), 7.57 (d, J = 8.8 Hz, 1 H), 7.63 (d, J = 4.6 Hz, 1 H), 7.64-7.71 (m, 2 H), 7.84 (d, J = 2.0 Hz, 1 H), 8.27 (d, J = 4.6 Hz, 1 H), 8.43 (s, 1 H); m/z = 584 (M + H)+ |
| 157 | 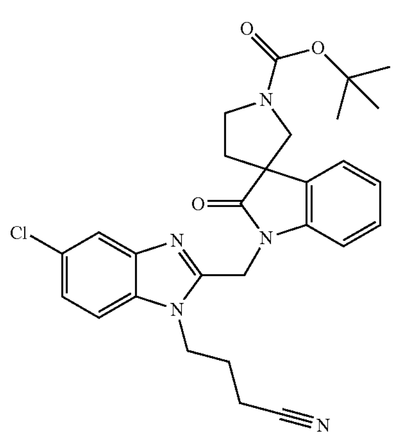 [SMILES: CC(C)(C)OC(=O)N1CCC2(C1)C(=O)N(Cc1nc3cc(Cl)ccc3n1CCCC#N)c1ccccc12] | tert-Butyl 1-{[5-chloro-1-(3-cyanopropyl)-1H-benzimidazol-2-yl]methyl}-2-oxo-1,2-dihydro-1'H-spiro[indole-3,3'-pyrrolidine]-1'-carboxylate<br>¹H-NMR (400 MHz, DMSO-d6) δ ppm 1.35-1.52 (m, 9 H), 2.02-2.14 (m, 2 H), 2.18-2.30 (m, 2 H), 2.62 (t, J = 7.4 Hz, 2 H), 3.50-3.62 (m, 2 H), 3.62-3.77 (m, 2 H), 4.39 (t, J = 7.6 Hz, 2 H), 5.17-5.33 (m, 2 H), 7.08 (td, J = 7.5, 0.9 Hz, 1 H), 7.16-7.21 (m, 1 H), 7.24-7.32 (m, 2 H), 7.35 (d, J = 7.3 Hz, 1 H), 7.62-7.69 (m, 2 H); m/z = 521 (M + H)+ |

| No | structure | Name/analytical details |
|---|---|---|
| 158 | 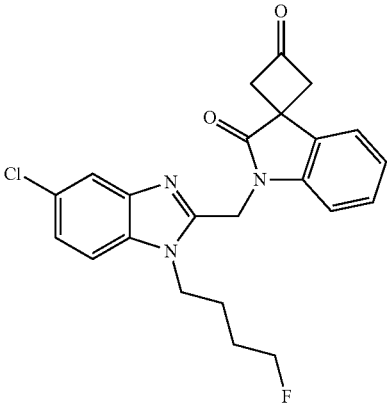 [SMILES: O=C1CC2(C1)C(=O)N(Cc1nc3cc(Cl)ccc3n1CCCCF)c1ccccc12] | 1-{[5-Chloro-1-(4-fluorobutyl)-1H-benzimidazol-2-yl]methyl}-3H-spiro[cyclobutane-1,3'-indole]-2',3(1'H)-dione<br>$^1$H-NMR (400 MHz, DMSO-d6) δ ppm 1.52-1.86 (m, 4 H) 3.39-3.50 (m, 2 H) 3.60-3.74 (m, 2 H) 4.32-4.42 (m, 3 H) 4.50 (t, J = 5.50 Hz, 1 H) 5.26 (s, 2 H) 7.11 (dd, J = 7.48, 0.88 Hz, 1 H) 7.19 (d, J = 7.92 Hz, 1 H) 7.24-7.30 (m, 2 H) 7.60-7.69 (m, 3 H); m/z = 426 (M + H)+ |
| 162 | 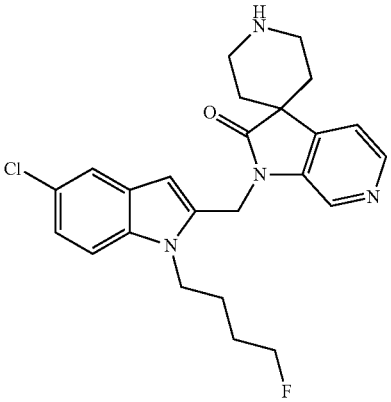 [SMILES: O=C1N(Cc2cc3cc(Cl)ccc3n2CCCCF)c2cnccc2C12CCNCC2] | 1'-[5-Chloro-1-(4-fluorobutyl)-1H-indol-2-yl]methyl}spiropiperidine-4,3'-pyrrolo[2,3-c]pyridin]-2'(1'H)-one<br>$^1$H-NMR (400 MHz, DMSO-d6) δ ppm 1.53-1.85 (m, 8 H) 2.77-3.00 (m, 2 H) 3.03-3.16 (m, 2 H) 4.26 (t, J = 6.93 Hz, 2 H) 4.40 (t, J = 5.72 Hz, 1 H) 4.47-4.56 (m, 1 H) 5.17 (s, 2 H) 6.40 (s, 1 H) 7.13 (dd, J = 8.80, 2.20 Hz, 1 H) 7.50 (d, J = 8.58 Hz, 1 H) 7.53 (d, J = 1.98 Hz, 1 H) 7.64 (d, J = 4.62 Hz, 1 H) 8.32 (d, J = 4.84 Hz, 1 H) 8.35 (s, 1 H); m/z = 441 (M + H)+ |
| 163 | 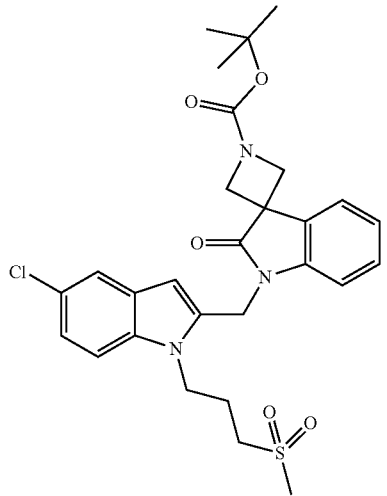 [SMILES: CC(C)(C)OC(=O)N1CC2(C1)C(=O)N(Cc1cc3cc(Cl)ccc3n1CCCS(C)(=O)=O)c1ccccc12] | tert-Butyl 1'-({5-chloro-1-[3-(methylsulfonyl)propyl]-1H-indol-2-yl}methyl)-2'-oxo-1',2'-dihydro-1H-spiro[azetidine-3,3'-indole]-1-carboxylate<br>$^1$H-NMR (400 MHz, DMSO-d6) δ ppm 1.45 (s, 9 H) 1.98-2.13 (m, 2 H) 2.99 (s, 3 H) 3.13-3.22 (m, 2 H) 4.01-4.24 (m, 4 H) 4.38 (t, J = 7.59 Hz, 2 H) 5.13 (s, 2 H) 6.39 (s, 1 H) 7.05-7.19 (m, 3 H) 7.24-7.33 (m, 1 H) 7.52 (d, J = 1.98 Hz, 1 H) 7.54 (d, J = 8.80 Hz, 1 H) 7.65-7.71 (m, 1 H); m/z = 558.23 (M + H)+ |

| No | structure | Name/analytical details |
|---|---|---|
| 164 | 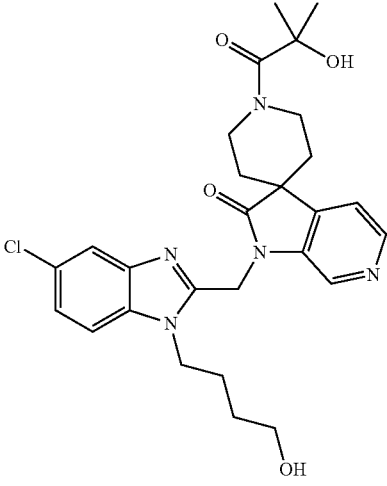 [SMILES: CC(C)(O)C(=O)N1CCC2(CC1)C(=O)N(Cc1nc3cc(Cl)ccc3n1CCCCO)c1cnccc12] | 1'-{[5-Chloro-1-(4-hydroxybutyl)-1H-benzimidazol-2-yl]methyl}-1-(2-hydroxy-2-methylpropanoyl)spiro[piperidine-4,3'-pyrrolo[2,3-c]pyridin]-2'(1'H)-one<br>$^1$H-NMR (360 MHz, DMSO-d6) δ ppm 1.37 (s, 6 H), 1.40-1.57 (m, 2 H), 1.63-1.79 (m, 2 H), 1.82 (br. s., 4 H), 3.42 (q, J = 6.1 Hz, 2 H), 3.85 (br. s., 2 H), 4.34 (m, J = 7.5, 7.5 Hz, 4 H), 4.50 (t, J = 5.1 Hz, 1 H), 5.29 (s, 2 H), 5.51 (s, 1 H), 7.28 (dd, J = 8.8, 1.8 Hz, 1 H), 7.55-7.75 (m, 3 H), 8.34 (d, J = 4.8 Hz, 1 H), 8.48 (s, 1 H); m/z = 526 (M + H)+; MP = 191.87° C. |
| 165 | 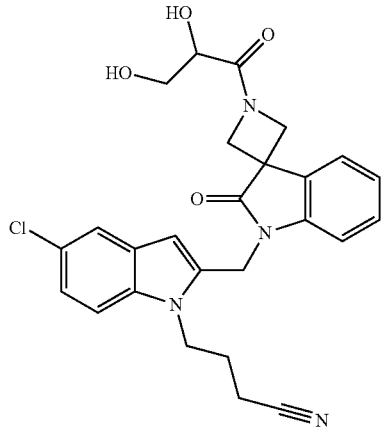 [SMILES: N#CCCCn1c(CN2C(=O)C3(CN(C(=O)C(O)CO)C3)c3ccccc32)cc2cc(Cl)ccc21] | 4-(5-chloro-2-((1-(2,3-dihydroxypropanoyl)-2'-oxospiro[azetidine-3,3'-indolin]-1'-yl)methyl)-1H-indol-1-yl)butanenitrile<br>$^1$H-NMR (400 MHz, DMSO-d6) δ ppm 1.83-2.05 (m, 2 H) 2.56 (t, J = 7.30 Hz, 2 H) 3.44-3.66 (m, 2 H) 4.01-4.24 (m, 3 H) 4.25-4.34 (m, 2 H) 4.43-4.67 (m, 2 H) 4.76-4.92 (m, 1 H) 5.13 (s, 2 H) 5.30 (dd, J = 49.08, 5.50 Hz, 1 H) 6.32 (d, J = 2.86 Hz, 1 H) 7.05 (br. d, J = 9.00 Hz, 1 H) 7.10-7.16 (m, 2 H) 7.22-7.31 (m, 1 H) 7.47-7.54 (m, 2 H) 7.59-7.69 (m, 1 H); m/z = 493 (M + H)+ |
| 166 | 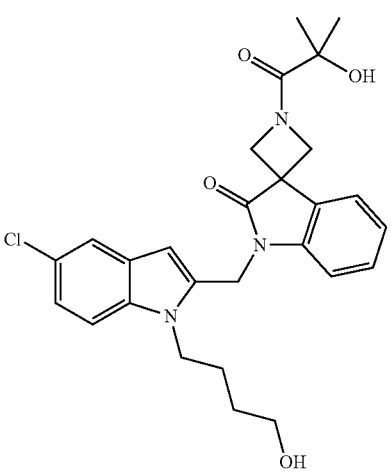 [SMILES: CC(C)(O)C(=O)N1CC2(C1)C(=O)N(Cc1cc3cc(Cl)ccc3n1CCCCO)c1ccccc12] | 1'-{[5-Chloro-1-(4-hydroxybutyl)-1H-indol-2-yl]methyl}-1-(2-hydroxy-2-methylpropanoyl)spiro[azetidine-3,3'-indol]-2'(1'H)-one<br>$^1$H-NMR (360 MHz, DMSO-d6) δ ppm 1.33 (d, J = 5.9 Hz, 6 H), 1.37-1.50 (m, 2 H), 1.61 (m, J = 7.0 Hz, 2 H), 3.39 (q, J = 6.2 Hz, 2 H), 4.06 (d, J = 9.5 Hz, 1 H), 4.17 (d, J = 9.5 Hz, 1 H), 4.24 (t, J = 7.7 Hz, 2 H), 4.46 (t, J = 5.1 Hz, 1 H), 4.59 (d, J = 9.9 Hz, 1 H), 4.72 (d, J = 9.5 Hz, 1 H), 5.12 (s, 2 H), 5.29 (s, 1 H), 6.42 (s, 1 H), 7.02-7.18 (m, 3 H), 7.27 (m, J = 7.0 Hz, 1 H), 7.47 (d, J = 8.8 Hz, 1 H), 7.52 (d, J = 2.2 Hz, 1 H), 7.63 (d, J = 7.0 Hz, 1 H); m/z = 496 (M + H)+; MP = 157.11° C. |

| No | structure | Name/analytical details |
|---|---|---|
| 167 | 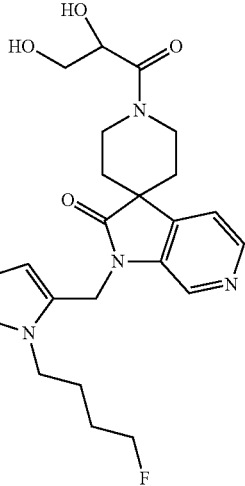 | 1'-{[5-Chloro-1-(4-fluorobutyl)-1H-indol-2-yl]methyl}-1-(2,3-dihydroxypropanoyl)spiro[piperidine-4,3'-pyrrolo[2,3-c]pyridin]-2'(1'H)-one<br>$^1$H-NMR (400 MHz, DMSO-d6) δ ppm 1.55-1.95 (m, 8 H) 3.42-3.52 (m, 1 H) 3.53-3.65 (m, 1 H) 3.74-4.02 (m, 4 H) 4.17-4.31 (m, 2 H) 4.38 (t, J = 6.40 Hz, 2 H) 4.46-4.55 (m, 1 H) 4.71 (t, J = 5.90 Hz, 1 H) 4.95 (dd, J = 21.13, 6.82 Hz, 1 H) 5.18 (s, 2 H) 6.40 (s, 1 H) 7.11 (dd, J = 8.80, 2.20 Hz, 1 H) 7.50 (d, J = 8.80 Hz, 1 H) 7.52 (d, J = 2.20 Hz, 1 H) 7.59-7.70 (m, 1 H) 8.32 (d, J = 4.62 Hz, 1 H) 8.37 (s, 1 H); m/z = 530 (M + H)+ |
| 168 | 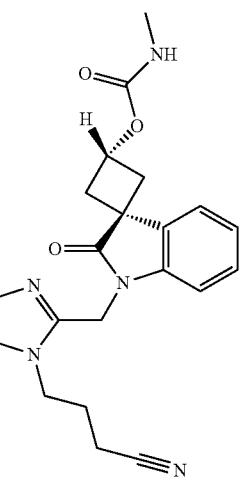 | (1r,3r)-1'-((5-chloro-1-(3-cyanopropyl)-1H-benzo[d]imidazol-2-yl)methyl)-2'-oxospiro[cyclobutane-1,3'-indolin]-3-yl methylcarbamate<br>$^1$H-NMR (400 MHz, DMSO-d6) δ ppm 2.07 (quin, J = 7.48 Hz, 2 H) 2.44-2.53 (m, 2 H) 2.56-2.67 (m, 5 H) 2.72-2.83 (m, 2 H) 4.40 (t, J = 7.50 Hz, 2 H) 5.23 (s, 2 H) 5.30 (quin, J = 7.37 Hz, 1 H) 7.06-7.19 (m, 3 H) 7.22-7.27 (m, 1 H) 7.29 (dd, J = 8.80, 1.98 Hz, 1 H) 7.48-7.55 (m, 1 H) 7.62-7.68 (m, 2 H); m/z = 478.10 (M + H)+ |
| 169 | 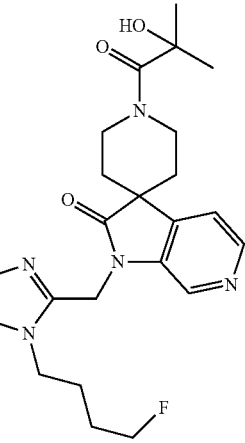 | 1'-{[5-Chloro-1-(4-fluorobutyl)-1H-benzimidazol-2-yl]methyl}-1-(2-hydroxy-2-methylpropanoyl)spiro[piperidine-4,3'-pyrrolo[2,3-c]pyridin]-2'(1'H)-one<br>$^1$H-NMR (400 MHz, DMSO-d6) δ ppm 1.40 (s, 6 H), 1.69-1.93 (m, 8 H), 4.05 (t, J = 5.6 Hz, 4 H), 4.35 (t, J = 7.5 Hz, 2 H), 4.40 (t, J = 6.1 Hz, 1 H), 4.52 (t, J = 5.8 Hz, 1 H), 5.06 (s, 1 H), 5.25 (s, 2 H), 7.24 (dd, J = 8.6, 2.0 Hz, 1 H), 7.53 (dd, J = 4.6, 0.7 Hz, 1 H), 7.55-7.61 (m, 1 H), 8.32 (d, J = 4.8 Hz, 1 H), 8.45 (s, 1 H); m/z = 528 (M + H)+; MP = 222.72° C. |

| No | structure | Name/analytical details |
|---|---|---|
| 170 | 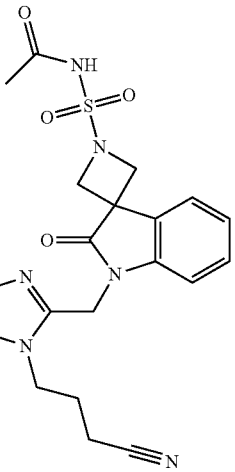 | N-[(1'-{[5-Chloro-1-(3-cyanopropyl)-1H-benzimidazol-2-yl]methyl}-2'-oxo-1',2'-dihydro-1H-spiro[azetidine-3,3'-indol]-1-yl)sulfonyl]acetamide<br>$^1$H-NMR (400 MHz, DMSO-d6) δ ppm 2.00-2.13 (m, 2 H) 2.16 (s, 3 H) 2.62 (t, J = 7.37 Hz, 2 H) 4.24 (d, J = 8.36 Hz, 2 H) 4.33-4.44 (m, 4 H) 5.21 (s, 2 H) 7.07-7.23 (m, 2 H) 7.25-7.35 (m, 2 H) 7.56 (d, J = 6.82 Hz, 1 H) 7.62-7.68 (m, 2 H) 11.73 (s, 1 H); m/z = 527 (M + H)+ |
| 172 | 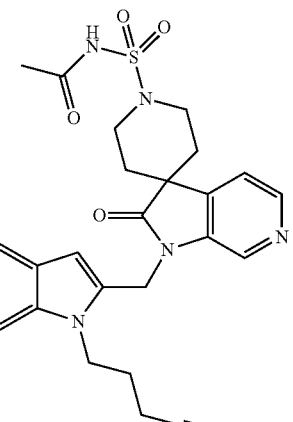 | N-[(1'-{[5-Chloro-1-(3-cyanopropyl)-1H-indol-2-yl]methyl}-2'-oxo-1',2'-dihydro-1H-spiro[piperidine-4,3'-pyrrolo[2,3-c]pyridin]-1-yl)sulfonyl]acetamide<br>$^1$H-NMR (400 MHz, DMSO-d6) δ ppm 1.84-2.08 (m, 9 H) 2.58 (t, J = 7.37 Hz, 2 H) 3.49-3.74 (m, 4 H) 4.24-4.37 (m, 2 H) 5.19 (s, 2 H) 6.34 (s, 1 H) 7.15 (dd, J = 8.69, 2.09 Hz, 1 H) 7.50-7.61 (m, 3 H) 8.36 (d, J = 4.84 Hz, 1 H) 8.39 (s, 1 H) 11.54 (s, 1 H); m/z = 555.06 (M + H)+; MP = 230.52° C. |
| 173 | 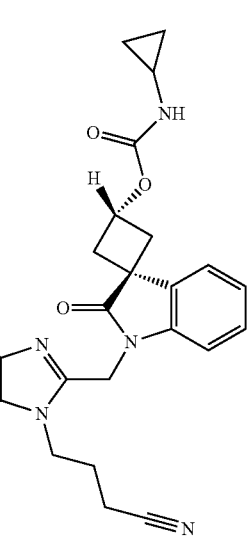 | (1r,3r)-1'-((5-chloro-1-(3-cyanopropyl)-1H-benzo[d]imidazol-2-yl)methyl)-2'-oxospiro[cyclobutane-1,3'-indolin]-3-yl cyclopropylcarbamate<br>$^1$H-NMR (400 MHz, DMSO-d6) δ ppm 0.36-0.50 (m, 2 H) 0.53-0.67 (m, 2 H) 2.06 (quin, J = 7.43 Hz, 2 H) 2.42-2.52 (m, 3 H) 2.62 (t, J = 7.37 Hz, 2 H) 2.70-2.83 (m, 2 H) 4.40 (t, J = 7.48 Hz, 2 H) 5.23 (s, 2 H) 5.31 (quin, J = 7.37 Hz, 1 H)<br>7.07-7.14 (m, 2 H) 7.22-7.27 (m, 1 H) 7.29 (dd, J = 8.58, 1.98 Hz, 1 H) 7.41-7.55 (m, 2 H) 7.62-7.69 (m, 2 H); m/z = 504.15 (M + H)+ |

-continued

| No | structure | Name/analytical details |
|---|---|---|
| 174 | 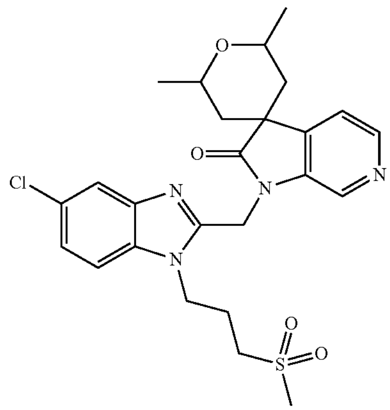 [SMILES: CC1CC2(CC(C)O1)C(=O)N(Cc1nc3cc(Cl)ccc3n1CCCS(C)(=O)=O)c1cnccc12] | 1'-({5-Chloro-1-[3-(methylsulfonyl)propyl]-1H-benzimidazol-2-yl}methyl)-2,6-dimethyl-2,3,5,6-tetrahydrospiro[pyran-4,3'-pyrrolo[2,3-c]pyridin]-2'(1'H)-one<br>$^1$H-NMR (400 MHz, CHLOROFORM-d) δ ppm 1.23 (d, J = 6.16 Hz, 6 H) 1.59-1.74 (m, 4 H) 2.30-2.41 (m, 2 H) 2.98 (s, 3 H) 3.12 (t, J = 7.04 Hz, 2 H) 4.33-4.43 (m, 2 H) 4.48-4.56 (m, 2 H) 5.18 (s, 2 H) 7.10-7.14 (m, 1 H) 7.27-7.35 (m, 2 H) 7.73 (d, J = 1.54 Hz, 1 H) 8.43 (d, J = 4.84 Hz, 1 H) 8.69-8.74 (m, 1 H); m/z = 517.05 (M + H)+ |
| 175 | 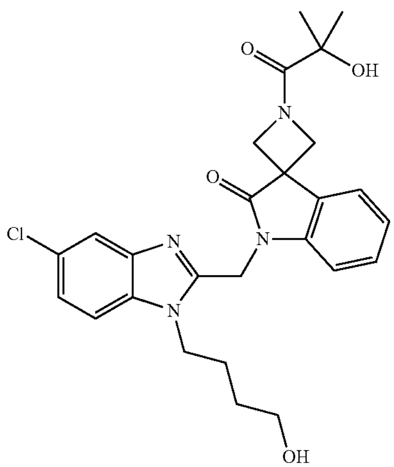 [SMILES: CC(C)(O)C(=O)N1CC2(C1)C(=O)N(Cc1nc3cc(Cl)ccc3n1CCCCO)c1ccccc12] | 1'-{[5-Chloro-1-(4-hydroxybutyl)-1H-benzimidazol-2-yl]methyl}-1-(2-hydroxy-2-methylpropanoyl)spiro[azetidine-3,3'-indol]-2'(1'H)-one<br>$^1$H-NMR (360 MHz, DMSO-d6): δ ppm 1.31 (s, 3 H), 1.33 (s, 3 H), 1.39-1.51 (m, 2 H), 1.61-1.75 (m, 2 H), 3.36-3.44 (m, 2 H), 4.02-4.18 (m, 2 H), 4.33 (t, J = 7.5 Hz, 2 H), 4.48 (t, J = 5.1 Hz, 1 H), 4.54-4.74 (m, 2 H), 5.21 (s, 2 H), 5.29 (s, 1 H), 7.10-7.21 (m, 2 H), 7.25-7.33 (m, 2 H), 7.59-7.65 (m, 2 H), 7.67 (d, J = 1.8 Hz, 1 H); m/z = 497 (M + H)+ |
| 176 | 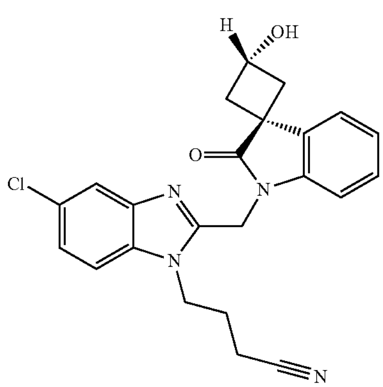 [SMILES: N#CCCCn1c(CN2c3ccccc3[C@]3(C[C@@H](O)C3)C2=O)nc2cc(Cl)ccc21] | 4-(5-chloro-2-(((1r,3r)-3-hydroxy-2'-oxospiro[cyclobutane-1,3'-indolin]-1'-yl)methyl)-1H-benzo[d]imidazol-1-yl)butanenitrile<br>$^1$H-NMR (400 MHz, DMSO-d6) δ ppm 2.03 (quin, J = 7.54 Hz, 2 H) 2.27-2.40 (m, 2 H) 2.57-2.73 (m, 4 H) 4.38 (t, J = 7.48 Hz, 2 H) 4.56 (sxt, J = 7.35 Hz, 1 H) 5.20 (s, 2 H) 5.45 (d, J = 7.26 Hz, 1 H) 7.05-7.14 (m, 2 H) 7.22 (td, J = 7.70, 1.10 Hz, 1 H) 7.29 (dd, J = 8.58, 1.76 Hz, 1 H) 7.48-7.54 (m, 1 H) 7.61-7.68 (m, 2 H); m/z = 421.01 (M + H)+; MP = 217.25° C. |

| No | structure | Name/analytical details |
|---|---|---|
| 178 | 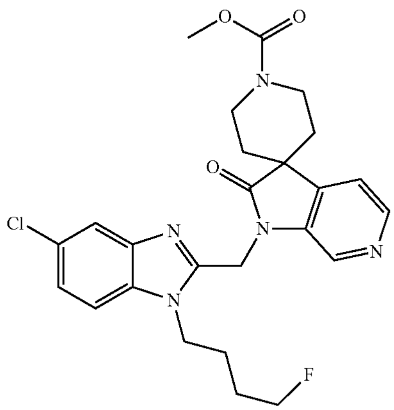 | Methyl 1'-{[5-chloro-1-(4-fluorobutyl)-1H-benzimidazol-2-yl]methyl}-2'-oxo-1',2'-dihydro-1H-spiro[piperidine-4,3'-pyrrolo[2,3-c]pyridine]-1-carboxylate<br>$^1$H-NMR (400 MHz, DMSO-d6) δ ppm 1.65-1.91 (m, 8 H), 3.66 (s, 3 H), 3.71-3.81 (m, 4 H), 4.37 (t, J = 7.3 Hz, 2 H), 4.43 (t, J = 5.9 Hz, 1 H), 4.55 (t, J = 5.6 Hz, 1 H), 5.29 (s, 2 H), 7.29 (dd, J = 8.7, 1.9 Hz, 1 H), 7.62-7.70 (m, 3 H), 8.33 (d, J = 4.8 Hz, 1 H), 8.49 (s, 1 H); m/z = 500 (M + H)+; MP = 182.68° C. |
| 179 | 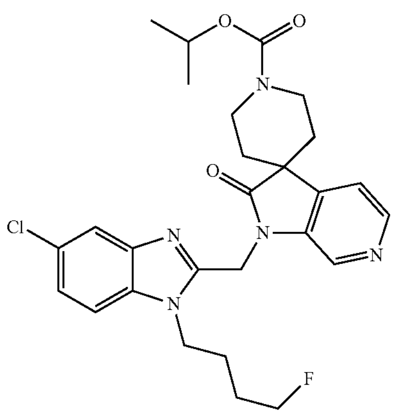 [SMILES: CC(C)OC(=O)N1CCC2(CC1)C(=O)N(Cc1nc3cc(Cl)ccc3n1CCCCF)c1cnccc12] | 1-Methylethyl 1'-{[5-chloro-1-(4-fluorobutyl)-1H-benzimidazol-2-yl]methyl}-2'-oxo-1',2'-dihydro-1H-spiro[piperidine-4,3'-pyrrool[2,3-c]pyridine]-1-carboxylate<br>$^1$H-NMR (400 MHz, DMSO-d6) δ ppm 1.23 (d, J = 6.2 Hz, 6 H), 1.65-1.91 (m, 8 H), 3.65-3.81 (m, 4 H), 4.37 (t, J = 7.3 Hz, 2 H), 4.43 (t, J = 5.9 Hz, 1 H), 4.54 (t, J = 5.6 Hz, 1 H), 4.78-4.90 (m, 1 H), 5.29 (s, 2 H), 7.28 (dd, J = 8.7, 1.9 Hz, 1 H), 7.65 (dd, J = 5.4, 3.2 Hz, 2 H), 7.68 (dd, J = 4.7, 0.6 Hz, 1 H), 8.33 (d, J = 4.8 Hz, 1 H), 8.48 (s, 1 H); m/z = 528 (M + H)+; MP = 198.92° C. |
| 180 | 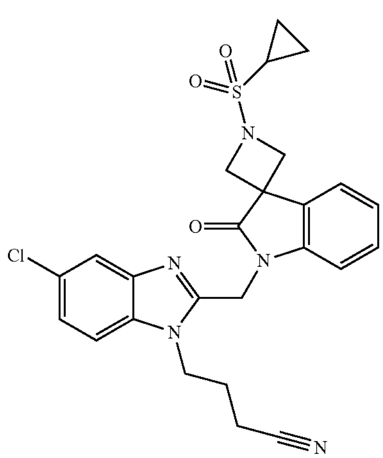 [SMILES: N#CCCCn1c(CN2C(=O)C3(CN(S(=O)(=O)C4CC4)C3)c3ccccc32)nc2cc(Cl)ccc21] | 4-(5-Chloro-2-{[1-(cyclopropylsulfonyl)-2'-oxospiro[azetidine-3,3'-indol]-1'(2'H)-yl]methyl}-1H-benzimidazol-1-yl)butanenitrile<br>$^1$H-NMR (400 MHz, DMSO-d6) δ ppm 1.01-1.19 (m, 4 H) 2.01-2.14 (m, 2 H) 2.63 (t, J = 7.26 Hz, 2 H) 2.93-3.03 (m, 1 H) 4.12-4.34 (m, 4 H) 4.40 (t, J = 7.59 Hz, 2 H) 5.23 (s, 2 H) 7.12-7.24 (m, 2 H) 7.27-7.37 (m, 2 H) 7.61-7.72 (m, 3 H); m/z = 510.10 (M + H)+; MP = 190.42° C. |

| No | structure | Name/analytical details |
|---|---|---|
| 181 | 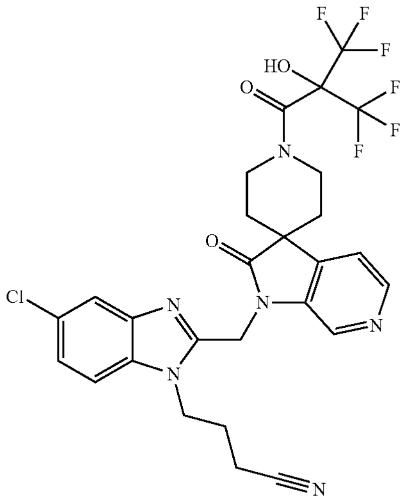 [SMILES: N#CCCCn1c(CN2C(=O)C3(CCN(C(=O)C(O)(C(F)(F)F)C(F)(F)F)CC3)c3ccncc32)nc2cc(Cl)ccc21] | 4-[5-Chloro-2-({2'-oxo-1-[3,3,3-trifluoro-2-hydroxy-2-(trifluoromethyl)propanoyl]spiro[piperidine-4,3'-pyrrolo[2,3-c]pyridin]-1'(2'H)-yl}methyl)-1H-benzimidazol-1-yl]butanenitrile<br>$^1$H-NMR (400 MHz, DMSO-d6) δ ppm 1.72-2.01 (m, 4 H) 2.03-2.16 (m, 2 H) 2.64 (t, J = 7.50 Hz, 2 H) 3.81-4.03 (m, 2 H) 4.22-4.35 (m, 2 H) 4.35-4.45 (m, 2 H) 5.32 (s, 2 H) 7.29 (dd, J = 8.58, 1.98 Hz, 1 H) 7.57-7.73 (m, 3 H) 8.35 (d, J = 4.62 Hz, 1 H) 8.49 (s, 1 H) 9.41 (s, 1 H); m/z = 629 (M + H)+; MP = 240.41° C. |
| 183 | 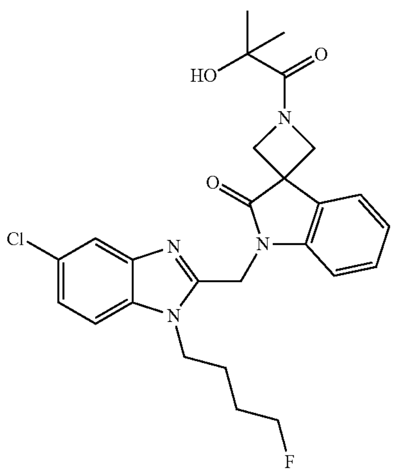 [SMILES: CC(C)(O)C(=O)N1CC2(C1)C(=O)N(Cc1nc3cc(Cl)ccc3n1CCCCF)c1ccccc12] | 1'-{[5-Chloro-1-(4-fluorobutyl)-1H-benzimidazol-2-yl]methyl}-1-(2-hydroxy-2-methylpropanoyl)spiro[azetidine-3,3'-indol]-2'(1'H)-one<br>$^1$H-NMR (400 MHz, DMSO-d$_6$) δ ppm 1.33 (d, J = 7.70 Hz, 6 H) 1.60-1.83 (m, 4 H) 4.06 (d, J = 9.68 Hz, 1 H) 4.16 (d, J = 9.68 Hz, 1 H) 4.27-4.45 (m, 3 H) 4.52 (t, J = 5.39 Hz, 1 H) 4.59 (d, J = 9.68 Hz, 1 H) 4.71 (d, J = 9.68 Hz, 1 H) 5.22 (s, 2 H) 7.10-7.23 (m, 2 H) 7.25-7.33 (m, 2 H) 7.59-7.66 (m, 2 H) 7.67 (d, J = 1.76 Hz, 1 H); m/z = 499 (M + H)+; MP = 219.71° C. |
| 184 | 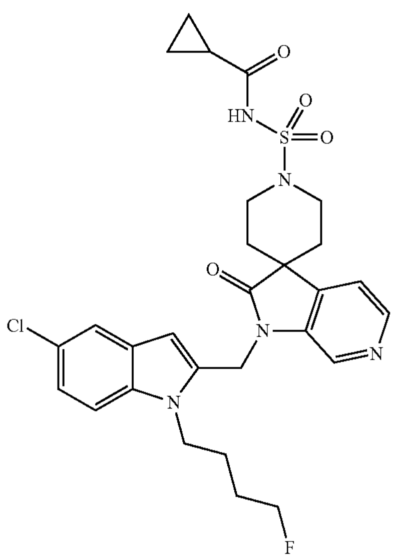 [SMILES: O=C(NS(=O)(=O)N1CCC2(CC1)C(=O)N(Cc1cc3cc(Cl)ccc3n1CCCCF)c1cnccc12)C1CC1] | N-[(1'-{[5-Chloro-1-(4-fluorobutyl)-1H-indol-2-yl]methyl}-2'-oxo-1',2'-dihydro-1H-spiro[piperidine-4,3'-pyrrolo[2,3-c]pyridin]-1-yl)sulfonyl]cyclopropanecarboxamide<br>m/z = 588 (M + H)+ |

Antiviral Activity

Black 96-well clear-bottom microtiter plates (Corning, Amsterdam, The Netherlands) were filled in duplicate using a customized robot system with serial 4-fold dilutions of compound in a final volume of 50 µl culture medium [RPMI medium without phenol red, 10% FBS, 0.04% gentamycin (50 mg/ml) and 0.5% DMSO]. Then, 100 µl of a HeLa cell suspension ($5 \times 10^4$ cells/ml) in culture medium was added to each well followed by the addition of 50 µl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% $CO_2$ atmosphere. Three days post-virus exposure, viral replication was quantified by measuring GFP expression in the cells by a MSM laser microscope (Tibotec, Beerse, Belgium). The $EC_{50}$ was defined as the 50% inhibitory concentration for GFP expression. In parallel, compounds were incubated for three days in a set of white 96-well microtitier plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity. SI is calculated as $CC_{50}/EC_{50}$.

REFERENCES

Hallak L K, Spillmann D, Collins P L, Peeples M E. Glycosaminoglycan sulfation requirements for respiratory syncytial virus infection. J. Virol. 740, 10508-10513 (2000).

| N° | pEC$_{50}$ | SI |
|---|---|---|
| 1 | 9.2 | 19370 |
| 2 | 7.3 | >2193.76 |
| 3 | 10.5 | >3.23668e+006 |
| 4 | 10.1 | 654998 |
| 5 | 8.3 | >20325 |
| 6 | 9.3 | >220491 |
| 7 | 10.6 | >3.59137e+006 |
| 8 | 9.1 | >127462 |
| 9 | 9.4 | >234634 |
| 10 | 8.7 | 49544 |
| 11 | 9.4 | >249735 |
| 12 | 9.3 | >194729 |
| 13 | 10.3 | >2.13334e+006 |
| 14 | >9.8 | >655360 |
| 15 | >9.8 | >655360 |
| 16 | >9.8 | >643591 |
| 17 | 9.5 | 79869 |
| 18 | 8.9 | >84288.8 |
| 19 | 8.4 | >21417.6 |
| 20 | 8.4 | 1880 |
| 21 | 8.3 | >21256.9 |
| 22 | 8.1 | 3515 |
| 23 | 8.1 | 606 |
| 24 | 8.1 | >13913.6 |
| 25 | 7.5 | 1386 |
| 26 | 6.5 | 164 |
| 27 | | — |
| 28 | >9.8 | >660861 |
| 29 | >9.8 | >660861 |
| 30 | 9.6 | >405070 |
| 31 | 8.5 | >34055.7 |
| 32 | 9.2 | >147839 |
| 33 | 9.8 | >563300 |
| 34 | 8.9 | >79744.4 |
| 35 | 9.1 | 65535 |
| 36 | 9.6 | 353419 |
| 37 | 10.0 | >935083 |
| 38 | 9.8 | >571387 |
| 39 | 9.2 | 59894 |
| 40 | 8.6 | >43461 |
| 41 | 7.34 | >2230.95 |
| 42 | >9.8 | >655360 |
| 43 | 9.6 | >419527 |
| 44 | 9.6 | >384096 |
| 45 | 9.4 | >227520 |
| 46 | 9.2 | >155253 |
| 47 | 8.8 | >61850 |
| 48 | 8.6 | >43054.6 |
| 49 | 8.3 | 2615 |
| 50 | 8.0 | >8995.8 |
| 51 | 7.2 | 595 |
| 52 | 8.6 | 22757 |
| 53 | >9.8 | >305014 |
| 54 | 8.8 | 20155 |
| 55 | 10.3 | 1382102 |
| 56 | 9.5 | >298202 |
| 57 | 7.08 | 842.91 |
| 58 | >9.7 | >386305 |
| 59 | 8.3 | 14980 |
| 60 | 9.6 | >390292 |
| 61 | 9.4 | >241324 |
| 62 | 9.0 | 46732 |
| 63 | 9.8 | 100580 |
| 64 | 9.6 | >379778 |
| 65 | 9.2 | 158245 |
| 66 | 8.5 | >29357.6 |
| 67 | 10.3 | 1260115 |
| 68 | 9.3 | >204235 |
| 69 | 8.3 | 4891 |
| 70 | >9.8 | >325484 |
| 70 | >9.8 | >313148 |
| 71 | 8.5 | 12968 |
| 72 | 9.6 | >405070 |
| 73 | 9.3 | 51488 |
| 74 | 9.7 | 342437 |
| 75 | 8.3 | >21707.5 |
| 76 | >9.8 | >263057 |
| 77 | >9.8 | >96511.7 |
| 78 | 9.2 | 24938 |
| 80 | >9.8 | >319161 |
| 81 | >9.8 | >655360 |
| 82 | >9.8 | >655360 |
| 83 | >9.8 | >655360 |
| 84 | 9.2 | >176673 |
| 85 | >9.8 | >655360 |
| 86 | >9.8 | >349849 |
| 88 | 9.4 | >253700 |
| 89 | 10.1 | >124385 |

| Compound Number | RSV-wt_pEC50 | SI_TOX-HELA_wt |
|---|---|---|
| 90 | 10.33 | >2.13954e+006 |
| 91 | 9.63 | >428924 |
| 92 | 10.16 | >1.43463e+006 |
| 93 | 8.79 | >62290.2 |
| 94 | 9.89 | >770442 |
| 95 | 10.10 | >1.25505e+006 |
| 96 | 9.37 | >233222 |
| 97 | 8.84 | 31764 |
| 98 | 10.17 | >1.46504e+006 |
| 99 | 10.62 | 2437755 |
| 100 | 6.58 | >380.041 |
| 101 | 9.05 | >111491 |
| 102 | 8.84 | >68433.7 |
| 103 | 9.58 | 76392 |
| 104 | 10.64 | 3927534 |
| 105 | 10.08 | 895262 |

193
-continued

| Compound Number | RSV-wt_pEC50 | SI_TOX-HELA_wt |
|---|---|---|
| 106 | 9.62 | 80390 |
| 107 | 10.10 | >1.25219e+006 |
| 108 | 9.06 | >57149.2 |
| 109 | 9.72 | >523866 |
| 110 | 8.84 | >69368.1 |
| 111 | 9.91 | 274530 |
| 112 | 10.60 | >3.96908e+006 |
| 113 | 7.18 | >1507.51 |
| 114 | 9.37 | 120036 |
| 115 | 10.16 | >1.45522e+006 |
| 116 | 10.15 | >1.42033e+006 |
| 117 | 8.0 | 6595 |
| 120 | 8.62 | 4817 |
| 121 | 8.07 | >11676.2 |
| 122 | 8.08 | >12032.3 |
| 123 | 9.47 | 33180 |
| 124 | 8.23 | >16849.6 |
| 125 | 9.54 | >342949 |
| 126 | 9.59 | 199719 |
| 129 | 9.45 | 144016 |
| 131 | 9.37 | 107026 |
| 132 | 10.19 | 281041 |
| 133 | 9.85 | >714628 |
| 134 | 8.70 | 21330 |
| 135 | 10.02 | >1.05419e+006 |
| 136 | 9.61 | 251299 |
| 137 | 9.97 | 232965 |
| 138 | 8.67 | >46631.6 |
| 143 | 8.48 | >30292.8 |
| 144 | 9.64 | >435994 |
| 145 | 9.52 | >330255 |
| 146 | 9.30 | >198577 |
| 147 | 10.26 | 872087 |
| 148 | 8.33 | 10550 |
| 149 | 8.92 | 43155 |
| 150 | 10.31 | 862700 |
| 152 | 8.80 | 31147 |
| 153 | 10.24 | 388687 |
| 154 | 8.93 | >85767 |
| 155 | 9.77 | 291340 |
| 156 | 10.17 | 178008 |
| 157 | 8.40 | 6934 |
| 158 | 9.24 | 78873 |
| 162 | 8.34 | 2405 |
| 163 | 9.70 | 95825 |
| 164 | 9.90 | >800424 |
| 165 | 9.84 | 288416 |
| 166 | 9.27 | 64805 |
| 167 | 9.91 | >408517 |
| 168 | 10.46 | 2134519 |
| 169 | 10.56 | — |
| 170 | 9.57 | >370143 |
| 172 | 10.18 | >1.51471e+006 |
| 173 | 10.65 | 2178763 |
| 174 | 7.75 | >5597.19 |
| 175 | 10.13 | >1.34645e+006 |
| 176 | 9.44 | >278272 |
| 178 | 10.54 | 3132492 |
| 179 | 10.36 | 1045996 |
| 180 | 9.93 | >847754 |
| 181 | 9.60 | 271188 |
| 183 | 10.12 | 1295538 |
| 184 | 9.66 | 215909 |

194

The invention claimed is:
1. The compound according to formula (RI)

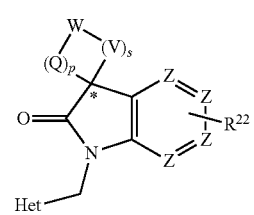

Formula (RI)

wherein Het is selected from the group consisting of: formula (a'), (b'), (c'), and (d'):

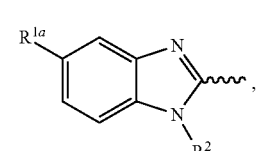

(a')

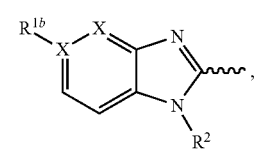

(b')

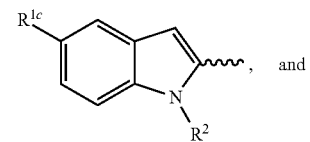

(c')

and

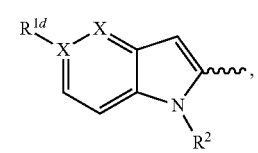

(d')

wherein each X independently is C or N; wherein at least one X is N;
each of $R^{1a}$, $R^{1b}$, $R^{1c}$, $R^{1d}$ is halogen; and $R^{1b}$ or $R^{1d}$ is absent when the X to which it is bound is N;
each $R^2$ is $—(CR^8R^9)_m—R^{10}$;
m is an integer from 0 to 6;
each $R^8$ and $R^9$ are independently selected from the group consisting of: H, $C_1$-$C_{10}$alkyl and $C_3$-$C_7$cycloalkyl; or $R^8$ and $R^9$ are taken together form a 4 to 6 membered saturated ring that optionally contains one or more heteroatoms selected from the group consisting of: N, S and O;
each $R^{10}$ is independently selected from the group consisting of: H, halogen, OH, CN, $CF_2H$, $CF_3$, $C_1$-$C_6$alkyl, $C_3$-$C_7$cycloalkyl, $C(=O)C_1$-$C_6$alkyl, $C(=O)C_3$-$C_7$cycloalkyl, $C(=O)NR^8R^9$, $C(=O)OR^8$, $SO_2R^8$, $C(=O)N(R^8)SO_2R^9$, $C(=O)N(R^8)SO_2N(R^8R^9)$, $NR^8R^9$, $NR^8C(=O)OR^9$, $OC(=O)R^8$, O-benzyl, $NR^8SO_2R^9$, $SO_2NR^8R^9$, $SO_2R^8$, $OC(=O)NR^8R^9$, $OC(=O)NR^8R^{12}$, $N(R^8)C(=O)N(R^8R^9)$, $R^{11}$, $N(R^8)C(=O)OR^{12}$, $OR^{11}$, $C(=O)R^{11}$, and a 4 to 6 membered saturated ring containing one oxygen atom;
$R^{11}$ phenyl, pyridinyl or pyrazolyl; wherein each phenyl, pyridinyl or pyrazolyl can be optionally substituted with one or more substituents each independently selected from the group consisting of: $CF_3$, $CH_3$, $OCH_3$, $OCF_3$, and halogen;

$R^{12}$ is $C_1$-$C_6$ alkyl or $C_3$-$C_7$cycloalkyl; wherein each $C_1$-$C_6$ alkyl or $C_3$-$C_7$cycloalkyl is substituted with one or more substituents each independently selected from the group consisting of: $CF_3$, $CH_3$, $OCH_3$, $OCF_3$, and halogen;

each Z independently is C or N, provided that at least two Z are C;

Q and V each independently represent C=O, $SO_2$ or $CR^{20}R^{21}$;

p and s independently represent an integer from 0 to 3, wherein the sum of p and s minimally should be 2, and when p=0 or s=0 then the carbon atom marked with * is directly bound to W;

$R^{20}$ and $R^{21}$ are each independently selected from the group consisting of: hydrogen, hydroxyl, $C_1$-$C_3$alkyl, $C_3$-$C_7$cycloalkyl, $CF_3$, $OCH_3$, $OCF_3$, and halogen;

$R^{22}$ is selected from the group consisting of: hydrogen, hydroxyl, $C_1$-$C_6$alkyl, $C_3$-$C_7$cycloalkyl, $CF_3$, $OCH_3$, $OCF_3$, and halogen;

W is selected from the group consisting of: SO, $SO_2$, S, C, O, and N, wherein such C or N is optionally substituted with one or more $R^{23}$;

$R^{23}$ is selected from the group consisting of: hydrogen, hydroxyl, $C_1$-$C_6$alkyl, $C_3$-$C_7$cycloalkyl, $C_1$-$C_6$alkyl-$R^{24}$, $SO_2R^{24}$ $SO_2N(R^{24})_2$, aryl, heteroaryl, C(=O)$OR^{24}$, $OR^{24}$, C(=O)$R^{24}$, C(=O)N($R^{24}$)$_2$, OC(=O)N($R^{24}$)$_2$, P(=O)—(O—$C_1$-$C_6$-alkyl)$_2$, N($R^{24}$)$_2$, $NR^{25}$C(=O)$OR^{24}$, $NR^{25}$C(=O)N($R^{24}$)$_2$, $NR^{25}SO_2R^{24}$, and a 4 to 6 membered saturated ring containing one oxygen atom, wherein any of such $C_1$-$C_6$alkyl, $C_3$-$C_7$cycloalkyl, aryl or heteroaryl is optionally substituted with one or more substituents each independently selected from the group consisting of: halogen, OH, CN, and $OCH_3$;

$R^{24}$ is selected from the group of: hydrogen, OH, halogen, $C_1$-$C_6$alkyl, $C_3$-$C_7$cycloalkyl, C(=O) $C_1$-$C_6$alkyl, C(=O) $C_3$-$C_7$cycloalkyl, aryl, heteroaryl, benzyl, and a 4 to 6 membered saturated ring containing one oxygen atom; wherein any of such $C_1$-$C_6$alkyl, $C_3$-$C_7$cycloalkyl, C(=O) $C_1$-$C_6$alkyl, C(=O) $C_3$-$C_7$cycloalkyl, aryl, heteroaryl, and benzyl is optionally substituted with one or more substituents each independently selected from the group consisting of: halogen, $CF_3$, OH, CN, $OCH_3$, OC(=O)$CH_3$), and $C_1$-$C_3$alkyl substituted with at least one CN;

$R^{25}$ is selected from the group consisting of hydrogen and $C_1$-$C_3$ alkyl;

aryl represents phenyl or naphthalenyl;

heteroaryl represents a monocyclic 5 to 6 membered aromatic heterocycle containing one or more heteroatoms each independently selected from the group consisting of: O, S and N; or a bicyclic 8 to 12 membered aromatic heterocycle containing one or more heteroatoms each independently selected from the group consisting of: O, S and N;

or a pharmaceutically acceptable addition salt or a solvate thereof.

2. The compound according to claim 1, wherein for Formula (b') and (d'), one X is N.

3. A compound according to claim 1, wherein each of $R^{1a}$, $R^{1b}$, $R^{1c}$ or $R^{1d}$ is independently selected from the group consisting of: chloro, bromo and fluoro.

4. A compound according to claim 1, wherein each of $R^{1a}$, $R^{1b}$, $R^{1c}$ or $R^{1d}$ is chloro.

5. A compound according to claim 1, wherein $R^2$ is —(CR$^8$R$^9$)$_m$—R$^{10}$; m is an integer from 1 to 4; and each of $R^8$ and $R^9$ is independently selected from: H or $C_1$-$C_6$alkyl.

6. A compound according to claim 1, wherein $R^2$ is $C_1$-$C_6$ alkyl-$R^{10}$.

7. A compound according to claim 6, wherein $R^{10}$ is selected from the group consisting of: $C_1$-$C_3$ alkyl, H, OH, CN, F, $CF_2H$, $CF_3$, $SO_2$—$C_1$-$C_3$alkyl, and $SO_2C_3$-$C_6$cycloalkyl.

8. A compound according to claim 1, wherein the compound has the Formula selected from the group consisting of: RII, RIII, RIV, RV, RVI and RVII:

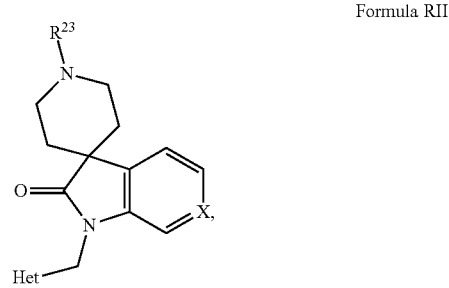

Formula RII

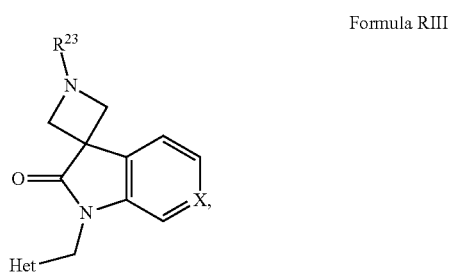

Formula RIII

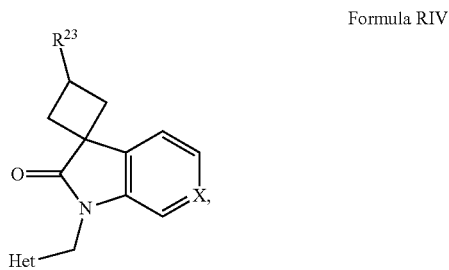

Formula RIV

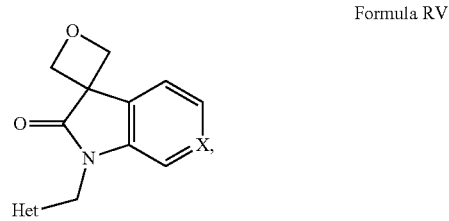

Formula RV

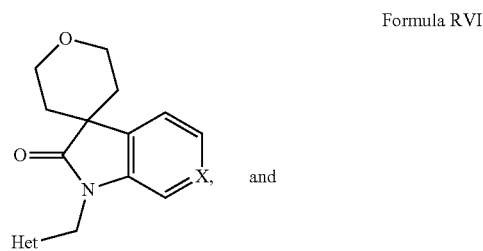

Formula RVI and

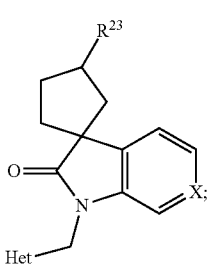

Formula RVII or any stereoisomeric form thereof.

9. The compound as claimed in claim 8 wherein $R^{23}$ is selected from the group consisting of hydrogen, hydroxyl, $C_1$-$C_6$alkyl, $C_1$-$C_3$alkyl-$R^{24}$, $SO_2R^{24}$, O—$R^{24}$, phenyl, pyridinyl pyrimidyl, pyrazolyl, C(=O)O$R^{24}$, and C(=O)$R^{24}$, wherein any of such $C_1$-$C_6$alkyl, phenyl, pyridinyl, pyrimidyl, and pyrazolyl is optionally substituted with one or more members each independently selected from the group consisting of: $OCH_3$, halogen, OH and CN.

10. A pharmaceutical composition comprising a pharmaceutically acceptable carrier, and as active ingredient a compound as claimed in claim 1.

11. A method for treating viral RSV infections comprising administering to a subject in need thereof, a therapeutically effective amount of a compound as claimed in claim 1.

12. A method for treating viral RSV infections comprising administering to a subject in need thereof, a therapeutically effective amount of a composition as claimed in claim 10.

13. The compound selected from the group consisting of:
tert-butyl 1'-({5-chloro-1-[3-(methylsulfonyl)propyl]-1H-indol-2-yl}methyl)-2'-oxo-1',2'-dihydro-1H-spiro[piperidine-4,3'-pyrrolo[2,3-c]pyridine]-1-carboxylate;
1'-({5-chloro-1-[3-(methylsulfonyl)propyl]-1H-indol-2-yl}methyl)spiro[piperidine-4,3'-pyrrolo[2,3-c]pyridin]-2'(1'H)-one;
1'-({5-chloro-1-[3-(methylsulfonyl)propyl]-1H-indol-2-yl}methyl)spiro[piperidine-4,3'-pyrrolo[2,3-c]pyridin]-2'(1'H)-one;
tert-butyl 1'-({5-chloro-1-[3-(methylsulfonyl)propyl]-1H-benzimidazol-2-yl}methyl)-2'-oxo-1',2'-dihydro-1H-spiro[azetidine-3,3'-indole]-1-carboxylate;
1'-({5-chloro-1-[3-(methylsulfonyl)propyl]-1H-benzimidazol-2-yl}methyl)spiro[azetidine-3,3'-indol]-2'(1'H)-one;
1'-({5-chloro-1-[3-(methylsulfonyl)propyl]-1H-benzimidazol-2-yl}methyl)-1-(2-hydroxy-2-methylpropanoyl)spiro[azetidine-3,3'-indol]-2'(1'H)-one;
1'-({5-chloro-1-[3-(methylsulfonyl)propyl]-1H-benzimidazol-2-yl}methyl)-1-(pyridin-3-yl)spiro[azetidine-3,3'-indol]-2'(1'H)-one;
1'-({5-chloro-1-[3-(methylsulfonyl)propyl]-1H-benzimidazol-2-yl}methyl)-1-(2-hydroxy-2-methylpropyl)spiro[azetidine-3,3'-indol]-2'(1'H)-one;
1'-[[5-chloro-1-(3-methylsulfonylpropyl)benzimidazol-2-yl]methyl]-1-(2,2,2-trifluoroethyl)spiro[azetidine-3,3'-indoline]-2'-one;
1-((5-chloro-1-(3-(methylsulfonyl)propyl)-1H-benzo[d]imidazol-2-yl)methyl)-6-fluoro-2',3',5',6'-tetrahydrospiro[indoline-3,4'-pyran]-2-one;
(3S)-1'-({5-chloro-1-[3-(methylsulfonyl)propyl]-1H-benzimidazol-2-yl}methyl)-3-hydroxyspiro[cyclobutane-1,3'-indol]-2'(1'H)-one;
(3R)-1'-({5-chloro-1-[3-(methylsulfonyl)propyl]-1H-benzimidazol-2-yl}methyl)-3-hydroxyspiro[cyclobutane-1,3'-indol]-2'(1'H)-one;
1'-((5-chloro-1-(3-(methylsulfonyl)propyl)-1H-benzo[d]imidazol-2-yl)methyl)-1-(quinoxalin-6-ylsulfonyl)spiro[piperidine-4,3'-pyrrolo[2,3-c]pyridin]-2'(1'H)-one;
tert-butyl 1'-((5-chloro-1-(3-(methylsulfonyl)propyl)-1H-benzo[d]imidazol-2-yl)methyl)-2'-oxo-1',2'-dihydrospiro[piperidine-4,3'-pyrrolo[2,3-c]pyridine]-1-carboxylate;
1-((5-chloro-1-(3-(methylsulfonyl)propyl)-1H-benzo[d]imidazol-2-yl)methyl)-1'-(6-chloropyridazin-3-yl)spiro[indoline-3,4'-piperidin]-2-one;
1-((5-chloro-1-(3-(methylsulfonyl)propyl)-1H-benzo[d]imidazol-2-yl)methyl)-1'-(quinoxalin-6-ylsulfonyl)spiro[indoline-3,4'-piperidin]-2-one;
tert-butyl 1-((5-bromo-1-(3-(methylsulfonyl)propyl)-1H-benzo[d]imidazol-2-yl)methyl)-2-oxospiro[indoline-3,4'-piperidine]-1'-carboxylate;
4-(1-((5-chloro-1-(3-(methylsulfonyl)propyl)-1H-benzo[d]imidazol-2-yl)methyl)-2-oxospiro[indoline-3,4'-piperidine]-1'-yl sulfonyl)benzonitrile;
1-((5-chloro-1-(3-(methylsulfonyl)propyl)-1H-benzo[d]imidazol-2-yl)methyl)-5-fluoro-2',3',5',6'-tetrahydrospiro[indoline-3,4'-pyran]-2-one;
5-bromo-1-((5-chloro-1-(3-(methylsulfonyl)propyl)-1H-benzo[d]imidazol-2-yl)methyl)-1'-(6-chloropyridazin-3-yl)spiro[indoline-3,4'-piperidin]-2-one;
1-((5-chloro-1-(3-(methylsulfonyl)propyl)-1H-benzo[d]imidazol-2-yl)methyl)spiro[indoline-3,4'-piperidin]-2-one;
5-bromo-1-((5-chloro-1-(3-(methylsulfonyl)propyl)-1H-benzo[d]imidazol-2-yl)methyl)-1'-isonicotinoylspiro[indoline-3,4'-piperidin]-2-one;
tert-butyl 5-bromo-1-((5-chloro-1-(3-(methylsulfonyl)propyl)-1H-benzo[d]imidazol-2-yl)methyl)-2-oxospiro[indoline-3,4'-piperidine]-1'-carboxylate;
1'-acetyl-5-chloro-1-((5-chloro-1-(3-(methylsulfonyl)propyl)-1H-benzo[d]imidazol-2-yl)methyl)spiro[indoline-3,4'-piperidin]-2-one;
5-chloro-1-((5-chloro-1-(3-(methylsulfonyl)propyl)-1H-benzo[d]imidazol-2-yl)methyl)-1'-(2-hydroxy-2-methylpropyl)spiro[indoline-3,4'-piperidin]-2-one;
4-chloro-1-({5-chloro-1-[3-(methylsulfonyl)propyl]-1H-benzimidazol-2-yl}methyl)spiro[indole-3,4'-piperidin]-2(1H)-one;
1'-acetyl-4-chloro-1-({5-chloro-1-[3-(methylsulfonyl)propyl]-1H-benzimidazol-2-yl}methyl)spiro[indole-3,4'-piperidin]-2(1H)-one;
1'-({5-chloro-1-[3-(methylsulfonyl)propyl]-1H-benzimidazol-2-yl}methyl)-1-(2-methylpropanoyl)spiro[azetidine-3,3'-indol]-2'(1'H)-one;
1'-({5-chloro-1-[3-(methylsulfonyl)propyl]-1H-benzimidazol-2-yl}methyl)-1-(cyclopropylsulfonyl)spiro[azetidine-3,3'-indol]-2'(1'H)-one;
1-acetyl-1'-({5-chloro-1-[3-(methylsulfonyl)propyl]-1H-benzimidazol-2-yl}methyl)spiro[azetidine-3,3'-indol]-2'(1'H)-one;
1'-({5-chloro-1-[3-(methylsulfonyl)propyl]-1H-benzimidazol-2-yl}methyl)-1-(trifluoroacetyl)spiro[azetidine-3,3'-indol]-2'(1'H)-one;
1'-acetyl-1-({5-chloro-1-[3-(methylsulfonyl)propyl]-1H-benzimidazol-2-yl}methyl)spiro[indole-3,4'-piperidin]-2(1H)-one;

1'-({5-chloro-1-[3-(methylsulfonyl)propyl]-1H-benzimidazol-2-yl}methyl)-1-[(4-fluorophenyl)sulfonyl]spiro[azetidine-3,3'-indol]-2'(1'H)-one;
1-({5-chloro-1-[3-(methylsulfonyl)propyl]-1H-benzimidazol-2-yl}methyl)-1'-[(4-fluorophenyl)sulfonyl]spiro[indole-3,4'-piperidin]-2(1H)-one;
1-({5-chloro-1-[3-(methylsulfonyl)propyl]-1H-benzimidazol-2-yl}methyl)-1'-(cyclopropylsulfonyl)spiro[indole-3,4'-piperidin]-2(1H)-one;
1-({5-chloro-1-[3-(methylsulfonyl)propyl]-1H-benzimidazol-2-yl}methyl)-1'-[(4-methoxyphenyl)sulfonyl]spiro[indole-3,4'-piperidin]-2(1H)-one;
1'-((5-chloro-1-(3-(methylsulfonyl)propyl)-1H-benzo[d]imidazol-2-yl)methyl)spiro[cyclopentane-1,3'-pyrrolo[2,3-c]pyridin]-2'(1'H)-one;
1'-((5-chloro-1-(3-(methylsulfonyl)propyl)-1H-benzo[d]imidazol-2-yl)methyl)-2,3,5,6-tetrahydrospiro[pyran-4,3'-pyrrolo[2,3-c]pyridin]-2'(1'H)-one;
tert-butyl 1-((5-chloro-1-(3-(methylsulfonyl)propyl)-1H-benzo[d]imidazol-2-yl)methyl)-2-oxospiro[indoline-3,4'-piperidine]-1'-carboxylate;
1-((5-chloro-1-(3-(methylsulfonyl)propyl)-1H-benzo[d]imidazol-2-yl)methyl)-2',3',5',6'-tetrahydrospiro[indoline-3,4'-pyran]-2-one;
1'-((5-chloro-1-(3-(methylsulfonyl)propyl)-1H-benzo[d]imidazol-2-yl)methyl)-2,3,5,6-tetrahydrospiro[pyran-4,3'-pyrrolo[3,2-c]pyridin]-2'(1'H)-one;
1-acetyl-1'-((5-chloro-1-(3-(methylsulfonyl)propyl)-1H-benzo[d]imidazol-2-yl)methyl)spiro[piperidine-4,3'-pyrrolo[2,3-c]pyridin]-2'(1'H)-one;
4-fluorophenyl 1'-((5-chloro-1-(4,4,4-trifluorobutyl)-1H-benzo[d]imidazol-2-yl)methyl)-2'-oxospiro[azetidine-3,3'-indoline]-1-carboxylate;
tert-butyl 1'-((5-chloro-1-(4,4,4-trifluorobutyl)-1H-benzo[d]imidazol-2-yl)methyl)-2'-oxospiro[azetidine-3,3'-indoline]-1-carboxylate;
isobutyl 1'-((5-chloro-1-(4,4,4-trifluorobutyl)-1H-benzo[d]imidazol-2-yl)methyl)-2'-oxospiro[azetidine-3,3'-indoline]-1-carboxylate;
1'-((5-chloro-1-(4,4,4-trifluorobutyl)-1H-benzo[d]imidazol-2-yl)methyl)spiro[azetidine-3,3'-indolin]-2'-one;
Cyclopentyl 1-((5-chloro-1-(4,4,4-trifluorobutyl)-1H-benzo[d]imidazol-2-yl)methyl)-2-oxospiro[indoline-3,4'-piperidine]-1'-carboxylate;
tert-butyl 1-((5-chloro-1-(4,4,4-trifluorobutyl)-1H-benzo[d]imidazol-2-yl)methyl)-2-oxospiro[indoline-3,4'-piperidine]-1'-carboxylate;
1-((5-chloro-1-(4,4,4-trifluorobutyl)-1H-benzo[d]imidazol-2-yl)methyl)spiro[indoline-3,4'-piperidin]-2-one;
benzyl 1-((5-chloro-1-(4,4,4-trifluorobutyl)-1H-benzo[d]imidazol-2-yl)methyl)-2-oxospiro[indoline-3,4'-piperidine]-1'-carboxylate;
1'-benzyl-1-((5-chloro-1-(4,4,4-trifluorobutyl)-1H-benzo[d]imidazol-2-yl)methyl)spiro[indoline-3,4'-piperidin]-2-one;
1-((5-chloro-1-(4,4,4-trifluorobutyl)-1H-benzo[d]imidazol-2-yl)methyl)-2',3',5',6'-tetrahydrospiro[indoline-3,4'-pyran]-2-one;
tert-butyl 1'-((5-chloro-1-(3-cyanopropyl)-1H-benzo[d]imidazol-2-yl)methyl)-2'-oxo-1',2'-dihydrospiro[piperidine-4,3'-pyrrolo[2,3-c]pyridine]-1-carboxylate;
1'-({5-chloro-1-[3-(methylsulfonyl)propyl]-1H-indol-2-yl}methyl)spiro[cyclopentane-1,3'-pyrrolo[2,3-c]pyridin]-2'(1'H)-one;
1'-({5-chloro-1-[3-(methylsulfonyl)propyl]-1H-indol-2-yl}methyl)-2'-oxo-1',2'-dihydro-1H-spiro[piperidine-4,3'-pyrrolo[2,3-c]pyridine]-1-carboxylate;
1-acetyl-1'-({5-chloro-1-[3-(methylsulfonyl)propyl]-1H-indol-2-yl}methyl)spiro[piperidine-4,3'-pyrrolo[2,3-c]pyridin]-2'(1'H)-one;
1'-((5-chloro-1-(3-(methylsulfonyl)propyl)-1H-indol-2-yl)methyl)-2,3,5,6-tetrahydrospiro[pyran-4,3'-pyrrolo[3,2-c]pyridin]-2'(1'H)-one;
tert-butyl 1'-{[5-chloro-1-(3-cyanopropyl)-1H-indol-2-yl]methyl}-2'-oxo-1',2'-dihydro-1H-spiro[azetidine-3,3'-indole]-1-carboxylate;
4-{5-chloro-2-[(2'-oxospiro[azetidine-3,3'-indol]-1'(2'H)-yl)methyl]-1H-indol-1-yl}butanenitrile;
1'-{[5-chloro-1-(3-cyanopropyl)-1H-indol-2-yl]methyl}-2'-oxo-1',2'-dihydro-1H-spiro[azetidine-3,3'-indole]-1-carboxylate;
4-(5-chloro-2-{[1-(cyclopropylsulfonyl)-2'-oxospiro[azetidine-3,3'-indol]-1'(2'H)-yl]methyl}-1H-indol-1-yl)butanenitrile;
4-{2-[(1-acetyl-2'-oxospiro[azetidine-3,3'-indol]-1'(2'H)-yl)methyl]-5-chloro-1H-indol-1-yl}butanenitrile;
tert-butyl 1'-((5-chloro-1-(3-cyanopropyl)-1H-indol-2-yl)methyl)-2'-oxo-1',2'-dihydrospiro[piperidine-4,3'-pyrrolo[2,3-c]pyridine]-1-carboxylate;
4-(2-((1-acetyl-2'-oxospiro[piperidine-4,3'-pyrrolo[2,3-c]pyridin]-1'(2'H)-yl)methyl)-5-chloro-1H-indol-1-yl)butanenitrile;
1'-((5-chloro-1-(4,4,4-trifluorobutyl)-1H-imidazo[4,5-b]pyridin-2-yl)methyl)spiro[cyclopentane-1,3'-pyrrolo[2,3-c]pyridin]-2'(1'H)-one;
tert-butyl-2'-oxo-1'-((1-(4,4,4-trifluorobutyl)-1H-imidazo[4,5-b]pyridine-2-yl)methyl)-1',2'-dihydrospiro[piperidine-4,3'-pyrrolo[2,3-c]pyridine]-1-carboxylate;
1'-((5-chloro-1-(4,4,4-trifluorobutyl)-1H-imidazo[4,5-b]pyridin-2-yl)methyl)-2,3,5,6-tetrahydrospiro[pyran-4,3'-pyrrolo[2,3-c]pyridin]-2'(1'H)-one;
tert-butyl-1' 4(5-chloro-1-(4,4,4-trifluorobutyl)-1H-imidazo[4,5-b]pyridin-2-yl)methyl)-2'-oxo-1',2'-dihydrospiro[piperidine-4,3'-pyrrolo[2,3-c]pyridine]-1-carboxylate;
tert-butyl 1'-((5-chloro-1-(4-fluorobutyl)-1H-pyrrolo[3,2-b]pyridin-2-yl)methyl)-2'-oxo-1',2'-dihydrospiro[piperidine-4,3'-pyrrolo[2,3-c]pyridine]-1-carboxylate;
tert-butyl 1'-((5-chloro-1-(3-cyanopropyl)-1H-benzo[d]imidazol-2-yl)methyl)-2'-oxospiro[azetidine-3,3'-indoline]-1-carboxylate;
1-((5-chloro-1-(4,4,4-trifluorobutyl)-1H-benzo[d]imidazol-2-yl)methyl)-6-fluoro-2',3',5',6'-tetrahydrospiro[indoline-3,4'-pyran]-2-one;
1-acetyl-1'-((5-chloro-1-(3-(methylsulfonyl)propyl)-1H-benzo[d]imidazol-2-yl)methyl)spiro[azetidine-3,3'-indolin]-2'-one;
4-(5-chloro-2-((1-(2-hydroxy-2-methylpropanoyl)-2'-oxospiro[azetidine-3,3'-indolin]-1'-yl)methyl)-1H-indol-1-yl)butanenitrile;
1'-((5-chloro-1-(3-(methylsulfonyl)propyl)-1H-indol-2-yl)methyl)-1-(2-hydroxy-2-methylpropanoyl)spiro[piperidine-4,3'-pyrrolo[2,3-c]pyridin]-2'(1'H)-one;
1'-((5-chloro-1-(4,4,4-trifluorobutyl)-1H-imidazo[4,5-b]pyridin-2-yl)methyl)-2,3,5,6-tetrahydrospiro[pyran-4,3'-pyrrolo[2,3-c]pyridin]-2'(1'H)-one;
methyl 1'-((5-chloro-1-(3-cyanopropyl)-1H-indol-2-yl)methyl)-2'-oxo-1',2'-dihydrospiro[piperidine-4,3'-pyrrolo[2,3-c]pyridine]-1-carboxylate;
isopropyl 1'-((5-chloro-1-(3-cyanopropyl)-1H-indol-2-yl)methyl)-2'-oxo-1',2'-dihydrospiro[piperidine-4,3'-pyrrolo[2,3-c]pyridine]-1-carboxylate;

4-(5-chloro-2-((2'-oxospiro[piperidine-4,3'-pyrrolo[2,3-c]pyridin]-1'(2'H)-yl)methyl)-1H-indol-1-yl)butanenitrilehydrochloride;

1-(1'-((5-chloro-1-(3-cyanopropyl)-1H-indol-2-yl)methyl)-2'-oxo-1',2'-dihydrospiro[piperidine-4,3'-pyrrolo[2,3-c]pyridin]-1-yl)-2-methyl-1-oxopropan-2-ylacetate;

oxetan-3-yl 1'-((5-chloro-1-(3-cyanopropyl)-1H-indol-2-yl)methyl)-2'-oxo-1',2'-dihydrospiro[piperidine-4,3'-pyrrolo[2,3-c]pyridine]-1-carboxylate;

4-(5-chloro-2-((1-(cyclopropylsulfonyl)-2'-oxospiro[piperidine-4,3'-pyrrolo[2,3-c]pyridin]-1'(2'H)-yl)methyl)-1H-indol-1-yl)butanenitrile;

oxetan-3-yl 1'-((5-chloro-1-(3-cyanopropyl)-1H-benzo[d]imidazol-2-yl)methyl)-2'-oxo-1',2'-dihydrospiro[piperidine-4,3'-pyrrolo[2,3-c]pyridine]-1-carboxylate;

4-(2-((1-acetyl-2'-oxospiro[piperidine-4,3'-c]pyridin]-1'(2'H)-yl)methyl)-5-chloro-1H-benzo[d]imidazol-1-yl)butanenitrile;

4-(5-chloro-2-((2'-oxospiro[piperidine-4,3'-pyrrolo[2,3-c]pyridin]-1'(2'H)-yl)methyl)-1H-benzo[d]imidazol-1-yl)butanenitrilehydrochloride;

1'-((5-chloro-1-(3-(methylsulfonyl)propyl)-1H-benzo[d]imidazol-2-yl)methyl)-1-(cyclopropyl sulfonyl)spiro[piperidine-4,3'-pyrrolo[2,3-c]pyridin]-2'(1'H)-one;

4-(5-chloro-2-((1-(2-hydroxy-2-methylpropanoyl)-2'-oxospiro[piperidine-4,3'-pyrrolo[2,3-c]pyridin]-1'(2'H)-yl)methyl)-1H-indol-1-yl)butanenitrile;

isopropyl 1'-((5-chloro-1-(3-(methylsulfonyl)propyl)-1H-benzo[d]imidazol-2-yl)methyl)-2'-oxo-1',2'-dihydrospiro[piperidine-4,3'-pyrrolo[2,3-c]pyridine]-1-carboxylate;

4-(2-((1-acetyl-2'-oxospiro[azetidine-3,3'-indolin]-1'-yl)methyl)-5-chloro-1H-benzo[d]imidazol-1-yl)butanenitrile;

1'-((5-chloro-1-(3-cyanopropyl)-1H-benzo[d]imidazol-2-yl)methyl)-2'-oxo-1',2'-dihydrospiro[piperidine-4,3'-pyrrolo[2,3-c]pyridine]-1-sulfonamide;

1'-({5-Chloro-1-[3-(methylsulfonyl)propyl]-1H-benzimidazol-2-yl}methyl)-1-(cyclopropylcarbonyl)spiro[piperidine-4,3'-pyrrolo[2,3-c]pyridin]-2'(1'H)-one;

4-(5-Chloro-2-{[2'-oxo-1-(thiophen-2-ylsulfonyl)spiro[azetidine-3,3'-indol]-1'(2'H)-yl]methyl}-1H-benzimidazol-1-yl)butanenitrile;

Oxetan-3-yl 1'-{[5-chloro-1-(3-cyanopropyl)-1H-benzimidazol-2-yl]methyl}-2'-oxo-1',2'-dihydro-1H-spiro[azetidine-3,3'-indole]-1-carboxylate;

4-[5-Chloro-2-({1-[(4-fluorophenyl)sulfonyl]-2'-oxospiro[azetidine-3,3'-indol]-1'(2'H)-yl}methyl)-1H-benzimidazol-1-yl]butanenitrile;

4-(5-Chloro-2-{[1-(methylsulfonyl)-2'-oxospiro[azetidine-3,3'-indol]-1'(2'H)-yl]methyl}-1H-benzimidazol-1-yl)butanenitrile;

N-[(1'-{[5-Chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl)sulfonyl]acetamide;

4-(5-Chloro-2-{[2'-oxo-1-(thiophen-2-ylsulfonyl)spiro[piperidine-4,3'-pyrrolo[2,3-c]pyridin]-1'(2'H)-yl]methyl}-1H-indol-1-yl)butanenitrile;

tert-Butyl 1'-{[1-(3-methylbutyl)-1H-pyrrolo[3,2-c]pyridin-2-yl]methyl}-2'-oxo-1',2'-dihydro-1H-spiro[piperidine-4,3'-pyrrolo[2,3-c]pyridine]-1-carboxylate;

Methyl 1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridine]-1-carboxylate;

1-Methylethyl 1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridine]-1-carboxylate;

4-{5-Chloro-2-[(2'-oxospiro[azetidine-3,3'-indol]-1'(2'H)-yl)methyl]-1H-benzimidazol-1-yl}butanamide;

4-{5-Chloro-2-[(2'-oxospiro[azetidine-3,3'-indol]-1'(2'H)-yl)methyl]-1H-benzimidazol-1-yl}butanenitrile;

1-({5-Chloro-1-[3-(methylsulfonyl)propyl]-1H-benzimidazol-2-yl}methyl)-1'-(thiophen-2-ylsulfonyl)spiro[indole-3,4'-piperidin]-2(1H)-one;

Cyclobutyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate;

(1R,3R)-1'-((5-chloro-1-(3-(methylsulfonyl)propyl)-1H-benzo[d]imidazol-2-yl)methyl)-2'-oxospiro[cyclobutane-1,3'-indoline]-3-ylmethylcarbamate;

4-(5-Chloro-2-{[1-(methylsulfonyl)-2'-oxospiro[piperidine-4,3'-pyrrolo[2,3-c]pyridin]-1'(2'H)-yl]methyl}-1H-indol-1-yl)butanenitrile;

1'-{[5-Chloro-1-(4-fluorobutyl)-1H-indol-2-yl]methyl}-1-(2-hydroxy-2-methylpropanoyl)spiro[piperidine-4,3'-pyrrolo[2,3-c]pyridin]-2'(1'H)-one;

4-(5-Chloro-2-{[1-(2-hydroxy-2-methylpropanoyl)-2'-oxospiro[piperidine-4,3'-pyrrolo[2,3-c]pyridin]-1'(2'H)-yl]methyl}-1H-benzimidazol-1-yl)butanenitrile;

4-{5-Chloro-2-[(1',1'-dioxido-2-oxo-2',3',5',6'-tetrahydrospiro[pyrrolo[2,3-c]pyridine-3,4'-thiopyran]-1(2H)-yl]methyl}-1H-benzimidazol-1-yl}butanenitrile;

4-{5-Chloro-2-[(3-hydroxy-2'-oxospiro[cyclobutane-1,3'-indol]-1'(2'H)-yl)methyl]-1H-benzimidazol-1-yl}butanenitrile;

4-(5-chloro-2-(((1S,3S)-1'-((5-chloro-1-(3-cyanopropyl)-1H-benzo[d]imidazol-2-yl)methyl)-2'-oxospiro[cyclobutane-1,3'-indoline]-3-yloxy)methyl)-1H-benzo[d]imidazol-1-yl)butanenitrile;

1'-{[5-Chloro-1-(4-fluorobutyl)-1H-indol-2-yl]methyl}-2'-oxo-1',2'-dihydro-1H-spiro[piperidine-4,3'-pyrrolo[2,3-c]pyridine]-1-sulfonamide;

4-(5-Chloro-2-{[1-(cyclopropylsulfonyl)-2'-oxospiro[piperidine-4,3'-pyrrolo[2,3-c]pyridin]-1'(2'H)-yl]methyl}-1H-benzimidazol-1-yl)butanenitrile;

tert-Butyl 2'-oxo-1'-{[1-(4,4,4-trifluorobutyl)-1H-indol-2-yl]methyl}-1',2'-dihydro-1H-spiro[piperidine-4,3'-pyrrolo[2,3-c]pyridine]-1-carboxylate;

N-[(1'-{[5-Chloro-1-(4-fluorobutyl)-1H-indol-2-yl]methyl}-2'-oxo-1',2'-dihydro-1H-spiro[piperidine-4,3'-pyrrolo[2,3-c]pyridin]-1-yl)sulfonyl]acetamide;

Diethyl (1'-{[5-chloro-1-(3-cyanopropyl)-1H-benzimidazol-2-yl]methyl}-2'-oxo-1',2'-dihydro-1H-spiro[piperidine-4,3'-pyrrolo[2,3-c]pyridin]-1-yl)phosphonate;

4-(5-Chloro-2-{[2'-oxo-1-(3,3,3-trifluoro-2-hydroxy-2-methylpropanoyl)spiro[piperidine-4,3'-pyrrolo[2,3-c]pyridin]-1'(2'H)-yl]methyl}-1H-benzimidazol-1-yl)butanenitrile;

N-[(1'-{[5-Chloro-1-(3-cyanopropyl)-1H-indol-2-yl]methyl}-2'-oxo-1',2'-dihydro-1H-spiro[azetidine-3,3'-indol]-1-yl)sulfonyl]acetamide;

(1r,3r)-1'-((5-chloro-1-(4-fluorobutyl)-1H-indol-2-yl)methyl)-2'-oxospiro[cyclobutane-1,3'-indolin]-3-ylmethylcarbamate;

(R)-1-({5-Chloro-1-[3-(methylsulfonyl)propyl]-1H-benzimidazol-2-yl}methyl)-1'-(2-hydroxy-2-methylpropanoyl)spiro[indole-3,3'-pyrrolidin]-2(1H)-one;

(S)-1-((5-chloro-1-(3-(methylsulfonyl)propyl)-1H-benzo[d]imidazol-2-yl)methyl)-1'-(2-hydroxy-2-methylpropanoyl)spiro[indoline-3,3'-pyrrolidin]-2-one;

(1r,3r)-1'-((5-chloro-1-(3-cyanopropyl)-1H-indol-2-yl)methyl)-2'-oxospiro[cyclobutane-1,3'-indolin]-3-ylmethylcarbamate;

cyclopropyl ((1s,3s)-1'-((5-chloro-1-(3-cyanopropyl)-1H-benzo[d]imidazol-2-yl)methyl)-2'-oxospiro[cyclobutane-1,3'-indolin]-3-yl)carbamate;

cyclopropyl ((1r,3r)-1'-((5-chloro-1-(3-cyanopropyl)-1H-benzo[d]imidazol-2-yl)methyl)-2'-oxospiro[cyclobutane-1,3'-indolin]-3-yl)carbamate;

(S)-4-(5-chloro-2-((1-(2,3-dihydroxypropanoyl)-2'-oxospiro[azetidine-3,3'-indolin]-1'-yl)methyl)-1H-indol-1-yl)butanenitrile;

(R)-4-(5-chloro-2-((1-(2,3-dihydroxypropanoyl)-2'-oxospiro[azetidine-3,3'-indolin]-1'-yl)methyl)-1H-indol-1-yl)butanenitrile;

Cyclopropyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate;

(1r,3r)-1'-((5-chloro-1-(3-(methylsulfonyl)propyl)-1H-benzo[d]imidazol-2-yl)methyl)-2'-oxospiro[cyclobutane-1,3'-indolin]-3-ylmorpholine-4-carboxylate;

1'-({5-Chloro-1-[3-(methylsulfonyl)propyl]-1H-indol-2-yl}methyl)spiro[azetidine-3,3'-indol]-2'(1'H)-one;

methyl ((1s,3s)-1'-((5-chloro-1-(3-cyanopropyl)-1H-benzo[d]imidazol-2-yl)methyl)-2'-oxospiro[cyclobutane-1,3'-indolin]-3-yl)carbamate;

methyl ((1r,3r)-1'-((5-chloro-1-(3-cyanopropyl)-1H-benzo[d]imidazol-2-yl)methyl)-2'-oxospiro[cyclobutane-1,3'-indolin]-3-yl)carbamate;

4-[5-Chloro-2-({1-[(1-hydroxycyclopropyl)carbonyl]-2'-oxospiro[azetidine-3,3'-indol]-1'(2'H)-yl}methyl)-1H-indol-1-yl]butanenitrile;

1-((5-chloro-1-(3-(methylsulfonyl)propyl)-1H-benzo[d]imidazol-2-yl)methyl)-1'-(2-hydroxy-2-methylpropanoyl)spiro[indoline-3,3'-pyrrolidin]-2-one;

1-((1s,3s)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea;

1-((1r,3r)-1'-((5-chloro-1-(3-cyanopropyl)-1H-benzo[d]imidazol-2-yl)methyl)-2'-oxospiro[cyclobutane-1,3'-indolin]-3-yl)-3-isopropylurea;

N-((1s,3s)-1'-((5-chloro-1-(3-cyanopropyl)-1H-benzo[d]imidazol-2-yl)methyl)-2'-oxospiro[cyclobutane-1,3'-indolin]-3-yl)acetamide;

N-((1r,3r)-1'-((5-chloro-1-(3-cyanopropyl)-1H-benzo[d]imidazol-2-yl)methyl)-2'-oxospiro[cyclobutane-1,3'-indolin]-3-yl)acetamide;

2-Hydroxyethyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate;

4-(2-(((1r,3r)-3-amino-2'-oxospiro[cyclobutane-1,3'-indolin]-1'-yl)methyl)-5-chloro-1H-benzo[d]imidazol-1-yl)butanenitrile;

4-(2-(((1s,3s)-3-amino-2'-oxospiro[cyclobutane-1,3'-indolin]-1'-yl)methyl)-5-chloro-1H-benzo[d]imidazol-1-yl)butanenitrile;

2-(Acetyloxy)ethyl 1'-{[5-chloro-1-(3-cyanopropyl)-1H-indol-2-yl]methyl}-2'-oxo-1',2'-dihydro-1H-spiro[piperidine-4,3'-pyrrolo[2,3-c]pyridine]-1-carboxylate;

1'-({5-Chloro-1-[3-(methylsulfonyl)propyl]-1H-indol-2-yl}methyl)-1-(2-hydroxy-2-methylpropanoyl)spiro[azetidine-3,3'-indol]-2'(1'H)-one;

5-Chloro-1-(4-fluorobutyl)-2-{[1-(2-hydroxy-2-methylpropanoyl)-2'-oxospiro[piperidine-4,3'-pyrrolo[2,3-c]pyridin]-1'(2'H)-yl]methyl}-1H-indole-3-carboxamide;

4-(5-Chloro-2-{[1'-(2-hydroxy-2-methylpropanoyl)-2-oxospiro[indole-3,3'-pyrrolidin]-1(2H)-yl]methyl}-1H-benzimidazol-1-yl)butanenitrile;

1'-{[5-Chloro-1-(4-hydroxybutyl)-1H-indol-2-yl]methyl}-1-(2-hydroxy-2-methylpropanoyl)spiro[piperidine-4,3'-pyrrolo[2,3-c]pyridin]-2'(1'H)-one;

tert-Butyl 1'-{[3-carbamoyl-5-chloro-1-(4-fluorobutyl)-1H-indol-2-yl]methyl}-2'-oxo-1',2'-dihydro-1H-spiro[piperidine-4,3'-pyrrolo[2,3-c]pyridine]-1-carboxylate;

tert-Butyl 1-{5-chloro-1-(3-cyanopropyl)-1H-benzimidazol-2-yl]methyl}-2-oxo-1,2-dihydro-1'H-spiro[indole-3,3'-pyrrolidine]-1'-carboxylate;

1'-{[5-Chloro-1-(4-fluorobutyl)-1H-benzimidazol-2-yl]methyl}-3H-spiro[cyclobutane-1,3'-indole]-2',3(1'H)-dione;

1'-{[5-Chloro-1-(4-fluorobutyl)-1H-indol-2-yl]methyl}spiro[piperidine-4,3'-pyrrolo[2,3-c]pyridin]-2'(1'H)-one;

tert-Butyl 1'-({5-chloro-1-[3-(methylsulfonyl)propyl]-1H-indol-2-yl}methyl)-2'-oxo-1',2'-dihydro-1H-spiro[azetidine-3,3'-indole]-1-carboxylate;

1'-{[5-Chloro-1-(4-hydroxybutyl)-1H-benzimidazol-2-yl]methyl}-1-(2-hydroxy-2-methylpropanoyl)spiro[piperidine-4,3'-pyrrolo[2,3-c]pyridin]-2'(1'H)-one;

4-(5-chloro-2-((1-(2,3-dihydroxypropanoyl)-2'-oxospiro[azetidine-3,3'-indolin]-1'-yl)methyl)-1H-indol-1-yl)butanenitrile;

1'-{[5-Chloro-1-(4-hydroxybutyl)-1H-indol-2-yl]methyl}-1-(2-hydroxy-2-methylpropanoyl)spiro[azetidine-3,3'-indol]-2'(1'H)-one;

1'-{[5-Chloro-1-(4-fluorobutyl)-1H-indol-2-yl]methyl}-dihydroxypropanoyl)spiro[piperidine-4,3'-pyrrolo[2,3-c]pyridin]-2'(1'H)-one;

(1r,3r)-1'-((5-chloro-1-(3-cyanopropyl)-1H-benzo[d]imidazol-2-yl)methyl)-2'-oxospiro[cyclobutane-1,3'-indolin]-3-ylmethylcarbamate;

1'-{[5-Chloro-1-(4-fluorobutyl)-1H-benzimidazol-2-yl]methyl}-1-(2-hydroxy-2-methylpropanoyl)spiro[piperidine-4,3'-pyrrolo[2,3-c]pyridin]-2'(1'H)-one;

N-[(1'-{[5-Chloro-1-(3-cyanopropyl)-1H-benzimidazol-2-yl]methyl}-2'-oxo-1',2'-dihydro-1H-spiro[azetidine-3,3'-indol]-1-yl)sulfonyl]acetamide;

N-[(1'-{[5-Chloro-1-(3-cyanopropyl)-1H-indol-2-yl]methyl}-2'-oxo-1',2'-dihydro-1H-spiro[piperidine-4,3'-pyrrolo[2,3-c]pyridin]-1-yl)sulfonyl]acetamide;

(1r,3r)-1'-((5-chloro-1-(3-cyanopropyl)-1H-benzo[d]imidazol-2-yl)methyl)-2'-oxospiro[cyclobutane-1,3'-indolin]-3-ylcyclopropylcarbamate;

1'-({5-Chloro-1-[3-(methylsulfonyl)propyl]-1H-benzimidazol-2-yl}methyl)-2,6-dimethyl-2,3,5,6-tetrahydrospiro[pyran-4,3'-pyrrolo[2,3-c]pyridin]-2'(1'H)-one;

1'-{[5-Chloro-1-(4-hydroxybutyl)-1H-benzimidazol-2-yl]methyl}-1-(2-hydroxy-2-methylpropanoyl)spiro[azetidine-3,3'-indol]-2'(1'H)-one;

4-(5-chloro-2-(((1r,3r)-3-hydroxy-2'-oxospiro[cyclobutane-1,3'-indolin]-1'-yl)methyl)-1H-benzo[d]imidazol-1-yl)butanenitrile;

Methyl 1'-{[5-chloro-1-(4-fluorobutyl)-1H-benzimidazol-2-yl]methyl}-2'-oxo-1',2'-dihydro-1H-spiro[piperidine-4,3'-pyrrolo[2,3-c]pyridine]-1-carboxylate;

1-Methylethyl 1'-{[5-chloro-1-(4-fluorobutyl)-1H-benzimidazol-2-yl]methyl}-2'-oxo-1',2'-dihydro-1H-spiro[piperidine-4,3'-pyrrolo[2,3-c]pyridine]-1-carboxylate;

4-(5-Chloro-2-{[1-(cyclopropylsulfonyl)-2'-oxospiro[azetidine-3,3'-indol]-1'(2'H)-yl]methyl}-1H-benzimidazol-1-yl)butanenitrile;

4-[5-Chloro-2-({2'-oxo-1-[3,3,3-trifluoro-2-hydroxy-2-(trifluoromethyl)propanoyl]spiro[piperidine-4,3'-pyrrolo[2,3-c]pyridin]-1'(2'H)-yl}methyl)-1H-benzimidazol-1-yl]butanenitrile;

1'-{[5-Chloro-1-(4-fluorobutyl)-1H-benzimidazol-2-yl]methyl}-1-(2-hydroxy-2-methylpropanoyl)spiro[azetidine-3,3'-indol]-2'(1'H-one; and N-[(1'-{[5-Chloro-1-(4-fluorobutyl)-1H-indol-2-yl]methyl}-2'-oxo-1',2'-dihydro-1H-spiro[piperidine-4,3'-pyrrolo[2,3-c]pyridin]-1-yl)sulfonyl]cyclopropanecarboxamide;

and pharmaceutically acceptable addition salts or solvates thereof.

14. The compound as claimed in claim 1, wherein the compound is

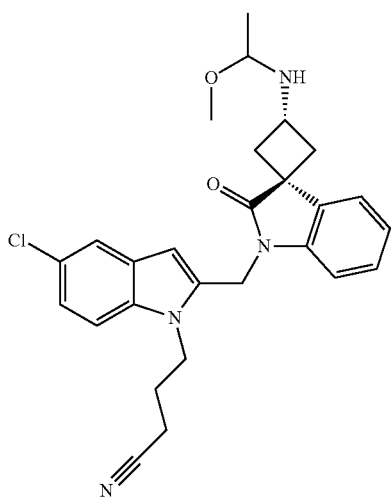 [SMILES: COC(C)N[C@H]1C[C@@]2(C1)C(=O)N(Cc1cc3cc(Cl)ccc3n1CCCC#N)c1ccccc12]

or a pharmaceutically acceptable addition salt or a solvate thereof.

15. A pharmaceutical composition comprising a pharmaceutically acceptable carrier, and a compound as claimed in claim 14.

16. A method for treating a viral RSV infection comprising administering to a subject in need thereof, a therapeutically effective amount of a compound as claimed in claim 14.

17. A method for treating a viral RSV infection comprising administering to a subject in need thereof, a therapeutically effective amount of a composition as claimed in claim 15.

\* \* \* \* \*